US008648074B2

(12) United States Patent
Li et al.

(10) Patent No.: US 8,648,074 B2
(45) Date of Patent: Feb. 11, 2014

(54) SUBSTITUTED OCTAHYDROPYRROLO[1,2-A]PYRAZINE SULFONAMIDES AS CALCIUM CHANNEL BLOCKERS

(71) Applicant: AbbVie Inc., North Chicago, IL (US)

(72) Inventors: Tao Li, Grayslake, IL (US); Sachin V. Patel, Round Lake, IL (US); Richard J. Perner, Gurnee, IL (US); John T. Randolph, Libertyville, IL (US); Michael R. Schrimpf, Grayslake, IL (US); Kevin R. Woller, Antioch, IL (US); Zhiren Xia, Gurnee, IL (US); Qingwei Zhang, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/627,536

(22) Filed: Sep. 26, 2012

(65) Prior Publication Data
US 2013/0085141 A1 Apr. 4, 2013

Related U.S. Application Data

(60) Provisional application No. 61/540,716, filed on Sep. 29, 2011.

(51) Int. Cl.
*A61K 31/495* (2006.01)
(52) U.S. Cl.
USPC ........... 514/249; 544/117; 544/238; 544/333; 544/336; 544/349; 546/268.1; 548/202; 548/335.1; 548/465; 549/59; 549/469
(58) Field of Classification Search
USPC .......... 514/249; 544/117, 238, 333, 336, 349; 546/268.1; 548/202, 335.1, 465; 549/59, 469
See application file for complete search history.

(56) References Cited

U.S. PATENT DOCUMENTS

| 6,316,626 | B1 * | 11/2001 | Swayze et al. ................ 546/207 |
| 8,044,069 | B2 | 10/2011 | Bhatia et al. |
| 8,101,614 | B2 | 1/2012 | Zhang et al. |
| 8,129,417 | B2 | 3/2012 | Stewart et al. |
| 2004/0147559 | A1 | 7/2004 | Taveras et al. |
| 2005/0148587 | A1 | 7/2005 | Fraser et al. |
| 2011/0230459 | A1 | 9/2011 | Drizin et al. |
| 2011/0281870 | A1 | 11/2011 | Searle et al. |
| 2011/0294854 | A1 | 12/2011 | Searle et al. |
| 2013/0085142 | A1 | 4/2013 | Li et al. |
| 2013/0178477 | A1 | 7/2013 | Zhang et al. |

FOREIGN PATENT DOCUMENTS

| EP | 2098526 A1 | 9/2009 |
| WO | 9912034 A1 | 3/1999 |
| WO | 0059882 A1 | 10/2000 |
| WO | 02055518 A1 | 7/2002 |
| WO | 03084955 A1 | 10/2003 |
| WO | 2005079574 A1 | 9/2005 |
| WO | 2007028654 A1 | 3/2007 |
| WO | 2010083264 A1 | 7/2010 |

OTHER PUBLICATIONS

Angeli et al., "Calcium channel blockade to prevent stroke in hypertension: A meta-analysis of 13 studies with 103,793 subjects," Am J Hypertens. 2004, 17(9): 817-822.
Arulmozhi, et al., "Migraine: current concepts and emerging therapies," Vascul Pharmacol. 2005, 43(3): 176-187.
Bao et al., "Differences in $Ca^{2+}$ channels governing generation of miniature and evoked excitatory synaptic currents in spinal laminae I and II," J Neurosci. 1998, 18(21): 8740-8750.
Barone et al., "SB 201823-A antagonizes calcium currents in central neurons and reduces the effects of focal ischemia in rats and mice," Stroke. 1995, 26(9): 1683-1690.
Bell et al., "Cell-specific alternative splicing increases calcium channel current density in the pain pathway," Neuron. 2004, 41(1): 127-138.
Benington et al., Cellular and molecular connections between sleep and synaptic plasticity, Prog Neurobiol. 2003, 69(2): 71-101.
Bennett et al., "A peripheral mononeuropathy in rat that produces disorders of pain sensation like those seen in man," Pain. 1988, 33(1):87-107.
Berge et al., "Pharmaceutical Salts," J Pharm Sci. 1977, 66(1):1-19.
Beuckmann et al., "N-type calcium channel $α_{1B}$ subunit ($Ca_v2.2$) knock-out mice display hyperactivity and vigilance state differences," J Neurosci. 2003, 23(17):6793-6797.
Bhatia et al., "Fresh and globular amyloid β protein (1-42) induces rapid cellular degeneration: evidence for AβP channel-mediated cellular toxicity," FASEB J. 2000, 14(9): 1233-1243.
Bhattacharjee et al., "T-type calcium channels facilitate insulin secretion by enhancing general excitability in the insulin-secreting β-cell line, INS-1," Endocrinology. 1997, 138(9): 3735-3740.
Bilici et al., "Protective effect of T-type calcium channel blocker in histamine-induced paw inflammation in rat," Pharmacol Res. 2001, 44(6): 257-231.
Bourinet et al., "Silencing of the $Ca_v3.2$ T-type calcium channel gene in sensory neurons demonstrates its major role in nociception," EMBO J. 2005, 24(2):315-324.

(Continued)

*Primary Examiner* — Douglas M Willis

(57) ABSTRACT

The present application relates to: (a) compounds of Formula (I):

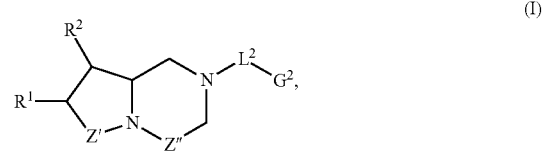

and salts thereof, wherein Z', Z", $L^2$, $G^2$, $R^1$, and $R^2$ are as defined in the specification; (b) compositions comprising such compounds and salts; and (c) methods of use of such compounds, salts, and compositions, particularly use as calcium channel blockers.

25 Claims, No Drawings

(56) References Cited

OTHER PUBLICATIONS

Bowersox et al., "Selective N-type neuronal voltage-sensitive calcium channel blocker, SNX-111, produces spinal antinociception in rat models of acute, persistent and neuropathic pain," J Pharmacol Exp Ther. 1996, 279(3):1243-1249.

Brennan et al., "Characterization of a rat model of incisional pain," 1996, Pain. 64: 493-501.

Castiglioni et al., "Alternative splicing in the C-terminus of $Ca_v2.2$ controls expression and gating of N-type calcium channels," J Physiol. 2006, 576(Pt 1):119-134.

Cavalli et al., "Multi-target-directed ligands to combat neurodegenerative diseases," J Med Chem. 2008, 51(3):347-372.

Chaplan et al., "Quantitative assessment of tactile allodynia in the rat paw," J Neurosci Methods. 1994, 53(1):55-63.

Chaplan et al., "Role of voltage-dependent calcium channel subtypes in experimental tactile allodynia," J Pharmacol Exp Ther. 1994, 269(3):1117-1123.

Chen et al., "Abnormal coronary function in mice deficient in $\alpha_{1H}$ T-type $Ca^{2+}$ channels," Science. 2003, 302(5649):1416-1418.

Choi et al., "Attenuated pain responses in mice lacking $Ca_v3.2$ T-type channels," Genes Brain Behav. 2007, 6(5):425-431.

Cizkova et al., "Localization of N-type $Ca^{2+}$ channels in the rat spinal cord following chronic constrictive nerve injury," Exp Brain Res. 2002, 147(4):456-463.

Colbourne et al., "Continuing postischemic neuronal death in CA1: influence of ischemia duration and cytoprotective doses of NBQX and SNX-111 in rats," Stroke. 1999, 30(3):662-668.

Croom et al., "Modified-release nifedipine: a review of the use of modified-release formulations in the treatment of hypertension and angina pectoris," Drugs. 2006, 66(4):497-528.

Darszon et al., "Ion channels in sperm physiology," Physiol Rev. 1999, 79(2):481-510.

Dixon, W.J., "Efficient analysis of experimental observations," Annu Rev Pharmacol Toxicol. 1980, 20:441-462.

Dolphin, A.C., "A short history of voltage-gated calcium channels," Br J Pharmacol. 2006, 147(Suppl. 1):S56-S62.

Eliel, E. L. and Wilen, S.H., Stereochemistry of Organic Compounds, John Wiley & Sons, Inc., New York, 1994, pp. 119-120 and 1206 (Table of Contents only).

Evans et al., "Differential regulation of evoked peptide release by voltage-sensitive calcium channels in rat sensory neurons," Brain Res. 1996, 712(2):265-273.

Feng et al., "Determinants of inhibition of transiently expressed voltage-gated calcium channels by omega-conotoxins GVIA and MVIIA," J Biol Chem. 2003, 278(22):20171-20178.

Geldenhuys et al., "Structure-activity relationships of pentacycloundecylamines at the N-methyl-d-aspartate receptor," Bioorg Med Chem. 2007, 15(3):1525-1532.

Gitlin, M., "Treatment-resistant bipolar disorder," Mol Psychiatry. 2006, 11(3):227-240.

Gladstone et al., "Current and emerging treatment options for migraine and other primary headache disorders," Expert Rev Neurother. 2003, 3(6):845-872.

Gould et al., "Antischizophrenic drugs of the diphenylbutylpiperidine type act as calcium channel antagonists," Proc Natl Acad Sci USA. 1983, 80(16):5122-5125.

Gray et al., "Neuronal calcium channels: splicing for optimal performance," Cell Calcium. 2007, 42(4-5):409-417.

Greene et al, Editors, Protective Groups in Organic Synthesis (3rd ed.), John Wiley & Sons, NY (1999) (52 pages).

Hatakeyama et al., "Differential nociceptive responses in mice lacking the $\alpha_{1B}$ subunit of N-type $Ca^{2+}$ channels," Neuroreport. 2001, 12(11):2423-2427.

Heinemann et al., "Extracellular free calcium and potassium during paroxsmal activity in the cerebral cortex of the cat," Exp Brain Res. 1977, 27(3-4):237-243.

Heinke et al., "Pre- and postsynaptic contributions of voltage-dependent $Ca^{2+}$ channels to nociceptive transmission in rat spinal lamina I neurons," Eur J Neurosci. 2004, 19(1):103-111.

Ino et al., "Functional disorders of the sympathetic nervous system in mice lacking the $\alpha_{1B}$ subunit ($Ca_v2.2$) of N-type calcium channels," Proc Natl Acad Sci USA. 2001, 98(9):5323-5328.

International Search Report for application No. PCT/US2012/057296, mailed on Nov. 20, 2012 (8 pages).

IUPAC 1974 Recommendations for Section E, Fundamental Stereochemistry, Pure Appl Chem. 1976, 45:13-30.

Jagodic et al., "Cell-specific alterations of T-type calcium current in painful diabetic neuropathy enhance excitability of sensory neurons," J Neurosci. 2007, 37(12):3305-3316.

Jagodic et al., "Upregulation of the T-type calcium current in small rat sensory neurons after chronic constrictive injury of the sciatic nerve," J Neurophysiol. 2008, 99(6):3151-3156.

Kim et al., "Altered nociceptive response in mice deficient in the $\alpha_{1B}$ subunit of the voltage-dependent calcium channel," Mol Cell Neurosci. 2001, 18(2):235-245.

Levy et al., "Calcium channel antagonists for the treatment of bipolar disorder," Bipolar Disord. 2000, 2(2):108-119.

Little et al., "Calcium channel antagonists decrease the ethanol withdrawal syndrome," Life Sci. 1986, 39(22):2059-2065.

Liu et al., "In vivo analysis of voltage-dependent calcium channels," J Bioenerg Biomembr. 2003, 35(6):671-685.

Lorton, D., "β-Amyloid-induced IL-1β release from an activated human monocyte cell line is calcium- and G-protein-dependent," Mech Ageing Dev. 1997, 94(1-3):199-211.

Lubin et al., "A nonadherent cell-based HTS assay for N-type calcium channel using calcium 3 dye," Assay Drug Dev Technol. 2006, 4(6):689-694.

Luebke et al., "Multiple calcium channel types control glutamatergic synaptic transmission in the hippocampus," Neuron. 1993, 11(5):895-902.

Luo et al., "Upregulation of dorsal root ganglion $\alpha_2\delta$ calcium channel subunit and its correlation with allodynia in spinal nerve-injured rats," J Neurosci. 2001, 21(6):1868-1875.

Malmberg et al., "Voltage-sensitive calcium channels in spinal nociceptive processing: blockade of N- and P-type channels inhibits formalin-induced nociception," J. Neurosci. 1994, 14(8):4882-4890.

Mason et al., "Antioxidant and cytoprotective activities of the calcium channel blocker mibefradil," Biochem Pharmacol. 1998, 55(11):1843-1852.

Matthews et al., "Effects of spinally delivered N- and P-type voltage-dependent calcium channel antagonists on dorsal horn neuronal responses in a rat model of neuropathy," Pain. 2001, 92(1-2):235-246.

McGivern J.G., "Targeting N-type and T-type calcium channels for the treatment of pain," Drug Discov Today. 2006, 11(5-6):245-253.

Miljanich et al., "Antagonists of neuronal calcium channels: structure, function, and therapeutic implications," Annu Rev Pharmacol Toxicol. 1995, 35:707-734.

Mogil et al., "Heritability of nociception I: responses of 11 inbred mouse strains on 12 measures of nociception.," Pain. 1999, 80(1-2):67-82.

Newton et al., "Dorsal root ganglion neurons show increased expression of the calcium channel $\alpha_2\delta$-1 subunit following partial sciatic nerve injury," Brain Res Mol Brain Res. 2001, 95(1-2):1-8.

Nordskog et al., "Diurnal gene expression patterns of T-type calcium channels and their modulation by ethanol," Neuroscience. 2006, 141(3):1365-1373.

Nozaki-Taguchi et al., "Vincristine-induced allodynia in the rat," Pain. 2001, 93(1):69-76.

Olivera et al., "Calcium channel diversity and neurotransmitter release: the omega-conotoxins and omega-agatoxins," Annu Rev Biochem. 1994, 63:823-867.

Otoom et al., "Nifedipine inhibits picrotoxin-induced seizure activity: further evidence on the involvement of L-type calcium channel blockers in epilepsy," Fundam Clin Pharmacol. 2006, 20(2):115-119.

Perez-Reyes et al., "Molecular pharmacology of human Cav3.2 T-type $Ca^{2+}$ channels: block by antihypertensives, antiarrhythmics, and their analogs," J Pharmacol Exp Ther. 2009, 328(2):621-627.

Pietrobon, D., "Function and dysfunction of synaptic calcium channels: insights from mouse models," Curr Opin Neurobiol. 2005, 15(3):257-265.

(56) References Cited

OTHER PUBLICATIONS

Prescott et al., Editors, Methods in Cell Biology, vol. XIV, Academic Press, New York, N.Y. (1976), pp. 33-71 (Table of Contents only).
Raingo et al., "Alternative splicing controls G protein-dependent inhibition of N-type calcium channels in nociceptors," Nat Neurosci. 2007, 10(3):285-292.
Rodnitzky, R.L., "Can calcium antagonists provide a neuroprotective effect in Parkinson's disease?" Drugs. 1999, 57(6):845-849.
Saade et al., "The L-type calcium channel blocker nimodipine mitigates "learned helplessness" in rats," Pharmacol Biochem Behav. 2003, 74(2):269-78.
Saegusa et al., "Suppression of inflammatory and neuropathic pain symptoms in mice lacking the N-type $Ca^{2+}$ channel," EMBO J. 2001, 20(10):2349-2356.
Scott et al., "Actions of intrathecal omega-conotoxins CVID, GVIA, MVIIA, and morphine in acute and neuropathic pain in the rat," Eur J Pharmacol. 2002, 451(3):279-286.
Shin et al., "T-type $Ca^{2+}$ channels as therapeutic targets in the nervous system," Curr Opin Pharmacol. 2008, 8(1):33-41.
Smith et al., "The novel N-type calcium channel blocker, AM336, produces potent dose-dependent antinociception after intrathecal dosing in rats and inhibits substance P release in rat spinal cord slices," Pain. 2002, 96(1-2):119-27.
Takahashi et al., "Different types of calcium channels mediate central synaptic transmission," Nature. 1993, 366(6451):156-158.
Takei et al, "Increased sensitivity to halothane but decreased sensitivity to propofol in mice lacking the N-type $Ca^{2+}$ channel," Neurosci Lett. 2003, 350(1):41-45.
Talley et al, "Differential distribution of three members of a gene family encoding low voltage-activated (T-type) calcium channels," J Neurosci. 1999, 19(6):1895-1911.
Tort et al., "Atypical antipsychotic profile of flunarizine in animal models," Psychopharmacology (Berl). 2005, 177(3):344-348.
Urban et al., "Medullary N-type and P/Q-type calcium channels contribute to neuropathy-induced allodynia," Neuroreport. 2005, 16(6):563-566.
Uslaner et al., "T-type calcium channel antagonism decreases motivation for nicotine and blocks nicotine- and cue-induced reinstatement for a response previously reinforced with nicotine," Biol Phychiatry. 2010, 68(8):712-718.
Uslaner et al., "T-type calcium channel antagonism produces antipsychotic-like effects and reduces stimulant-induced glutamate release in the nucleus accumbens of rats," Neuropharmacology. 2012, 62(3):1413-1421.
Vagnucci et al., "Alzheimer's disease and angiogenesis," Lancet. 2003, 361(9357):605-608.
Veng et al., "Age-related working memory impairment is correlated with increases in the L-type calcium channel protein $\alpha_{1D}$ ($Ca_v1.3$) in area CA1 of the hippocampus and both are ameliorated by chronic nimodipine treatment," Brain Res Mol Brain Res. 2003, 110(2):193-202.
Vezzani et al., "Effect of various calcium channel blockers on three different models of limbic seizures in rats," Neuropharmacology. 1988, 27(5):451-458.
Wang et al., "Effects of intrathecal administration of ziconotide, a selective neuronal N-type calcium channel blocker, on mechanical allodynia and heat hyperalgesia in a rat model of postoperactive pain," Pain. 2000, 84(2-3):151-158.
Westenbroek et al., "Localization of $Ca^{2+}$ channel subtypes on rat spinal motor neurons, interneurons, and nerve terminals," J Neurosci. 1998, 18(16):6319-6330.
Yamamoto et al., "Differential effects of intrathecally administered N- and P-type voltage-sensitive calcium channel blockers upon two models of experimental mononeuropathy in the rat," Brain Res. 1998, 794(2):329-332.
Yokoyama et al., "Plastic change of N-type Ca channel expression after preconditioning is responsible for prostaglandin E2-induced long-lasting allodynia," Anesthesiology. 2003, 99(6):1364-1370.
Zanchetti et al., "Calcium antagonist lacidipine slows down progression of asymptomatic carotid atherosclerosis: principal results of the European Lacidipine Study on Atherosclerosis (ELSA), a randomized, double-blind, long-term trial," Circulation. 2002, 106(19):2422-2427.
U.S. Appl. No. 13/627,541, filed Sep. 26, 2013, File History.

\* cited by examiner

SUBSTITUTED OCTAHYDROPYRROLO[1,2-*A*]PYRAZINE SULFONAMIDES AS CALCIUM CHANNEL BLOCKERS

CROSS-REFERENCE TO RELATED PATENT APPLICATIONS

This patent application claims priority to U.S. Provisional Patent Application No. 61/540,716 (filed Sep. 29, 2011). The entire text of that provisional application is incorporated by reference into this application.

TECHNICAL FIELD

The present application relates to compounds that are calcium channel blockers, compositions comprising such compounds, and methods of treating conditions and disorders using such compounds and compositions.

BACKGROUND

Voltage-gated calcium channels (VGCC) play an integral role in the regulation of membrane ion conductance, neurotransmitter release, and cellular excitability. VGCC are composed of the pore-forming α1 subunit and auxiliary α2δ and β subunits that modulate channel expression and functional properties (Dolphin, A. C. British Journal of Pharmacology 2006, 147 (Suppl. 1), S56-S62). These channels can be classified into low-voltage activated (LVA; T-type or $Ca_v3.x$) and high-voltage activated (HVA; L-type or $Ca_v1.x$ and N-, P/Q- and R-types or $Ca_v2.x$) channels. N-, P/Q and R channels typically activate at more positive membrane potentials (~−30 mV) and are involved in "presynaptic" neurotransmission (McGivern J. G. Drug Discovery Today 2006, 11, 245-253). T-type channels are activated at relatively negative membrane potentials (~−60 mV) and are primarily involved in "postsynaptic" excitability (Shin, H.-S.; et al. Curr. Opin. in Pharmacology 2008, 8, 33-41).

N-type channel $α_1$ subunits are encoded by a single gene ($α_1$B or $Ca_v2.2$) in contrast to pharmacologically defined L- and T-type currents that are encoded by multiple $α_1$-subunit genes. A diversity of N-type channels arises due to extensive alternative splicing of the α subunit gene that generates variants with different expression patterns and GPCR-modulated biophysical properties (Gray, A. C.; et al. Cell Calcium, 2007, 42(4-5), 409-417). The primary sequence for $Ca_v2.2$ is highly conserved across species (rat and human share 91% identity at the amino acid level).

N-type channels are widely expressed in the central nervous system (CNS) (cortex, hippocampus, striatum, thalamus, brain stem nuclei and spinal cord) and in the peripheral nervous system (PNS) (adult sympathetic nervous system and dorsal root ganglia) (Ino, M.; et al. Proc. Natl. Acad. Sci. USA 2001, 98(9), 5323-5328). In pain pathways, N-type channels are expressed in the rostral ventral medulla, an important site of descending pain modulation (Urban, M. O.; et al. Neuroreport 2005, 16(6), 563-566) and are a major contributor to the synaptic neurotransmission that occurs between C/Aδ nociceptors and spinal lamina I neurons (Bao, J.; et al. J. Neurosci. 1998, 18(21), 8740-50. Heinke, B.; et al. Eur. J. Neurosci. 2004, 19(1), 103-111). In contrast, P/Q type channels are expressed almost exclusively in laminae II-IV of the spinal cord and show little co-localization with Substance P and N-type channels (Westenbroek, R. E.; et al. J. Neurosci. 1998, 18(16), 6319-6330).

Following nerve injury there is increased expression of $Ca_v2.2$ (Westenbroek, R. E.; et al. J. Neurosci. 1998, 18(16), 6319-6330. Cizkova, D.; et al. Exp. Brain Res. 2002, 147, 456-463. Yokoyama, K.; et al. Anesthesiology 2003, 99(6), 1364-1370) and α2δ1 subunits (Luo, Z. D.; et al. J. Neurosci. 2001, 21(6), 1868-1875. Newton, R. A.; et al. Mol. Brain. Res. 2001, 95(1-2), 1-8) in addition to increases in the superficial layers of the dorsal horn of the spinal cord supporting a role for N-type channels in neuropathic pain. Recently a nociceptor-specific $Ca_v2.2$ splice variant has been identified in the dorsal root ganglion (Bell, T. J.; et al. Neuron 2004, 41(1), 127-138). These channels have distinct electrophysiological properties and current densities (Castiglioni, A. J.; et al. J. Physiol. 2006, 576(Pt 1), 119-134) compared to wild-type $Ca_v2.2$ channels. While G-protein coupled receptor inhibition of wildtype N-type channels is typically mediated by Gβγ and is voltage-dependent, the nociceptor specific splice variant is inhibited by GPCR activation (e.g. opioids) in a voltage-independent fashion (Raingo, J.; et al. Nat. Neurosci. 2007, 10(3), 285-292). This mechanism substantially increases the sensitivity of $Ca_v2.2$ channels to opiates and gamma-aminobutyric acid (GABA) suggesting that cell-specific alternative splicing of mRNA for $Ca_v2.2$ channels serves as a molecular switch that controls the sensitivity of N-type channels to neurotransmitters and drugs that modulate nociception. Collectively these data provide further support for the role of $Ca_v2.2$ channels in pain states.

The relative contributions of various HVA $Ca^{2+}$ channels in nociceptive signaling have been evaluated using knockout mice studies. $Ca_v2.2$ knockout mice are healthy, fertile, and do not display overt neurological deficits (Ino, M.; et al. Proc. Natl. Acad. Sci. USA 2001, 98(9), 5323-5328. Kim, C.; et al. Mol. Cell. Neurosci. 2001, 18(2), 235-245. Hatakeyama, S.; et al. Neuroreport 2001, 12(11), 2423-2427. Liu; L.; et al. J. Bioenerg. Biomembr. 2003, 35(6), 671-685). This finding suggests that other types of $Ca_v$ channels are able to compensate for the lack of $Ca_v2.2$ channels at most synapses in these mice (Pietrobon, D. Curr. Opin. Neurobiol. 2005, 15(3), 257-265). $Ca_v2.2$ deficient mice are resistant to the development of inflammatory and neuropathic pain (Kim, C.; et al. Mol. Cell. Neurosci. 2001, 18(2), 235-245. Hatakeyama, S.; et al. Neuroreport 2001, 12(11), 2423-2427. Saegusa, H.; et al. EMBO J. 2001, 20(10), 2349-2356), have decreased sympathetic nervous system function (Ino, M.; et al. Proc. Natl. Acad. Sci. USA 2001, 98(9), 5323-5328), and altered responses to both ethanol and anesthetics (Newton, R. A.; et al. Brain Res. Mol. Brain. Res. 2001, 95(1-2), 1-8. Takei, R. et al. Neurosci. Lett. 2003, 350(1), 41-45). Additional behavioral studies indicate that $Ca_v2.2$ knockout mice are less anxious, are hyperactive, and show enhanced vigilance compared to wild-type littermates (Beuckmann, C. T.; et al. J. Neurosci. 2003, 23(17), 6793-6797).

N- and P/Q-type channels are localized at neuronal synaptic junctions and contribute significantly to neurotransmitter release (Olivera, B. M.; et al. Annu. Rev. Biochem. 1994, 63, 823-867. Miljanich, G P.; et al. Annu. Rev. Pharmacol. Toxicol. 1995, 35, 707-734). N-type channels play a major role in the release of glutamate, acetylcholine, dopamine, norepinephrine, GABA, substance P and calcitonin gene-related protein (CGRP). P/Q-type channels may be involved in the release of glutamate, aspartate, 5HT, GABA and probably glycine (Pietrobon, D. Curr. Opin. Neurobiol. 2005, 15(3), 257-265).

L, P/Q and N-type channels are blocked by channel specific antagonists i.e., dihydropyridines, ω-agatoxin WA and ω-conotoxin MVIIA/ziconotide, respectively. Agatoxin IVa has been shown to block excitatory (Luebke, J. I.; et al.

Neuron 1993, 11(5), 895-902) as well as inhibitory neurotransmission (Takahashi, T.; et al. Nature 1993, 366(6451), 156-158). Intrathecal injection of selective N-type channel blockers (e.g. conotoxin-derived peptides such as GVIA, MVIIA (ziconotide), and CVID) significantly attenuates pain responses in animal models of neuropathic pain, formalin-induced pain, and post-operative pain (Chaplan, S. R.; et al. J. Pharmacol. Exp. Ther. 1994, 269(3), 1117-1123. Malmberg, A. B.; et al. J. Neurosci. 1994, 14(8), 4882-4890. Bowersox, S. S.; et al. J. Pharmacol. Exp. Ther. 1996, 279(3), 1243-1249. Wang, Y. X.; et al. Pain 2000, 84(2-3), 151-158. Scott, D. A.; et al. Eur. J. Pharmacol. 2002, 451(3), 279-286). These peptide blockers bind to the pore region of the channel, do not show voltage- or frequency-dependent activity, and show irreversible channel block (Feng, Z. P.; et al. J. Biol. Chem. 2003, 278(22), 20171-20178). Ziconotide potently blocks neurotransmitter release in the spinal cord dorsal horn (Matthews, E. A.; et al. Pain 2001, 92(1-2), 235-246. Smith, M. T.; et al. Pain 2002, 96(1-2), 119-127. Heinke, B.; et al. Eur. J. Neurosci. 2004, 19(1), 103-111) and in dorsal root ganglion (DRG) neurons (Evans, A. R.; et al. Brain Res. 1996, 712(2), 265-273. Smith, M. T.; et al. Pain 2002, 96(1-2), 119-127). It also potently and fully blocks depolarization-induced release of substance P from rat spinal cord slices. In contrast, intrathecal delivery of the selective P/Q type blocker ω-agatoxin IVA had no effects on mechanical allodynia in the spinal nerve ligation model (Chaplan, S. R.; et al. J. Pharmacol. Exp. Ther. 1994, 269(3), 1117-1123) or thermal hyperalgesia in the chronic constriction injury model (Yamamoto, T.; et al. Brain Res. 1998, 794(2), 329-332) of neuropathic pain.

T-Type or LVA calcium channels are composed of a single pore forming $\alpha_1$ subunit of which there are three subtypes: Cav3.1, Cav3.2 and Cav3.3 (Perez-Reyes, E.; et al. J. Pharmacol. Exp. Ther. 2009, 328(2), 621-7). These channels are activated at relatively hyperpolarized cell membrane potentials and contribute to membrane depolarization following action potential generation. As a result, T-type calcium channel activation triggers secondary bursts of neuronal action potentials with increased action potential duration. Evidence supporting a role of T-type calcium channels in neuropathic pain comes from studies that have shown a concurrent increase in the expression of Cav3.2 channels after-depolarization potentials in medium diameter Aδ high threshold mechanoreceptor dorsal root ganglia (DRG) neurons in diabetic neuropathy (Jagodic, M. M.; et al. J Neurosci 2007, 27, 3305-3316) and in small diameter neurons from the chronic constriction injury (CCI) neuropathic pain model (Jagodic, M. M.; et al. J Neurophysiol 2008, 99, 3151-3156). Additional support comes from gene knockdown studies whereby intrathecal Cav3.2 antisense administration produces a significant knockdown (~80-90%) of T-type calcium currents in small and medium diameter DRG neurons, and produces robust anti-allodynic and antihyperalgesic effects in the CCI rat model of neuropathic pain (Bourinet, E.; et al. Embo J 2005, 24, 315-324). Moreover, Cav3.2 knockout mice show decreased pain responses compared to wild-type mice in acute mechanical, thermal, and chemical pain models (Choi, S.; et al. Genes Brain Behav 2007, 6, 425-431).

Recently, T-type calcium channel blockers have been proposed to have potential in treating schizophrenia and substance dependence. The T-type calcium channels are located in brain regions that have relevance to schizophrenia and substance dependence (Talley, E. M.; et al. J Neurosci 1999, 19, 1895-1911). More importantly, it has been demonstrated that selective T-type calcium channel blockers, such as TTA-A2, have antipsychotic-like effects in preclinical animal models of psychosis (Uslaner, J. M.; et al. Neuropharmacology 2012, 62, 1413-1421) and were able to decrease nicotine seeking behavior in rats trained to self-administer nicotine (Uslaner, J. M.; et al. Biol Psychiatry 2010, 68, 712-718).

In addition to a role in nociception, T-type calcium channels have also been implicated to play roles in sleep disorders and absence epilepsy (Shin, H.-S.; et al. Curr Opin Pharmacol, 2008, 8, 33-41). Based on expression in the thalamus, T-type calcium channels may play a role in arousal from sleep (Benington, J. H.; et al. Prog Neurobiol 2003, 69, 71-101; Nordskog, B. K.; et al. Neuroscience 2006, 141, 1365-1373). Expression in the adrenal, pituitary and pineal glands suggests that these channels modulate hormone secretion. Notably, Cav3.2 knockout mice appear normal and healthy, although smaller than wild-type mice (Chen, C.-C.; et al. Science 2003, 302, 1416-1418; Choi, S.; et al. Genes Brain Behav 2007, 6, 425-431).

Pain is the most common symptom of disease and the most frequent complaint with which patients present to physicians. Inadequate pain management across the spectrum of pain etiologies remains a major public health problem. Going forward, the development of novel therapeutics with new mechanisms of action for the treatment of pain including calcium channel blockade will have a significant impact on the ongoing struggle to balance efficacy and safety for those patients most in need. The compounds of the present invention are novel calcium channel blockers that have utility in treating pain, amongst other conditions.

SUMMARY OF THE INVENTION

The invention is directed to compounds of Formula (I):

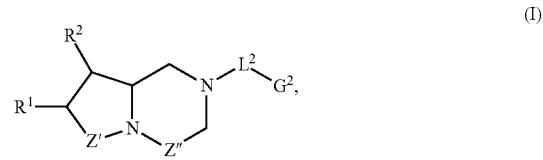

and salts thereof, wherein:
one of Z' and Z" is $CH_2$ and the other of Z' and Z" is $CH_2$ or C(O);
one of $R^1$ and $R^2$ is hydrogen and the other of $R^1$ and $R^2$ is $G^1$-$L^1$—;
$L^1$ is —C($R^c$)($R^d$)—, —C(O)N$R^a$—, —N$R^a$C(O)—, —S(O)$_2$N$R^a$—, —N$R^a$S(O)$_2$—; —N$R^a$—, or —O—;
$G^1$ is $C_1$-$C_8$-alkyl, $C_1$-$C_8$-haloalkyl, Ar$^1$, —(C$R^a$$R^b$)$_j$—Ar$^1$, —CH(Ar$^1$)$_2$, or —Ar$^1$-G$^a$;
$R^a$ and $R^b$, at each occurrence, are each independently hydrogen, $C_1$-$C_4$-alkyl, or $C_1$-$C_4$-haloalkyl;
$R^c$ and $R^d$ are each independently hydrogen, hydroxy, $C_1$-$C_4$-alkyl, or $C_1$-$C_4$-haloalkyl;
j is 1, 2, 3, 4, or 5;
Ar$^1$ is, at each occurrence, independently aryl or heteroaryl, wherein Ar$^1$ is unsubstituted or substituted with 1, 2, 3, 4, or 5 substituents selected from the group consisting of $C_1$-$C_4$-alkyl, $C_2$-$C_4$-alkenyl, $C_2$-$C_4$-alkynyl, halogen, cyano, —NO$_2$, —OR$^s$, —OC(O)R$^s$, —OC(O)N(R$^s$)(R$^t$), —SR$^s$, —S(O)R$^s$, —S(O)$_2$R$^s$, —S(O)$_2$N(R$^s$)(R$^t$), —C(O)R$^s$, —C(O)OR$^s$, —C(O)N(R$^s$)(R$^t$), —N(R$^s$)(R$^t$), —N(R$^s$)C(O)R$^t$, —N(R$^s$)C(O)O(R), —N(R$^s$)S(O)$_2$(R), $C_1$-$C_4$-cyanoalkyl, and $C_1$-$C_4$-haloalkyl;
$R^s$ and $R^t$ are, at each occurrence, independently hydrogen, $C_1$-$C_4$-alkyl, $C_2$-$C_4$-alkenyl, $C_2$-$C_4$-alkynyl or $C_1$-$C_4$-haloalkyl;

G$^a$ is C$_3$-C$_7$-cycloalkyl, C$_3$-C$_7$-cycloalkenyl, heterocycle, or heteroaryl, wherein the C$_3$-C$_7$-cycloalkyl, C$_3$-C$_7$-cycloalkenyl, heterocycle, or heteroaryl are unsubstituted or substituted with 1, 2, or 3 C$_1$-C$_4$-alkyl, C$_1$-C$_4$-haloalkyl, or halogen;

L$^2$ is —S(O)$_2$—, —S(O)$_2$CH$_2$—, or —S(O)—;

G$^2$ is C$_1$-C$_8$-alkyl, C$_1$-C$_8$-haloalkyl, C$_1$-C$_8$-cycloalkyl, Ar$^2$ or Ar$^3$;

Ar$^2$ is aryl or heteroaryl, wherein Ar$^2$ is unsubstituted or substituted with 1, 2, 3, 4, or 5 substituents selected from the group consisting of C$_1$-C$_4$-alkyl, C$_2$-C$_4$-alkenyl, C$_2$-C$_4$-alkynyl, halogen, cyano, —NO$_2$, —OR$^u$, -alkyl-OR$^u$, —OC(O)R$^u$, —OC(O)N(R$^u$)(R$^v$), —SR$^u$, —S(O)R$^u$, —S(O)$_2$R$^u$, —S(O)$_2$N(R$^u$)(R$^v$), —C(O)R$^u$, —C(O)OR$^u$, —C(O)N(R$^u$)(R$^v$), —N(R$^u$)(R$^v$), —N(R$^u$)C(O)R$^v$, —N(R$^u$)C(O)O(R$^v$), —N(R$^u$)S(O)$_2$(R$^v$), C$_1$-C$_4$-cyanoalkyl, C$_1$-C$_4$-haloalkyl and -G$^b$;

G$^b$ is C$_3$-C$_7$-cycloalkyl, C$_3$-C$_7$-cycloalkenyl, heterocycle, aryl or heteroaryl, wherein the C$_3$-C$_7$-cycloalkyl, C$_3$-C$_7$-cycloalkenyl, heterocycle, aryl or heteroaryl are unsubstituted or substituted with 1, 2, or 3 C$_1$-C$_4$-alkyl, C$_1$-C$_4$-haloalkyl, or halogen;

R$^u$ and R$^v$ are, at each occurrence, independently hydrogen, C$_1$-C$_4$-alkyl, C$_2$-C$_4$-alkenyl, C$_2$-C$_4$-alkynyl or C$_1$-C$_4$-haloalkyl;

Ar$^3$ is (i), wherein:

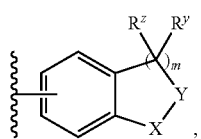

X is O, S, NR$^w$, or CH$_2$; wherein R$^w$ is hydrogen or alkyl;

Y is C(O) or CH$_2$;

R$^z$ and R$^y$ are independently, at each occurrence, hydrogen or C$_1$-C$_4$-alkyl; and m is 1, 2 or 3.

Another aspect of the invention relates to pharmaceutical compositions comprising therapeutically effective amount of compound(s) of the invention or pharmaceutically acceptable salts thereof, in combination with one or more pharmaceutically acceptable carrier. Such compositions can be administered in accordance with a method of the invention, typically as part of a therapeutic regimen for treatment or prevention of conditions and disorders related to calcium channels. More particularly, the method is useful for treating conditions related to a method of treating pain in a subject in need thereof. The method comprises administering to the subject a therapeutically suitable amount of a compound of Formula (I), or a pharmaceutically acceptable salt thereof. Conditions related to pain include acute pain, chronic pain, neuropathic pain, inflammatory pain, visceral pain, cancer pain, osteoarthritis pain, allodynia, fibromyalgia, sciatica, back pain, and headache pain including migraine, or combinations thereof.

Another aspect of the invention provides a method of treating disorders of the central nervous system in a subject in need thereof. The method comprising the step of: administering a therapeutically suitable amount of a compound of Formula (I), or a pharmaceutically acceptable salt thereof. The disorders of the central nervous system include stroke; epilepsy; absence epilepsy; manic depression; bipolar disorders; depression; anxiety; schizophrenia; migraine; psychoses; neural degenerative disorders including Alzheimer's disease, AIDS related dementia, Parkinson's disease, neuropathy caused by head injury, and dementia caused by cerebrovascular disorders; and substance dependence and drug addiction withdrawal symptoms, including ethanol addiction withdrawal symptoms; or combinations thereof.

Another aspect of the invention provides a method of treating disorders of the lower urinary tract including overactive bladder, prostatis, prostadynia, interstitial cystitis, and benign prostatic hyperplasia; disorders caused by psychogenic stress including bronchial asthma, unstable angina, and hypersensitive colon inflammation; cardiovascular disorders including hypertension, atherosclerosis, heart failure, and cardiac arrhythmias; skin disorders including pruritis and allergic dermatitis, inflammatory bowel disease; sleep disorders; cancer; diabetes; and infertility and sexual dysfunction, or combinations thereof. The method comprising the step of: administering a therapeutically suitable amount of a compound of Formula (I), or a pharmaceutically acceptable salt thereof.

The compounds, compositions comprising the compounds, and methods for treating or preventing conditions and disorders by administering the compounds are further described herein.

These and other objects of the invention are described in the following paragraphs. These objects should not be deemed to narrow the scope of the invention.

DETAILED DESCRIPTION OF THE INVENTION

The present invention includes compounds of Formula (I):

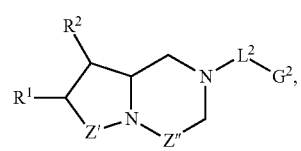

and salts thereof, wherein Z', Z", L$^2$, G$^2$, R$^1$, and R$^2$ are as defined above in the Summary of the Invention. The invention further includes compositions comprising such compounds and methods for treating conditions and disorders using such compounds and compositions.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

A. DEFINITIONS

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched chain hydrocarbon of 2 to 4 carbon atoms and contains at least one carbon-carbon double bond. Representative examples of alkenylene include, but are not limited to, —CH═CH— and —CH$_2$CH═CH—.

The term "alkyl" as used herein, means a straight or branched, saturated hydrocarbon chain containing from 1 to 10 carbon atoms. The term "lower alkyl" or "C$_{1-6}$ alkyl" means a straight or branched chain hydrocarbon containing 1 to 6 carbon atoms. The term "C$_{1-3}$ alkyl" means a straight or branched chain hydrocarbon containing 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the biaryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 3-phenylpropyl, and 2-naphth-2-ylethyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1] nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "cycloalkylalkyl" as used herein, means a cycloalkyl group appended to the parent molecular moiety through an alkyl group, as defined herein.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring can contain one or two alkylene bridges, each consisting of one, two or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 3,4-dihydrobenzothienyl, 2,3-dihydroisoquinolinyl or indolinyl, 2,3-dihydroisoquinolinyl, 1,1-dioxidoisothiazolidinyl, azabicyclo[2.2.1]heptyl (including 2-azabicyclo[2.2.1]hept-2-yl), 2,3-dihydro-1H-indolyl, isoindolinyl, octahydro-1H-indolyl, octahydrocyclopenta[c]-pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring can contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,2-oxazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, 2,1,3-benzothiadiazolyl, benzimidazolyl, benzoxadiazolyl, 6,7-dihydro-1,3-benzothiazolyl, furo[3,2-b]pyrrolyl, imidazo[1,2-a]pyridinyl, indazolyl, indolyl, isoindolyl, isoquinolinyl, naphthyridinyl, pyridoimidazolyl, pyrrolopyridinyl, quinolinyl, thiazolo[5,4-b]pyridin-2-yl, thiazolo[5,4-d]pyrimidin-2-yl, thienopyridinyl and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroarylalkyl," as used herein, means a heteroaryl group appended to the parent molecular moiety through an alkyl group, as defined herein.

The term "heteroatom" as used herein, means a nitrogen, oxygen, or sulfur atom.

The term "hydroxyl" or "hydroxy" as used herein, means an —OH group.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "nitro" as used herein, means a —NO$_2$ group.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by an alkyl anhydride (alkyl-OC=O)$_2$O, a diaryl anhydride, for example as represented by (aryl-OC=O)$_2$O, an acyl halide, an alkylchloroformate, or an alkylsulfonylhalide, an arylsulfonylhalide, or halo-CON(alkyl)$_2$, for example acetyl chloride, benzoyl chloride, benzyl bromide, benzyloxycarbonyl chloride, formylfluoride, phenylsulfonyl chloride, pivaloyl chloride, (tert-butyl-O—C=O)$_2$O, trifluoroacetic anhydride, and triphenylmethyl chloride.

The term "oxo" as used herein, means a =O group.

When cycloalkyl, heterocycle, heteroaryl, aryl, and the like are "substituted", it means there are one or more substituents other than hydrogen on the respective ring. "Unsubstituted" rings have no substituents other than hydrogen.

In some instances, the number of carbon atoms in a hydrocarbon substituent (e.g., alkyl, alkenyl, alkynyl, cycloalkyl or cycloalkenyl) is indicated by the prefix "$C_x$—$C_y$," wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbon ring containing from 3 to 6 carbon ring atoms.

B. COMPOUNDS

Compounds of the invention have the Formula (I) as described above.

Particular values of variable groups in compounds of Formula (I) are as follows. Such values can be used where appropriate with any of the other values, definitions, claims or embodiments defined hereinbefore or hereinafter.

More particularly, compounds of Formula (I) can include, but are not limited to compounds wherein both of Z' and Z" are CH$_2$. Such compounds can be shown as having the alternative structure of Formula (I-A):

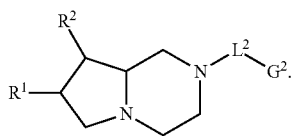

(I-A)

In another embodiment, Z' is CH$_2$ and Z" is C(O).

In another embodiment, Z' is C(O) and Z" is CH$_2$.

In another embodiment, R$^1$ is hydrogen and R$^2$ is G$^1$-L$^1$-.

In another embodiment, R$^1$ is G$^1$-L$^1$- and R$^2$ is hydrogen.

In another embodiment, the invention is directed to compounds of Formula (I-A) wherein:

one of R$^1$ and R$^2$ is hydrogen and the other of R$^1$ and R$^2$ is G$^1$-L$^1$-;

L$^1$ is —C(O)NR$^a$—, —NR$^a$C(O)—, —S(O)$_2$NR$^a$—, —NR$^a$S(O)$_2$—; —NR$^a$—, or —O—;

G$^1$ is C$_1$-C$_8$-alkyl, C$_1$-C$_8$ haloalkyl Ar$^1$, —(CR$^a$R$^b$)$_j$—Ar$^1$, —CH(Ar$^1$)$_2$ or —Ar$^1$-G$^a$;

R$^a$ and R$^b$, at each occurrence, are each independently hydrogen, C$_1$-C$_4$-alkyl, or C$_1$-C$_4$-haloalkyl;

j is 1, 2, 3, 4, or 5;

Ar$^1$ is, at each occurrence, independently aryl or heteroaryl, wherein Ar$^1$ is unsubstituted or substituted with 1, 2, 3, 4, or 5 substituents selected from the group consisting of C$_1$-C$_4$-alkyl, C$_2$-C$_4$-alkenyl, C$_2$-C$_4$-alkynyl, halogen, cyano, —NO$_2$, —OR$^s$, —OC(O)R$^s$, —OC(O)N(R$^s$)(R$^t$), —SR$^s$, —S(O)R$^s$, —S(O)$_2$R$^s$, —S(O)$_2$N(R$^s$)(R$^t$), —C(O)R$^s$, —C(O)OR$^s$, —C(O)N(R$^s$)(R$^t$), —N(R$^s$)(R$^t$), —N(R$^s$)C(O)R$^t$, —N(R$^s$)C(O)O(R$^t$), —N(R$^s$)S(O)$_2$(R$^t$), C$_1$-C$_4$-cyanoalkyl, and C$_1$-C$_4$-haloalkyl;

R$^s$ and R$^t$ are, at each occurrence, independently hydrogen, C$_1$-C$_4$-alkyl, C$_2$-C$_4$-alkenyl, C$_2$-C$_4$-alkynyl or C$_1$-C$_4$-haloalkyl;

G$^a$ is C$_3$-C$_7$-cycloalkyl, C$_3$-C$_7$-cycloalkenyl, heterocycle, or heteroaryl, wherein the C$_3$-C$_7$-cycloalkyl, C$_3$-C$_7$-cycloalkenyl, heterocycle, or heteroaryl are unsubstituted or substituted with 1, 2, or 3 C$_1$-C$_4$-alkyl, C$_1$-C$_4$-haloalkyl, or halogen;

L$^2$ is —S(O)$_2$—, or —S(O)—;

G$^2$ is C$_1$-C$_8$-alkyl, C$_1$-C$_8$-haloalkyl, C$_1$-C$_8$-cycloalkyl, Ar$^2$ or Ar$^3$;

Ar$^2$ is aryl or heteroaryl, wherein Ar$^2$ is unsubstituted or substituted with 1, 2, 3, 4, or 5 substituents selected from the group consisting of C$_1$-C$_4$-alkyl, C$_2$-C$_4$-alkenyl, C$_2$-C$_4$-alkynyl, halogen, cyano, —NO$_2$, —OR$^u$, -alkyl-OR$^u$, —OC(O)R$^u$, —OC(O)N(R$^u$)(R$^v$), —SR$^u$, —S(O)R$^u$, —S(O)$_2$R$^u$, —S(O)$_2$N(R$^u$)(R$^v$), —C(O)R$^u$, —C(O)OR$^u$, —C(O)N(R$^u$)(R$^v$), —N(R$^u$)(R$^v$), —N(R$^u$)C(O)R$^v$, —N(R$^u$)C(O)O(R$^v$), —N(R$^u$)S(O)$_2$(R$^v$), C$_1$-C$_4$-cyanoalkyl, C$_1$-C$_4$-haloalkyl and -G$^b$;

G$^b$ is C$_3$-C$_7$-cycloalkyl, C$_3$-C$_7$-cycloalkenyl, heterocycle, aryl or heteroaryl, wherein the C$_3$-C$_7$-cycloalkyl, C$_3$-C$_7$-cycloalkenyl, heterocycle, aryl or heteroaryl are unsubstituted or substituted with 1, 2, or 3 C$_1$-C$_4$-alkyl, C$_1$-C$_4$-haloalkyl, or halogen;

R$^u$ and R$^v$ are, at each occurrence, independently hydrogen, C$_1$-C$_4$-alkyl, C$_2$-C$_4$-alkenyl, C$_2$-C$_4$-alkynyl or C$_1$-C$_4$-haloalkyl;

Ar$^3$ is (i), wherein:

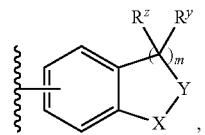

(i)

X is O, S, NR$^w$, or CH$_2$; wherein R$^w$ is hydrogen or alkyl;
Y is C(O) or CH$_2$;
R$^z$ and R$^y$ are hydrogen; and
m is 1, 2 or 3.

In one embodiment, L$^1$ is —C(O)NR$^a$—, —NR$^a$C(O)—, —S(O)$_2$NR$^a$—, —NR$^a$S(O)$_2$—; —NR$^a$—, or —O—.

In another embodiment, L$^1$ is —C(O)NR$^a$—, —NR$^a$C(O)—, —NR$^a$—, or —O—.

In another embodiment, L$^1$ is —S(O)$_2$NR$^a$— or —NR$^a$S(O)$_2$—.

In another embodiment, L$^1$ is —C(O)NR$^a$— or —NR$^a$C(O)—.

In another embodiment, L$^1$ is —C(O)NR$^a$— or —NR$^a$C(O)—, wherein R$^a$ is hydrogen.

In another embodiment, L$^1$ is —NR$^a$—.

In another embodiment, L$^1$ is —NR$^a$—, wherein R$^a$ is hydrogen.

In a further embodiment, L$^1$ is —O—.

In one embodiment, G$^1$ is C$_1$-C$_8$-alkyl, C$_1$-C$_8$-haloalkyl, Ar$^1$, —(CR$^a$R$^b$)$_j$—Ar$^1$, —CH(Ar$^1$)$_2$ or —Ar$^1$-G$^a$.

In another embodiment, G$^1$ is C$_1$-C$_8$-alkyl.

In another embodiment, G$^1$ is C$_1$-C$_8$-haloalkyl, Ar$^1$, —(CR$^a$R$^b$)$_j$—Ar$^1$, —CH(Ar$^1$)$_2$ or —Ar$^1$-G$^a$.

In another embodiment, G$^1$ is C$_1$-C$_8$-haloalkyl.

In another embodiment, G$^1$ is Ar$^1$.

In another embodiment, G$^1$ is Ar$^1$, wherein Ar$^1$ is aryl or heteroaryl optionally substituted as described below.

In another embodiment, G$^1$ is —(CR$^a$R$^b$)$_j$—Ar$^1$.

In another embodiment, G$^1$ is —(CR$^a$R$^b$)$_j$—Ar$^1$, wherein R$^a$ and R$^b$ are each hydrogen, j is 1, and Ar$^1$ is aryl or heteroaryl optionally substituted as described below.

In another embodiment, G$^1$ is —CH(Ar$^1$)$_2$.

In another embodiment, G$^1$ is —CH(Ar$^1$)$_2$, wherein Ar$^1$ is, at each occurrence, independently aryl or heteroaryl optionally substituted as described below.

In another embodiment, G$^1$ is —Ar$^1$-G$^a$.

In another embodiment, G$^1$ is —Ar$^1$-G$^a$, wherein Ar$^1$ is aryl or heteroaryl optionally substituted as described below, and G$^a$ is C$_3$-C$_7$-cycloalkyl, C$_3$-C$_7$-cycloalkenyl, heterocycle, or heteroaryl, wherein the C$_3$-C$_7$-cycloalkyl, C$_3$-C$_7$-cycloalkenyl, heterocycle, or heteroaryl are unsubstituted or substituted with 1, 2, or 3 C$_1$-C$_4$-alkyl, C$_1$-C$_4$-haloalkyl, or halogen.

In another embodiment, G$^1$ is —Ar$^1$-G$^a$, wherein Ar$^1$ is aryl or heteroaryl optionally substituted as described below, and G$^a$ is C$_3$-C$_7$-cycloalkyl or heteroaryl, wherein the C$_3$-C$_7$-cycloalkyl or heteroaryl are unsubstituted or substituted with 1, 2, or 3 C$_1$-C$_4$-alkyl, C$_1$-C$_4$-haloalkyl, or halogen.

In another embodiment, G$^1$ is —Ar$^1$-G$^a$, wherein Ar$^1$ is aryl or heteroaryl optionally substituted as described below, and G$^a$ is heteroaryl, wherein the heteroaryl is unsubstituted or substituted with 1, 2, or 3 C$_1$-C$_4$-alkyl, C$_1$-C$_4$-haloalkyl, or halogen.

In a further embodiment, G$^1$ is —Ar$^1$-G$^a$, wherein Ar$^1$ is aryl or heteroaryl optionally substituted as described below, and G$^a$ is cyclopropyl or cyclobutyl, wherein the cyclopropyl or cyclobutyl are unsubstituted or substituted with 1, 2, or 3 $C_1$-$C_4$-alkyl, $C_1$-$C_4$-haloalkyl, or halogen.

In one embodiment, $R^a$ and $R^b$, at each occurrence, are each independently hydrogen, $C_1$-$C_4$-alkyl, or $C_1$-$C_4$-haloalkyl.

In another embodiment, $R^a$ and $R^b$, at each occurrence, are each independently hydrogen or $C_1$-$C_4$-alkyl.

In another embodiment, $R^a$ and $R^b$, at each occurrence, are each $C_1$-$C_4$-haloalkyl.

In another embodiment, $R^a$ and $R^b$, at each occurrence, are each $C_1$-$C_4$-alkyl.

In a further embodiment, $R^a$ and $R^b$, at each occurrence, are each hydrogen.

In one embodiment, j is 1, 2, 3, 4, or 5.

In another embodiment, j is 1, 2 or 3.

In a further embodiment, j is 1.

In one embodiment, $Ar^1$ is, at each occurrence, independently aryl or heteroaryl, wherein $Ar^1$ is unsubstituted or substituted with 1, 2, 3, 4, or 5 substituents selected from the group consisting of $C_1$-$C_4$-alkyl, $C_2$-$C_4$-alkenyl, $C_2$-$C_4$-alkynyl, halogen, cyano, —$NO_2$, —$OR^s$, —OC(O)$R^s$, —OC(O)N($R^s$)($R^t$), —$SR^s$, —S(O)$R^s$, —S(O)$_2R^s$, —S(O)$_2$N($R^s$)($R^t$), —C(O)$R^s$, —C(O)O$R^s$, —C(O)N($R^s$)($R^t$), —N($R^s$)($R^t$), —N($R^s$)C(O)$R^t$, —N($R^s$)C(O)O($R^t$), —N($R^s$)S(O)$_2$($R^t$), $C_1$-$C_4$-cyanoalkyl, and $C_1$-$C_4$-haloalkyl; wherein $R^s$ and $R^t$ are, at each occurrence, independently hydrogen, $C_1$-$C_4$-alkyl, $C_2$-$C_4$-alkenyl, $C_2$-$C_4$-alkynyl or $C_1$-$C_4$-haloalkyl.

In another embodiment, $Ar^1$ is aryl, wherein $Ar^1$ is unsubstituted or substituted with 1, 2 or 3 substituents selected from the group consisting of $C_1$-$C_4$-alkyl, $C_2$-$C_4$-alkenyl, halogen, cyano, —$OR^s$, and $C_1$-$C_4$-haloalkyl; wherein $R^s$ is hydrogen, $C_1$-$C_4$-alkyl or $C_1$-$C_4$-haloalkyl.

In a further embodiment, $Ar^1$ is heteroaryl, wherein $Ar^1$ is unsubstituted or substituted with 1, 2 or 3 substituents selected from the group consisting of $C_1$-$C_4$-alkyl, $C_2$-$C_4$-alkenyl, halogen, cyano, —$OR^s$, and $C_1$-$C_4$-haloalkyl; wherein $R^s$ is hydrogen, $C_1$-$C_4$-alkyl or $C_1$-$C_4$-haloalkyl.

In one embodiment, $G^a$ is $C_3$-$C_7$-cycloalkyl, $C_3$-$C_7$-cycloalkenyl, heterocycle, or heteroaryl, wherein the $C_3$-$C_7$-cycloalkyl, $C_3$-$C_7$-cycloalkenyl, heterocycle, or heteroaryl are unsubstituted or substituted with 1, 2, or 3 $C_1$-$C_4$-alkyl, $C_1$-$C_4$-haloalkyl, or halogen.

In another embodiment, $G^a$ is $C_3$-$C_7$-cycloalkyl or heteroaryl, wherein the $C_3$-$C_7$-cycloalkyl or heteroaryl are unsubstituted or substituted with 1, 2, or 3 $C_1$-$C_4$-alkyl, $C_1$-$C_4$-haloalkyl, or halogen.

In another embodiment, $G^a$ is heteroaryl, wherein the heteroaryl is unsubstituted or substituted with 1, 2, or 3 $C_1$-$C_4$-alkyl, $C_1$-$C_4$-haloalkyl, or halogen.

In another embodiment, $G^a$ is $C_3$-$C_7$-cycloalkyl, wherein the $C_3$-$C_7$-cycloalkyl is unsubstituted or substituted with 1, 2, or 3 $C_1$-$C_4$-alkyl, $C_1$-$C_4$-haloalkyl, or halogen.

In a further embodiment, $G^a$ is cyclopropyl or cyclobutyl, wherein the cyclopropyl or cyclobutyl are unsubstituted or substituted with 1, 2, or 3 $C_1$-$C_4$-alkyl, $C_1$-$C_4$-haloalkyl, or halogen.

In one embodiment, $L^2$ is —S(O)$_2$—, or —S(O)—.

In another embodiment, $L^2$ is —S(O)—.

In a further embodiment, $L^2$ is —S(O)$_2$—.

In one embodiment, $G^2$ is $C_1$-$C_8$-alkyl, $C_1$-$C_8$-haloalkyl, $C_1$-$C_8$-cycloalkyl, $Ar^2$ or $Ar^3$.

In another embodiment, $G^2$ is $C_1$-$C_8$-alkyl, $C_1$-$C_8$-haloalkyl or $C_1$-$C_8$-cycloalkyl.

In another embodiment, $G^2$ is $Ar^2$ or $Ar^3$, wherein $Ar^2$ and $Ar^3$ are as described below.

In another embodiment, $G^2$ is $Ar^2$, wherein $Ar^2$ is as described below.

In a further embodiment, $G^2$ is $Ar^3$, wherein $Ar^3$ is as described below.

In one embodiment, $Ar^2$ is aryl or heteroaryl, wherein $Ar^2$ is unsubstituted or substituted with 1, 2, 3, 4, or 5 substituents selected from the group consisting of $C_1$-$C_4$-alkyl, $C_2$-$C_4$-alkenyl, $C_2$-$C_4$-alkynyl, halogen, cyano, —$NO_2$, —$OR^u$, -alkyl-$OR^u$, —OC(O)$R^u$, —OC(O)N($R^u$)($R^v$), —$SR^u$, —S(O)$R^u$, —S(O)$_2R^u$, —S(O)$_2$N($R^u$)($R^v$), —C(O)$R^u$, —C(O)O$R^u$, —C(O)N($R^u$)($R^v$), —N($R^u$)($R^v$), —N($R^u$)C(O)$R^v$, —N($R^u$)C(O)O($R^v$), —N($R^u$)S(O)$_2$($R^v$), $C_1$-$C_4$-cyanoalkyl, $C_1$-$C_4$-haloalkyl and -$G^b$; $G^b$ is $C_3$-$C_7$-cycloalkyl, $C_3$-$C_7$-cycloalkenyl, heterocycle, aryl or heteroaryl, wherein the $C_3$-$C_7$-cycloalkyl, $C_3$-$C_7$-cycloalkenyl, heterocycle, aryl or heteroaryl are unsubstituted or substituted with 1, 2, or 3 $C_1$-$C_4$-alkyl, $C_1$-$C_4$-haloalkyl, or halogen; and $R^u$ and $R^v$ are, at each occurrence, independently hydrogen, $C_1$-$C_4$-alkyl, $C_2$-$C_4$-alkenyl, $C_2$-$C_4$-alkynyl or $C_1$-$C_4$-haloalkyl.

In another embodiment, $Ar^2$ is aryl wherein $Ar^2$ is unsubstituted or substituted with 1, 2, 3, 4, or 5 substituents selected from the group consisting of $C_1$-$C_4$-alkyl, $C_2$-$C_4$-alkenyl, $C_2$-$C_4$-alkynyl, halogen, cyano, —$NO_2$, —$OR^u$, -alkyl-$OR^u$, —OC(O)$R^u$, —OC(O)N($R^u$)($R^v$), —$SR^u$, —S(O)$R^u$, —S(O)$_2$ $R^u$, —S(O)$_2$N($R^u$)($R^v$), —C(O)$R^u$, —C(O)O$R^u$, —C(O)N($R^u$)($R^v$), —N($R^u$)($R^v$), —N($R^u$)C(O)$R^v$, —N($R^u$)C(O)O($R^v$), —N($R^u$)S(O)$_2$($R^v$), $C_1$-$C_4$-cyanoalkyl, $C_1$-$C_4$-haloalkyl and -$G^b$; $G^b$ is $C_3$-$C_7$-cycloalkyl, $C_3$-$C_7$-cycloalkenyl, heterocycle, aryl or heteroaryl, wherein the $C_3$-$C_7$-cycloalkyl, $C_3$-$C_7$-cycloalkenyl, heterocycle, aryl or heteroaryl are unsubstituted or substituted with 1, 2, or 3 $C_1$-$C_4$-alkyl, $C_1$-$C_4$-haloalkyl, or halogen; and $R^u$ and $R^v$ are, at each occurrence, independently hydrogen, $C_1$-$C_4$-alkyl, $C_2$-$C_4$-alkenyl, $C_2$-$C_4$-alkynyl or $C_1$-$C_4$-haloalkyl.

In another embodiment, $Ar^2$ is phenyl or naphthyl, wherein $Ar^2$ is unsubstituted or substituted with 1, 2, or 3 substituents selected from the group consisting of $C_1$-$C_4$-alkyl, halogen, cyano, —$OR^u$, -alkyl-$OR^u$, —C(O)$R^u$, $C_1$-$C_4$-haloalkyl and -$G^b$; $G^b$ is $C_3$-$C_7$-cycloalkyl, heterocycle, aryl or heteroaryl, wherein the $C_3$-$C_7$-cycloalkyl, heterocycle, aryl or heteroaryl are unsubstituted or substituted with 1, 2, or 3 $C_1$-$C_4$-alkyl, $C_1$-$C_4$-haloalkyl, or halogen; and $R^u$ and $R^v$ are, at each occurrence, independently hydrogen, $C_1$-$C_4$-alkyl or $C_1$-$C_4$-haloalkyl.

In another embodiment, $Ar^2$ is phenyl or naphthyl, wherein $Ar^2$ is unsubstituted or substituted with 1, 2, or 3 substituents selected from the group consisting of $C_1$-$C_4$-alkyl, halogen, cyano, —$OR^u$, -alkyl-$OR^u$, —C(O)$R^u$, $C_1$-$C_4$-haloalkyl and -$G^b$; $G^b$ is $C_3$-$C_7$-cycloalkyl, heterocycle, aryl or heteroaryl, wherein the $C_3$-$C_7$-cycloalkyl, heterocycle, aryl or heteroaryl are unsubstituted or substituted with 1, 2, or 3 $C_1$-$C_4$-alkyl, $C_1$-$C_4$-haloalkyl, or halogen; and $R^u$ is hydrogen, $C_1$-$C_4$-alkyl or $C_1$-$C_4$-haloalkyl.

In a further embodiment, $Ar^2$ is heteroaryl, wherein $Ar^2$ is unsubstituted or substituted with 1, 2, or 3 substituents selected from the group consisting of $C_1$-$C_4$-alkyl, halogen, cyano, —$OR^u$, -alkyl-$OR^u$, —C(O)$R^u$, $C_1$-$C_4$-haloalkyl and -$G^b$; $G^b$ is $C_3$-$C_7$-cycloalkyl, heterocycle, aryl or heteroaryl, wherein the $C_3$-$C_7$-cycloalkyl, heterocycle, aryl or heteroaryl are unsubstituted or substituted with 1, 2, or 3 $C_1$-$C_4$-alkyl, $C_1$-$C_4$-haloalkyl, or halogen; and $R^u$ is hydrogen, $C_1$-$C_4$-alkyl or $C_1$-$C_4$-haloalkyl.

In one embodiment, Ar³ is (i), wherein:

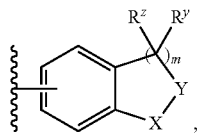

X is O, S, NR$^w$, or CH$_2$; 127 is hydrogen or alkyl; Y is C(O) or CH$_2$; R$^z$ and R$^y$ are hydrogen; and m is 1, 2 or 3.

In another embodiment, Ar³ is (i), wherein:

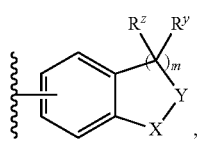

X is O, NR$^w$, or CH$_2$; R$^w$ is hydrogen or alkyl; Y is C(O) or CH$_2$; R$^z$ and R$^y$ are hydrogen; and m is 1, 2 or 3.

In another embodiment, Ar³ is (i), wherein:

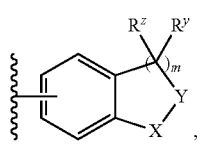

X is O or S; Y is CH$_2$; R$^z$ and R$^y$ are hydrogen; and m is 1 or 2.

In another embodiment, Ar³ is (i), wherein:

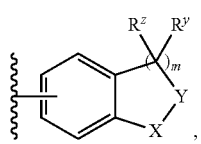

X is NR$^w$; R$^w$ is hydrogen or alkyl; Y is C(O) or CH$_2$; R$^z$ and R$^y$ are hydrogen; and m is 1, 2 or 3.

In another embodiment, Ar³ is (i), wherein:

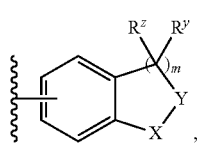

X is NR$^w$; R$^w$ is alkyl; Y is C(O); R$^z$ and R$^y$ are hydrogen; and m is 1.

In another embodiment, Ar³ is (i), wherein:

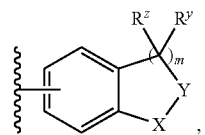

X is CH$_2$; Y is C(O) or CH$_2$; R$^z$ and R$^y$ are hydrogen; and m is 1, 2 or 3.

In another embodiment, Ar³ is (i), wherein:

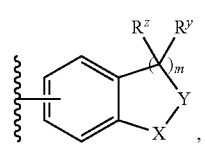

X is CH$_2$; Y is CH$_2$; R$^z$ and R$^y$ are hydrogen; and m is 1 or 2.

In one embodiment, in a compound of Formula (I) or Formula (I-A): R¹ is G¹-L¹-; L¹ is —C(O)NR$^a$—, —NR$^a$C(O)—, —S(O)$_2$NR$^a$—, or —NR$^a$S(O)$_2$—; R² is hydrogen; and L² is —S(O)$_2$—.

In another embodiment, in a compound of Formula (I) or Formula (I-A): R¹ is G¹-L¹-; R² is hydrogen; L¹ is —C(O)NR$^a$— or —NR$^a$C(O)—; G¹ is C$_1$-C$_8$-alkyl, C$_1$-C$_8$-haloalkyl, Ar¹, —(CR$^a$R$^b$)$_j$—Ar¹, or —CH(Ar¹)$_2$; R$^a$ and R$^b$, at each occurrence, are each independently hydrogen or C$_1$-C$_4$-alkyl; L² is —S(O)$_2$— and G² is Ar² or Ar³.

In further embodiment, in a compound of Formula (I) or Formula (I-A): R¹ is G¹-L¹-; R² is hydrogen; L¹ is —C(O)NR$^a$— or —NR$^a$C(O)—; G¹ is C$_1$-C$_8$-alkyl, C$_1$-C$_8$-haloalkyl, Ar¹, —(CR$^a$R$^b$)$_j$—Ar¹, or —CH(Ar¹)$_2$; R$^a$ and R$^b$, at each occurrence, are each independently hydrogen or C$_1$-C$_4$-alkyl; Ar¹ is, at each occurrence, independently aryl or heteroaryl, wherein Ar¹ is unsubstituted or substituted with 1, 2, or 3 substituents selected from the group consisting of C$_1$-C$_4$-alkyl, C$_2$-C$_4$-alkenyl, C$_2$-C$_4$-alkynyl, halogen, cyano, —OR$^s$, —SR$^s$, —C(O)R$^s$, C$_1$-C$_4$-cyanoalkyl, and C$_1$-C$_4$-haloalkyl; R$^s$ is hydrogen, C$_1$-C$_4$-alkyl, C$_2$-C$_4$-alkenyl or C$_1$-C$_4$-haloalkyl; L² is —S(O)$_2$—; G² is Ar²; Ar² is aryl or heteroaryl, wherein Ar² is unsubstituted or substituted with 1, 2, or 3, substituents selected from the group consisting of C$_1$-C$_4$-alkyl, halogen, cyano, —C(O)R$^u$, C$_1$-C$_4$-cyanoalkyl, C$_1$-C$_4$-haloalkyl and -G$^b$; G$^b$ is C$_3$-C$_2$-cycloalkyl, heterocycle, aryl or heteroaryl, wherein the C$_3$-C$_2$-cycloalkyl, C$_3$-C$_2$-cycloalkenyl, heterocycle, aryl or heteroaryl are unsubstituted or substituted with 1, 2, or 3 C$_1$-C$_4$-alkyl, C$_1$-C$_4$-haloalkyl, or halogen; and R" is C$_1$-C$_4$-alkyl, or C$_1$-C$_4$-haloalkyl.

In one embodiment, in a compound of Formula (I) or Formula (I-A): R¹ is G¹-L¹-; L¹ is NR$^a$—; R$^a$ is hydrogen, C$_1$-C$_4$-alkyl, or C$_1$-C$_4$-haloalkyl; R² is hydrogen; and L² is —S(O)$_2$—.

In another embodiment, in a compound of Formula (I) or Formula (I-A): R¹ is G¹-L¹-; L¹ is NR$^a$; R$^a$ is hydrogen; R² is hydrogen; L² is —S(O)$_2$—; G¹ is Ar¹; Ar¹ is aryl or heteroaryl, wherein Ar¹ is unsubstituted or substituted with 1, 2, or 3 substituents selected from the group consisting of C$_1$-C$_4$-alkyl, C$_2$-C$_4$-alkenyl, C$_2$-C$_4$-alkynyl, halogen, cyano, —OR$^s$, —SR$^s$, —C(O)R$^s$, C$_1$-C$_4$-cyanoalkyl, and C$_1$-C$_4$-haloalkyl; R$^s$ is, at each occurrence, independently hydrogen, C$_1$-C$_4$- alkyl, $C_2$-$C_4$-alkenyl or $C_1$-$C_4$-haloalkyl; $G^2$ is $Ar^2$; $Ar^2$ is aryl or heteroaryl, wherein $Ar^2$ is unsubstituted or substituted with 1, 2, or 3, substituents selected from the group consisting of $C_1$-$C_4$-alkyl, halogen, cyano, —C(O)$R^u$, $C_1$-$C_4$-cyanoalkyl, $C_1$-$C_4$-haloalkyl and -$G^b$; $G^b$ is $C_3$-$C_7$-cycloalkyl, heterocycle, aryl or heteroaryl, wherein the $C_3$-$C_7$-cycloalkyl, heterocycle, aryl or heteroaryl are unsubstituted or substituted with 1, 2, or 3 $C_1$-$C_4$-alkyl, $C_1$-$C_4$-haloalkyl, or halogen; and is $C_1$-$C_4$-alkyl, or $C_1$-$C_4$-haloalkyl.

In one embodiment, in a compound of Formula (I) or Formula (I-A): $R^1$ is hydrogen; $R^2$ is $G^1$-$L^1$-; $L^1$ is —O—; and $L^2$ is —S(O)$_2$—.

In another embodiment, in a compound of Formula (I) or Formula (I-A): $R^1$ is hydrogen; $R^2$ is $G^1$-$L^1$-; $L^1$ is —O—; $G^1$ is $Ar^1$; $Ar^1$ is aryl or heteroaryl, wherein $Ar^1$ is unsubstituted or substituted with 1, 2, or 3 substituents selected from the group consisting of $C_1$-$C_4$-alkyl, $C_2$-$C_4$-alkenyl, $C_2$-$C_4$-alkynyl, halogen, cyano, —OR$^s$, —SR$^s$, —C(O)R$^s$, $C_1$-$C_4$-cyanoalkyl, and $C_1$-$C_4$-haloalkyl; $R^s$ is, at each occurrence, independently hydrogen, $C_1$-$C_4$-alkyl, $C_2$-$C_4$-alkenyl or $C_1$-$C_4$-haloalkyl; $L^2$ is —S(O)$_2$—; $G^2$ is $Ar^2$; $Ar^2$ is aryl or heteroaryl, wherein $Ar^2$ is unsubstituted or substituted with 1, 2, or 3, substituents selected from the group consisting of $C_1$-$C_4$-alkyl, halogen, cyano, —C(O)R$^u$, $C_1$-$C_4$-cyanoalkyl, $C_1$-$C_4$-haloalkyl and -$G^b$; $G^b$ is $C_3$-$C_7$-cycloalkyl, heterocycle, aryl or heteroaryl, wherein the $C_3$-$C_7$-cycloalkyl, heterocycle, aryl or heteroaryl are unsubstituted or substituted with 1, 2, or 3 $C_1$-$C_4$-alkyl, $C_1$-$C_4$-haloalkyl, or halogen; and is $C_1$-$C_4$-alkyl, or $C_1$-$C_4$-haloalkyl.

In one embodiment, in a compound of Formula (I) or Formula (I-A): $R^1$ is $G^1$-$L^1$-; $L^1$ is —O—; $R^2$ is hydrogen; and $L^2$ is —S(O)$_2$—.

In another embodiment, in a compound of Formula (I) or Formula (I-A): $R^1$ is $G^1$-$L^1$-; $L^1$ is —O—; $G^1$ is $Ar^1$, —(CR$^a$R$^b$)$_j$—Ar$^1$, —CH(Ar$^1$)$_2$, and —Ar$^1$-$G^a$; $R^a$ and $R^b$, at each occurrence, are each independently hydrogen or $C_1$-$C_4$-alkyl; $R^2$ is hydrogen; $L^2$ is —S(O)$_2$—; and $G^2$ is $Ar^2$ or $Ar^3$.

In another embodiment, in a compound of Formula (I) or Formula (I-A): $R^1$ is $G^1$-$L^1$-; $L^1$ is —O—; $G^1$ is $Ar^1$; $Ar^1$ is aryl or heteroaryl, wherein $Ar^1$ is unsubstituted or substituted with 1, 2, or 3 substituents selected from the group consisting of $C_1$-$C_4$-alkyl, $C_2$-$C_4$-alkenyl, halogen, cyano, —OR$^s$, —C(O)R$^s$, $C_1$-$C_4$-cyanoalkyl, and $C_1$-$C_4$-haloalkyl; $R^s$ is $C_1$-$C_4$-alkyl or $C_1$-$C_4$-haloalkyl; $R^2$ is hydrogen; $L^2$ is —S(O)$_2$—; $G^2$ is $Ar^2$; $Ar^2$ is aryl or heteroaryl, wherein $Ar^2$ is unsubstituted or substituted with 1, 2, or 3 substituents selected from the group consisting of $C_1$-$C_4$-alkyl, halogen, cyano, —C(O)R$^u$, $C_1$-$C_4$-cyanoalkyl, and $C_1$-$C_4$-haloalkyl; and R$^u$ is $C_1$-$C_4$-alkyl or $C_1$-$C_4$-haloalkyl.

In another embodiment, in a compound of Formula (I) or Formula (I-A): $R^1$ is $G^1$-$L^1$-; $L^1$ is —O—; $G^1$ is —(CR$^a$R$^b$)$_j$—Ar$^1$; $R^a$ and $R^b$, at each occurrence, are each independently hydrogen or $C_1$-$C_4$-alkyl; j is 1, 2 or 3; $Ar^1$ is aryl or heteroaryl, wherein $Ar^1$ is unsubstituted or substituted with 1, 2, or 3 substituents selected from the group consisting of $C_1$-$C_4$-alkyl, $C_2$-$C_4$-alkenyl, halogen, cyano, —OR$^s$, —C(O)R$^s$, $C_1$-$C_4$-cyanoalkyl, and $C_1$-$C_4$-haloalkyl; $R^s$ is $C_1$-$C_4$-alkyl or $C_1$-$C_4$-haloalkyl; $R^2$ is hydrogen; $L^2$ is —S(O)$_2$—; $G^2$ is $Ar^2$; $Ar^2$ is aryl or heteroaryl, wherein $Ar^2$ is unsubstituted or substituted with 1, 2, or 3 substituents selected from the group consisting of $C_1$-$C_4$-alkyl, halogen, cyano, —C(O)R$^u$, $C_1$-$C_4$-cyanoalkyl, and $C_1$-$C_4$-haloalkyl; and is $C_1$-$C_4$-alkyl or $C_1$-$C_4$-haloalkyl.

In another embodiment, in a compound of Formula (I) or Formula (I-A): $R^1$ is $G^1$-$L^1$-; $L^1$ is —O—; $G^1$ is —Ar$^1$-$G^a$; $Ar^1$ is aryl or heteroaryl, wherein $Ar^1$ is unsubstituted or substituted with 1, 2, or 3 substituents selected from the group consisting of $C_1$-$C_4$-alkyl, $C_2$-$C_4$-alkenyl, halogen, cyano, —OR$^s$, —C(O)R$^s$, $C_1$-$C_4$-cyanoalkyl, and $C_1$-$C_4$-haloalkyl; $R^s$ is $C_1$-$C_4$-alkyl or $C_1$-$C_4$-haloalkyl; $G^a$ is heteroaryl, wherein the heteroaryl is unsubstituted or substituted with 1, 2, or 3 $C_1$-$C_4$-alkyl, $C_1$-$C_4$-haloalkyl, or halogen; $R^2$ is hydrogen; $L^2$ is —S(O)$_2$—; $G^2$ is $Ar^2$; $Ar^2$ is aryl or heteroaryl, wherein $Ar^2$ is unsubstituted or substituted with 1, 2, or 3 substituents selected from the group consisting of $C_1$-$C_4$-alkyl, halogen, cyano, —C(O)R$^u$, $C_1$-$C_4$-cyanoalkyl, and $C_1$-$C_4$-haloalkyl; and $R^a$ is $C_1$-$C_4$-alkyl or $C_1$-$C_4$-haloalkyl.

In another embodiment in a compound of Formula (I) or Formula (I-A): $R^1$ is $G^1$-$L^1$-; $L^1$ is —O—; $G^1$ is —Ar$^1$-$G^a$; $Ar^1$ is aryl or heteroaryl, wherein $Ar^1$ is unsubstituted or substituted with 1, 2, or 3 substituents selected from the group consisting of $C_1$-$C_4$-alkyl, $C_2$-$C_4$-alkenyl, halogen, cyano, —OR$^s$, —C(O)R$^s$, $C_1$-$C_4$-cyanoalkyl, and $C_1$-$C_4$-haloalkyl; $R^s$ is $C_1$-$C_4$-alkyl or $C_1$-$C_4$-haloalkyl; $G^a$ is $C_3$-$C_2$-cycloalkyl, wherein the $C_3$-$C_2$-cycloalkyl is unsubstituted or substituted with 1, 2, or 3 $C_1$-$C_4$-alkyl, $C_1$-$C_4$-haloalkyl, or halogen; $R^2$ is hydrogen; $L^2$ is —S(O)$_2$—; $G^2$ is $Ar^2$; $Ar^2$ is aryl or heteroaryl, wherein $Ar^2$ is unsubstituted or substituted with 1, 2, 3, or 4 substituents selected from the group consisting of $C_1$-$C_4$-alkyl, $C_2$-$C_4$-alkenyl, halogen, cyano, —C(O)R$^a$, $C_1$-$C_4$-cyanoalkyl, $C_1$-$C_4$-haloalkyl and -$G^b$; $G^b$ is $C_3$-$C_2$-cycloalkyl, heterocycle, aryl or heteroaryl, wherein the $C_3$-$C_7$-cycloalkyl, heterocycle, aryl or heteroaryl are unsubstituted or substituted with 1, 2, or 3 $C_1$-$C_4$-alkyl, $C_1$-$C_4$-haloalkyl, or halogen; and $R^u$ is $C_1$-$C_4$-alkyl or $C_1$-$C_4$-haloalkyl.

In another embodiment, in a compound of Formula (I) or Formula (I-A): $R^1$ is $G^1$-$L^1$-; $L^1$ is —O—; $G^1$ is —Ar$^1$-$G^a$; $Ar^1$ is aryl or heteroaryl, wherein $Ar^1$ is unsubstituted or substituted with 1, 2, or 3 substituents selected from the group consisting of $C_1$-$C_4$-alkyl, $C_2$-$C_4$-alkenyl, halogen, cyano, —OR$^u$, —C(O)R$^s$, $C_1$-$C_4$-cyanoalkyl, and $C_1$-$C_4$-haloalkyl; $R^5$ is $C_1$-$C_4$-alkyl or $C_1$-$C_4$-haloalkyl; $G^a$ is $C_3$-$C_7$-cycloalkyl, wherein the $C_3$-$C_7$-cycloalkyl is unsubstituted or substituted with 1, 2, or 3 $C_1$-$C_4$-alkyl, $C_1$-$C_4$-haloalkyl, or halogen; $R^2$ is hydrogen; $L^2$ is —S(O)$_2$—; $G^2$ is $Ar^3$; $Ar^3$ is (i):

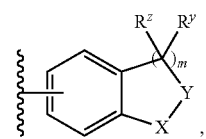

(i)

wherein X is O, NR$^w$, or CH$_2$; R$^w$ is hydrogen or alkyl; Y is C(O) or CH$_2$; R$^z$ and R$^y$ are hydrogen; and m is 1, 2 or 3.

(i) Additional Embodiments $G^1$ and $G^2$ Aryl and Heteroaryl Substituents

In one embodiment, the invention is directed to compounds of Formula (I) or Formula (I-A) wherein:

$R^1$ is $G^1$-$L^1$-;

$R^2$ is hydrogen;

$L^1$ is —C(R$^c$)(R$^d$)—, —C(O)NR$^a$—, —NR$^a$C(O)—, —NR$^a$—, or —O—;

$G^1$ is $C_1$-$C_8$-alkyl, $C_1$-$C_8$-haloalkyl, Ar$^1$, —(CR$^a$R$^b$)—Ar$^1$, —CH(Ar$^1$)$_2$, or —Ar$^1$-$G^a$;

$R^a$ and $R^b$, at each occurrence, are each hydrogen;

$R^c$ and $R^d$ are each independently hydrogen or hydroxy;

Ar$^1$ is, at each occurrence, independently selected from the group consisting of phenyl, thiazolyl, pyridinyl, pyrimidinyl, pyrazinyl, pyridazinyl, and benzoxazolyl; wherein $Ar^1$ is unsubstituted or substituted with 1, 2, 3, 4, or 5 substituents selected from the group consisting of halogen, cyano, $C_1$-$C_4$-alkyl, $C_2$-$C_4$-alkenyl, $C_1$-$C_4$-haloalkyl, and $C_1$-$C_4$-haloalkoxy;

$G^a$ is cyclopropyl, cyclobutyl, or imidazolyl;

$L^2$ is —S(O)$_2$— or —S(O)$_2$CH$_2$—;

$G^2$ is $C_1$-$C_8$-alkyl, $C_1$-$C_8$-haloalkyl, $C_1$-$C_8$-cycloalkyl, $Ar^2$, or $Ar^3$;

$Ar^2$ is aryl or heteroaryl; wherein the $Ar^2$ aryl is selected from the group consisting of phenyl, naphthyl, and tetrahydronaphthylenyl; the $Ar^2$ heteroaryl is selected from the group consisting of furyl, thienyl, pyrazolyl, and pyridinyl; and $Ar^2$ is unsubstituted or substituted with 1, 2, 3, 4, or 5 substituents selected from the group consisting of halogen, cyano, $C_1$-$C_4$-alkyl, $C_1$-$C_4$-haloalkyl, —OR$^u$, —C(O)R$^u$, —C(O)OR$^u$, —C(O)N(R$^u$)(R$^v$), and -G$^b$;

$G^b$ is selected from the group consisting of cyclopropyl, phenyl, pyrrolidinyl, piperidinyl, morpholinyl, and pyrazolyl; wherein the cyclopropyl, phenyl, pyrrolidinyl, piperidinyl, morpholinyl, and pyrazolyl are unsubstituted or substituted with 1, 2, or 3 $C_1$-$C_4$-alkyl;

$R^u$ and $R^v$ are, at each occurrence, independently hydrogen, $C_1$-$C_4$-alkyl, or $C_1$-$C_4$-haloalkyl;

$Ar^3$ is dihydroindenyl, dihydrobenzofuranyl, or hexahydropyrrolo[1,2-a]-pyrazinyl; wherein the dihydroindenyl, dihydrobenzofuranyl, and hexahydropyrrolo[1,2-a]-pyrazinyl are unsubstituted or substituted with 1, 2, or 3 $C_1$-$C_4$-alkyl or oxo.

In another embodiment, the invention is directed to compounds of Formula (I) or Formula (I-A) wherein:

$R^1$ is $G^1$-$L^1$-;

$R^2$ is hydrogen;

$L^1$ is —C(R$^c$)(R$^d$)—, —C(O)NR$^a$—, —NR$^a$C(O)—, —NR$^a$—, or —O—;

$G^1$ is —Ar$^1$ or —Ar$^1$-G$^a$;

$R^a$, at each occurrence, is hydrogen;

$R^c$ and $R^d$ are each independently hydrogen or hydroxy;

$Ar^1$ is, at each occurrence, independently selected from the group consisting of phenyl, thiazolyl, pyridinyl, pyrimidinyl, pyrazinyl, pyridazinyl, and benzoxazolyl; wherein $Ar^1$ is unsubstituted or substituted with 1, 2, or 3 substituents selected from the group consisting of halogen, cyano, $C_1$-$C_4$-alkyl, $C_2$-$C_4$-alkenyl, $C_1$-$C_4$-haloalkyl, and $C_1$-$C_4$-haloalkoxy;

$G^a$ is cyclopropyl, cyclobutyl, or imidazolyl;

$L^2$ is —S(O)$_2$— or —S(O)$_2$CH$_2$—;

$G^2$ is $C_1$-$C_8$-alkyl, $C_1$-$C_8$-haloalkyl, $C_1$-$C_8$-cycloalkyl, $Ar^2$, or $Ar^3$;

$Ar^2$ is aryl or heteroaryl; wherein the $Ar^2$ aryl is selected from the group consisting of phenyl, naphthyl, and tetrahydronaphthylenyl; the $Ar^2$ heteroaryl is selected from the group consisting of furyl, thienyl, pyrazolyl, and pyridinyl; and $Ar^2$ is unsubstituted or substituted with 1, 2, or 3 substituents selected from the group consisting of halogen, cyano, $C_1$-$C_4$-alkyl, $C_1$-$C_4$-haloalkyl, —OR$^u$, —C(O)R$^u$, —C(O)OR$^u$, —C(O)N(R$^u$)(R$^v$), and -G$^b$;

$G^b$ is selected from the group consisting of cyclopropyl, phenyl, pyrrolidinyl, piperidinyl, morpholinyl, and pyrazolyl; wherein the cyclopropyl, phenyl, pyrrolidinyl, piperidinyl, morpholinyl, and pyrazolyl are unsubstituted or substituted with 1, 2, or 3 $C_1$-$C_4$-alkyl;

$R^u$ and $R^v$ are, at each occurrence, independently hydrogen, $C_1$-$C_4$-alkyl, or $C_1$-$C_4$-haloalkyl;

$Ar^3$ is dihydroindenyl, dihydrobenzofuranyl, or hexahydropyrrolo[1,2-a]pyrazinyl; wherein the dihydroindenyl, dihydrobenzofuranyl, and hexahydropyrrolo[1,2-a]pyrazinyl are unsubstituted or substituted with 1, 2, or 3 $C_1$-$C_4$-alkyl or oxo.

In another embodiment, the compound is a compound of Formula (I) or Formula (I-A) wherein:

$R^1$ is $G^1$-$L^1$-;

$R^2$ is hydrogen;

$L^1$ is —C(R$^c$)(R$^d$)—, —C(O)NR$^a$—, —NR$^a$C(O)—, —NR$^a$—, or —O—;

$G^1$ is $C_1$-$C_8$-alkyl, $C_1$-$C_8$-haloalkyl, Ar$^1$, —(CR$^a$R$^b$)—Ar$^1$, —CH(Ar$^1$)$_2$, or —Ar$^1$-G$^a$;

$R^a$ and $R^b$, at each occurrence, are each hydrogen;

$R^c$ and $R^d$ are each independently hydrogen or hydroxy;

$Ar^1$ is, at each occurrence, independently selected from the group consisting of phenyl, thiazolyl, pyridinyl, pyrimidinyl, pyrazinyl, pyridazinyl, and benzoxazolyl; wherein $Ar^1$ is unsubstituted or substituted with 1, 2, 3, 4, or 5 substituents selected from the group consisting of halogen, cyano, $C_1$-$C_4$-alkyl, $C_2$-$C_4$-alkenyl, $C_1$-$C_4$-haloalkyl, and $C_1$-$C_4$-haloalkoxy;

$G^a$ is cyclopropyl, cyclobutyl, or imidazolyl;

$L^2$ is —S(O)$_2$— or —S(O)$_2$CH$_2$—;

$G^2$ is $Ar^2$;

$Ar^2$ is aryl or heteroaryl; wherein the $Ar^2$ aryl is selected from the group consisting of phenyl, naphthyl, and tetrahydronaphthylenyl; the $Ar^2$ heteroaryl is selected from the group consisting of furyl, thienyl, pyrazolyl, and pyridinyl; and $Ar^2$ is unsubstituted or substituted with 1, 2, 3, 4, or 5 substituents selected from the group consisting of halogen, cyano, $C_1$-$C_4$-alkyl, $C_1$-$C_4$-haloalkyl, —OR$^u$, —C(O)R$^u$, —C(O)OR$^u$, —C(O)N(R$^u$)(R$^v$), and -G$^b$;

$G^b$ is selected from the group consisting of cyclopropyl, phenyl, pyrrolidinyl, piperidinyl, morpholinyl, and pyrazolyl; wherein the cyclopropyl, phenyl, pyrrolidinyl, piperidinyl, morpholinyl, and pyrazolyl are unsubstituted or substituted with 1, 2, or 3 $C_1$-$C_4$-alkyl; and $R^u$ and $R^v$ are, at each occurrence, independently hydrogen, $C_1$-$C_4$-alkyl, or $C_1$-$C_4$-haloalkyl.

In further embodiments of each of the above embodiments, $L^1$ is —C(O)N(H)—. In further embodiments of each of the above embodiments, $L^1$ is —N(H)C(O)—. In further embodiments of each of the above embodiments, $L^1$ is —O—.

(ii) Additional Embodiments $G^1$=$Ar^1$ or $Ar^1$-$G^a$ and $G^2$=$Ar^2$

In one embodiment, the invention is directed to compounds of Formula (I) or Formula (I-A) wherein:

$R^1$ is $G^1$-$L^1$-;

$R^2$ is hydrogen;

$L^1$ is —C(O)NR$^a$—, —NR$^a$C(O)—, or —O—;

$G^1$ is Ar$^1$ or —Ar$^1$-G$^a$;

$R^a$, at each occurrence, is hydrogen;

$Ar^1$ is, at each occurrence, independently phenyl, pyridinyl, or pyrazinyl; wherein $Ar^1$ is unsubstituted or substituted with 1, 2, or 3 substituents selected from the group consisting of halogen, cyano, $C_1$-$C_4$-alkyl, $C_2$-$C_4$-alkenyl, $C_1$-$C_4$-haloalkyl, and $C_1$-$C_4$-haloalkoxy;

$G^a$ is cyclopropyl, cyclobutyl, or imidazolyl;

$L^2$ is —S(O)$_2$—;

$G^2$ is $Ar^2$;

$Ar^2$ is phenyl or pyridinyl; wherein $Ar^2$ is unsubstituted or substituted with 1, 2, or 3 substituents selected from the group consisting of halogen, cyano, $C_1$-$C_4$-alkyl, $C_1$-$C^4$-haloalkyl, —OR$^u$, —C(O)R$^u$, —C(O)OR$^u$, —C(O)N(R$^u$)(R$^v$), and -G$^b$;

$G^b$ is selected from the group consisting of cyclopropyl, phenyl, pyrrolidinyl, piperidinyl, morpholinyl, and pyrazolyl; wherein the cyclopropyl, phenyl, pyrrolidinyl, piperidinyl, morpholinyl, and pyrazolyl are unsubstituted or substituted with 1, 2, or 3 $C_1$-$C_4$-alkyl; and $R^u$ and $R^v$ are, at each occurrence, independently hydrogen, $C_1$-$C_4$-alkyl, or $C_1$-$C_4$-haloalkyl.

In another embodiment, the compound is a compound of Formula (I) or Formula (I-A) wherein:

$R^1$ is $G^1$-$L^1$-;
$R^2$ is hydrogen;
$L^1$ is —C(O)NR$^a$—, —NR$^a$C(O)—, or —O—;
$G^1$ is Ar$^1$ or —Ar$^1$-G$^a$;
$R^a$, at each occurrence, is hydrogen;
Ar$^1$ is, at each occurrence, independently phenyl, pyridin-2-yl, or pyrazin-2-yl; wherein Ar$^1$ is unsubstituted or substituted with 1 or 2 substituents selected from the group consisting of halogen, $C_1$-$C_4$-alkyl, halomethyl, and halomethoxy;
$G^a$ is cyclopropyl;
$L^2$ is —S(O)$_2$—;
$G^2$ is Ar$^2$; and
Ar$^2$ is phenyl or pyridinyl; wherein Ar$^2$ is unsubstituted or substituted with 1 or 2 substituents selected from the group consisting of halogen, cyano, $C_1$-$C_4$-alkyl, halomethyl, methoxy, and halomethoxy.

In another embodiment, the compound is a compound of Formula (I) or Formula (I-A) wherein:

$R^1$ is $G^1$-$L^1$-;
$R^2$ is hydrogen;
$L^1$ is —C(O)NR$^a$—, —NR$^a$C(O)—, or —O—;
$G^1$ is —Ar$^1$-G$^a$;
$R^a$, at each occurrence, is hydrogen;
Ar$^1$ is pyrazin-2-yl; wherein Ar$^1$ is unsubstituted or substituted with 1 or 2 substituents selected from the group consisting of halogen, $C_1$-$C_4$-alkyl, halomethyl, and halomethoxy;
$G^a$ is cyclopropyl;
$L^2$ is —S(O)$_2$—;
$G^2$ is Ar$^2$; and
Ar$^2$ is phenyl or pyridinyl; wherein Ar$^2$ is substituted with 1 or 2 substituents selected from the group consisting of chloro, fluoro, trifluoromethyl, and trifluoromethoxy.

In another embodiment, the compound is a compound of Formula (I) or Formula (I-A) wherein:

$R^1$ is $G^1$-$L^1$-;
$R^2$ is hydrogen;
$L^1$ is —C(O)NR$^a$—, —NR$^a$C(O)—, or —O—;
$G^1$ is Ar$^1$ or —Ar$^1$-G$^a$;
$R^a$, at each occurrence, is hydrogen;
Ar$^1$ is phenyl, pyridin-2-yl, or pyrazin-2-yl; wherein Ar$^1$ substituted with 1 or 2 substituents selected from the group consisting of chloro, fluoro, trifluoromethyl, and trifluoromethoxy;
$G^a$ is cyclopropyl;
$L^2$ is —S(O)$_2$—; and
Ar$^2$ is phenyl; wherein Ar$^2$ is substituted with 1 or 2 substituents selected from the group consisting of chloro, fluoro, trifluoromethyl, and trifluoromethoxy.

In another embodiment, the compound is a compound of Formula (I) or Formula (I-A) wherein:

$R^1$ is $G^1$-$L^1$-;
$R^2$ is hydrogen;
$L^1$ is —C(O)NR$^a$—, —NR$^a$C(O)—, or —O—;
$G^1$ is Ar$^1$ or —Ar$^1$-G$^a$;
$R^a$, at each occurrence, is hydrogen;
Ar$^1$ is phenyl, pyridin-2-yl, or pyrazin-2-yl; wherein Ar$^1$ substituted with 1 or 2 substituents selected from the group consisting of chloro, fluoro, trifluoromethyl, and trifluoromethoxy;
$G^a$ is cyclopropyl;
$L^2$ is —S(O)$_2$—;
Ar$^2$ is pyridinyl; wherein Ar$^2$ is substituted with 1 or 2 substituents selected from the group consisting of chloro, fluoro, trifluoromethyl, and trifluoromethoxy.

In further embodiments of each of the above embodiments, $L^1$ is —C(O)N(H)—.

In further embodiments of each of the above embodiments, $L^1$ is —N(H)C(O)—. In further embodiments of each of the above embodiments, $L^1$ is —O—.

(iii) Additional Embodiments $G^1$=$C_1$-$C_8$-Alkyl or $C_1$-$C_8$-Haloalkyl

In one embodiment, the invention is directed to compounds of Formula (I) or Formula (I-A) wherein:

$R^1$ is $G^1$-$L^1$-;
$R^2$ is hydrogen;
$L^1$ is —C(R$^c$)(R$^d$)—, —C(O)NR$^a$—, —NR$^a$C(O)—, —NR$^a$—, or —O—;
$G^1$ is $C_1$-$C_8$-alkyl or $C_1$-$C_8$-haloalkyl;
$R^c$ and $R^d$ are each independently hydrogen or hydroxy;
Ar$^1$ is, at each occurrence, independently selected from the group consisting of phenyl, thiazolyl, pyridinyl, pyrimidinyl, pyrazinyl, pyridazinyl, and benzoxazolyl; wherein Ar$^1$ is unsubstituted or substituted with 1, 2, or 3 substituents selected from the group consisting of halogen, cyano, $C_1$-$C_4$-alkyl, $C_2$-$C_4$-alkenyl, $C_1$-$C_4$-haloalkyl, and $C_1$-$C_4$-haloalkoxy;
$G^a$ is cyclopropyl, cyclobutyl, or imidazolyl;
$L^2$ is —S(O)$_2$— or —S(O)$_2$—;
$G^2$ is $C_1$-$C_8$-alkyl, $C_1$-$C_8$-haloalkyl, $C_1$-$C_8$-cycloalkyl, Ar$^2$, or Ar$^3$;
Ar$^2$ is aryl or heteroaryl; wherein the Ar$^2$ aryl is selected from the group consisting of phenyl, naphthyl, and tetrahydronaphthylenyl; the Ar$^2$ heteroaryl is selected from the group consisting of furyl, thienyl, pyrazolyl, and pyridinyl; and Ar$^2$ is unsubstituted or substituted with 1, 2, or 3 substituents selected from the group consisting of halogen, cyano, $C_1$-$C_4$-alkyl, $C_1$-$C_4$-haloalkyl, —OR$^u$, —C(O)R$^u$, —C(O)OR$^u$, —C(O)N(R$^u$)(R$^v$), and -G$^b$;
$G^b$ is selected from the group consisting of cyclopropyl, phenyl, pyrrolidinyl, piperidinyl, morpholinyl, and pyrazolyl; wherein the cyclopropyl, phenyl, pyrrolidinyl, piperidinyl, morpholinyl, and pyrazolyl are unsubstituted or substituted with 1, 2, or 3 $C_1$-$C_4$-alkyl;
$R^u$ and $R^v$ are, at each occurrence, independently hydrogen, $C_1$-$C_4$-alkyl, or $C_1$-$C_4$-haloalkyl;
Ar$^3$ is dihydroindenyl, dihydrobenzofuranyl, or hexahydropyrrolo[1,2-a]-pyrazinyl; wherein the dihydroindenyl, dihydrobenzofuranyl, and hexahydropyrrolo[1,2-a]-pyrazinyl are unsubstituted or substituted with 1, 2, or 3 $C_1$-$C_4$-alkyl or oxo.

In another embodiment, the compound is a compound of Formula (I) or Formula (I-A) wherein:

$R^1$ is $G^1$-$L^1$-;
$R^2$ is hydrogen;
$L^1$ is —C(O)NR$^a$—, —NR$^a$C(O)—, or —O—;
$G^1$ is $C_1$-$C_8$-alkyl or $C_1$-$C_8$-haloalkyl;
$R^a$, at each occurrence, is hydrogen;
$L^2$ is —S(O)$_2$—;
$G^2$ is Ar$^2$;

$Ar^2$ is phenyl or pyridinyl; wherein $Ar^2$ is unsubstituted or substituted with 1, 2, or 3 substituents selected from the group consisting of halogen, cyano, $C_1$-$C_4$-alkyl, $C_1$-$C_4$-haloalkyl, —$OR^u$, —$C(O)R^u$, —$C(O)OR^u$, —$C(O)N(R^u)(R^v)$, and -$G^b$;

$G^b$ is selected from the group consisting of cyclopropyl, phenyl, pyrrolidinyl, piperidinyl, morpholinyl, and pyrazolyl; wherein the cyclopropyl, phenyl, pyrrolidinyl, piperidinyl, morpholinyl, and pyrazolyl are unsubstituted or substituted with 1, 2, or 3 $C_1$-$C_4$-alkyl; and $R^u$ and $R^v$ are, at each occurrence, independently hydrogen, $C_1$-$C_4$-alkyl, or $C_1$-$C_4$-haloalkyl.

In another embodiment, the compound is a compound of Formula (I) or Formula (I-A) wherein:
$R^1$ is $G^1$-$L^1$-;
$R^2$ is hydrogen;
$L^1$ is —$C(O)NR^a$—, —$NR^aC(O)$—, or —O—;
$G^1$ is $C_1$-$C_8$-alkyl or $C_1$-$C_8$-haloalkyl;
$R^a$, at each occurrence, is hydrogen;
$L^2$ is —$S(O)_2$—;
$G^2$ is $Ar^2$;

$Ar^2$ is phenyl or pyridinyl; wherein $Ar^2$ is unsubstituted or substituted with 1 or 2 substituents selected from the group consisting of halogen, cyano, $C_1$-$C_4$-alkyl, halomethyl, methoxy, and halomethoxy.

In further embodiments of each of the above embodiments, $L^1$ is —$C(O)N(H)$—. In further embodiments of each of the above embodiments, $L^1$ is —$N(H)C(O)$—. In further embodiments of each of the above embodiments, $L^1$ is —O—.

(iv) Additional Embodiments $G^2$=$C_1$-$C_8$-Alkyl, $C_1$-$C_8$-Haloalkyl, or $C_1$-$C_8$-Cycloalkyl In one embodiment, the invention is directed to compounds of Formula (I) or Formula (I-A) wherein:
$R^1$ is $G^1$-$L^1$-;
$R^2$ is hydrogen;
$L^1$ is —$C(R^c)(R^d)$—, —$C(O)NR^a$—, —$NR^aC(O)$—, —$NR^a$—, or —O—;
$G^1$ is $C_1$-$C_8$-alkyl, $C_1$-$C_8$-haloalkyl, $Ar^1$, —$(CR^aR^b)$—$Ar^1$, —$CH(Ar^1)_2$, or —$Ar^1$-$G^a$;
$R^a$ and $R^b$, at each occurrence, are each hydrogen;
$R^c$ and $R^d$ are each independently hydrogen or hydroxy;
$Ar^1$ is, at each occurrence, independently selected from the group consisting of phenyl, thiazolyl, pyridinyl, pyrimidinyl, pyrazinyl, pyridazinyl, and benzoxazolyl; wherein $Ar^1$ is unsubstituted or substituted with 1, 2, 3, 4, or 5 substituents selected from the group consisting of halogen, cyano, $C_1$-$C_4$-alkyl, $C_2$-$C_4$-alkenyl, $C_1$-$C_4$-haloalkyl, and $C_1$-$C_4$-haloalkoxy;
$G^a$ is cyclopropyl, cyclobutyl, or imidazolyl;
$L^2$ is —$S(O)_2$—; and
$G^2$ is $C_1$-$C_8$-alkyl, $C_1$-$C_8$-haloalkyl, or $C_1$-$C_8$-cycloalkyl.

In another embodiment, the compound is a compound of Formula (I) or Formula (I-A) wherein:
$R^1$ is $G^1$-$L^1$-;
$R^2$ is hydrogen;
$L^1$ is —$C(O)NR^a$—, —$NR^aC(O)$—, or —O—;
$G^1$ is $Ar^1$ or —$Ar^1$-$G^a$;
$R^a$, at each occurrence, is hydrogen;
$Ar^1$ is, at each occurrence, independently phenyl, pyridinyl, or pyrazinyl; wherein $Ar^1$ is unsubstituted or substituted with 1, 2, or 3 substituents selected from the group consisting of halogen, $C_1$-$C_4$-alkyl, $C_1$-$C_4$-haloalkyl, and $C_1$-$C_4$-haloalkoxy;

$G^a$ is cyclopropyl or cyclobutyl;
$L^2$ is —$S(O)_2$—; and
$G^2$ is $C_1$-$C_8$-alkyl, $C_1$-$C_8$-haloalkyl, or $C_1$-$C_8$-cycloalkyl.

In another embodiment, the compound is a compound of Formula (I) wherein: $L^1$ is —$C(O)NR^a$—, —$NR^aC(O)$—, or —O—; $G^1$ is —$Ar^1$-$G^a$; $R^a$, at each occurrence, is hydrogen; $Ar^1$ is pyrazin-2-yl; $G^a$ is cyclopropyl; $L^2$ is —$S(O)_2$—; and $G^2$ is $C_1$-$C_8$-alkyl, $C_1$-$C_8$-haloalkyl, or $C_1$-$C_8$-cycloalkyl.

In further embodiments of each of the above embodiments, $L^1$ is —$C(O)N(H)$—. In further embodiments of each of the above embodiments, $L^1$ is —$N(H)C(O)$—. In further embodiments of each of the above embodiments, $L^1$ is —O—.

(v) Additional Embodiments $G^2$=$Ar^3$

In one embodiment, the invention is directed to compounds of Formula (I) or Formula (I-A) wherein:
$R^1$ is $G^1$-$L^1$-;
$R^2$ is hydrogen;
$L^1$ is —$C(R^c)(R^d)$—, —$C(O)NR^a$—, —$NR^aC(O)$—, —$NR^a$—, or —O—;
$G^1$ is $C_1$-$C_8$-alkyl, $C_1$-$C_8$-haloalkyl, $Ar^1$, —$(CR^aR^b)$—$Ar^1$, —$CH(Ar^1)_2$, or —$Ar^1$-$G^a$;
$R^a$ and $R^b$, at each occurrence, are each hydrogen;
$R^c$ and $R^d$ are each independently hydrogen or hydroxy;
$Ar^1$ is, at each occurrence, independently selected from the group consisting of phenyl, thiazolyl, pyridinyl, pyrimidinyl, pyrazinyl, pyridazinyl, and benzoxazolyl; wherein $Ar^1$ is unsubstituted or substituted with 1, 2, or 3 substituents selected from the group consisting of halogen, cyano, $C_1$-$C_4$-alkyl, $C_2$-$C_4$-alkenyl, $C_1$-$C_4$-haloalkyl, and $C_1$-$C_4$-haloalkoxy;
$G^a$ is cyclopropyl, cyclobutyl, or imidazolyl;
$L^2$ is —$S(O)_2$—; and
$G^2$ is $Ar^3$; and
$Ar^3$ is dihydroindenyl, dihydrobenzofuranyl, or hexahydropyrrolo[1,2-a]-pyrazinyl; wherein the dihydroindenyl, dihydrobenzofuranyl, and hexahydropyrrolo[1,2-a]-pyrazinyl are unsubstituted or, in the case of compounds of Formula I, substituted with 1, 2, or 3 $C_1$-$C_4$-alkyl or oxo.

In another embodiment, the compound is a compound of Formula (I) or Formula (I-A) wherein:
$R^1$ is $G^1$-$L^1$-;
$R^2$ is hydrogen;
$L^1$ is —$C(O)NR^a$—, —$NR^aC(O)$—, or —O—;
$G^1$ is $Ar^1$ or —$Ar^1$-$G^a$;
$R^a$, at each occurrence, is hydrogen;
$Ar^1$ is, at each occurrence, independently phenyl, pyridin-2-yl, or pyrazin-2-yl; wherein $Ar^1$ is unsubstituted or substituted with 1 or 2 substituents selected from the group consisting of halogen, $C_1$-$C_4$-alkyl, halomethyl, and halomethoxy;
$G^a$ is cyclopropyl;
$L^2$ is —$S(O)_2$—;
$G^2$ is $Ar^3$; and
$Ar^3$ is dihydroindenyl, dihydrobenzofuranyl, or hexahydropyrrolo[1,2-a]-pyrazinyl; wherein the dihydroindenyl, dihydrobenzofuranyl, and hexahydropyrrolo[1,2-a]-pyrazinyl are unsubstituted or, in the case of compounds of Formula I, substituted with 1, 2, or 3 $C_1$-$C_4$-alkyl or oxo.

In another embodiment, the compound is a compound of Formula (I) wherein:
$L^1$ is —$C(O)NR^a$—, —$NR^aC(O)$—, or —O—;
$G^1$ is —$Ar^1$-$G^a$;
$R^a$, at each occurrence, is hydrogen;

Ar¹ is pyrazin-2-yl;
$G^a$ is cyclopropyl;
$L^2$ is —S(O)₂—;
$G^2$ is $Ar^3$; and
$Ar^3$ is dihydroindenyl, dihydrobenzofuranyl, or hexahydropyrrolo[1,2-a]-pyrazinyl; wherein the dihydroindenyl, dihydrobenzofuranyl, and hexahydropyrrolo[1,2-a]-pyrazinyl are unsubstituted or, in the case of compounds of Formula I, substituted with 1, 2, or 3 $C_1$-$C_4$-alkyl or oxo.

In further embodiments of each of the above embodiments, $L^1$ is —C(O)N(H)—. In further embodiments of each of the above embodiments, $L^1$ is —N(H)C(O)—. In further embodiments of each of the above embodiments, $L^1$ is —O—.

(vi) Additional Embodiments $G^1$=-$Ar^1$-$G^a$ and $G^a$=Cyclopropyl

In one embodiment, the invention is directed to compounds of Formula (I) or Formula (I-A) wherein $G^1$ is —$Ar^1$-$G^a$; $Ar^1$ is $Ar^1$ pyridinyl or pyrazinyl; and $G^a$ is cyclopropyl.

In another embodiment, the compound is a compound of Formula (I) or Formula (I-A) wherein $G^1$ is —$Ar^1$-$G^a$; $Ar^1$ is pyrazinyl; and $G^a$ is cyclopropyl.

In another embodiment, the compound is a compound of Formula (I) or Formula (I-A) wherein $G^1$ is —$Ar^1$-$G^a$; and —$Ar^1$-$G^a$ is 5-cyclopropylpyrazin-2-yl.

In further embodiments of each of the above embodiments, $L^1$ is —C(O)N(H)—. In further embodiments of each of the above embodiments, $L^1$ is —N(H)C(O)—. In further embodiments of each of the above embodiments, $L^1$ is —O—.

(vii) Additional Embodiments $G^2$=$Ar^2$ and $Ar^2$=Phenyl or Pyridinyl

In one embodiment, the invention is directed to compounds of Formula (I) or Formula (I-A) wherein $G^2$ is $Ar^2$; and $Ar^2$ is phenyl or pyridinyl; wherein $Ar^2$ is unsubstituted or substituted with 1 or 2 substituents selected from the group consisting of halogen, cyano, $C_1$-$C_4$-alkyl, halomethyl, methoxy, and halomethoxy.

In another embodiment, the compound is a compound of Formula (I) or Formula (I-A) wherein $G^2$ is $Ar^2$; and $Ar^2$ is phenyl; wherein $Ar^2$ is unsubstituted or substituted with 1 or 2 substituents selected from the group consisting of halogen, cyano, $C_1$-$C_4$-alkyl, halomethyl, methoxy, and halomethoxy.

In another embodiment, the compound is a compound of Formula (I) or Formula (I-A) wherein $G^2$ is $Ar^2$; and $Ar^2$ is pyridinyl; wherein $Ar^2$ is unsubstituted or substituted with 1 or 2 substituents selected from the group consisting of halogen, cyano, $C_1$-$C_4$-alkyl, halomethyl, methoxy, and halomethoxy.

In further embodiments of each of the above embodiments, $L^1$ is —C(O)N(H)—. In further embodiments of each of the above embodiments, $L^1$ is —N(H)C(O)—. In further embodiments of each of the above embodiments, $L^1$ is —O—.

(viii) Additional Embodiments

Compounds of Formula (II)

In one embodiment, the invention is directed to compounds of Formula (II):

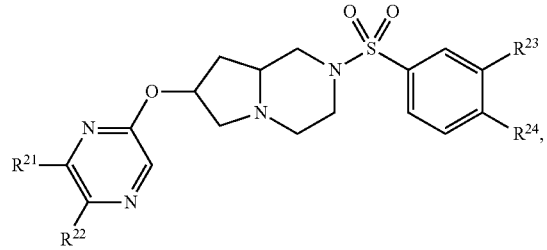

(II)

wherein:
$R^{21}$ and $R^{22}$ are independently selected from the group consisting of hydrogen, $C_{1-3}$ alkyl, and cyclopropyl; and
one of $R^{23}$ and $R^{24}$ is hydrogen, and the other of $R^{23}$ and $R^{24}$ is halomethyl.

In another embodiment, the invention is directed to compounds of Formula (II), wherein:
$R^{21}$ and $R^{22}$ are independently selected from the group consisting of hydrogen, $C_{1-3}$ alkyl, and cyclopropyl; and
one of $R^{23}$ and $R^{24}$ is hydrogen, and the other of $R^{23}$ and $R^{24}$ is trifluoromethyl.

In another embodiment, the invention is directed to compounds of Formula (II-A):

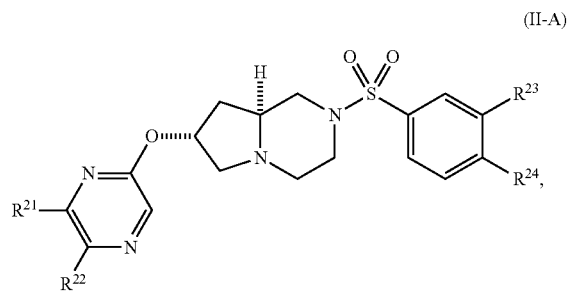

(II-A)

wherein:
$R^{21}$ and $R^{22}$ are independently selected from the group consisting of hydrogen, $C_{1-3}$ alkyl, and cyclopropyl; and
one of $R^{23}$ and $R^{24}$ is hydrogen, and the other of $R^{23}$ and $R^{24}$ is halomethyl.

In another embodiment, the compound is a compound of Formula (II-A) wherein: $R^{21}$ is hydrogen; $R^{22}$ is selected from the group consisting of hydrogen, $C_{1-3}$ alkyl, and cyclopropyl; $R^{23}$ is hydrogen; and $R^{24}$ is halomethyl.

In another embodiment, the compound is a compound of Formula (II-A) wherein: $R^{21}$ is hydrogen; $R^{22}$ is selected from the group consisting of hydrogen, $C_{1-3}$ alkyl, and cyclopropyl; $R^{23}$ is halomethyl; and $R^{24}$ is hydrogen.

In another embodiment, the compound is a compound of Formula (II-A) wherein: $R^{21}$ is selected from the group consisting of hydrogen, $C_{1-3}$ alkyl, and cyclopropyl; $R^{22}$ is hydrogen; $R^{23}$ is hydrogen; and $R^{24}$ is halomethyl.

In another embodiment, the compound is a compound of Formula (II-A) wherein: $R^{21}$ is selected from the group consisting of hydrogen, $C_{1-3}$ alkyl, and cyclopropyl; $R^{22}$ is hydrogen; $R^{23}$ is halomethyl; and $R^{24}$ is hydrogen.

In another embodiment, the compound is a compound of Formula (II-A) wherein: $R^{21}$ and $R^{22}$ are independently selected from the group consisting of hydrogen, isopropyl, and cyclopropyl; and one of $R^{23}$ and $R^{24}$ is hydrogen, and the other of $R^{23}$ and $R^{24}$ is halomethyl.

In another embodiment, the compound is a compound of Formula (II-A) wherein: $R^{21}$ is hydrogen; $R^{22}$ is selected from the group consisting of hydrogen, isopropyl, and cyclopropyl; and one of $R^{23}$ and $R^{24}$ is hydrogen, and the other of $R^{23}$ and $R^{24}$ is halomethyl.

In another embodiment, the compound is a compound of Formula (II-A) wherein: $R^{21}$ is $C_{1-3}$ alkyl; $R^{22}$ is selected from the group consisting of hydrogen, isopropyl, and cyclopropyl; and one of $R^{23}$ and $R^{24}$ is hydrogen, and the other of $R^{23}$ and $R^{24}$ is halomethyl.

In another embodiment, the compound is a compound of Formula (II-A), or a pharmaceutically acceptable salt thereof, wherein: $R^{21}$ is cyclopropyl; $R^{22}$ is selected from the group consisting of hydrogen, isopropyl, and cyclopropyl; and one of $R^{23}$ and $R^{24}$ is hydrogen, and the other of $R^{23}$ and $R^{24}$ is halomethyl.

In another embodiment, the compound is a compound of Formula (II-A) wherein: $R^{21}$ is selected from the group consisting of hydrogen isopropyl, and cyclopropyl; $R^{22}$ is hydrogen; and one of $R^{23}$ and $R^{24}$ is hydrogen, and the other of $R^{23}$ and $R^{24}$ is halomethyl.

In another embodiment, the compound is a compound of Formula (II-A) wherein: $R^{21}$ is selected from the group consisting of hydrogen, isopropyl, and cyclopropyl; $R^{22}$ is $C_{1-3}$ alkyl; and one of $R^{23}$ and $R^{24}$ is hydrogen, and the other of $R^{23}$ and $R^{24}$ is halomethyl.

In another embodiment, the compound is a compound of Formula (II-A) wherein: $R^{21}$ is selected from the group consisting of hydrogen, isopropyl, and cyclopropyl; $R^{22}$ is cyclopropyl; and one of $R^{23}$ and $R^{24}$ is hydrogen, and the other of $R^{23}$ and $R^{24}$ is halomethyl.

In another embodiment, the compound is a compound of Formula (II-A) wherein: $R^{21}$ and $R^{22}$ are independently selected from the group consisting of hydrogen, $C_{1-3}$ alkyl, and cyclopropyl; $R^{23}$ is hydrogen; and $R^{24}$ is halomethyl.

In another embodiment, the compound is a compound of Formula (II-A) wherein: $R^{21}$ and $R^{22}$ are independently selected from the group consisting of hydrogen, $C_{1-3}$ alkyl, and cyclopropyl; $R^{23}$ is halomethyl; and $R^{24}$ is hydrogen.

In another embodiment, the compound is a compound of Formula (II-A) wherein: one of $R^{21}$ and $R^{22}$ is hydrogen, and the other of $R^{21}$ and $R^{22}$ is selected from the group consisting of isopropyl and cyclopropyl; and one of $R^{23}$ and $R^{24}$ is hydrogen, and the other of $R^{23}$ and $R^{24}$ is trifluoromethyl.

In another embodiment, the compound is a compound of Formula (II-A) wherein: $R^{21}$ is hydrogen; $R^{22}$ is selected from the group consisting of hydrogen, isopropyl, and cyclopropyl; $R^{23}$ is hydrogen; and $R^{24}$ is trifluoromethyl.

In another embodiment, the compound is a compound of Formula (II-A) wherein: $R^{21}$ is hydrogen; $R^{22}$ is selected from the group consisting of isopropyl and cyclopropyl; $R^{23}$ is hydrogen; and $R^{24}$ is trifluoromethyl.

In another embodiment, the compound is a compound of Formula (II-A) wherein: $R^{21}$ is hydrogen; $R^{22}$ is selected from the group consisting of hydrogen, isopropyl, and cyclopropyl; $R^{23}$ is trifluoromethyl; and $R^{24}$ is hydrogen.

In another embodiment, the compound is a compound of Formula (II-A) wherein: $R^{21}$ is hydrogen; $R^{22}$ is selected from the group consisting of isopropyl and cyclopropyl; $R^{23}$ is trifluoromethyl; and $R^{24}$ is hydrogen.

In another embodiment, the compound is a compound of Formula (II-A) wherein: $R^{21}$ is selected from the group consisting of hydrogen, isopropyl and cyclopropyl; $R^{22}$ is hydrogen; $R^{23}$ is hydrogen; and $R^{24}$ is trifluoromethyl.

In another embodiment, the compound is a compound of Formula (II-A) wherein: $R^{21}$ is selected from the group con-sisting of isopropyl and cyclopropyl; $R^{22}$ is hydrogen; $R^{23}$ is hydrogen; and $R^{24}$ is trifluoromethyl.

In another embodiment, the compound is a compound of Formula (II-A) wherein: $R^{21}$ is selected from the group consisting of hydrogen, isopropyl, and cyclopropyl; $R^{22}$ is hydrogen; $R^{23}$ is trifluoromethyl; and $R^{24}$ is hydrogen.

In another embodiment, the compound is a compound of Formula (II-A) wherein: $R^{21}$ is selected from the group consisting of isopropyl and cyclopropyl; $R^{22}$ is hydrogen; $R^{23}$ is trifluoromethyl; and $R^{24}$ is hydrogen.

In another embodiment, the compound of Formula (II-A) is selected from the group consisting of:
(7R,8aS)-7-[(5-cyclopropylpyrazin-2-yl)oxy]-2-{[3-(trifluoromethyl)phenyl]-sulfonyl}octahydropyrrolo[1,2-a]pyrazine;
(7R,8aS)-7-(pyrazin-2-yloxy)-2-{[3-(trifluoromethyl)phenyl]sulfonyl}-octahydropyrrolo[1,2-a]pyrazine;
(7R,8aS)-7-[(6-cyclopropylpyrazin-2-yl)oxy]-2-{[3-(trifluoromethyl)phenyl]-sulfonyl}octahydropyrrolo[1,2-a]pyrazine;
(7R,8aS)-7-[(5-cyclopropylpyrazin-2-yl)oxy]-2-{[4-(trifluoromethyl)phenyl]-sulfonyl}octahydropyrrolo[1,2-a]pyrazine;
(7R,8aS)-7-[(6-cyclopropylpyrazin-2-yl)oxy]-2-{[4-(trifluoromethyl)phenyl]-sulfonyl}octahydropyrrolo[1,2-a]pyrazine; and
(7R,8aS)-7-[(5-isopropylpyrazin-2-yl)oxy]-2-{[4-(trifluoromethyl)phenyl]-sulfonyl}octahydropyrrolo[1,2-a]pyrazine.

(ix) Additional Embodiments

Z' or Z"=C(O)

In one embodiment, the invention is directed to compounds of Formula (I):

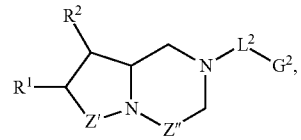

(I)

wherein:
one of $Z^1$ and $Z^2$ is $CH_2$ and the other of $Z^1$ and $Z^2$ is C(O);
$R^1$ is $G^1$-$L^1$-;
$L^1$ is —C($R^c$)($R^d$)—, —C(O)$NR^a$—, —$NR^a$C(O)—, —$NR^a$—, or —O—;
$G^1$ is $C_1$-$C_8$-alkyl, $C_1$-$C_8$-haloalkyl, $Ar^1$, —(C$R^a R^b$)—$Ar^1$, —CH($Ar^1$)$_2$, or —$Ar^1$-$G^a$;
$R^a$ and $R^b$, at each occurrence, are each hydrogen;
$R^c$ and $R^d$ are each independently hydrogen or hydroxy;
$Ar^1$ is, at each occurrence, independently selected from the group consisting of phenyl, thiazolyl, pyridinyl, pyrimidinyl, pyrazinyl, pyridazinyl, and benzoxazolyl; wherein $Ar^1$ is unsubstituted or substituted with 1, 2, 3, or 4 substituents selected from the group consisting of halogen, cyano, $C_1$-$C_4$-alkyl, $C_2$-$C_4$-alkenyl, $C_1$-$C_4$-haloalkyl, and $C_1$-$C_4$-haloalkoxy;
$G^a$ is cyclopropyl, cyclobutyl, or imidazolyl;
$L^2$ is —S(O)$_2$— or —S(O)$_2$CH$_2$—;
$G^2$ is $C_1$-$C_8$-alkyl, $C_1$-$C_8$-haloalkyl, $C_1$-$C_8$-cycloalkyl, $Ar^2$, or $Ar^3$;

$Ar^2$ is aryl or heteroaryl; wherein the $Ar^2$ aryl is selected from the group consisting of phenyl, naphthyl, and tetrahydronaphthylenyl; the $Ar^2$ heteroaryl is selected from the group consisting of furyl, thienyl, pyrazolyl, and pyridinyl; and $Ar^2$ is unsubstituted or substituted with 1, 2, 3, or 4 substituents selected from the group consisting of halogen, cyano, $C_1$-$C_4$-alkyl, $C_1$-$C_4$-haloalkyl, —$OR^u$, —$C(O)R^u$, —$C(O)R^u$, —$C(O)N(R^u)(R^v)$, and -$G^b$;

$G^b$ is selected from the group consisting of cyclopropyl, phenyl, pyrrolidinyl, piperidinyl, morpholinyl, and pyrazolyl, wherein the cyclopropyl, phenyl, pyrrolidinyl, piperidinyl, morpholinyl, and pyrazolyl are unsubstituted or substituted with 1, 2, or 3 $C_1$-$C_4$-alkyl;

$R^u$ and $R^v$ are, at each occurrence, independently hydrogen, $C_1$-$C_4$-alkyl, or $C_1$-$C_4$-haloalkyl;

$Ar^3$ is dihydroindenyl, dihydrobenzofuranyl, or hexahydropyrrolo[1,2-a]pyrazinyl; wherein the dihydroindenyl, dihydrobenzofuranyl, and hexahydropyrrolo[1,2-a]pyrazinyl are unsubstituted or substituted with 1, 2, or 3 $C_1$-$C_4$-alkyl or oxo.

In one embodiment of the above compounds of Formula (I), $Z^1$ is $CH_2$; $Z^2$ is $C(O)$; and $L^1$ is —O—. In another embodiment of the above compounds of Formula (I), $Z^1$ is $C(O)$; $Z^2$ is $CH_2$; and $L^1$ is —O—.

In one embodiment of the above compounds of Formula (I), —$Ar^1$-$G^a$ is 5-cyclopropylpyrazinyl.

In one embodiment of the above compounds of Formula (I), $L^2$ is —$S(O)_2$—; $G^2$ is $Ar^2$; and $Ar^2$ is trifluoromethylphenyl or trifluoromethylpyridinyl.

In another embodiment, the compound is a compound of Formula (I) wherein:
one of $Z^1$ and $Z^2$ is $CH_2$ and the other of $Z^1$ and $Z^2$ is $C(O)$;
$L^1$ is —O—;
$G^1$ is $Ar^1$ or —$Ar^1$-$G^a$;
$Ar^1$ is, at each occurrence, independently phenyl, pyridinyl, or pyrazinyl; wherein $Ar^1$ is unsubstituted or substituted with 1, 2, or 3 substituents selected from the group consisting of halogen, cyano, $C_1$-$C_4$-alkyl, $C_2$-$C_4$-alkenyl, $C_1$-$C_4$-haloalkyl, and $C_1$-$C_4$-haloalkoxy;
$G^a$ is cyclopropyl, cyclobutyl, or imidazolyl;
$L^2$ is —$S(O)_2$— or —$S(O)_2CH_2$—;
$G^2$ is $Ar^2$;
$Ar^2$ is phenyl or pyridinyl; wherein $Ar^2$ is unsubstituted or substituted with 1, 2, or 3 substituents selected from the group consisting of halogen, cyano, $C_1$-$C_4$-alkyl, $C_1$-$C_4$-haloalkyl, —$OR^u$, —$C(O)R^u$, —$C(O)R^u$, —$C(O)N(R^u)(R^v)$, and -$G^b$;
$G^b$ is selected from the group consisting of cyclopropyl, phenyl, pyrrolidinyl, piperidinyl, morpholinyl, and pyrazolyl; wherein the cyclopropyl, phenyl, pyrrolidinyl, piperidinyl, morpholinyl, and pyrazolyl are unsubstituted or substituted with 1, 2, or 3 $C_1$-$C_4$-alkyl; and
$R^u$ and $R^v$ are, at each occurrence, independently hydrogen, $C_1$-$C_4$-alkyl, or $C_1$-$C_4$-haloalkyl.

In another embodiment, the compound is a compound of Formula (I) wherein:
one of $Z^1$ and $Z^2$ is $CH_2$ and the other of $Z^1$ and $Z^2$ is $C(O)$;
$L^1$ is —O—;
$G^1$ is $Ar^1$ or —$Ar^1$-$G^a$;
$Ar^1$ is, at each occurrence, independently phenyl, pyridinyl, or pyrazinyl;
wherein $Ar^1$ is unsubstituted or substituted with 1, 2, or 3 substituents selected from the group consisting of halogen, $C_1$-$C_4$-alkyl, $C_1$-$C_4$-haloalkyl, and $C_1$-$C_4$-haloalkoxy;
$G^a$ is cyclopropyl or cyclobutyl;
$L^2$ is —$S(O)_2$—;
$G^2$ is $Ar^2$;

$Ar^2$ is phenyl or pyridinyl; wherein $Ar^2$ is unsubstituted or substituted with 1, 2, or 3 substituents selected from the group consisting of halogen, cyano, $C_1$-$C_4$-alkyl, $C_1$-$C_4$-haloalkyl, $C_1$-$C_4$-alkoxy, $C_1$-$C_4$-haloalkoxy, and -$G^b$; and $G^b$ is selected from the group consisting of cyclopropyl, phenyl, pyrrolidinyl, piperidinyl, morpholinyl, and pyrazolyl, wherein the cyclopropyl, phenyl, pyrrolidinyl, piperidinyl, morpholinyl, and pyrazolyl are unsubstituted or substituted with 1, 2, or 3 $C_1$-$C_4$-alkyl.

In another embodiment, the compound is a compound of Formula (I) wherein:
one of $Z^1$ and $Z^2$ is $CH_2$ and the other of $Z^1$ and $Z^2$ is $C(O)$;
$L^1$ is —$C(O)N(H)$—, —$N(H)C(O)$—, or —O—;
$G^1$ is $Ar^1$ or —$Ar^1$-$G^a$;
$Ar^1$ is, at each occurrence, independently phenyl, pyridin-2-yl, or pyrazin-2-yl; wherein $Ar^1$ is unsubstituted or substituted with 1 or 2 substituents selected from the group consisting of halogen, $C_1$-$C_4$-alkyl, halomethyl, and halomethoxy;
$G^a$ is cyclopropyl;
$L^2$ is —$S(O)_2$—;
$G^2$ is $Ar^2$; and
$Ar^2$ is phenyl or pyridinyl; wherein $Ar^2$ is unsubstituted or substituted with 1 or 2 substituents selected from the group consisting of halogen, cyano, $C_1$-$C_4$-alkyl, halomethyl, methoxy, and halomethoxy.

In another embodiment, the compound is a compound of Formula (I) wherein:
one of $Z^1$ and $Z^2$ is $CH_2$ and the other of $Z^1$ and $Z^2$ is $C(O)$;
$L^1$ is —O—;
$G^1$ is —$Ar^1$-$G^a$;
$Ar^1$ is pyrazin-2-yl;
$G^a$ is cyclopropyl; and
$Ar^2$ is phenyl or pyridinyl; wherein $Ar^2$ is substituted with 1 or 2 substituents selected from the group consisting of chloro, fluoro, trifluoromethyl, and trifluoromethoxy.

Specific embodiments of compounds contemplated as part of the invention include, but are not limited to:

4-fluoro-N-[(7S,8aS)-2-{[3-(trifluoromethyl)phenyl]sulfonyl}octahydropyrrolo[1,2-a]pyrazin-7-yl]benzamide;

4-fluoro-N-[(7S,8aS)-2-{[4-(trifluoromethyl)phenyl]sulfonyl}octahydropyrrolo[1,2-a]pyrazin-7-yl]benzamide;

N-[(7S,8aS)-2-{[2-chloro-4-(trifluoromethyl)phenyl]sulfonyl}octahydropyrrolo[1,2-a]pyrazin-7-yl]-4-fluorobenzamide;

N-[(7S,8aS)-2-{[2-chloro-5-(trifluoromethyl)phenyl]sulfonyl}-octahydropyrrolo[1,2-a]pyrazin-7-yl]-4-fluorobenzamide;

4-chloro-N-[(7S,8aS)-2-{[3-(trifluoromethyl)phenyl]sulfonyl}-octahydropyrrolo[1,2-a]pyrazin-7-yl]benzamide;

4-chloro-N-[(7S,8aS)-2-{[4-(trifluoromethyl)phenyl]sulfonyl}octahydropyrrolo[1,2-a]pyrazin-7-yl]benzamide;

4-chloro-N-[(7S,8aS)-2-{[2-chloro-4-(trifluoromethyl)phenyl]sulfonyl}-octahydropyrrolo[1,2-a]pyrazin-7-yl]benzamide;

4-chloro-N-[(7S,8aS)-2-{[4-fluoro-2-(trifluoromethyl)phenyl]sulfonyl}-octahydropyrrolo[1,2-a]pyrazin-7-yl]benzamide;

4-chloro-N-[(7S,8aS)-2-{[2-(trifluoromethyl)phenyl]sulfonyl}-octahydropyrrolo[1,2-a]pyrazin-7-yl]benzamide;

N-[(7S,8aS)-2-{[2-chloro-4-(trifluoromethyl)phenyl]sulfonyl}-octahydropyrrolo[1,2-a]pyrazin-7-yl]-2,4-difluorobenzamide;

2,4-difluoro-N-[(7S,8aS)-2-{[4-(trifluoromethyl)phenyl] sulfonyl}octahydropyrrolo[1,2-a]pyrazin-7-yl]benzamide;

N-{(7S,8aS)-2-[(2,4-dichlorophenyl)sulfonyl]octahydropyrrolo[1,2-a]pyrazin-7-yl}-2,4-difluorobenzamide;

N-[(7S,8aS)-2-{[2-chloro-4-(trifluoromethyl)phenyl] sulfonyl}octahydropyrrolo[1,2-a]pyrazin-7-yl]-3,4-difluorobenzamide;

3,4-difluoro-N-[(7S,8aS)-2-{[4-(trifluoromethyl)phenyl] sulfonyl}octahydropyrrolo[1,2-a]pyrazin-7-yl]benzamide;

(7S,8aS)-2-[(3,5-dichlorophenyl)sulfonyl]-N-[6-(trifluoromethyl)pyridin-2-yl]octahydropyrrolo[1,2-a]pyrazin-7-amine;

(7S,8aS)-2-{[2-chloro-4-(trifluoromethyl)phenyl]sulfonyl}-N-[6-(trifluoromethyl)-pyridin-2-yl]octahydropyrrolo[1,2-a]pyrazin-7-amine;

(7S,8aR)-7-[(5-cyclopropylpyrazin-2-yl)oxy]-2-{[3-(trifluoromethyl)phenyl]-sulfonyl}octahydropyrrolo[1,2-a]pyrazine;

(7R,8aS)-2-{[2-chloro-4-(trifluoromethyl)phenyl]sulfonyl}-7-{[6-(trifluoromethyl)pyridin-2-yl]oxy}octahydropyrrolo[1,2-a]pyrazine;

(7R,8aS)-7-[(5-cyclopropylpyrazin-2-yl)oxy]-2-{[3-(trifluoromethyl)phenyl]sulfonyl}octahydropyrrolo[1,2-a]pyrazine;

(7R,8aS)-7-(pyrazin-2-yloxy)-2-{[3-(trifluoromethyl)phenyl]-sulfonyl}-octahydropyrrolo[1,2-a]pyrazine;

(7R,8aS)-7-[(6-cyclopropylpyrazin-2-yl)oxy]-2-{[3-(trifluoromethyl)phenyl]-sulfonyl}octahydropyrrolo[1,2-a]pyrazine;

(7R,8aS)-7-[(5-cyclopropylpyrazin-2-yl)oxy]-2-{[4-(trifluoromethyl)phenyl]sulfonyl}octahydropyrrolo[1,2-a]pyrazine;

(7R,8aS)-7-[(6-cyclopropylpyrazin-2-yl)oxy]-2-{[4-(trifluoromethyl)phenyl]sulfonyl}octahydropyrrolo[1,2-a]pyrazine;

(7R,8aS)-7-[(5-cyclopropylpyrazin-2-yl)oxy]-2-{[2-(trifluoromethyl)phenyl]-sulfonyl}octahydropyrrolo[1,2-a]pyrazine;

(7R,8aS)-7-[(5-cyclopropylpyrazin-2-yl)oxy]-2-{[4-(trifluoromethoxy)-phenyl]-sulfonyl}octahydropyrrolo[1,2-a]pyrazine;

(7R,8aS)-7-[(5-cyclopropylpyrazin-2-yl)oxy]-2-{[4-(difluoromethoxy)-phenyl]-sulfonyl}octahydropyrrolo[1,2-a]pyrazine;

(7R,8aS)-7-[(5-cyclopropylpyrazin-2-yl)oxy]-2-{[3-(difluoromethoxy)-phenyl]-sulfonyl}octahydropyrrolo[1,2-a]pyrazine;

(7R,8aS)-7-[(5-cyclopropylpyrazin-2-yl)oxy]-2-[(2-fluorophenyl)-sulfonyl]octahydropyrrolo[1,2-a]pyrazine;

(7R,8aS)-7-[(5-cyclopropylpyrazin-2-yl)oxy]-2-{[2-fluoro-5-(trifluoromethyl)phenyl]-sulfonyl}octahydropyrrolo[1,2-a]pyrazine;

(7R,8aS)-7-[(5-cyclopropylpyrazin-2-yl)oxy]-2-(2-furylsulfonyl)-octahydropyrrolo-[1,2-a]pyrazine;

(7R,8aS)-7-[(5-cyclopropylpyrazin-2-yl)oxy]-2-{[3-(trifluoromethoxy)-phenyl]-sulfonyl}octahydropyrrolo[1,2-a]pyrazine;

(8R*,8aS*)-8-[(5-chloropyridin-2-yl)oxy]-2-{[3-(trifluoromethyl)phenyl]-sulfonyl}octahydropyrrolo[1,2-a]pyrazine;

(8R*,8aR*)-8-[(5-chloropyridin-2-yl)oxy]-2-[(3-(trifluoromethyl)phenyl]-sulfonyl}octahydropyrrolo[1,2-a]pyrazine;

(7S,8aS)—N-(diphenylmethyl)-2-{[3-(trifluoromethyl)phenyl]sulfonyl}-octahydropyrrolo[1,2-a]pyrazine-7-carboxamide;

(7S,8aS)—N-(diphenylmethyl)-2-{[4-(trifluoromethyl)phenyl]sulfonyl}-octahydropyrrolo[1,2-a]pyrazine-7-carboxamide;

(7S,8aS)—N-(diphenylmethyl)-2-{[4-fluoro-3-(trifluoromethyl)phenyl]-sulfonyl}-octahydropyrrolo[1,2-a]pyrazine-7-carboxamide;

(7S,8aS)—N-(4,4,4-trifluorobutyl)-2-{[3-(trifluoromethyl)phenyl]sulfonyl}-octahydropyrrolo[1,2-a]pyrazine-7-carboxamide;

(7S,8aS)-7-[4-(trifluoromethoxy)phenoxy]-2-{[3-(trifluoromethyl)-phenyl]sulfonyl}-octahydropyrrolo[1,2-a] pyrazine;

(7S,8aS)-7-(4-tert-butylphenoxy)-2-{[3-(trifluoromethyl)phenyl]sulfonyl}-octahydropyrrolo[1,2-a]pyrazine;

(7S,8aS)-7-[4-(1H-imidazol-1-yl)phenoxy]-2-{[3-(trifluoromethyl)-phenyl]sulfonyl}-octahydropyrrolo[1,2-a] pyrazine;

(7R,8aS)-7-[(6-cyclopropylpyridazin-3-yl)oxy]-2-{[3-(trifluoromethyl)-phenyl]sulfonyl}octahydropyrrolo[1,2-a] pyrazine;

(7R,8aS)-7-[(6-cyclopropylpyridazin-3-yl)oxy]-2-{[4-(trifluoromethyl)-phenyl]-sulfonyl}octahydropyrrolo[1,2-a] pyrazine;

(7R,8aS)-7-[(4-cyclopropylpyrimidin-2-yl)oxy]-2-{[3-(trifluoromethyl)-phenyl]-sulfonyl}octahydropyrrolo[1,2-a] pyrazine;

(7R,8aS)-7-[(4-cyclopropylpyrimidin-2-yl)oxy]-2-{[4-(trifluoromethyl)-phenyl]-sulfonyl}octahydropyrrolo[1,2-a] pyrazine;

1-(4-{[(7R,8aS)-7-[(5-cyclopropylpyrazin-2-yl)oxy] hexahydropyrrolo[1,2-a]pyrazin-2(1H)-yl] sulfonyl}phenyl)ethanone;

(7S,8aS)-7-[(5-cyclopropylpyrazin-2-yl)oxy]-2-{[3-(trifluoromethyl)phenyl]-sulfonyl}octahydropyrrolo[1,2-a]pyrazine;

(7S,8aS)-7-[(5-cyclopropylpyrazin-2-yl)oxy]-2-{[4-(trifluoromethyl)phenyl]-sulfonyl}octahydropyrrolo[1,2-a]pyrazine;

(7R,8aS)-7-[(5-cyclopropylpyrazin-2-yl)oxy]-2-{[3-fluoro-5-(trifluoromethyl)phenyl]-sulfonyl}octahydropyrrolo[1,2-a]pyrazine;

(7R,8aS)-7-[(5-cyclopropylpyrazin-2-yl)oxy]-2-{[4-fluoro-3-(trifluoromethyl)phenyl]-sulfonyl}octahydropyrrolo[1,2-a]pyrazine;

(7R,8aS)-2-[(3-tert-butylphenyl)sulfonyl]-7-[(5-cyclopropylpyrazin-2-yl)-oxy]-octahydropyrrolo[1,2-a]pyrazine;

(7S,8aR)-7-[(5-cyclopropylpyrazin-2-yl)oxy]-2-{[4-(trifluoromethyl)phenyl]-sulfonyl}octahydropyrrolo[1,2-a]pyrazine;

(7R,8aS)-2-[(3-chlorophenyl)sulfonyl]-7-[(5-cyclopropylpyrazin-2-yl)-oxy]octahydropyrrolo[1,2-a]pyrazine;

(7R,8aS)-2-[(4-tert-butylphenyl)sulfonyl]-7-[(5-cyclopropylpyrazin-2-yl)-oxy]-octahydropyrrolo[1,2-a]pyrazine;

(7R,8aS)-2-[(3-tert-butyl-4-methoxyphenyl)sulfonyl]-7-[(5-cyclopropylpyrazin-2-yl)oxy]octahydropyrrolo[1,2-a] pyrazine;

(7R,8aS)-2-[(6-tert-butylpyridin-2-yl)sulfonyl]-7-[(5-cyclopropylpyrazin-2-yl)oxy]octahydropyrrolo[1,2-a]pyrazine;

(7R,8aS)-7-[(5-cyclopropylpyrazin-2-yl)oxy]-2-{[6-(morpholin-4-yl)pyridin-2-yl]sulfonyl}octahydropyrrolo[1,2-a]pyrazine;

(7R,8aS)-7-[(5-cyclopropylpyrazin-2-yl)oxy]-2-{[6-(piperidin-1-yl)pyridin-2-yl]sulfonyl}octahydropyrrolo[1,2-a]pyrazine;

(7R,8aS)-7-[(5-cyclopropylpyrazin-2-yl)oxy]-2-{[6-(pyrrolidin-1-yl)pyridin-2-yl]sulfonyl}octahydropyrrolo[1,2-a]pyrazine;

(7R,8aS)-7-[(5-cyclopropylpyrazin-2-yl)oxy]-2-[(2,4-difluorophenyl)-sulfonyl]octahydropyrrolo[1,2-a]pyrazine;

(7R,8aS)-7-[(5-cyclopropylpyrazin-2-yl)oxy]-2-{[4-(trifluoromethyl)pyridin-2-yl]sulfonyl}octahydropyrrolo[1,2-a]pyrazine;

3-{[(7R,8aS)-7-[(5-cyclopropylpyrazin-2-yl)oxy]hexahydropyrrolo[1,2-a]-pyrazin-2(1H)-yl]sulfonyl}-5-(trifluoromethyl)benzonitrile;

4-{[(7R,8aS)-7-[(5-cyclopropylpyrazin-2-yl)oxy]hexahydropyrrolo[1,2-a]-pyrazin-2(1H)-yl]sulfonyl}-2-(trifluoromethyl)benzonitrile;

(7R,8aS)-7-[(5-cyclopropylpyrazin-2-yl)oxy]-2-{[6-(trifluoromethyl)pyridin-2-yl]sulfonyl}octahydropyrrolo[1,2-a]pyrazine;

(7R,8aS)-7-[(5-cyclopropylpyrazin-2-yl)oxy]-2-{[5-(trifluoromethyl)pyridin-2-yl]sulfonyl}octahydropyrrolo[1,2-a]pyrazine;

2-chloro-5-{[(7R,8aS)-7-[(5-cyclopropylpyrazin-2-yl)oxy]hexahydropyrrolo[1,2-a]pyrazin-2(1H)-yl]sulfonyl}benzonitrile;

(7R,8aS)-7-{[6-(trifluoromethyl)pyridin-3-yl]oxy}-2-{[6-(trifluoromethyl)-pyridin-2-yl]sulfonyl}octahydropyrrolo[1,2-a]pyrazine;

(7R,8aS)-7-[(5-cyclopropylpyrazin-2-yl)oxy]-2-{[6-(morpholin-4-yl)pyridin-3-yl]sulfonyl}octahydropyrrolo[1,2-a]pyrazine;

(7R,8aS)-2-[(5-tert-butyl-2-methoxyphenyl)sulfonyl]-7-[(5-cyclopropylpyrazin-2-yl)oxy]octahydropyrrolo[1,2-a]pyrazine;

(7R,8aS)-7-[(5-cyclopropylpyrazin-2-yl)oxy]-2-[(5-methyl-2-thienyl)-sulfonyl]-octahydropyrrolo[1,2-a]pyrazine;

(7R,8aS)-2-[(5-bromopyridin-3-yl)sulfonyl]-7-[(5-cyclopropylpyrazin-2-yl)oxy]-octahydropyrrolo[1,2-a]pyrazine;

(7R,8aS)-7-[(5-cyclopropylpyrazin-2-yl)oxy]-2-[(5-cyclopropylpyridin-3-yl)sulfonyl]-octahydropyrrolo[1,2-a]pyrazine;

(7R,8aS)-2-[(6-chloropyridin-3-yl)sulfonyl]-7-[(5-cyclopropylpyrazin-2-yl)oxy]-octahydropyrrolo[1,2-a]pyrazine;

5-{[(7S,8aS)-2-{[3-(trifluoromethyl)phenyl]sulfonyl}octahydropyrrolo[1,2-a]pyrazin-7-yl]oxy}-1,3-benzoxazole;

(7S,8aS)-2-{[3-(trifluoromethyl)phenyl]sulfonyl}-7-{[6-(trifluoromethyl)-pyridin-3-yl]oxy}octahydropyrrolo[1,2-a]pyrazine;

2-methyl-6-{[(7S,8aS)-2-{[3-(trifluoromethyl)phenyl]sulfonyl}-octahydropyrrolo[1,2-a]pyrazin-7-yl]oxy}-1,3-benzoxazole;

(7S,8aS)-7-(4-fluoro-3-methylphenoxy)-2-{[3-(trifluoromethyl)phenyl]-sulfonyl}-octahydropyrrolo[1,2-a]pyrazine;

(7R,8aS)-7-[(5-methylpyrazin-2-yl)oxy]-2-{[3-(trifluoromethyl)phenyl]-sulfonyl}-octahydropyrrolo[1,2-a]pyrazine;

(7R,8aS)-7-[(6-methylpyrazin-2-yl)oxy]-2-{[3-(trifluoromethyl)phenyl]-sulfonyl}-octahydropyrrolo[1,2-a]pyrazine;

(7R,8aS)-7-{[6-chloro-5-(trifluoromethyl)pyridin-3-yl]oxy}-2-{[3-(trifluoromethyl)phenyl]sulfonyl}octahydropyrrolo[1,2-a]pyrazine;

(7R,8aS)-2-{[3-(trifluoromethyl)phenyl]sulfonyl}-7-{[5-(trifluoromethyl)-pyridin-2-yl]oxy}octahydropyrrolo[1,2-a]pyrazine;

(7R,8aS)-2-{[3-(trifluoromethyl)phenyl]sulfonyl}-7-{[6-(trifluoromethyl)-pyridin-3-yl]oxy}octahydropyrrolo[1,2-a]pyrazine;

6-{[(7R,8aS)-2-{[3-(trifluoromethyl)phenyl]sulfonyl}octahydropyrrolo[1,2-a]pyrazin-7-yl]oxy}nicotinonitrile;

5-{[(7R,8aS)-2-{[3-(trifluoromethyl)phenyl]sulfonyl}octahydropyrrolo[1,2-a]pyrazin-7-yl]oxy}pyridine-2-carbonitrile;

(7R,8aS)-7-[(6-bromopyridin-3-yl)oxy]-2-{[3-(trifluoromethyl)phenyl]-sulfonyl}octahydropyaolo[1,2-a]pyrazine;

(7R,8aS)-7-[(6-cyclopropylpyridin-3-yl)oxy]-2-{[3-(trifluoromethyl)phenyl]-sulfonyl}octahydropyaolo[1,2-a]pyrazine;

(7R,8aS)-7-[(5-bromopyridin-2-yl)oxy]-2-{[3-(trifluoromethyl)phenyl]-sulfonyl}octahydropyaolo[1,2-a]pyrazine;

(7R,8aS)-7-[(5-cyclopropylpyridin-2-yl)oxy]-2-{[3-(trifluoromethyl)phenyl]-sulfonyl}octahydropyaolo[1,2-a]pyrazine;

(7R,8aS)-7-[(6-bromopyridin-2-yl)oxy]-2-{[3-(trifluoromethyl)phenyl]-sulfonyl}octahydropyaolo[1,2-a]pyrazine;

(7R,8aS)-7-[(6-cyclopropylpyridin-2-yl)oxy]-2-{[3-(trifluoromethyl)phenyl]-sulfonyl}octahydropyaolo[1,2-a]pyrazine;

(7R,8aS)-7-[(5-bromo-1,3-thiazol-2-yl)oxy]-2-{[3-(trifluoromethyl)phenyl]-sulfonyl}octahydropyaolo[1,2-a]pyrazine;

(7R,8aS)-7-[(5-cyclopropyl-1,3-thiazol-2-yl)oxy]-2-{[3-(trifluoromethyl)-phenyl]sulfonyl}octahydropyrrolo[1,2-a]pyrazine;

(7R,8aS)-7-[(5-cyclopropylpyrazin-2-yl)oxy]-2-[(2,3-difluorophenyl)-sulfonyl]octahydropyrrolo[1,2-a]pyrazine;

(7R,8aS)-7-[(5-cyclopropylpyrazin-2-yl)oxy]-2-{[3-fluoro-2-(piperidin-1-yl)-phenyl]sulfonyl}octahydropyrrolo[1,2-a]pyrazine;

(7R,8aS)-7-[(4-tert-butylbenzyl)oxy]-2-{[3-(trifluoromethyl)-phenyl]sulfonyl}octahydropyrrolo[1,2-a]pyrazine;

(7R,8aS)-7-{[4-(trifluoromethoxy)benzyl]oxy}-2-{[3-(trifluoromethyl)-phenyl]sulfonyl}octahydropyrrolo[1,2-a]pyrazine;

(7R,8aS)-7-{[4-(trifluoromethyl)benzyl]oxy}-2-{[3-(trifluoromethyl)phenyl]-sulfonyl}octahydropyrrolo[1,2-a]pyrazine;

(7R,8aS)-7-[(5-cyclopropylpyrazin-2-yl)oxy]-2-{[4-(1,1-difluoroethyl)-phenyl]sulfonyl}octahydropyrrolo[1,2-a]pyrazine;

(7R,8aS)-7-[(5-cyclobutylpyrazin-2-yl)oxy]-2-{[3-(trifluoromethyl)phenyl]-sulfonyl}octahydropyrrolo[1,2-a]pyrazine;

(7R,8aS)-7-[(5-cyclobutylpyrazin-2-yl)oxy]-2-{[4-(trifluoromethyl)phenyl]-sulfonyl}octahydropyrrolo[1,2-a]pyrazine;

(7R,8aS)-2-(biphenyl-3-ylsulfonyl)-7-[(5-cyclopropylpyrazin-2-yl)oxy]-octahydropyrrolo[1,2-a]pyrazine;

(7R,8aS)-7-[(5-cyclopropylpyrazin-2-yl)oxy]-2-[(4-isopropylphenyl)-sulfonyl]octahydropyrrolo[1,2-a]pyrazine;

(7R,8aS)-7-[(5-cyclopropylpyrazin-2-yl)oxy]-2-[(3-methoxyphenyl)sulfonyl]-octahydropyrrolo[1,2-a]pyrazine;

(7R,8aS)-7-[(5-cyclopropylpyrazin-2-yl)oxy]-2-{[4-methoxy-3-(trifluoromethyl)-phenyl]sulfonyl}octahydropyrrolo[1,2-a]pyrazine;

1-(3-{[(7R,8aS)-7-[(5-cyclopropylpyrazin-2-yl)oxy]hexahydropyrrolo[1,2-a]-pyrazin-2(1H)-yl]sulfonyl}phenyl)ethanone;

(7R,8aS)-7-[(5-cyclopropylpyrazin-2-yl)oxy]-2-{[3-(1,1-difluoroethyl)-phenyl]sulfonyl}octahydropyrrolo[1,2-a]pyrazine;

(7R,8aS)-7-[(5-cyclopropylpyrazin-2-yl)oxy]-2-[(4-methylphenyl)sulfonyl]-octahydropyrrolo[1,2-a]pyrazine;

(7R,8aR)-7-[(5-cyclopropylpyrazin-2-yl)oxy]-2-{[3-(trifluoromethyl)phenyl]-sulfonyl}octahydropyrrolo[1,2-a]pyrazine;

(7R,8aS)-2-{[3-bromo-5-(trifluoromethyl)phenyl]sulfonyl}-7-[(5-cyclopropylpyrazin-2-yl)oxy]octahydropyrrolo[1,2-a]pyrazine;

(7R,8aS)-2-[(3-tert-butylphenyl)sulfonyl]-7-{[5-(prop-1-en-2-yl)pyrazin-2-yl]oxy}-octahydropyrrolo[1,2-a]pyrazine;

(7R,8aS)-7-[(5-cyclopropylpyrazin-2-yl)oxy]-2-(2,3-dihydro-1-benzofuran-5-yl-sulfonyl)octahydropyrrolo[1,2-a]pyrazine;

(7R,8aS)-7-{[5-(prop-1-en-2-yl)pyrazin-2-yl]oxy}-2-{[3-(trifluoromethyl)-phenyl]-sulfonyl}octahydropyrrolo[1,2-a]pyrazine;

(7R,8aS)-7-{[5-(prop-1-en-2-yl)pyrazin-2-yl]oxy}-2-{[4-(trifluoromethyl)-phenyl]-sulfonyl}octahydropyrrolo[1,2-a]pyrazine;

(7R,8aS)-2-[(3-tert-butylphenyl)sulfonyl]-7-[(5-isopropylpyrazin-2-yl)oxy]-octahydropyrrolo[1,2-a]pyrazine;

(7R,8aS)-7-[(5-isopropylpyrazin-2-yl)oxy]-2-{[3-(trifluoromethyl)phenyl]-sulfonyl}octahydropyrrolo[1,2-a]pyrazine;

(7R,8aS)-7-[(5-cyclopropylpyrazin-2-yl)oxy]-2-[(3,4,5-trifluorophenyl)-sulfonyl]-octahydropyrrolo[1,2-a]pyrazine;

(7R,8aS)-2-[(3-chloro-2-fluorophenyl)sulfonyl]-7-[(5-cyclopropylpyrazin-2-yl)oxy]-octahydropyrrolo[1,2-a]pyrazine;

(7R,8aS)-7-[(5-cyclopropylpyrazin-2-yl)oxy]-2-[(2-fluoro-5-methylphenyl)-sulfonyl]-octahydropyrrolo[1,2-a]pyrazine;

(7R,8aS)-7-[(5-cyclopropylpyrazin-2-yl)oxy]-2-[(2,6-difluorophenyl)-sulfonyl]-octahydropyrrolo[1,2-a]pyrazine;

(7R,8aS)-7-[(5-cyclopropylpyrazin-2-yl)oxy]-2-[(2,3,4-trifluorophenyl)-sulfonyl]-octahydropyrrolo[1,2-a]pyrazine;

(7R,8aS)-2-[(5-chloro-2-fluorophenyl)sulfonyl]-7-[(5-cyclopropylpyrazin-2-yl)oxy]-octahydropyrrolo[1,2-a]pyrazine;

(7R,8aS)-7-[(5-cyclopropylpyrazin-2-yl)oxy]-2-[(3-fluoro-4-methylphenyl)-sulfonyl]-octahydropyrrolo[1,2-a]pyrazine;

(7R,8aS)-7-[(5-cyclopropylpyrazin-2-yl)oxy]-2-[(3,5-difluorophenyl)-sulfonyl]-octahydropyrrolo[1,2-a]pyrazine;

(7R,8aS)-7-[(5-cyclopropylpyrazin-2-yl)oxy]-2-[(3,5-dimethylphenyl)-sulfonyl]-octahydropyrrolo[1,2-a]pyrazine;

(7R,8aS)-2-{[4-bromo-3-(trifluoromethyl)phenyl]sulfonyl}-7-[(5-cyclopropylpyrazin-2-yl)oxy]octahydropyrrolo[1,2-a]pyrazine;

(7R,8aS)-7-[(5-cyclopropylpyrazin-2-yl)oxy]-2-[(4-fluoro-2-methylphenyl)-sulfonyl]-octahydropyrrolo[1,2-a]pyrazine;

(7R,8aS)-2-[(4-chloro-2-fluorophenyl)sulfonyl]-7-[(5-cyclopropylpyrazin-2-yl)oxy]octahydropyrrolo[1,2-a]pyrazine;

(7R,8aS)-7-[(5-cyclopropylpyrazin-2-yl)oxy]-2-[(2,5-difluorophenyl)-sulfonyl]-octahydropyrrolo[1,2-a]pyrazine;

(7R,8aS)-2-[(3-chloro-4-methylphenyl)sulfonyl]-7-[(5-cyclopropylpyrazin-2-yl)oxy]-octahydropyrrolo[1,2-a]pyrazine;

(7R,8aS)-2-[(4-bromo-3-methylphenyl)sulfonyl]-7-[(5-cyclopropylpyrazin-2-yl)oxy]octahydropyrrolo[1,2-a]pyrazine;

(7R,8aS)-2-{[2-bromo-5-(trifluoromethyl)phenyl]sulfonyl}-7-[(5-cyclopropylpyrazin-2-yl)oxy]octahydropyaolo[1,2-a]pyrazine;

(7R,8aS)-7-[(5-cyclopropylpyrazin-2-yl)oxy]-2-(mesitylsulfonyl)-octahydropyrrolo-[1,2-a]pyrazine;

(7R,8aS)-2-(biphenyl-4-ylsulfonyl)-7-[(5-cyclopropylpyrazin-2-yl)oxy]octahydropyrrolo[1,2-a]pyrazine;

(7R,8aS)-2-[(3-bromophenyl)sulfonyl]-7-[(5-cyclopropylpyrazin-2-yl)-oxy]octahydropyrrolo[1,2-a]pyrazine;

(7R,8aS)-2-{[2,5-bis(trifluoromethyl)phenyl]sulfonyl}-7-[(5-cyclopropylpyrazin-2-yl)oxy]octahydropyrrolo[1,2-a]pyrazine;

(7R,8aS)-7-[(5-cyclopropylpyrazin-2-yl)oxy]-2-[(5-fluoro-2-methylphenyl)-sulfonyl]-octahydropyrrolo[1,2-a]pyrazine;

(7R,8aS)-7-[(5-cyclopropylpyrazin-2-yl)oxy]-2-[(2,5-dichloro-3-thienyl)-sulfonyl]-octahydropyrrolo[1,2-a]pyrazine;

(7R,8aS)-2-[(5-chloro-2-thienyl)sulfonyl]-7-[(5-cyclopropylpyrazin-2-yl)-oxy]-octahydropyrrolo[1,2-a]pyrazine;

(7R,8aS)-2-[(4-chlorophenyl)sulfonyl]-7-[(5-cyclopropylpyrazin-2-yl)oxy]-octahydropyrrolo[1,2-a]pyrazine;

(7R,8aS)-7-[(5-cyclopropylpyrazin-2-yl)oxy]-2-[(4-fluorophenyl)sulfonyl]-octahydropyrrolo[1,2-a]pyrazine;

(7R,8aS)-7-[(5-cyclopropylpyrazin-2-yl)oxy]-2-[(3-fluorophenyl)sulfonyl]-octahydropyrrolo[1,2-a]pyrazine;

(7R,8aS)-7-[(5-cyclopropylpyrazin-2-yl)oxy]-2-[(3-methylphenyl)sulfonyl]-octahydropyrrolo[1,2-a]pyrazine;

2-{[(7R,8aS)-7-[(5-cyclopropylpyrazin-2-yl)oxy]hexahydropyrrolo[1,2-a]pyrazin-2(1H)-yl]sulfonyl}benzonitrile;

(7R,8aS)-7-[(5-cyclopropylpyrazin-2-yl)oxy]-2-[(4-methoxyphenyl)sulfonyl]-octahydropyrrolo[1,2-a]pyrazine;

(7R,8aS)-7-[(5-cyclopropylpyrazin-2-yl)oxy]-2-[(3,5-dichlorophenyl)-sulfonyl]-octahydropyrrolo[1,2-a]pyrazine;

(7R,8aS)-7-[(5-cyclopropylpyrazin-2-yl)oxy]-2-[(2,3-dichlorophenyl)-sulfonyl]-octahydropyrrolo[1,2-a]pyrazine;

(7R,8aS)-2-[(4-bromophenyl)sulfonyl]-7-[(5-cyclopropylpyrazin-2-yl)oxy]octahydropyrrolo[1,2-a]pyrazine;

(7R,8aS)-7-[(5-cyclopropylpyrazin-2-yl)oxy]-2-[(3,4-dichlorophenyl)-sulfonyl]-octahydropyrrolo[1,2-a]pyrazine;

(7R,8aS)-7-[(5-cyclopropylpyrazin-2-yl)oxy]-2-[(2,5-dichlorophenyl)-sulfonyl]-octahydropyrrolo[1,2-a]pyrazine;

4-{[(7R,8aS)-7-[(5-cyclopropylpyrazin-2-yl)oxy]hexahydropyrrolo[1,2-a]-pyrazin-2(1H)-yl]sulfonyl}benzonitrile;

(7R,8aS)-7-[(5-cyclopropylpyrazin-2-yl)oxy]-2-[(2,4-dichlorophenyl)-sulfonyl]-octahydropyrrolo[1,2-a]pyrazine;

(7R,8aS)-7-[(5-cyclopropylpyrazin-2-yl)oxy]-2-(1-naphthylsulfonyl)-octahydropyrrolo[1,2-a]pyrazine;

(7R,8aS)-7-[(5-cyclopropylpyrazin-2-yl)oxy]-2-(2-naphthylsulfonyl)-octahydropyrrolo[1,2-a]pyrazine;

(7R,8aS)-7-[(5-cyclopropylpyrazin-2-yl)oxy]-2-[(4-propylphenyl)-sulfonyl]octahydropyrrolo[1,2-a]pyrazine;

(7R,8aS)-7-[(5-cyclopropylpyrazin-2-yl)oxy]-2-[(2-methylphenyl)-sulfonyl]octahydropyrrolo[1,2-a]pyrazine;

3-{[(7R,8aS)-7-[(5-cyclopropylpyrazin-2-yl)oxy]hexahydropyrrolo[1,2-a]-pyrazin-2(1H)-yl]sulfonyl}benzonitrile;

(7R,8aS)-7-[(5-cyclopropylpyrazin-2-yl)oxy]-2-[(2,5-dimethoxyphenyl)-sulfonyl]-octahydropyrrolo[1,2-a]pyrazine;

(7R,8aS)-2-[(3-chloro-4-fluorophenyl)sulfonyl]-7-[(5-cyclopropylpyrazin-2-yl)oxy]-octahydropyrrolo[1,2-a]pyrazine;

(7R,8aS)-7-[(5-isopropylpyrazin-2-yl)oxy]-2-{[4-(trifluoromethyl)-phenyl]sulfonyl}-octahydropyrrolo[1,2-a]pyrazine;

5-{[(7R,8aS)-7-[(5-cyclopropylpyrazin-2-yl)oxy]hexahydropyrrolo[1,2-a]-pyrazin-2(1H)-yl]sulfonyl}-1-methyl-1,3-dihydro-2H-indol-2-one;

(7R,8aS)-7-[(5-cyclopropylpyrazin-2-yl)oxy]-2-[(5-ethyl-2-thienyl)sulfonyl-octahydropyrrolo[1,2-a]pyrazine;

(7R,8aS)-7-[(5-cyclopropylpyrazin-2-yl)oxy]-2-[(1-ethyl-1H-pyrazol-4-yl)-sulfonyl]-octahydropyrrolo[1,2-a]pyrazine;

(7R,8aS)-7-[(2-cyclopropylpyrimidin-4-yl)oxy]-2-{[3-(trifluoromethyl)-phenyl]sulfonyl}octahydropyrrolo[1,2-a]pyrazine;

(7R,8aS)-7-[(2-cyclopropylpyrimidin-4-yl)oxy]-2-{[4-(trifluoromethyl)-phenyl]sulfonyl}octahydropyrrolo[1,2-a]pyrazine;

(7R,8aS)-2-[(5-tert-butyl-2-methylphenyl)sulfonyl]-7-[(5-cyclopropylpyrazin-2-yl)oxy]octahydropyrrolo[1,2-a]pyrazine;

(7R,8aS)-7-[(5-cyclopropylpyrazin-2-yl)oxy]-2-(5,6,7,8-tetrahydronaphthalen-2-ylsulfonyl)octahydropyrrolo[1,2-a]pyrazine;

(7R,8aS)-7-[(5-cyclopropylpyrazin-2-yl)oxy]-2-[(4-methoxy-3-methylphenyl)-sulfonyl]octahydropyrrolo[1,2-a]pyrazine;

(7R,8aS)-2-{[4-chloro-3-(trifluoromethyl)phenyl]sulfonyl}-7-[(5-cyclopropylpyrazin-2-yl)oxy]octahydropyrrolo[1,2-a]pyrazine;

(7R,8aS)-2-{[2-chloro-5-(trifluoromethyl)phenyl]sulfonyl}-7-[(5-cyclopropylpyrazin-2-yl)oxy]octahydropyrrolo[1,2-a]pyrazine;

(7R,8aS)-7-[(5-cyclopropylpyrazin-2-yl)oxy]-2-{[2-methoxy-5-(trifluoromethyl)-phenyl]sulfonyl}octahydropyrrolo[1,2-a]pyrazine;

(7R,8aS)-7-[(5-cyclopropylpyrazin-2-yl)oxy]-2-(2,3-dihydro-1H-inden-5-yl-sulfonyl)octahydropyrrolo[1,2-a]pyrazine;

(7R,8aS)-7-[(5-cyclopropylpyrazin-2-yl)oxy]-2-[(3,4-dimethylphenyl)-sulfonyl]-octahydropyrrolo[1,2-a]pyrazine;

(7R,8aS)-7-[(5-cyclopropylpyrazin-2-yl)oxy]-2-{[3-(1-methyl-1H-pyrazol-5-yl)-phenyl]sulfonyl}octahydropyrrolo[1,2-a]pyrazine;

(7R,8aS)-7-[(5-cyclopropylpyrazin-2-yl)oxy]-2-{[2-methyl-6-(trifluoromethyl)-pyridin-3-yl]sulfonyl}octahydropyrrolo[1,2-a]pyrazine;

(7R,8aS)-7-[(5-cyclopropylpyrazin-2-yl)oxy]-2-{[2-(morpholin-4-yl)-5-(trifluoromethyl)phenyl]sulfonyl}octahydropyrrolo[1,2-a]pyrazine;

(7R,8aS)-7-[(5-cyclopropylpyrazin-2-yl)oxy]-2-{[3-(methoxymethyl)phenyl]-sulfonyl}octahydropyrrolo[1,2-a]pyrazine;

(7R,8aS)-7-[(5-cyclopropylpyrazin-2-yl)oxy]-2-{[4-methyl-3-(trifluoromethyl)-phenyl]sulfonyl}octahydropyrrolo[1,2-a]pyrazine;

5-{[(7R,8aS)-7-[(5-cyclopropylpyrazin-2-yl)oxy]hexahydropyrrolo[1,2-a]-pyrazin-2(1H)-yl]sulfonyl}-2-fluorobenzonitrile;

2-{[(7R,8aS)-7-[(5-cyclopropylpyrazin-2-yl)oxy]hexahydropyrrolo[1,2-a]-pyrazin-2(1H)-yl]sulfonyl}-4-methylbenzonitrile;

(7R,8aS)-7-[(5-cyclopropylpyrazin-2-yl)oxy]-2-[(1-isopropyl-3-methyl-1H-pyrazol-4-yl)sulfonyl]octahydropyrrolo[1,2-a]pyrazine;

(7R,8aS)-2-{[4-chloro-3-(trifluoromethyl)phenyl]sulfonyl}-7-ethoxy-octahydropyrrolo[1,2-a]pyrazine;

(7R,8aS)-7-[(5-cyclopropylpyrazin-2-yl)oxy]-2-[(3,3,3-trifluoropropyl)-sulfonyl]octahydropyrrolo[1,2-a]pyrazine;

(7R,8aS)-2-(butylsulfonyl)-7-[(5-cyclopropylpyrazin-2-yl)oxy]octahydropyrrolo[1,2-a]pyrazine;

(7R,8aS)-7-[(5-cyclopropylpyrazin-2-yl)oxy]-2-(2-thienylsulfonyl)octahydropyrrolo[1,2-a]pyrazine;

(7R,8aS)-2-(benzylsulfonyl)-7-[(5-cyclopropylpyrazin-2-yl)oxy]octahydropyrrolo[1,2-a]pyrazine;

(7R,8aS)-7-[(5-cyclopropylpyrazin-2-yl)oxy]-2-(isopropylsulfonyl)octahydropyrrolo[1,2-a]pyrazine;

(7R,8aS)-7-[(5-cyclopropylpyrazin-2-yl)oxy]-2-{[6-(trifluoromethyl)pyridin-3-yl]sulfonyl}octahydropyrrolo[1,2-a]pyrazine;

(7R,8aS)-7-[(5-cyclopropylpyrazin-2-yl)oxy]-2-[(4-methylpyridin-2-yl)-sulfonyl]-octahydropyrrolo[1,2-a]pyrazine;

(7R,8aS)-7-[(5-cyclopropylpyrazin-2-yl)oxy]-2-[(6-methoxypyridin-3-yl)-sulfonyl]-octahydropyrrolo[1,2-a]pyrazine;

3-{[(7R,8aS)-7-[(5-cyclopropylpyrazin-2-yl)oxy]hexahydropyrrolo[1,2-a]-pyrazin-2(1H)-yl]sulfonyl}-N,N-dimethylbenzamide;

(7R,8aS)-7-[(5-cyclopropylpyrazin-2-yl)oxy]-2-[(5-fluoropyridin-3-yl)-sulfonyl]-octahydropyrrolo[1,2-a]pyrazine;

5-{[(7R,8aS)-7-[(5-cyclopropylpyrazin-2-yl)oxy]hexahydropyrrolo[1,2-a]-pyrazin-2(1H)-yl]sulfonyl}-3,3-dimethyl-1,3-dihydro-2H-indol-2-one;

2-{[(7R,8aS)-7-[(5-cyclopropylpyrazin-2-yl)oxy]hexahydropyrrolo[1,2-a]-pyrazin-2(1H)-yl]sulfonyl}-4-(trifluoromethyl)benzonitrile;

(7R,8aS)-2-[(6-tert-butylpyridin-2-yl)sulfonyl]-7-{[5-(prop-1-en-2-yl)-pyrazin-2-yl]oxy}octahydropyrrolo[1,2-a]pyrazine;

(7R,8aS)-2-[(6-tert-butylpyridin-2-yl)sulfonyl]-7-[(5-isopropylpyrazin-2-yl)-oxy]octahydropyrrolo[1,2-a]pyrazine;

(7R,8aS)-7-{[5-(prop-1-en-2-yl)pyrazin-2-yl]oxy}-2-{[6-(trifluoromethyl)-pyridin-2-yl]sulfonyl}octahydropyrrolo[1,2-a]pyrazine;

(7R,8aS)-7-[(5-isopropylpyrazin-2-yl)oxy]-2-{[6-(trifluoromethyl)pyridin-2-yl]-sulfonyl}octahydropyrrolo[1,2-a]pyrazine;

(7R,8aS)-7-{[5-(1-methylcyclopropyl)pyrazin-2-yl]oxy}-2-{[3-(trifluoromethyl)-phenyl]sulfonyl}octahydropyrrolo[1,2-a]pyrazine;

7-[(5-cyclopropylpyrazin-2-yl)oxy]-2-{[3-(trifluoromethyl)phenyl]-sulfonyl}hexahydropyrrolo[1,2-a]pyrazin-6(2H)-one;

(7S,8aR)-7-[(5-cyclopropylpyrazin-2-yl)oxy]-2-{[3-(trifluoromethyl)phenyl]-sulfonyl}hexahydropyrrolo[1,2-a]pyrazin-6(2H)-one;

(7S,8aS)-7-[(5-cyclopropylpyrazin-2-yl)oxy]-2-{[3-(trifluoromethyl)phenyl]-sulfonyl}hexahydropyrrolo[1,2-a]pyrazin-6(2H)-one;

(7R,8aR)-7-[(5-cyclopropylpyrazin-2-yl)oxy]-2-{[3-(trifluoromethyl)phenyl]-sulfonyl}hexahydropyaolo[1,2-a]pyrazin-6(2H)-one;

(7R,8aS)-7-[(5-cyclopropylpyrazin-2-yl)oxy]-2-{[3-(trifluoromethyl)phenyl]-sulfonyl}hexahydropyrrolo[1,2-a]pyrazin-6(2H)-one;

7-[(5-cyclopropylpyrazin-2-yl)oxy]-2-{[4-(trifluoromethyl)phenyl]sulfonyl}-hexahydropyrrolo[1,2-a]pyrazin-6(2H)-one;

(8aS)-7-(3-fluorobenzyl)-2-{[4-(trifluoromethyl)phenyl]-sulfonyl}hexahydropyrrolo[1,2-a]pyrazin-6(2H)-one;

(8aS)-7-(3-fluorobenzyl)-2-{[3-(trifluoromethyl)phenyl]-sulfonyl}hexahydropyrrolo[1,2-a]pyrazin-6(2H)-one;

(7S,8aS)-7-[(3-fluorophenyl)(hydroxy)methyl]-2-{[3-(trifluoromethyl)-phenyl]-sulfonyl}hexahydropyrrolo[1,2-a]pyrazin-6(2H)-one;

(7R,8aS)-7-[(3-fluorophenyl)(hydroxy)methyl]-2-{[3-(trifluoromethyl)-phenyl]-sulfonyl}hexahydropyrrolo[1,2-a]pyrazin-6(2H)-one;

2-{[3-(trifluoromethyl)phenyl]sulfonyl}-7-{[5-(trifluoromethyl)pyridin-2-yl]-oxy}hexahydropyrrolo[1,2-a]pyrazin-6(2H)-one;

(7R,8aS)-7-[(5-cyclopropylpyrazin-2-yl)oxy]-2-{[3-(trifluoromethyl)benzyl]-sulfonyl}octahydropyaolo[1,2-a]pyrazine;

(7R,8aS)-7-[(5-cyclopropylpyrazin-2-yl)oxy]-2-[(4,4,4-trifluorobutyl)-sulfonyl]-octahydropyrrolo[1,2-a]pyrazine;

(7R,8aS)-7-[(5-cyclopropylpyrazin-2-yl)oxy]-2-{[3-(trifluoromethyl)phenyl]-sulfonyl}hexahydropyrrolo[1,2-a]pyrazin-4(1H)-one;

(7R,8aS)-7-[(5-cyclopropylpyrazin-2-yl)oxy]-2-{[4-(trifluoromethyl)phenyl]-sulfonyl}hexahydropyrrolo[1,2-a]pyrazin-4(1H)-one;

(8aR)-7-[(5-cyclopropylpyrazin-2-yl)oxy]-2-{[3-(trifluoromethyl)phenyl]-sulfonyl}hexahydropyrrolo[1,2-a]pyrazin-6(2H)-one;

(8aS)-7-[3-(trifluoromethyl)benzyl]-2-{[3-(trifluoromethyl)phenyl]sulfonyl}-hexahydropyrrolo[1,2-a]pyrazin-6(2H)-one;

(8aS)-7-[3-(trifluoromethyl)benzyl]-2-{[4-(trifluoromethyl)phenyl]sulfonyl}-hexahydropyrrolo[1,2-a]pyrazin-6(2H)-one;

3-{[[(8aS)-6-oxo-7-[3-(trifluoromethyl)benzyl]hexahydropyrrolo[1,2-a]pyrazin-2(1H)-yl]sulfonyl}benzonitrile;

(7R,8aS)-2-{[4-(trifluoromethyl)phenyl]sulfonyl}-7-{[5-(trifluoromethyl)-pyridin-2-yl]oxy}octahydropyrrolo[1,2-a]pyrazine;

3-{[(7R,8aS)-7-{[5-(trifluoromethyl)pyridin-2-yl]oxy}hexahydropyrrolo[1,2-a]pyrazin-2(1H)-yl]sulfonyl}benzonitrile;

(7R,8aS)-2-{[4-(trifluoromethyl)phenyl]sulfonyl}-7-{[6-(trifluoromethyl)-pyridin-3-yl]oxy}octahydropyrrolo[1,2-a]pyrazine;

3-{[(7R,8aS)-7-{[6-(trifluoromethyl)pyridin-3-yl]oxy}hexahydropyrrolo[1,2-a]pyrazin-2(1H)-yl]sulfonyl}benzonitrile;

(7R,8aS)-2-{[3-(trifluoromethyl)phenyl]sulfonyl}-7-{[6-(trifluoromethyl)-pyridin-2-yl]oxy}octahydropyrrolo[1,2-a]pyrazine; and (7R,8aS)-2-{[3-(trifluoromethyl)phenyl]sulfonyl}-7-{[5-(trifluoromethyl)-pyridin-3-yl]oxy}octahydropyrrolo[1,2-a]pyrazine.

Compounds of the present application can exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The stereoisomers of Formula (I) wherein $R^2$ is hydrogen include those depicted below as Formula (I-1), (I-2), (I-3), and (I-4):

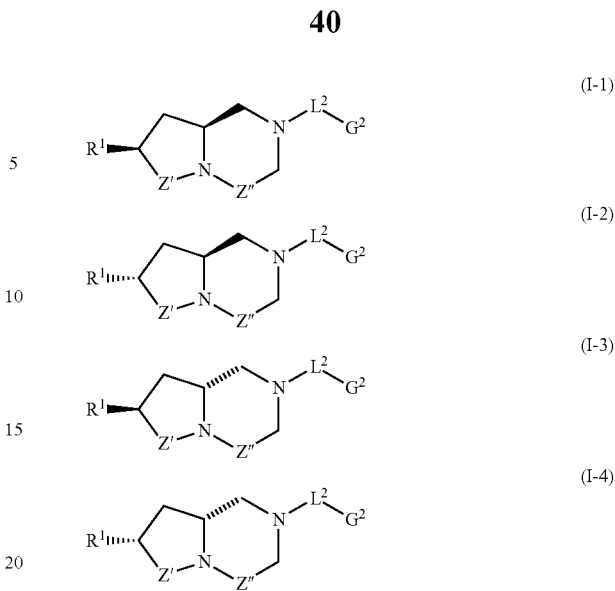

The stereoisomers of Formula (I) wherein $R^1$ is hydrogen include those depicted below as Formula (I-4), (I-5), (I-6), (I-7), and (I-8):

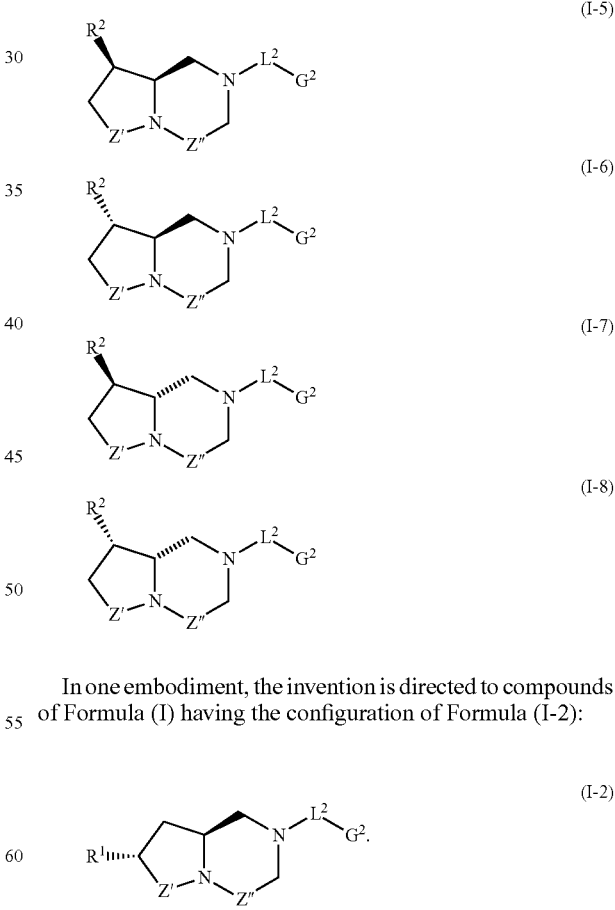

In one embodiment, the invention is directed to compounds of Formula (I) having the configuration of Formula (I-2):

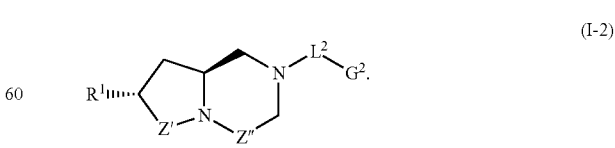

In another embodiment, the invention is directed to compounds of Formula (I) wherein Z' and Z" are $CH_2$, $R^2$ is hydrogen, and the compounds have the configuration of Formula (I-2A):

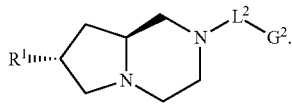

(I-2A)

On occasion, the relative stereochemistry of an enantiomeric pair is known, however, the absolute configuration is not known. In that circumstance, the relative stereochemistry descriptor terms "R*" and "S*" are used. The terms "R*" and "S*" used herein are defined in Eliel, E. L.; Wilen, S. H. Stereochemistry of Organic Compounds; John Wiley & Sons, Inc.: New York, 1994; pp 119-120 and 1206. In a particular enantiomeric pair, the relative descriptors are reversed to indicate that this pair of enantiomers is of unknown absolute stereochemistry.

The present application contemplates various stereoisomers and mixtures thereof and these are specifically included within the scope of this application. Stereoisomers include enantiomers and diastereomers, and mixtures of enantiomers or diastereomers. Individual stereoisomers of compounds of the present application can be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers can exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein can exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

The present invention also includes isotopically-labeled compounds, which are identical to those recited in Formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, fluorine, and chlorine, such as, but not limited to $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Compounds incorporating positron-emitting isotopes are useful in medical imaging and positron-emitting tomography (PET) studies for determining the distribution of receptors. Suitable positron-emitting isotopes that can be incorporated in compounds of Formula (I) are $^{11}C$, $^{13}N$, $^{15}O$, and $^{18}F$. Isotopically-labeled compounds of Formula (I) can generally be prepared by conventional techniques known to those skilled in the art or by processes analogous to those described in the accompanying Examples using appropriate isotopically-labeled reagent in place of non-isotopically-labeled reagent.

C. BIOLOGICAL DATA

Abbreviations which have been used in the descriptions of Biological Data that follow are: EDTA for ethylenediaminetetraacetic acid; FBS for fetal bovine serum; FLIPR for fluorometric imaging plate reader; HBSS for Hank's balanced salt solution; HEPES for 4-(2-hydroxyethyl)-1-piperazineethanesulfonic acid; i.p. for intraperitoneal; MEM for minimum essential medium; MEM NEAA for minimum essential medium non-essential amino acid; p.o. for per orem (by mouth).

(i) In Vitro Assessment of Calcium Channel Activity Using FLIPR

IMR32 cells endogenously expressing human $Ca_v2.2$ were assayed for $Ca^{2+}$ influx using a no-wash calcium indicator dye (Calcium 4 dye: Molecular Probes) and FLIPR technology (Lubin, M L; et al. Assay and Drug Development Technologies, 2006, 4(6), 689-694). The IMR32 cells were maintained in MEM media containing 10% (v/v) FBS, 1% (v/v) antibiotic/antimitotic, 1% (v/v) sodium pyruvate and 1% (v/v) MEM NEAA. Following dissociation in 0.05% (v/v) trypsin/EDTA, cells were seeded into black 1×96-well plates (Corning Cellbind) at a density of $1-1.2\times10^5$ cells/well and incubated in the maintenance media above for 48 hours at 37° C. Immediately prior to performing the assay the media was removed and cells were loaded for 1.5 hours with 1× Calcium 4 dye prepared in HBSS (137 mM NaCl, 5.4 mM KCl, 0.25 mM $Na_2HPO_4$, 0.44 mM $KH_2PO_4$, 1.3 mM $CaCl_2$, 1 mM $MgSO_4$, 4.2 mM $NaHCO_3$) containing HEPES pH 7.4 at room temperature. After dye loading and a subsequent 60 minute pre-incubation with compounds (full log dilutions from 10 µM to 0.1 nM) in the presence of 1.3 mM $CaCl_2$ and 2 µM nifedipine to block endogenous L-type channels, the external $Ca^{2+}$ concentration was increased to 5 mM $CaCl_2$ and the cells concomitantly depolarized with 80 mM KCl to assay channel activity. To determine the $IC_{50}$ values, the percent inhibition of the compound at each concentration was determined relative to the activity in the absence of inhibitor, and data was fitted using non-linear regression sigmoidal dose response curve analysis with GraphPad Prism®. Unless otherwise indicated (*), the reported values are average values from at least two runs (i.e., n≥2).

| Example | $IC_{50}$ (µM) |
| --- | --- |
| 1 | 1.15 |
| 2 | 1.73 |
| 3 | 1.01 |
| 4 | 3.83 |
| 5 | 0.75 |
| 6 | 1.60 |
| 7 | 1.75 |
| 8 | 3.56 |

| Example | IC$_{50}$ (μM) |
|---|---|
| 9 | 5.12 |
| 19 | 1.83 |
| 11 | 2.41 |
| 12 | 2.53 |
| 13 | 0.95 |
| 14 | 1.93 |
| 15 | 1.86 |
| 16 | 0.55 |
| 18 | 0.53 |
| 20 | 1.56 |
| 21 | 0.49 |
| 22 | 2.98 |
| 23 | 0.79 |
| 25 | 1.33 |
| 26 | 1.36 |
| 27 | 1.63 |
| 28 | 1.15 |
| 29 | 1.46 |
| 30 | 0.75 |
| 31 | 2.31 |
| 32 | 1.28 |
| 33 | 6.33 |
| 34 | 0.58 |
| 35 | 0.85 |
| 36 | 0.85 |
| 37 | 0.92 |
| 38 | 1.02 |
| 39 | 1.89 |
| 40 | 1.40 |
| 41 | 0.72 |
| 42 | 1.21 |
| 43 | 1.09 |
| 44 | 1.30 |
| 45 | 3.04 |
| 46 | 1.23 |
| 47 | 2.17 |
| 48 | 9.66 |
| 49 | 0.28 |
| 50 | 1.57 |
| 51 | 1.39 |
| 52 | 0.51 |
| 53 | 0.18 |
| 54 | 1.46 |
| 55 | 1.14 |
| 56 | 2.90 |
| 57 | 1.83 |
| 58 | 0.25 |
| 59 | 1.62 |
| 60 | 0.48 |
| 61 | 1.04 |
| 62 | 1.38* |
| 63 | 1.38 |
| 64 | 0.81 |
| 65 | 1.65 |
| 66 | 0.46 |
| 67 | 1.80 |
| 68 | 1.04 |
| 69 | 0.46 |
| 70 | 6.97 |
| 71 | 2.35 |
| 72 | 3.76* |
| 73 | 4.68 |
| 74 | 4.53 |
| 75 | 19.40 |
| 76 | 0.81 |
| 77 | 0.33 |
| 78 | 1.31 |
| 79 | 1.12 |
| 80 | 2.99 |
| 81 | 3.18 |
| 82 | 0.75 |
| 83 | 1.22 |
| 84 | 0.40 |
| 85 | 0.96 |
| 86 | 2.95 |
| 87 | 1.12 |
| 88 | 1.10 |
| 89 | 1.13 |
| 90 | 0.72 |
| 91 | 2.69 |
| 92 | 2.38 |
| 93 | 1.57 |
| 94 | 1.44 |
| 95 | 2.54 |
| 96 | 0.78 |
| 97 | 1.85 |
| 98 | 1.04 |
| 99 | 1.14 |
| 100 | 3.00 |
| 101 | 0.93 |
| 102 | 1.90 |
| 103 | 2.29 |
| 104 | 1.66 |
| 105 | 3.99 |
| 106 | 1.06 |
| 108 | 4.36 |
| 109 | 1.61 |
| 110 | 4.90* |
| 111 | 2.90 |
| 112 | 5.89 |
| 113 | 0.94 |
| 114 | 6.81 |
| 115 | 1.96 |
| 116 | 2.57 |
| 117 | 0.47 |
| 118 | 0.49 |
| 119 | 3.15 |
| 120 | 0.72 |
| 121 | 1.55 |
| 122 | 3.14 |
| 123 | 3.13* |
| 124 | 3.05* |
| 125 | 1.51 |
| 126 | 3.46* |
| 127 | 1.19* |
| 128 | 4.14 |
| 129 | 0.89 |
| 130 | 1.30 |
| 131 | 3.94 |
| 132 | 2.40* |
| 133 | 1.93* |
| 134 | 11.10* |
| 135 | 1.75* |
| 136 | 0.99 |
| 137 | 0.91 |
| 138 | 0.99 |
| 139 | 1.32 |
| 140 | >30 |
| 141 | 1.99* |
| 142 | 3.03* |
| 143 | 2.84 |
| 144 | 3.85* |
| 145 | 3.12* |
| 146 | 4.35 |
| 147 | 6.15* |
| 148 | 1.75* |
| 149 | 0.43 |
| 150 | 1.41 |
| 151 | 1.34 |
| 152 | 1.15 |
| 153 | 5.50* |
| 154 | 1.26* |
| 155 | 1.04 |
| 156 | 1.91 |
| 157 | 1.36 |
| 158 | 2.58* |
| 159 | 4.68* |
| 160 | 7.08* |
| 161 | 1.71 |
| 162 | 1.29 |
| 163 | 16.67 |
| 164 | 1.91 |
| 165 | 16.42 |
| 166 | 1.12 |
| 167 | 4.37 |
| 168 | 0.74 |

-continued

| Example | IC$_{50}$ (μM) |
|---|---|
| 169 | 1.14 |
| 170 | 2.64 |
| 171 | 5.74 |
| 172 | 1.21 |
| 173 | >30 |
| 174 | 1.52 |
| 175 | 1.33 |
| 176 | 1.33 |
| 177 | 0.95 |
| 178 | 3.02 |
| 179 | 1.64 |
| 180 | 0.50 |
| 181 | >30 |
| 182 | 1.64 |
| 183 | 4.30 |
| 188 | >30 |
| 189 | >30 |
| 191 | ND |
| 192 | ND |
| 193 | ND |
| 194 | ND |
| 195 | ND |
| 196 | ND |
| 197 | ND |
| 198 | ND |
| 199 | ND |
| 200 | ND |
| 201 | 0.76 |
| 202 | ND |
| 203 | 0.13 |
| 204 | 0.38 |
| 205 | 0.28 |
| 206 | 1.52 |
| 207 | 0.88 |
| 208 | 1.56 |
| 209 | 0.61 |
| 210 | 1.66 |
| 211 | 1.56 |
| 212 | 10.69 |
| 213 | 1.22 |
| 214 | 0.44 |
| 215 | 1.11 |
| 216 | 1.66 |
| 217 | 0.78 |
| 218 | 16 |
| 219 | >30 |
| 220 | 0.66 |
| 221 | >30 |
| 222 | 1.25 |
| 223 | 0.127 |
| 224 | 0.353 |
| 225 | 0.625 |
| 226 | 2.28 |
| 227 | 2.62 |
| 228 | 0.654 |
| 229 | 4.43 |
| 230 | 0.629 |
| 231 | 0.383 |

ND = not determined (ii) In Vivo Assessment of Analgesic Effect Against Neuropathic Pain (Bennett Model)

Animals were prepared for testing, by use of a surgical procedure that induces neuropathic pain in one paw. IACUC guidelines for rodent survival surgery were followed. All surgical procedures were conducted on a clean, uncluttered surgical station. The area was wiped with a 70% ethanol solution before and after use. All instruments were sterilized by either autoclave or chemical sterilant (such as 2% glutaraldehyde>10 hours). Surgeons wore sterile gloves (for the initial procedure), clean lab coat or scrubs, hairnet or cap, and a half-mask respirator (when not working under a hood). Surgeons thoroughly washed their hands prior to donning sterile gloves. Gloves were disinfected in-between animals by cleansing with povidone iodine, chlorhexidine or 70% alcohol for at least 30 seconds. If multiple surgeries were performed, the instruments were cleaned and sterilized between procedures with hot glass beads (>10 seconds). To prevent thermal or chemical burns, the instruments were cooled by rinsing in sterile saline before use.

Male, Sprague Dawley® rats, 175-200 g were used for surgeries. To minimize post-operative dehydration/maintain blood volume during the surgery, warmed sterile saline or Lactate Ringers solution at 10-15 mL/kg was administered subcutaneously immediately before or after surgery. This facilitated better renal function and presumably anesthesia product excretion post surgery. For all surgical procedures, anesthesia was induced with 4-5% isoflurane. Anesthesia was maintained during surgery with 1-3% isoflurane. Following induction, the surgical site was carefully shaved and the exposed area was aseptically prepared with povidone-iodine scrub solution and 70% ethanol 2-3 times.

Chronic constriction injury (CCI), a model of neuropathic pain, was produced by following the method of Bennett and Xie (Bennett, G, et al. Pain, 1988, 33, 87-107). After site sterilization and anesthetic procedures outline above were completed, a 1.5 cm incision was made at the mid-thigh level to expose the biceps femoris and gluteous superficialis (right side), which were then separated by blunt dissection. The common sciatic nerve was exposed, isolated, and loosely ligated by four 5-0 chromic gut ligatures with <1 mm spacing between each. The surgical site was closed in layers—muscle was closed with 6.0 absorbable sutures, and the skin closed with wound clips. Animals were allowed to recover on a warming plate and were returned to their home cages when fully ambulatory. Animals were not be used for testing until at least 10 days following surgery.

To measure mechanical sensitivity, tactile allodynia was measured using calibrated von Frey filaments (Stoelting, Wood Dale, Ill.) as described by Chaplan et al. (Chaplan S., et al. J of Neuroscience Methods 1994, 53, 55-63). Filament strengths used were: 0.4, 0.6, 1.0, 2, 4, 6, 8, and 15 g. Rats were placed into inverted individual plastic containers (20× 12.5×20 cm) on top of a suspended wire mesh grid, and acclimated to the test chambers for at least 20 minutes. Filaments were applied perpendicular to the mid-plantar paw surface with enough force to cause slight buckling and held in place for 6-8 seconds. Positive responses included an abrupt withdrawal of the paw from the stimulus or flinching behavior immediately following removal of the stimulus. The maximum force applied was 15 g. The 50% paw withdrawal threshold (PWT) was calculated in grams (g) using the up-down method of Dixon (Dixon W. Ann Rev Pharmacol Toxicol 1980, 20, 441-462). Only rats exhibiting increased mechanical sensitivity were used (threshold responses below 5 g). All compounds were orally administered in at a dose of 10 mg/kg in 10% dimethyl sulfoxide/polyethylene glycol at a volume of 2.0 mL/kg, and mechanical allodynia was determined 60 minutes following compound administration. Data were reported as log g values and the percentage of maximum possible effect (% MPE) was calculated using log g values with the formula:

% MPE=(log [observed PWT in grams]−log [mean PWT vehicle])/(log [15]−log [mean PWT vehicle])*100

All statistical procedures were run on log g values.

| Example | % MPE |
|---------|-------|
| 21 | 43 |
| 25 | 42 |
| 44 | 40 |
| 49 | 19 |
| 50 | 25 |
| 51 | 32 |
| 52 | 38 |
| 54 | 34 |
| 62 | 29 |
| 64 | 37 |
| 67 | 5 |
| 86 | 0 |

The ability of the compounds of the present invention to reduce nociceptive pain can be evaluated using conventional in vivo nociceptive pain models known in the art. Such models include, for example, those described in Pain (1996) 64:493-501; and Pain (2001) 93:69-76.

The ability of the compounds of the present invention to reduce inflammatory pain can be evaluated using conventional in vivo nociceptive pain models known in the art. Such models include, for example, those described in Pain (1999) 80:67-82.

D. METHODS OF USING THE COMPOUNDS

One embodiment of the present invention provides a method of treating pain in a subject in need thereof. The method comprises administering to the subject, including a mammal, such as a human, a therapeutically suitable amount of a compound of Formula (I), or a pharmaceutically acceptable salt thereof. Conditions related to pain include, for example, acute pain, chronic pain, neuropathic pain, nociceptive pain, allodynia, inflammatory pain, inflammatory hyperalgesia, post herpetic neuralgia, post-operative pain, post-stroke pain, neuropathies, neuralgia, diabetic neuropathy, HIV-related neuropathy, nerve injury, rheumatoid arthritic pain, osteoarthritic pain, burns, back pain, eye pain, visceral pain, cancer pain, dental pain, headache, migraine, carpal tunnel syndrome, fibromyalgia, neuritis, sciatica, pelvic hypersensitivity, pelvic pain, menstrual pain. In one embodiment, the condition related to pain is selected from the group consisting of acute pain, chronic pain, neuropathic pain, inflammatory pain, visceral pain, cancer pain, osteoarthritis pain, allodynia, fibromyalgia, sciatica, back pain, and headache pain including migraine, or combinations thereof. Preferably, the method comprises administering to the mammal a therapeutically effective amount of any of the compounds as described herein, or a pharmaceutically acceptable salt thereof.

Pain generally can be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain include neuropathic pain (e.g. painful diabetic neuropathy, postherpetic neuralgia), carpal tunnel syndrome, back pain, headache, cancer pain, arthritic pain and chronic post-surgical pain. In one embodiment, the condition related to pain is chronic pain. In another embodiment, the condition related to pain is acute pain.

Pain also can be divided into a number of different subtypes according to differing pathophysiology, including neuropathic, nociceptive, and inflammatory pain. Some types of pain have multiple etiologies and can be classified in more than one area, e.g., back pain and cancer pain have both nociceptive and neuropathic components. In one embodiment, the condition related to pain is selected from the subtypes of neuropathic pain, nociceptive pain, and inflammatory pain.

In another embodiment, the condition related to pain is neuropathic pain. Neuropathic pain generally is defined as pain initiated or caused by a primary lesion or dysfunction in the nervous system and can result, for example, from trauma or disease. The term neuropathic pain encompasses many conditions with diverse etiologies including peripheral neuropathy, diabetic neuropathy, post-herpetic neuralgia, trigeminal neuralgia, back pain, cancer neuropathy, HIV-neuropathy, phantom limb pain, carpal tunnel syndrome, central post-stroke pain, and pain associated with chronic alcoholism, hypothyroidism, uremia, multiple sclerosis, spinal cord injury, Parkinson's disease, epilepsy and vitamin deficiency.

In another embodiment, the condition related to pain is nociceptive pain. Nociceptive pain is induced by tissue injury or by intense stimuli with the potential to cause injury. When a substantial injury occurs to body tissue through trauma or disease, the characteristics of nociceptor activation are altered and there is sensitization in the periphery leading to a heightened sensation of pain in the subject. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain can be chronic pain such as tumor related pain (e.g., bone pain, headache, facial pain or visceral pain) or pain associated with cancer therapy (e.g., post-chemotherapy syndrome, chronic postsurgical pain syndrome or post radiation syndrome). Cancer pain can also occur in response to chemotherapy, immunotherapy, hormonal therapy or radiotherapy. Back pain can be due to herniated or ruptured intervertebral discs or abnormalities of the lumber facet joints, sacroiliac joints, paraspinal muscles or the posterior longitudinal ligament.

In another embodiment, the condition related to pain is inflammatory pain. A common type of inflammatory pain is arthritic pain arising from rheumatoid disease (such as ankylosing spondylitis) or symptomatic osteoarthritis or degenerative joint disease. Another type of inflammatory pain is visceral pain. Visceral pain is pain associated with the viscera, which encompass the organs of the abdominal cavity including the sex organs, spleen and part of the digestive system. Pain associated with the viscera can be divided into digestive visceral pain and non-digestive visceral pain. Commonly encountered gastrointestinal disorders that cause pain include functional bowel disorder and inflammatory bowel disease. These gastrointestinal disorders include a wide range of disease states that are currently only moderately controlled, including, with respect to functional bowel disorder, gastroesophageal reflux, dyspepsia, irritable bowel syndrome, and functional abdominal pain syndrome, and, in respect of inflammatory bowel disease, Crohn's disease, ileitis and ulcerative colitis, all of which regularly produce visceral pain. Other types of visceral pain include the pain associated with dysmenorrhea, cystitis and pancreatitis and pelvic pain.

In another embodiment, the condition related to pain results from a musculo-skeletal condition such as myalgia, fibromyalgia, spondylitis, sero-negative (non-rheumatoid)

arthropathies, non-articular rheumatism, dystrophinopathy, glycogenolysis, polymyositis and pyomyositis; heart and vascular pain, including pain caused by angina, myocardical infarction, mitral stenosis, pericarditis, Raynaud's phenomenon, scleredoma and skeletal muscle ischemia; head pain, such as migraine (including migraine with aura and migraine without aura), cluster headache, tension-type headache mixed headache and headache associated with vascular disorders; and orofacial pain, including dental pain, otic pain, burning mouth syndrome and temporomandibular myofascial pain.

In certain embodiments, the method comprises administering to the mammal a therapeutically effective amount of any of the compounds as described herein, or a pharmaceutically acceptable salt thereof, in combination with one or more of the following: nonsteroidal anti-inflammatory drug (NSAID), opioid analgesic, barbiturate, benzodiazapine, histamine antagonist, sedative, skeletal muscle relaxant, transient receptor potential ion channel antagonist, α-adrenergic, tricyclic antidepressant, anticonvulsant, tachykinin antagonist, muscarinic antagonist, cyclooxygenase-2 selective inhibitor, neuroleptic, vanilloid receptor agonist, vanilloid receptor antagonist, β-adrenergic, local anesthetic, corticosteroid, 5-HT receptor agonist, 5-HT receptor antagonist, 5-HT$_{2A}$ receptor antagonist, cholinergic analgesic, $\alpha_2\delta$ ligand such as gabapentin or pregabalin, cannabinoid receptor ligand, metabotropic glutamate subtype 1 receptor antagonist, serotonin reuptake inhibitor, norepinephrine reuptake inhibitor, dual serotonin-noradrenaline reuptake inhibitor, Rho kinase inhibitor, inducible nitric oxide synthase inhibitor, acetylcholinesterase inhibitor, prostaglandin $E_2$ subtype 4 antagonist, leukotriene B4 antagonist, 5-lipoxygenase inhibitor, sodium channel blocker, 5-HT3 antagonist, N-methyl-D-aspartic acid receptor antagonist, and phosphodiesterase V inhibitor. In one embodiment, the method comprises administering to the subject a therapeutically effective amount of a compound described herein, or a pharmaceutically acceptable salt, with or without a pharmaceutically acceptable carrier, in combination with a second therapeutic agent selected from the group consisting of acetaminophen, opioid analgesics, NSAIDs, and combinations thereof.

Yet another embodiment of the present invention relates to a method for providing a method for treating disorders of the central nervous system including stroke, epilepsy, manic depression, bipolar disorders, depression, anxiety, schizophrenia, migraine, and psychoses; neural degenerative disorders including Alzheimer's disease, AIDS related dementia, Parkinson's disease, neuropathy caused by head injury, and dementia caused by cerebrovascular disorders; disorders of the lower urinary tract including overactive bladder, prostatis, prostadynia, interstitial cystitis, and benign prostatic hyperplasia; disorders caused by psychogenic stress including bronchial asthma, unstable angina, and hypersensitive colon inflammation; cardiovascular disorders including hypertension, atherosclerosis, heart failure, and cardiac arrhythmias; drug addiction withdrawal symptoms, including ethanol addiction withdrawal symptoms; skin disorders including pruritis and allergic dermatitis, inflammatory bowel disease; cancer; diabetes; and infertility and sexual dysfunction in a mammal in need of such treatment. This method comprises administering to the mammal (including human) a therapeutically effective amount of a compound of the invention or a pharmaceutically acceptable salt thereof.

Calcium channel blockers have been associated with a slightly greater decreased risk of stroke compared to other types of antihypertensive agents (Angeli, F.; et al. American Journal of Hypertension 2004, 17(9), 817-822). The enhanced effect did not correlate with differences in systolic blood pressure and the mechanism of action remains unknown. However, calcium channel blockers have been associated with blockade of central neuronal calcium influx and subsequent ischemic injury in two rodent models (Barone, F. C.; et al. Stroke 1995, 26, 1683-1690). In another model of global ischemia, a calcium channel blocker offered neuroprotection although not permanently (Colbourne, F.; et al. Stroke 1999, 30(3), 662-668). Additionally, diminished progression of carotid atherosclerosis has been observed with calcium channel blocker use (Zanchetti, A.; et al. Circulation 2002, 106, r47-r52).

An increase in intracellular calcium concentration has been correlated with seizure activity (Heinemann, U.; et al. Exp. Brain Res. 1977, 27, 237-243). Several studies have indicated that calcium channel blockers produce anticonvulsant activity (Vezzani, A.; et al. Neuropharmacology 1988, 27(5), 451-458. Otoom, S.; et al. Fundamental & Clinical Pharmacology 2006, 20, 115-119).

Calcium channel blockers have been evaluated in the treatment of bipolar disorders and manic depression for decades. There are suggestions that the calcium channel subtype has influence on efficacy of these disorders (Gitlin, M. Molecular Psychiatry 2006, 11, 227-240. Levy, N. A.; Janicak, P. G Bipolar Disorders 2000, 2, 108-119).

Calcium channel blockers have also been associated with the treatment of anxiety and depression (Saade, S.; et al. Pharmacology, Biochemistry and Behavior 2003, 74, 269-278).

Antischizophrenic drugs have been found to be calcium channel antagonists (Gould, R. J.; et al. Proc. Natl. Acad. Sci. USA 1983, 80, 5122-5125). Other calcium channel blockers have been suggested for the treatment of schizophrenia (Tort, A. B. L.; et al. Psychopharmacology 2005, 177, 344-348). T-type calcium channels have been located in brain regions with relevance to schizophrenia and substance dependence (Talley, E. M.; et al. J Neurosci 1999, 19, 1895-1911).

Migraines are treated with calcium channel blockers (Arulmoshi, D. K.; et al. Vascular Pharmacology 2005, 43, 176-187. Gladstone, J. P.; et al. Expert Rev. Neurotherapeutics 2003, 3(6), 845-872).

Disorders of the lower urinary tract including overactive bladder, prostatis, prostadynia, interstitial cystitis, and benign prostatic hyperplasia can be treated with calcium channel blockers (Fraser, M. O.; et al. US20050148587, 2005).

Ethanol withdrawal syndrome is decreased with calcium channel blockers (Little, H. J.; et al. Life Sciences 1986, 39, 2059-2065).

Dependence on nicotine has been decreased upon treatment with T-type calcium channel blockers (Uslaner, J M; et al. Biological Psychiatry 2010, 68(8), 712-718).

Several cardiac disorders are treated with calcium channel blockers. Atherosclerosis can be reduced by a decrease in free radical-mediated damage as a result of influence on the biophysical properties of membranes (Mason, R. P.; et al. Biochemical Pharmacology 1998, 55, 1843-1852). Hypertension and angina are both successfully treated with calcium channel blockers (Croom, K. F.; et al. Drugs 2006, 66(4), 497-528).

There is data suggesting that calcium channel blockers inhibit the proliferation of cancer cells (Gray, L. S.; et al. International Publication No. WO200059882, 2000).

Calcium channels have been suggested as a target for the treatment of diabetes (Bhattacharjee, A.; et al. Endocrinology 1997, 138(9), 3735-3740).

Ion channels including calcium channels play an important role in sperm physiology and fertilization (Darszon, A.; et al. Physiological Reviews 1999, 79(2), 481-510).

Calcium channel blockers modulate inflammation (Bilici, D.; et al. Pharmacological Research 2001, 44(6), 527-531).

Increased calcium levels in neurones has been implicated in Alzheimer's disease. Two suggested mechanisms of increased calcium influx are that β-amyloid can form calcium permeable channels (Bhatia, R.; et al. FASEB J. 2000, 14(9), 1233-1243) or a G-protein-coupled receptor can be activated by β-amyloid (Lorton, D. Mech. Ageing Dev. 1997, 94(1-3), 199-211).

Neurodegenerative diseases, including Parkinson's and Alzheimer's diseases can be modulated by calcium channel blockers (Rodnitzky, R. L. Drugs 1999, 57(6), 845-849. Vagnucci, A. H., Jr.; et al. The Lancet 2003, 361(9357), 605-608. Veng, L. M.; et al. Molecular Brain Research 2203, 110, 193-202. Geldenhuys, W. J.; et al. Bioorganic and Medicinal Chemistry 2007, 15, 1525-1532. Cavalli, A.; et al. J. Med. Chem. 2008, 51(3), 347-372).

Sleep disorders and absence epilepsy have been associated with calcium channels (Shin, H.-S.; et al. Curr Opin Pharmacol, 2008, 8, 33-41).

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level can depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It can be understood, however, that the total daily usage of the compounds and compositions of the invention can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or other animal range from about 0.01 mg/kg body weight to about 100 mg/kg body weight. More preferable doses can be in the range of from about 0.01 mg/kg body weight to about 30 mg/kg body weight. If desired, the effective daily dose can be divided into multiple doses for purposes of administration. Consequently, single dose compositions can contain such amounts or submultiples thereof to make up the daily dose.

The present invention also is directed, in part, to a use of one or more compounds and/or salts of the invention, and, optionally one or more additional therapeutic agents to prepare a medicament. In some embodiments, the medicament is for co-administration with one or more additional therapeutic agents. In some embodiments, the medicament is for treating pain. In some embodiments, the medicament is for treating neuropathic pain. In some embodiments, the medicament is for treating nociceptive pain. In some embodiments, the medicament is for treating inflammatory pain.

This invention also is directed, in part, to one or more compounds and/or salts of the invention, and, optionally one or more additional therapeutic agents, for use as a medicament. In some embodiments, the medicament is for treating pain. In another embodiment, the medicament is for treating neuropathic pain. In another embodiment, the medicament is for treating nociceptive pain. In another embodiment, the medicament is for treating inflammatory pain.

E. PHARMACEUTICAL COMPOSITIONS

The present invention further provides pharmaceutical compositions that comprise compounds of the present invention or a pharmaceutically acceptable salt or solvate thereof. The pharmaceutical compositions comprise compounds of the present invention that can be formulated together with one or more non-toxic pharmaceutically acceptable carriers.

Another aspect of the present invention is a pharmaceutical composition comprising compounds of the invention, or a pharmaceutically acceptable salt thereof, and one or more pharmaceutically acceptable carriers, alone or in combination with one or more nonsteroidal anti-inflammatory drugs (NSAID), opioid analgesics, barbiturates, benzodiazepines, histamine antagonists, sedatives, skeletal muscle relaxants, transient receptor potential ion channel antagonists, α-adrenergics, tricyclic antidepressants, anticonvulsants, tachykinin antagonists, muscarinic antagonists, cyclooxygenase-2 selective inhibitors, neuroleptics, vanilloid receptor agonists, vanilloid receptor antagonists, β-adrenergics, local anesthetics, corticosteroids, 5-HT receptor agonists, 5-HT receptor antagonists, 5-$HT_{2A}$ receptor antagonists, cholinergic analgesics, $\alpha_2\delta$ ligands such as gabapentin or pregabalin, cannabinoid receptor ligands, metabotropic glutamate subtype 1 receptor antagonists, serotonin reuptake inhibitors, norepinephrine reuptake inhibitors, dual serotonin-noradrenaline reuptake inhibitors, Rho kinase inhibitors, inducible nitric oxide synthase inhibitors, acetylcholinesterase inhibitors, prostaglandin $E_2$ subtype 4 antagonists, leukotriene B4 antagonists, 5-lipoxygenase inhibitors, sodium channel blockers, 5-HT3 antagonists, N-methyl-D-aspartic acid receptor antagonists, and phosphodiesterase V inhibitors.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound can be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form can also comprise buffering agents.

Solid compositions of a similar type can also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They can optionally contain opacifying agents and can also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring and perfuming agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound can be mixed under sterile conditions with a pharmaceutically acceptable carrier and any needed preservatives, buffers or propellants which can be required. Ophthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, piperazine and the like.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The present invention also is directed, in part, to a kit comprising one or more compounds and/or salts of the invention. The kit can optionally contain one or more additional therapeutic agents and/or instructions for, for example, using the kit.

F. GENERAL SYNTHESIS

This invention is intended to encompass compounds of the invention when prepared by synthetic processes or by metabolic processes. Preparation of the compounds by metabolic processes includes those occurring in the human or animal body (in vivo) or processes occurring in vitro.

This invention is directed, in part, to the synthetic processes for preparing compounds of Formula I as shown in Schemes 1 through 14 and the Examples below. This invention also is directed, in part, to novel intermediates that can be used to prepare the compounds of Formula I (and their salts) as shown in Schemes 1 through 14 and the Examples below.

The compounds of the invention can be prepared by a variety of processes well known for the preparation of compounds of this class. For example, the compounds of the invention wherein the groups $Ar^1$, $G^1$, $G^2$, $Z'$, $Z''$, $R^a$ and $R^b$, have the meanings as set forth in the Summary of the Invention section unless otherwise noted, can be synthesized as shown in Schemes 1-14.

Abbreviations which have been used in the descriptions of the Schemes and the Examples that follow are: APCI for atmospheric pressure chemical ionization; DMSO for dimethyl sulfoxide; ESI for electrospray ionization; LCMS for liquid chromatography-mass spectrometry; HPLC for high performance liquid chromatography; Ph for phenyl; and psi for pounds per square inch.

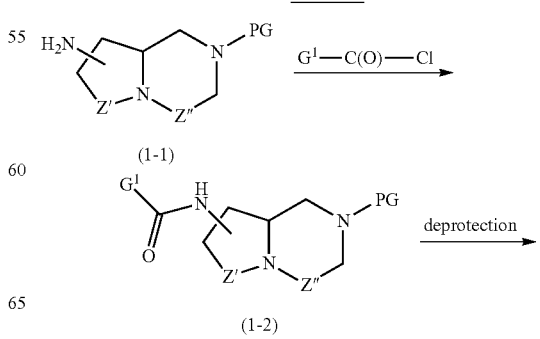

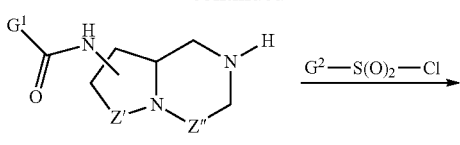

(1-3)

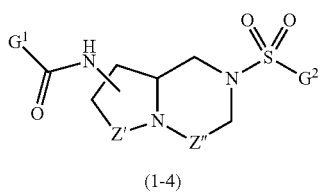

(1-4)

Compounds of Formula (I-4), wherein Z', Z'', $G^1$ and $G^2$ are as defined in the Summary of the Invention, can be prepared as illustrated in Scheme 1. Compounds of Formula (I-1), wherein the primary amine can be located at either the position of $R^1$ or $R^2$ in compounds of Formula (I) shown the Summary of the Invention and PG is a nitrogen protecting group, can be reacted with an acid chloride, $G^1$-C(O)—Cl, in the presence of a base such as but not limited to sodium carbonate in a suitable solvent at ambient or elevated temperature to afford compounds of Formula (1-2). The protecting group can be removed from compounds of Formula (1-2) under suitable conditions known to one skilled in the art to deliver compounds of Formula (1-3). For example, if the protecting group is a benzyl group, it can be removed by catalytic hydrogenation in the presence of a palladium or palladium hydroxide catalyst. Alternatively, if the protecting group is ten-butoxycarbonyl, exposure to acids such as hydrochloric acid or trifluoroacetic acid will remove the protecting group. Compounds of Formula (1-3) can be reacted with sulfonyl chlorides, $G^2$-S(O)$_2$—Cl, in the presence of a base in a suitable solvent at or near room temperature to give compounds of Formula (1-4) which are representative of compounds of Formula (I).

Scheme 2

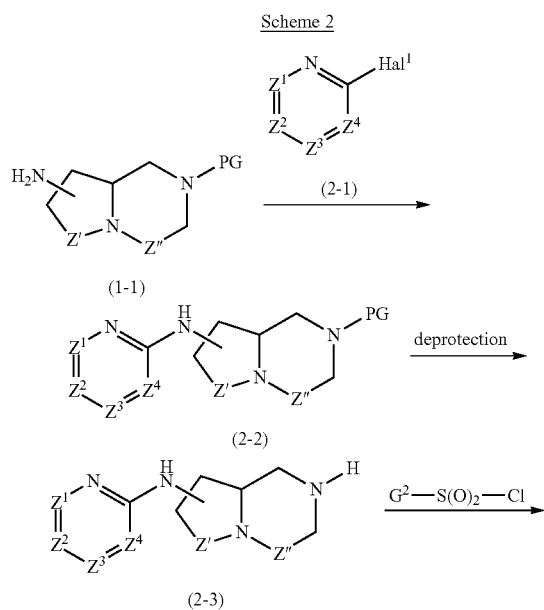

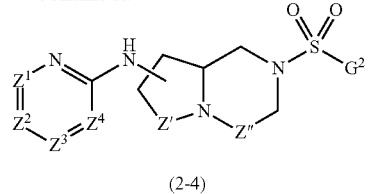

(2-4)

As shown in Scheme 2, compounds of Formula (1-1) can be transformed to compounds of Formula (2-4) which are representative of compounds of Formula (I). Compounds of Formula (1-1) can be reacted with compounds of Formula (2-1) in the presence of a base such as but not limited to sodium carbonate in a solvent such as heated dimethyl sulfoxide to give compounds of Formula (2-2). In compounds of Formula (2-1), Hal$^1$ is fluorine, chlorine, bromine or iodine. Also in compounds of Formula (2-1) one or none of $Z^1$, $Z^2$, $Z^3$ and $Z^4$ can be nitrogen and the others of $Z^1$, $Z^2$, $Z^3$ and $Z^4$ are CR', wherein R' is either hydrogen or the substituents described for Ar$^1$ in the Summary of the Invention. Compounds of Formula (2-3) can be deprotected to give compounds of Formula (2-3) and subsequently sulfonylated to give compounds of Formula (2-4) as described in Scheme 1.

Scheme 3

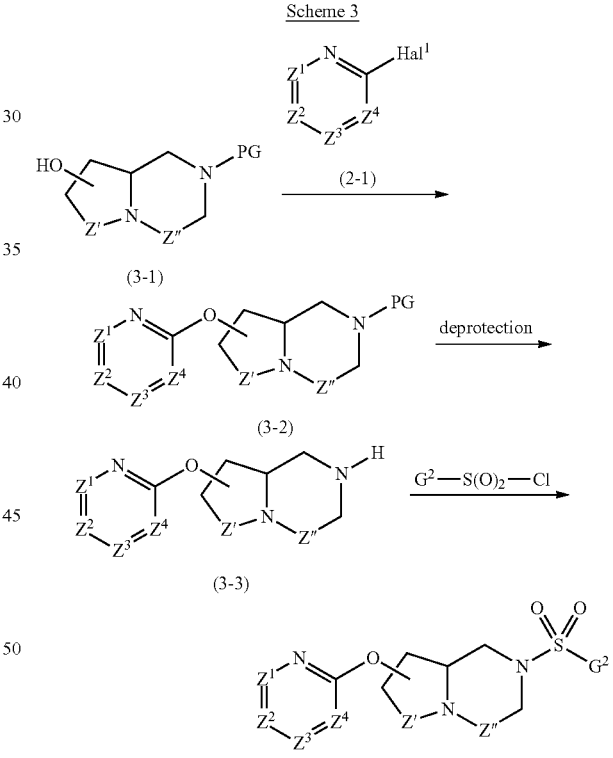

As shown in Scheme 3, compounds of Formula (3-1) can be reacted with compounds of Formula (2-1) in the presence of a base in an optionally heated solvent to give compounds of Formula (3-2). The protecting group can be removed from compounds of Formula (3-2) under suitable conditions known to one skilled in the art to deliver compounds of Formula (3-3). Compounds of Formula (3-3) can be reacted with sulfonyl chlorides, $G^2$-S(O)$_2$—Cl, in the presence of a base in a suitable solvent at or near room temperature to give compounds of Formula (3-4) which are representative of compounds of Formula (I).

Scheme 4

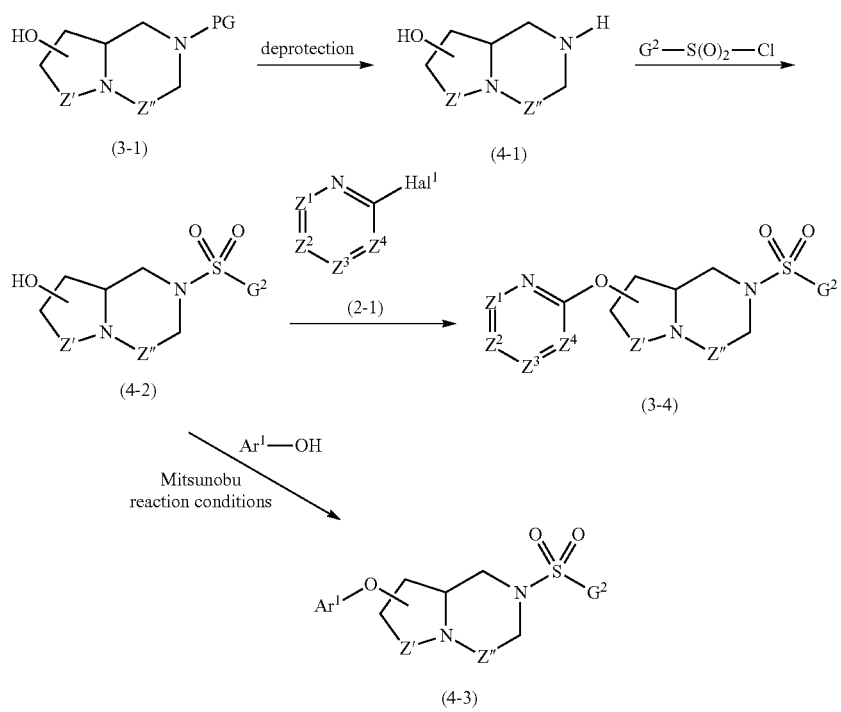

Scheme 4 depicts the alternative transformation of compounds of Formula (3-1) to compounds of Formula (3-4) as well as the sequence to deliver compounds of Formula (4-3). Compounds of Formula (3-1) can be deprotected to give compounds of Formula (4-1). Compounds of Formula (4-1) can be sulfonylated with sulfonyl chlorides, $G^2$-S(O)$_2$—Cl, in the presence of a base in a suitable solvent at or near room temperature to give compounds of Formula (4-2). Compounds of Formula (4-2) can be reacted with compounds of Formula (2-1) in the presence of a base such as potassium tert-butoxide in a suitable solvent to give compounds of Formula (3-4). Compounds of Formula (4-2) can be reacted with compounds, $Ar^1$—OH, wherein $Ar^1$ is as defined in the Summary of the Invention, under Mitsunobu reaction conditions to give compounds of Formula (4-3). Compounds of Formula (3-4) and compounds of Formula (4-3) are representative of compounds of Formula (I).

Scheme 5

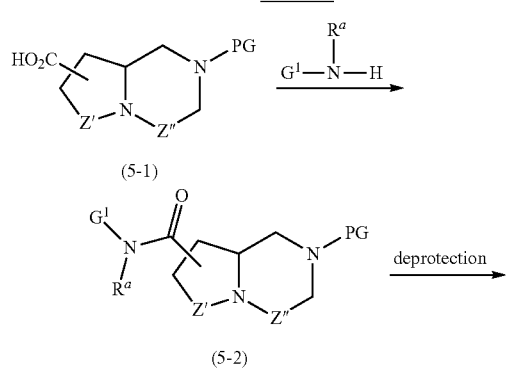

-continued

As shown in Scheme 5, compounds of Formula (5-1) can supply compounds of Formula (5-4) which are representative of compounds of Formula (I). Compounds of Formula (5-1) can be coupled with amines, $G^1$-N($R^a$)H, to give compounds of Formula (5-2). Examples of conditions known to generate amides from a mixture of a carboxylic acid and an amine include but are not limited to adding a coupling reagent such as but not limited to N-(3-dimethylaminopropyl)-N'-ethyl-carbodiimide (EDC or EDCI), 1,3-dicyclohexyl-carbodiimide (DCC), bis(2-oxo-3-oxazolidinyl)phosphinic chloride (BOPCl), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), and 2-(1H-benzo[d][1,2,3]triazol-1-yl)-1,1,3,3-tetramethylisouronium hexafluorophosphate(V) (HBTU). The coupling reagents can be added as a solid, a solution or as the reagent bound to a solid support resin. In addition to the coupling reagents, auxiliary-coupling reagents can facilitate the coupling reaction. Auxiliary coupling reagents that are often used in the coupling reactions include but are not limited to (dimethylamino)pyridine (DMAP), 1-hydroxy-7-azabenzotriazole (HOAT) and 1-hydroxybenzotriazole (HOBT). The reaction can be carried out optionally in the presence of a base such as triethylamine or diisopropylethylamine. The coupling reaction can be carried out in solvents such as but not limited to tetrahydrofuran, N,N-dimethylformamide, dichloromethane, and ethyl acetate. The reaction can be conducted at ambient or elevated temperatures.

Alternatively, compounds of Formula (5-1) can be converted to the corresponding carboxylic acid chloride and then reacted with amines, $G^1$-N($R^a$)H, to give compounds of Formula (5-2) optionally in the presence of a base in a suitable solvent.

Compounds of Formula (5-2) can be deprotected to give compounds of Formula (5-3) and then sulfonylated to give compounds of Formula (5-4) as described in Scheme 1.

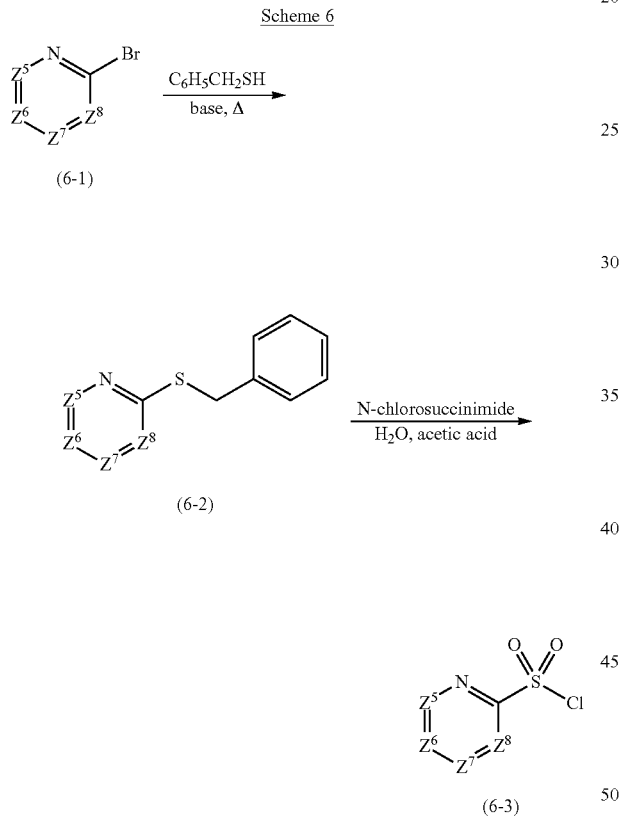

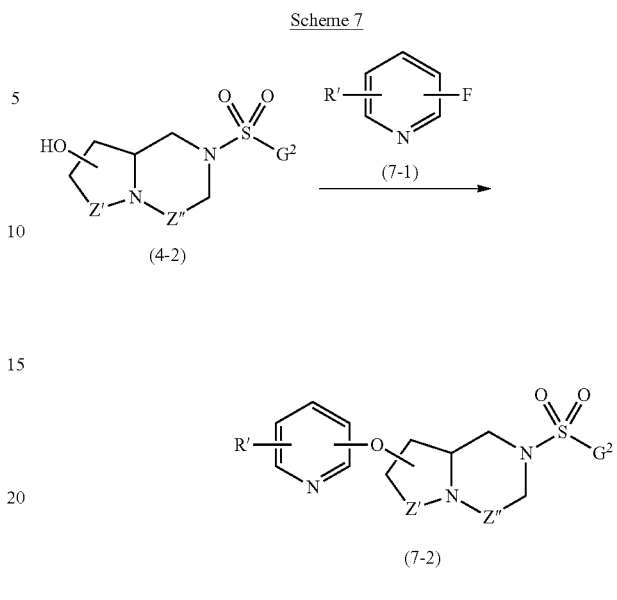

As shown in Scheme 7, compounds of Formula (7-2) can be prepared from compounds of Formula (4-2). Compounds of Formula (4-2) can be treated with a base such as potassium t-butoxide in a solvent such as dimethyl sulfoxide in the presence of compounds of Formula (7-1), wherein R' is either hydrogen or the substituents described for $Ar^1$ in the Summary of the Invention, to give compounds of Formula (7-2). Compounds of Formula (7-2) are representative of compounds of Formula (I).

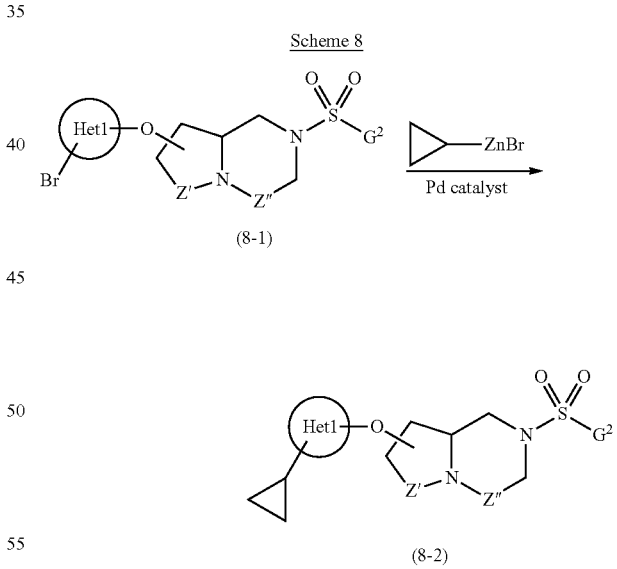

As shown in Scheme 6, sulfonyl chlorides of Formula (6-3) can be prepared from compounds of Formula (6-1), wherein one or none of $Z^5$, $Z^6$, $Z^7$ and $Z^8$ can be nitrogen and the others of $Z^5$, $Z^6$, $Z^7$ and $Z^8$ are CR", wherein R" is either hydrogen or the substituents described for $Ar^2$ in the Summary of the Invention. Compounds of Formula (6-1) can be treated with benzyl mercaptan in the presence of a base such as potassium tert-butoxide in an optionally heated solvent such as N,N-dimethylformamide to give compounds of Formula (6-2). Compounds of Formula (6-2) can then be reacted either with N-chlorosuccinimide or chlorine gas in a mixture of water and acetic acid to give compounds of Formula (6-3). Compounds of Formula (6-3) are compounds of formula $G^2$-S(O)$_2$—Cl and can be used in reactions described in Schemes 1-5, 12 and 13.

As shown in Scheme 8, compounds of Formula (8-2) can be prepared from compounds of Formula (8-1). Compounds of Formula (8-1), wherein Het1 is a 5- or 6-membered heteroaryl that contains one nitrogen atom and optionally a second heteroatom, can be reacted with cyclopropylzinc(II) bromide in the presence of a palladium catalyst such as [1,3-bis(2,6-diisopropylphenyl)imidazol-2-ylidene](3-chloropyridyl)palladium(II) dichloride to give compounds of Formula (8-2). Compounds of Formula (8-2) are representative a compounds of Formula (I).

Scheme 9

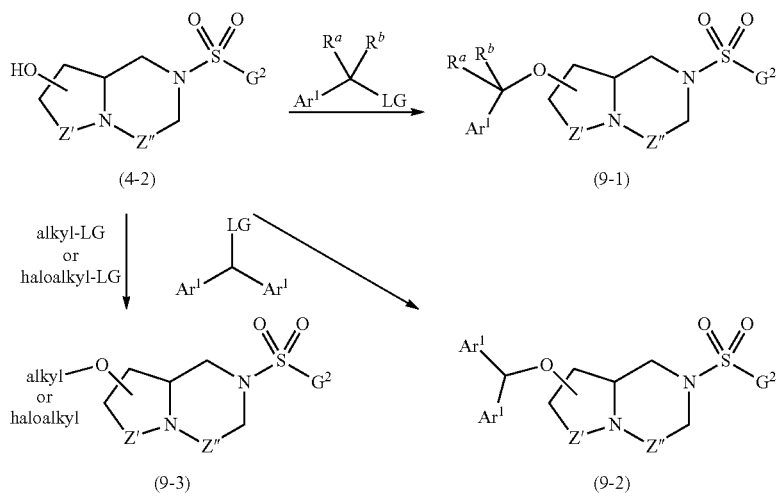

As shown in Scheme 9, compounds of Formula (9-1), Formula (9-2) and Formula (9-3) can be prepared from compounds of Formula (4-2). Compounds of Formula (4-2) can be reacted with $Ar^1C(R^a)R^b$-LG; wherein $Ar^1$, $R^a$ and $R^b$ are as described in the Summary, and LG is a suitable leaving group such as bromine, chlorine, iodine, or a sulfonate; in the presence of a base to give compounds of Formula (9-1). Similarly, compounds of Formula (4-2) can be reacted with $(Ar^1)_2$CH-LG in the presence of a base to give compounds of Formula (9-2). Compounds of Formula (4-2) can also be reacted with alkyl-LG or haloalkyl-LG in the presence of a base to give compounds of Formula (9-3). Compounds of Formula (9-1), Formula (9-2), and Formula (9-3) are representative of compounds of Formula (I).

Scheme 10

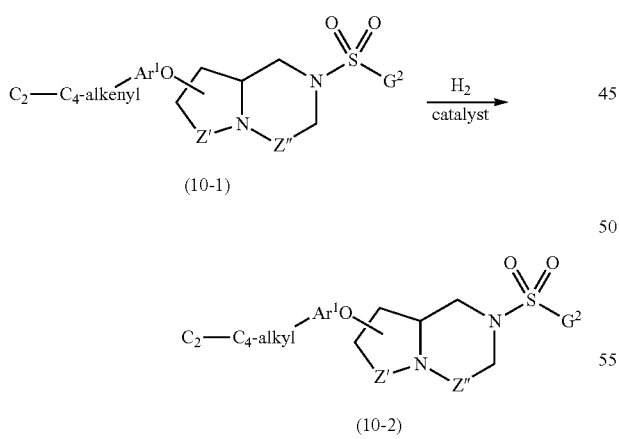

As shown in Scheme 10, compounds of Formula (10-2) can be prepared from compounds of Formula (10-1). Compounds of Formula (10-1), wherein $Ar^1$ is substituted with a $C_2$-$C_4$-alkenyl, can be reduced with hydrogen in the presence of a catalyst such as palladium on carbon, palladium hydroxide on carbon, or Raney® nickel to give compounds of Formula (10-2). Compounds of Formula (10-2) are representative a compounds of Formula (I).

Scheme 11

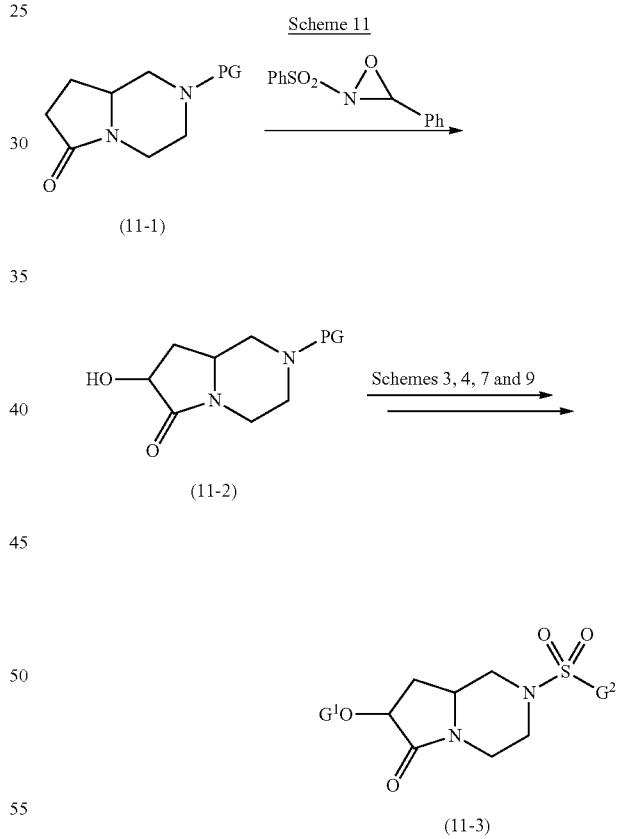

As shown in Scheme 11, compounds of Formula (11-3) can be prepared from compounds of Formula (11-1). Compounds of Formula (11-1) can be deprotonated with a base such as lithium bis(trimethylsilyl)amide and then treated with 3-phenyl-2-(phenylsulfonyl)-1,2-oxaziridine to give compounds of Formula (11-2). Compounds of Formula (11-2) can be reacted in the sequences described in Schemes 3, 4, 7 and 9 to give compounds of Formula (11-3). Compounds of Formula (11-3) are representative of compounds of Formula (I).

Scheme 12

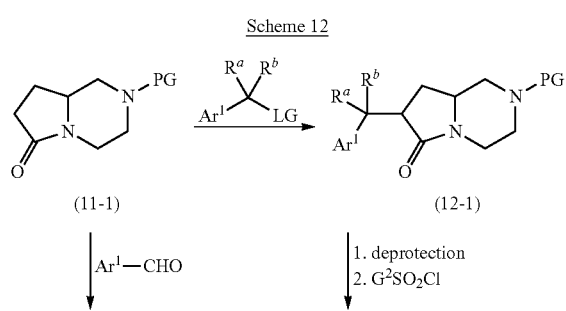

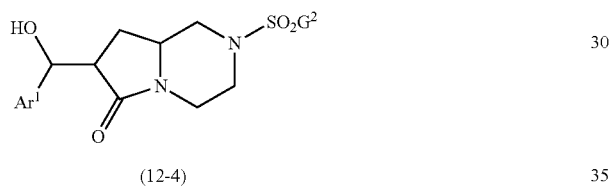

As shown in Scheme 12, compounds of Formula (12-2) and Formula (12-4) can be prepared from compounds of Formula (11-1). Compounds of Formula (11-1) can be deprotonated and then treated with $Ar^1C(R^a)(R^b)$-LG to give compounds of Formula (12-1). The protecting group of compounds of Formula (12-1) can be removed under suitable conditions known to one skilled in the art, and then the intermediate can be reacted with sulfonyl chlorides, $G^2$-S(O)$_2$—Cl, in the presence of a base in a suitable solvent at or near room temperature to give compounds of Formula (12-2) which are representative of compounds of Formula (I). Compounds of Formula (11-1) can also be deprotonated and then treated with aldehydes, $Ar^1CHO$, to give compounds of Formula (12-3). The protecting group of compounds of Formula (12-3) can be removed under suitable conditions known to one skilled in the art, and then the intermediate can be reacted with sulfonyl chlorides, $G^2$-S(O)$_2$—Cl, in the presence of a base in a suitable solvent at or near room temperature to give compounds of Formula (12-4) which are representative of compounds of Formula (I).

Scheme 13

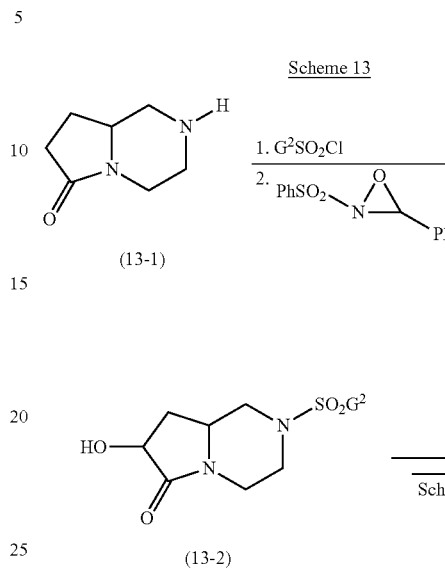

As shown in Scheme 13, compounds of Formula (11-3) can be prepared from compounds of Formula (13-1). Compounds of Formula (13-1) can be reacted with sulfonyl chlorides, $G^2$-S(O)$_2$—Cl, in the presence of a base in a suitable solvent at or near room temperature to give sulfonylated compounds and then subsequently can be deprotonated and then treated with 3-phenyl-2-(phenylsulfonyl)-1,2-oxaziridine to give compounds of Formula (13-2). Compounds of Formula (13-2) can be reacted in the sequences described in Schemes 4, 7 and 9 to give compounds of Formula (11-3). Compounds of Formula (11-3) are representative of compounds of Formula (I).

Scheme 14

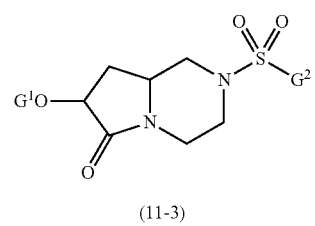

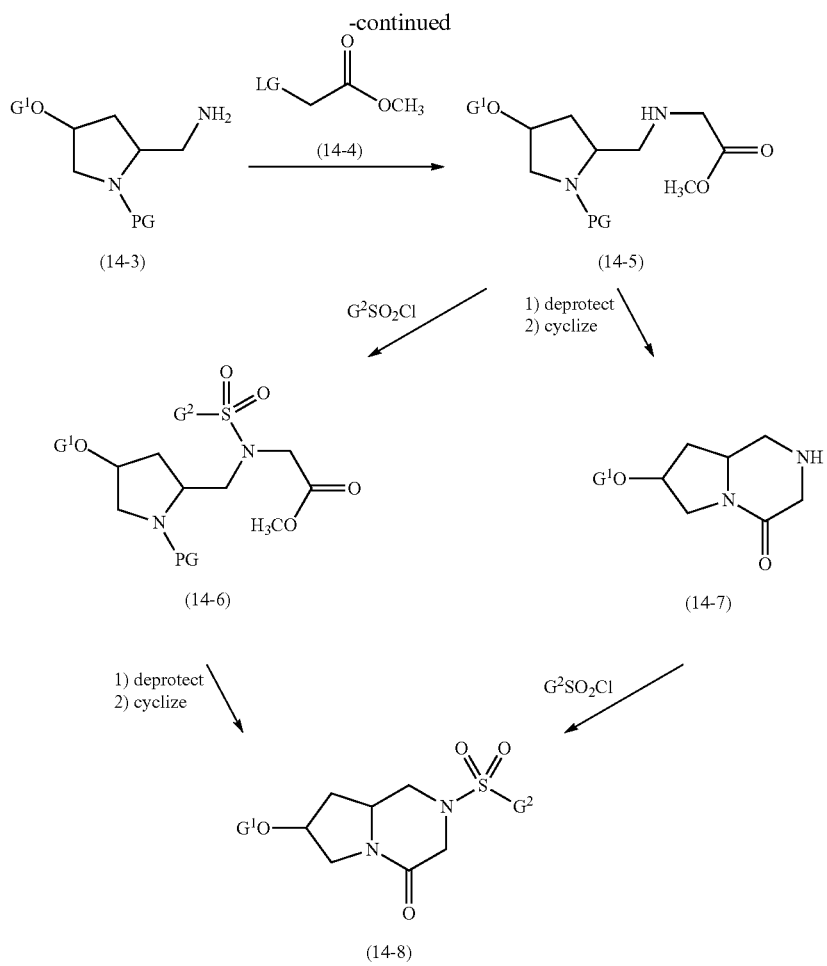

As shown in Scheme 14, compounds of Formula (14-8) can be prepared from compounds of Formula (14-1). Compounds of Formula (14-1), wherein PG is a nitrogen protecting group, can be converted to compounds of Formula (14-2) by selective activation of the primary alcohol and subsequent displacement with azide. Compounds of Formula (14-2) can then be converted to compounds of Formula (14-3) by first introducing a $G^1$ group, wherein $G^1$ is as defined in the Summary, using the methodologies previously described in Schemes 3, 4, 7, or 9; and second, reducing the azide to the corresponding amine Compounds of Formula (14-3) can be reacted with compounds of Formula (14-4), wherein LG is a suitable leaving group such as bromine, chlorine, iodine, or a sulfonate, to give compounds of Formula (14-5). Compounds of Formula (14-5) can be treated with $G^2SO_2Cl$ optionally in the presence of a base to give compounds of Formula (14-6). After removal of the protecting group and cyclization of that intermediate, compounds of Formula (14-6) are transformed to compounds of Formula (14-8). Alternatively, removal of the protecting group on compounds of Formula (14-5) and cyclization of that intermediate gives compounds of Formula (14-7). Compounds of Formula (14-7) can be treated with $G^2SO_2Cl$ optionally in the presence of a base to give compounds of Formula (14-8). Compounds of Formula (14-8) are representative of compounds of Formula (I).

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protective Groups in Organic Synthesis ($3^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

G. EXAMPLES

Example 1

4-fluoro-N-[(7S,8aS)-2-{[3-(trifluoromethyl)phenyl] sulfonyl}octahydropyrrolo[1,2-a]pyrazin-7-yl]benzamide

Example 1A tert-butyl (7S,8aS)-7-[(4-fluorobenzoyl)amino] hexahydropyrrolo[1,2-a]-pyrazine-2(1H)-carboxylate To (7S,8aS)-tert-butyl 7-aminohexahydropyrrolo[1,2-a] pyrazine-2(1H)-carboxylate (0.241 g, 1 mmol) in dichloromethane (6 mL) was added sodium carbonate (0.127 g, 1.2 mmol) and 4-fluorobenzoyl chloride (0.174 g, 1.1 mmol). The mixture was stirred at room temperature for 4 hours. The mixture was concentrated. The residue was purified by chromatography on silica gel (ethyl acetate, then ethyl acetate/methanol=10:1) to give the title compound. $^1$H NMR (300 MHz, CDCl$_3$) δ ppm 1.40 (m, 1H), 1.47 (s, 9H), 1.63 (m, 2H), 2.05-2.20 (m, 2H), 2.50-2.65 (m, 2H), 3.00 (m, 2H), 4.20 (m, 2H), 4.70 (m, 1H), 6.68 (m, 1H), 7.10 (m, 2H), 7.80 (m, 2H); MS (ESI) m/z 364 (M+H)$^+$.

Example 1B 4-fluoro-N-[(7S,8aS)-2-{[3-(trifluoromethyl)phenyl] sulfonyl}octahydropyrrolo[1,2-a]pyrazin-7-yl]benzamide To a solution of Example 1A (200 mg, 0.55 mmol) in dichloromethane (2 mL) was added trifluoroacetic acid (1 mL). The mixture was stirred at room temperature for 3 hours, and then concentrated to give a crude intermediate where the t-butoxycarbonyl protective group has been removed from the starting material. To the above crude intermediate (0.12 mmol) in dichloromethane (2 mL) and N,N-dimethylformamide (0.5 mL) was added sodium carbonate (51 mg, 0.48 mmol), and 3-(trifluoromethyl)benzene-1-sulfonyl chloride (53 mg, 0.216 mol) in dichloromethane (0.5 mL). The mixture was stirred at room temperature for 3 hours, and then concentrated. The residue was purified by chromatography on silica gel (ethyl acetate, then ethyl acetate/methanol=50:1) to give the title compound. $^1$H NMR (500 MHz, DMSO-d$_6$) δ ppm 1.41 (m, 1H), 2.10 (m, 3H), 2.30 (m, 1H), 2.40 (m, 2H), 2.84 (m, 1H), 3.00 (m, 1H), 3.68 (m, 1H), 3.82 (m, 1H), 4.32 (m, 1H), 7.23 (m, 2H), 7.90 (m, 3H), 8.00 (s, 1H), 8.16 (m, 2H), 8.38 (m, 1H); MS (ESI) m/z 472 (M+H)$^+$.

Example 2

4-fluoro-N-[(7S,8aS)-2-{[4-(trifluoromethyl)phenyl] sulfonyl}-octahydropyrrolo[1,2-a]pyrazin-7-yl]benzamide The title compound was prepared according to the procedure described in Example 1 substituting 4-(trifluoromethyl) benzene-1-sulfonyl chloride for 3-(trifluoromethyl)benzene-1-sulfonyl chloride. $^1$H NMR (500 MHz, DMSO-d$_6$) δ ppm 1.41 (m, 1H), 2.05-2.20 (m, 3H), 2.30 (m, 1H), 2.40 (m, 2H), 2.84 (m, 1H), 3.00 (m, 1H), 3.62 (m, 1H), 3.80 (m, 1H), 4.34 (m, 1H), 7.23 (m, 2H), 7.88 (m, 2H), 8.00 (d, 2H, J=7 Hz), 8.08 (d, 2H, J=7 Hz), 8.39 (m, 1H); MS (ESI) m/z 472 (M+H)$^+$.

Example 3

N-[(7S,8aS)-2-{[2-chloro-4-(trifluoromethyl)phenyl] sulfonyl}octahydropyrrolo[1,2-a]pyrazin-7-yl]-4-fluorobenzamide The title compound was prepared according to the procedure described in Example 1 substituting 2-chloro-4-(trifluoromethyl)benzene-1-sulfonyl chloride for 3-(trifluoromethyl)benzene-1-sulfonyl chloride. $^1$H NMR (500 MHz, DMSO-d$_6$) δ ppm 1.42 (m, 1H), 2.00-2.10 (m, 2H), 2.27 (m, 1H), 2.42 (m, 1H), 2.64 (m, 1H), 2.90-3.00 (m, 3H), 3.69 (m, 1H), 3.83 (m, 1H), 4.35 (m, 1H), 7.25 (m, 2H), 7.92 (m, 3H), 8.20 (m, 2H), 8.42 (m, 1H); MS (ESI) m/z 506 (M+H)$^+$.

Example 4

N-[(7S,8aS)-2-{[2-chloro-5-(trifluoromethyl)phenyl] sulfonyl}octahydropyrrolo[1,2-a]pyrazin-7-yl]-4-fluorobenzamide The title compound was prepared according to the procedure described in Example 1 substituting 2-chloro-5-(trifluoromethyl)benzene-1-sulfonyl chloride for 3-(trifluoromethyl)benzene-1-sulfonyl chloride. $^1$H NMR (500 MHz, DMSO-d$_6$) δ ppm 1.45 (m, 1H), 2.00-2.10 (m, 2H), 2.28 (m, 1H), 2.40 (m, 1H), 2.62 (m, 1H), 2.88-3.00 (m, 3H), 3.71 (m, 1H), 3.85 (m, 1H), 4.34 (m, 1H), 7.24 (m, 2H), 7.90 (m, 2H), 7.99 (m, 1H), 8.10 (m, 1H), 8.20 (s, 1H), 8.45 (m, 1H); MS (ESI) m/z 506 (M+H)$^+$.

Example 5

4-chloro-N-[(7S,8aS)-2-{[3-(trifluoromethyl)phenyl] sulfonyl}octahydropyrrolo[1,2-a]pyrazin-7-yl]benzamide The title compound was prepared according to the procedure described in Example 1A, substituting 4-chlorobenzoyl chloride for 4-fluorobenzoyl chloride followed by the procedure described in Example 1B. $^1$H NMR (500 MHz, DMSO-$d_6$) δ ppm 1.41 (m, 1H), 2.10 (m, 3H), 2.28 (m, 1H), 2.38 (m, 2H), 2.85 (m, 1H), 2.99 (m, 1H), 3.68 (m, 1H), 3.82 (m, 1H), 4.32 (m, 1H), 7.46 (m, 2H), 7.82 (m, 2H), 7.92 (m, 1H), 8.00 (s, 1H), 8.15 (m, 2H), 8.42 (m, 1H); MS (ESI) m/z 488 (M+H)$^+$.

Example 6

4-chloro-N-[(7S,8aS)-2-{[4-(trifluoromethyl)phenyl]sulfonyl}octahydropyrrolo[1,2-a]pyrazin-7-yl]benzamide The title compound was prepared according to the procedure described in Example 1A, substituting 4-chlorobenzoyl chloride for 4-fluorobenzoyl chloride followed by the procedure described in Example 1B, substituting 4-(trifluoromethyl)benzene-1-sulfonyl chloride for 3-(trifluoromethyl)benzene-1-sulfonyl chloride. $^1$H NMR (500 MHz, DMSO-$d_6$) δ ppm 1.41 (m, 1H), 2.07-2.20 (m, 3H), 2.29 (m, 1H), 2.39 (m, 2H), 2.84 (m, 1H), 3.00 (m, 1H), 3.63 (m, 1H), 3.80 (m, 1H), 4.34 (m, 1H), 7.48 (d, 2H, J=7 Hz), 7.82 (d, 2H, J=7 Hz), 8.00 (d, 2H, J=7 Hz), 8.07 (d, 2H, J=7 Hz), 8.42 (m, 1H); MS (ESI) m/z 488 (M+H)$^+$.

Example 7

4-chloro-N-[(7S,8aS)-2-{[2-chloro-4-(trifluoromethyl)phenyl]sulfonyl}-octahydropyrrolo[1,2-a]pyrazin-7-yl]benzamide The title compound was prepared according to the procedure described in Example 1A, substituting 4-chlorobenzoyl chloride for 4-fluorobenzoyl chloride followed by the procedure described in Example 1B, substituting 2-chloro-4-(trifluoromethyl)benzene-1-sulfonyl chloride for 3-(trifluoromethyl)benzene-1-sulfonyl chloride. $^1$H NMR (500 MHz, DMSO-$d_6$) δ ppm 1.44 (m, 1H), 2.00-2.12 (m, 2H), 2.29 (m, 1H), 2.41 (m, 1H), 2.63 (m, 1H), 2.86-3.00 (m, 3H), 3.71 (m, 1H), 3.83 (m, 1H), 4.34 (m, 1H), 7.51 (d, 2H, J=7 Hz), 7.83 (d, 2H, J=7 Hz), 7.98 (d, 1H, J=7 Hz), 8.21 (m, 2H), 8.55 (m, 1H); MS (ESI) m/z 522 (M+H)$^+$.

Example 8

4-chloro-N-[(7S,8aS)-2-{[4-fluoro-2-(trifluoromethyl)phenyl]sulfonyl}-octahydropyrrolo[1,2-a]pyrazin-7-yl]benzamide The title compound was prepared according to the procedure described in Example 1A, substituting 4-chlorobenzoyl chloride for 4-fluorobenzoyl chloride followed by the procedure described in Example 1B, substituting 4-fluoro-2-(trifluoromethyl)-benzene-1-sulfonyl chloride for 3-(trifluoromethyl)benzene-1-sulfonyl chloride. $^1$H NMR (500 MHz, DMSO-$d_6$) δ ppm 1.46 (m, 1H), 2.00-2.18 (m, 2H), 2.28 (m, 1H), 2.41 (m, 1H), 2.57 (m, 1H), 2.79 (m, 1H), 2.96 (m, 1H), 3.02 (m, 1H), 3.68 (m, 1H), 3.81 (m, 1H), 4.35 (m, 1H), 7.52 (d, 2H, J=7 Hz), 7.78 (m, 1H), 7.84 (d, 2H, J=7 Hz), 7.99 (d, 1H, J=7 Hz), 8.19 (m, 1H), 8.54 (m, 1H); MS (ESI) m/z 506 (M+H)$^+$.

Example 9

4-chloro-N-[(7S,8aS)-2-{[2-(trifluoromethyl)phenyl]sulfonyl}octahydropyrrolo[1,2-a]pyrazin-7-yl]benzamide The title compound was prepared according to the procedure described in Example 1A, substituting 4-chlorobenzoyl chloride for 4-fluorobenzoyl chloride followed by the procedure described in Example 1B, substituting 2-(trifluoromethyl)benzene-1-sulfonyl chloride for 3-(trifluoromethyl)benzene-1-sulfonyl chloride. $^1$H NMR (500 MHz, DMSO-$d_6$) δ ppm 1.45 (m, 1H), 2.02-2.18 (m, 2H), 2.28 (m, 1H), 2.41 (m, 1H), 2.57 (m, 1H), 2.79 (m, 1H), 2.94 (m, 1H), 2.99 (m, 1H), 3.68 (m, 1H), 3.82 (m, 1H), 4.36 (m, 1H), 7.52 (d, 2H, J=7 Hz), 7.84 (d, 2H, J=7 Hz), 7.92 (m, 1H), 8.02 (m, 1H), 8.09 (m, 1H), 8.52 (m, 1H); MS (ESI) m/z 488 (M+H)$^+$.

Example 10

N-[(7S,8aS)-2-{[2-chloro-4-(trifluoromethyl)phenyl]sulfonyl}octahydropyrrolo[1,2-a]pyrazin-7-yl]-2,4-difluorobenzamide The title compound was prepared according to the procedure described in Example 1A, substituting 2,4-difluorobenzoyl chloride for 4-fluorobenzoyl chloride followed by the procedure described in Example 1B, substituting 2-chloro-4-(trifluoromethyl)benzene-1-sulfonyl chloride for 3-(trifluoromethyl)benzene-1-sulfonyl chloride. $^1$H NMR (500 MHz, DMSO-$d_6$) δ ppm 1.37 (m, 1H), 2.00-2.12 (m, 2H), 2.29 (m, 1H), 2.41 (m, 1H), 2.62 (m, 1H), 2.84-3.00 (m, 3H), 3.71 (m, 1H), 3.83 (m, 1H), 4.34 (m, 1H), 7.15 (m, 1H), 7.31 (m, 1H), 7.60 (m, 1H), 7.97 (m, 1H), 8.20 (m, 2H), 8.43 (m, 1H); MS (ESI) m/z 524 (M+H)$^+$.

Example 11

2,4-difluoro-N-[(7S,8aS)-2-{[4-(trifluoromethyl)phenyl]sulfonyl}octahydropyrrolo[1,2-a]pyrazin-7-yl]benzamide The title compound was prepared according to the procedure described in Example 1A, substituting 2,4-difluorobenzoyl chloride for 4-fluorobenzoyl chloride followed by the procedure described in Example 1B, substituting 4-(trifluoromethyl)-benzene-1-sulfonyl chloride for 3-(trifluoromethyl)benzene-1-sulfonyl chloride. $^1$H NMR (500 MHz, DMSO-$d_6$) δ ppm 1.35 (m, 1H), 2.03-2.17 (m, 3H), 2.29-2.39 (m, 3H), 2.62 (m, 1H), 2.98 (m, 1H), 3.68 (m, 1H), 3.80 (m, 1H), 4.30 (m, 1H), 7.10 (m, 1H), 7.30 (m, 1H), 7.58 (m, 1H), 7.97-8.02 (m, 4H), 8.38 (m, 1H); MS (ESI) m/z 490 (M+H)$^+$.

Example 12

N-{(7S,8aS)-2-[(2,4-dichlorophenyl)sulfonyl]octahydropyrrolo[1,2-a]pyrazin-7-yl}-2,4-difluorobenzamide The title compound was prepared according to the procedure described in Example 1A, substituting 2,4-difluorobenzoyl chloride for 4-fluorobenzoyl chloride followed by the procedure described in Example 1B, substituting 2,4-dichlorobenzene-1-sulfonyl chloride for 3-(trifluoromethyl)benzene-1-sulfonyl chloride. $^1$H NMR (500 MHz, DMSO-$d_6$) δ ppm 1.37 (m, 1H), 2.00-2.10 (m, 2H), 2.29 (m, 1H), 2.40 (m, 1H), 2.58 (m, 1H), 2.82 (m, 1H), 2.90 (m, 1H), 2.99 (m, 1H), 3.64 (m, 1H), 3.80 (m, 1H), 4.30 (m, 1H), 7.12 (m, 1H), 7.30

Example 13

N-[(7S,8aS)-2-{[2-chloro-4-(trifluoromethyl)phenyl]sulfonyl}octahydropyrrolo[1,2-a]pyrazin-7-yl]-3,4-difluorobenzamide The title compound was prepared according to the procedure described in Example 1A, substituting 3,4-difluorobenzoyl chloride for 4-fluorobenzoyl chloride followed by the procedure described in Example 1B, substituting 2-chloro-4-(trifluoromethyl)benzene-1-sulfonyl chloride for 3-(trifluoromethyl)benzene-1-sulfonyl chloride. $^1$H NMR (500 MHz, DMSO-d$_6$) δ ppm 1.42 (m, 1H), 2.00-2.15 (m, 2H), 2.28 (m, 1H), 2.41 (m, 1H), 2.64 (m, 1H), 2.86-3.00 (m, 3H), 3.71 (m, 1H), 3.83 (m, 1H), 4.35 (m, 1H), 7.54 (m, 1H), 7.75 (m, 1H), 7.90-7.97 (m, 2H), 8.20 (m, 2H), 8.58 (m, 1H); MS (ESI) m/z 524 (M+H)$^+$.

Example 14

3,4-difluoro-N-[(7S,8aS)-2-{[4-(trifluoromethyl)phenyl]sulfonyl}octahydropyrrolo[1,2-a]pyrazin-7-yl]benzamide The title compound was prepared according to the procedure described in Example 1A, substituting 3,4-difluorobenzoyl chloride for 4-fluorobenzoyl chloride followed by the procedure described in Example 1B, substituting 4-(trifluoromethyl)-benzene-1-sulfonyl chloride for 3-(trifluoromethyl)benzene-1-sulfonyl chloride. $^1$H NMR (500 MHz, DMSO-d$_6$) δ ppm 1.40 (m, 1H), 2.05-2.20 (m, 3H), 2.25-2.41 (m, 3H), 2.84 (m, 1H), 3.00 (m, 1H), 3.68 (m, 1H), 3.81 (m, 1H), 4.31 (m, 1H), 7.50 (m, 1H), 7.70 (m, 1H), 7.91 (m, 1H), 8.02 (m, 4H), 8.48 (m, 1H); MS (ESI) m/z 490 (M+H)$^+$.

Example 15

(7S,8aS)-2-[(3,5-dichlorophenyl)sulfonyl]-N-[6-(trifluoromethyl)pyridin-2-yl]octahydropyrrolo[1,2-a]pyrazin-7-amine

Example 15A tert-butyl (7S,8aS)-7-{[6-(trifluoromethyl)pyridin-2-yl]amino}hexahydropyrrolo[1,2-a]pyrazine-2(1H)-carboxylate To (7S,8aS)-tert-butyl 7-aminohexahydropyrrolo[1,2-a]pyrazine-2(1H)-carboxylate (310 mg, 1.29 mmol) and sodium carbonate (0.26 g, 2.5 mmol) in dimethyl sulfoxide (1 mL) was added 2-chloro-6-(trifluoromethyl)pyridine (0.35 g, 1.93 mmol). The mixture was stirred at 100° C. for 3 days and then concentrated. The residue was purified by chromatography on silica gel (100% ethyl acetate) to provide the title compound. MS (ESI) m/z 387 (M+H)$^+$.

Example 15B (7S,8aS)—N-(6-(trifluoromethyl)pyridin-2-yl)octahydropyrrolo[1,2-a]pyrazin-7-amine To Example 15A (0.43 g, 1.113 mmol) in methanol (5 mL) was added 4 N hydrochloric acid in dioxane (5 mL). The mixture was heated at 80° C. for 1 hour and then concentrated to provide the title compound as the hydrochloric acid salt. MS (ESI) m/z 287 (M+H)$^+$.

Example 15C (7S,8aS)-2-[(3,5-dichlorophenyl)sulfonyl]-N-[6-(trifluoromethyl)pyridin-2-yl]octahydropyrrolo[1,2-a]pyrazin-7-amine To a solution of Example 15B (70 mg, 0.217 mmol) in triethylamine (40 mg, 0.4 mmol) and dichloromethane (1 mL) was added a solution of 3,5-dichlorobenzene-1-sulfonyl chloride (53 mg, 0.217 mmol) in dichloromethane (1 mL). The mixture was stirred at room temperature for 18 hours and then concentrated. The residue was purified by chromatography on silica gel (ethyl acetate/methanol=20:1) to give the title compound. $^1$NMR (500 MHz, DMSO-d$_6$) δ ppm 1.23 (m, 2H), 2.14 (m, 2H), 2.38 (m, 3H), 2.78 (m, 1H), 2.96 (m, 1H), 3.64 (m, 1H), 3.81 (m, 1H), 4.20 (m, 1H), 6.65 (d, 1H, J=7 Hz), 6.86 (d, 1H, J=7 Hz), 7.15 (d, 1H, J=7 Hz), 7.52 (t, 1H, J=7 Hz), 7.78 (s, 2H), 8.04 (m, 1H); MS (ESI) m/z 496 (M+H)$^+$.

Example 16

(7S,8aS)-2-{[2-chloro-4-(trifluoromethyl)phenyl]sulfonyl}-N-[6-(trifluoromethyl)pyridin-2-yl]octahydropyrrolo[1,2-a]pyrazin-7-amine The title compound was prepared according to the procedure described in Example 15C, substituting 2-chloro-4-(trifluoromethyl)benzene-1-sulfonyl chloride for 3,5-dichlorobenzene-1-sulfonyl chloride. $^1$H NMR (500 MHz, DMSO-d$_6$) δ ppm 1.23 (m, 2H), 2.14 (m, 2H), 2.38 (m, 3H), 2.78 (m, 1H), 2.96 (m, 1H), 3.64 (M, 1H), 3.81 (m, 1H), 4.20 (m, 1H), 6.65 (d, 1H, J=7 Hz), 6.86 (d, 1H, J=7 Hz), 7.21 (d, 1H, J=7 Hz), 7.52 (t, 1H, J=7 Hz), 7.94 (d, 1H, J=7 Hz), 8.18 (m, 2H); MS (ESI) m/z 529 (M+H)$^+$.

Example 17

(7S,8aR)-2-{[3-(trifluoromethyl)phenyl]sulfonyl}octahydropyrrolo[1,2-a]-pyrazin-7-ol

Example 17A (2R,4S)-methyl 4-hydroxypyrrolidine-2-carboxylate hydrochloride To a suspension of trans-4-hydroxy-D-proline hydrochloride (150 g, 0.89 mol, 1 equivalent) in methanol (1.25 L), thionyl chloride (130 mL, 1.79 mol, 2 equivalents) was added drop-wise at 0-5° C. Then the reaction mixture was stirred for 4 hours at 20-25° C. The reaction mixture was concentrated under reduced pressure. This crude material was stirred in a mixture of ethanol-methyl tert-butyl ether (1:4, 750 mL) for 30 minutes and the solid was collected by filtration. The wet cake was dried in a vacuum tray dryer for 8 hours at about 50° C. to afford the title compound. $^1$H NMR (300 MHz, DMSO-d$_6$) δ ppm 2.03-2.23 (m, 2H), 3.06 (d, 1H, J=12.0 Hz), 3.37 (dd, 2H, J=4.5 Hz, J=12.0 Hz), 3.75 (s, 3H), 4.41-4.48 (m, 2H), 5.64 (bs, 1H), 9.43 (bs, 1H), 10.48 (bs, 1H).

Example 17B (2R,4S)-methyl 1-(2-chloroacetyl)-4-hydroxypyrrolidine-2-carboxylate To a suspension of Example 17A (100 g, 0.55 mol, 1 equivalent) in benzene (2.5 L), chloroacetyl chloride (62.4 g, 0.50 mol, 1 equivalent) was added dropwise at 20-25° C. The reaction mixture was refluxed for 3 hours. Then charcoal (2 g) was added, and the mixture was hot filtered through diatomaceous earth. The filtrate was concentrated under reduced pressure to get a solid. To this crude material, methyl tert-butyl ether (500 mL) was added and stirred for 30 minutes. The solid was collected by filtration, and the wet cake was dried in a vacuum tray dryer for 5 hours at about 50° C. to afford the title compound. $^1$H NMR (300 MHz, DMSO-$d_6$) δ ppm 2.06-2.15 (m, 1H), 2.31-2.39 (m, 1H), 3.64 (d, 1H, J=11.1 Hz), 3.76 (s, 3H), 3.76-3.86 (m, 2H), 4.09 (s, 2H), 4.6-4.65 (m, 2H).

Example 17C (7S,8aR)-2-benzyl-7-hydroxyhexahydropyrrolo[1,2-a]pyrazine-1,4-dione To a solution of Example 17B (200 g, 0.90 mol, 1 equivalent) in 2-ethoxyethanol (3.2 L), benzylamine (120 mL, 1.09 mol, 1.2 equivalents) was added. To this mixture, triethylamine (152 mL, 1.08 mol, 1.28 equivalents) was added, and the mixture was refluxed for 20 hours. The reaction mixture was cooled and concentrated under reduced pressure to afford crude product. This crude material was purified by column chromatography on silica gel using a mixture of methanol-ethyl acetate gradient (0-10%) to afford the title compound. $^1$H NMR (300 MHz, CDCl$_3$) δ ppm 2.11 (m, 1H), 2.46 (m, 1H), 3.50 (m, 2H), 3.73 (d, 1H, J=16), 3.76 (m, 1H), 4.00 (d, 1H, J=16), 4.45 (d, 1H, J=15), 4.50 (m, 1H), 4.72 (d, 1H, J=15), 7.30 (m, 5H).

Example 17D (7S,8aR)-2-benzyloctahydropyrrolo[1,2-a]pyrazin-7-ol

To a suspension of lithium aluminum hydride (50.7 g, 1.33 mol, 4 equivalents) in tetrahydrofuran (1.3 L), Example 17C (87 g, 0.33 mol, 1 equivalent) in tetrahydrofuran (1.3 L) was added slowly at about 15° C. Then the mixture was stirred at about 65° C. for 78 hours. The reaction mixture was cooled to 0-5° C. and quenched using ethyl acetate (430 mL), water (87 mL), 10% NaOH solution (175 mL), followed by water (260 mL) and stirred at 20-25° C. for 30 minutes. The suspension was filtered through diatomaceous earth, and the filtrate was concentrated. This crude material was purified by column chromatography on silica gel using a gradient of methanol-ethyl acetate (0-10%) to afford the title compound. $^1$H NMR (300 MHz, DMSO-$d_6$) δ ppm 1.46-1.52 (m, 2H), 1.68 (t, 1H, J=8.4 Hz), 1.918 (dd, 1H, J=5.7 Hz, J=7.2 Hz), 2.04-2.27 (m, 3H), 2.67 (d, 1H, J=10.5 Hz), 2.79 (d, 2H, J=10.2 Hz), 3.23 (dd, 1H, J=6.9 Hz, J=4.9 Hz), 3.47 (dd, 2H, J=4.2 Hz, J=17.7 Hz), 4.15-4.25 (m, 1H), 4.73 (bs, 1H), 7.23-7.34 (m, 5H); $^{13}$C NMR (75 MHz, DMSO-$d_6$) δ ppm 40.0, 51.32, 52.62, 57.58, 60.72, 62.49, 63.12, 68.42, 127.29, 128.57, 129.23, 138.83; MS (ESI) m/z 233 (M+H)$^+$.

Example 17E (7S,8aR)-2-{[3-(trifluoromethyl)phenyl]sulfonyl}octahydropyrrolo[1,2-a]-pyrazin-7-ol To (7S,8aR)-2-benzyloctahydropyrrolo[1,2-a]pyrazin-7-ol (Example 17D, 5 g, 21.52 mmol) and solvent 2,2,2-trifluoroethanol (50 mL) were added to 20% palladium hydroxide on carbon, wet (0.500 g) in a pressure bottle. The mixture was stirred at 50° C. for 16 hours under 30 psi of hydrogen. The mixture was filtered through a nylon membrane to give a crude (7S,8aR)-octahydropyrrolo[1,2-a]pyrazin-7-ol. To a solution of the above crude (7S,8aR)-octahydropyrrolo[1,2-a]pyrazin-7-ol (1.0 g, 7 mmol) and triethylamine (1.13 g, 11.2 mmol) in dichloromethane (40 mL) was slowly added a solution of 3-(trifluoromethyl)benzene-1-sulfonyl chloride (1.712 g, 7 mmol) in dichloromethane (2 mL). The solution was stirred at room temperature for 4 hours. The solution was concentrated, diluted with ethyl acetate (100 mL), washed with water (20 mL), dried over sodium sulfate, filtered, and concentrated. The residue was purified by chromatography on silica gel (dichloromethane/methanol=10:1) to give the title compound. $^1$H NMR (400 MHz, DMSO-$d_6$) δ ppm 1.43-1.58 (m, 2H), 1.97 (m, 2H), 2.10-2.35 (m, 3H), 2.90 (m, 1H), 3.20 (m, 1H), 3.62 (m, 1H), 3.77 (m, 1H), 4.14 (m, 1H), 4.80 (m, 1H), 7.92 (m, 2H), 8.10 (m, 2H); MS (ESI) m/z 351 (M+H)$^+$.

Example 18

(7S,8aR)-7-[(5-cyclopropylpyrazin-2-yl)oxy]-2-{[3-(trifluoromethyl)phenyl]-sulfonyl}octahydropyrrolo[1,2-a]pyrazine To a solution of Example 17 (140 mg, 0.4 mmol) in tetrahydrofuran (5 mL) was added potassium tert-butoxide (0.7 mL, 1 M in tetrahydrofuran, 0.7 mmol) followed by a solution of 2-bromo-5-cyclopropylpyrazine (88 mg, 0.44 mmol) in tetrahydrofuran (1 mL). The mixture was stirred at room temperature for 2 days. The mixture was concentrated, and the residue was purified by chromatography on silica gel (dichloromethane/methanol=15:1) to give the title compound. $^1$H NMR (400 MHz, DMSO-$d_6$) δ ppm 0.80 (m, 2H), 0.92 (m, 2H), 1.70-1.95 (m, 2H), 2.08-2.40 (m, 6H), 2.98 (m, 1H), 3.57 (m, 1H), 3.69 (m, 1H), 3.82 (m, 1H), 5.20 (m, 1H), 7.92 (m, 2H), 8.15 (m, 4H); MS (ESI) m/z 469 (M+H)$^+$.

Example 19

(7R,8aS)-2-{[3-(trifluoromethyl)phenyl]sulfonyl}octahydropyrrolo[1,2-a]-pyrazin-7-ol

Example 19A (2S,4R)-methyl 4-hydroxypyrrolidine-2-carboxylate hydrochloride

To a suspension of trans-4-hydroxy-L-proline (100 g, 0.76 mol, 1 equivalent) in methanol (850 mL), thionyl chloride (110 mL, 1.53 mol, 2 equivalents) was added drop-wise at 0-5° C. Then the reaction mixture was stirred for 4 hours at 20-25° C. The reaction mixture was concentrated under reduced pressure. The crude material was stirred in a mixture of ethanol-methyl tert-butyl ether (1:4, 500 mL) for 30 minutes and the solid was collected by filtration. The wet cake was dried in a vacuum tray dryer for 8 hours at about 50° C. to afford the title compound. $^1$H NMR (300 MHz, DMSO-$d_6$)

δ ppm 2.09-2.24 (m, 2H), 3.07 (d, 1H, J=12.3 Hz), 3.35 (dd, 2H, J=4.2 Hz, J=11.7 Hz), 3.76 (s, 3H), 4.42-4.51 (m, 2H), 5.59 (bs, 1H), 9.3 (bs, 1H), 10.3 (bs, 1H).

Example 19B (2S,4R)-methyl 1-(2-chloroacetyl)-4-hydroxypyrrolidine-2-carboxylate To a suspension of Example 19A (130 g, 0.72 mol, 1 equivalent) in benzene (3.9 L), chloroacetyl chloride (81.1 g, 0.72 mol, 1 equivalent) was added dropwise at 20-25° C. The reaction mixture was refluxed for 5 hours. Then, charcoal (500 mg) was added, and the reaction mixture was hot filtered through diatomaceous earth. The filtrate was concentrated under reduced pressure. To this crude material, methyl tert-butyl ether (650 mL) was added, and the mixture was stirred for 30 minutes. The solid was collected by filtration, and the wet cake was dried in a vacuum tray dryer for 5 hours at about 50° C. to afford the title compound. $^1$H NMR (300 MHz, DMSO-$d_6$) δ ppm 1.9-1.96 (m, 1H), 2.08-2.19 (m, 1H), 3.36 (d, 1H, J=14.4 Hz), 3.65 (s, 3H), 3.66 (m, 2H), 4.33 (s, 2H), 4.35 (m, 1H), 5.25 (bs, 1H); MS (ESI) m/z 222 (M+H)$^+$.

Example 19C (7R,8aS)-2-benzyl-7-hydroxyhexahydropyrrolo[1,2-a]pyrazine-1,4-dione To a solution of Example 19B (75 g, 0.34 mol, 1 equivalent) in 2-ethoxyethanol (1.2 L), benzylamine (44 mL, 0.41 mol, 1.2 equivalents) was added. Triethylamine (60 mL, 0.43 mol, 1.28 equivalents) was then added, and the resultant mixture was refluxed for 12 hours. The reaction mixture was cooled and concentrated under reduced pressure. This crude material was purified by column chromatography on silica gel using a gradient of 0-10% methanol-ethyl acetate to provide the title compound. $^1$H NMR (300 MHz, DMSO-$d_6$) δ ppm 1.93-2.03 (m, 1H), 2.1-2.17 (m, 1H), 3.23 (d, 1H, J=12.3 Hz), 3.55 (d, 1H, J=4.2 Hz), 3.63 (d, 1H, J=16.5 Hz), 4.15 (m, 1H), 4.32 (bs, 1H), 4.47-4.59 (m, 3H), 5.16 (s, 1H), 7.24-7.37 (m, 5H).

Example 19D (7R,8aS)-2-benzyloctahydropyrrolo[1,2-a]pyrazin-7-ol

To a suspension of Example 19C (60 g, 0.23 mol, 1 equivalent) in tetrahydrofuran (900 mL), lithium aluminum hydride (2 M in tetrahydrofuran, 460 mL, 0.92 mol, 4 equivalents) was added slowly at about 15° C. Then, the mixture was stirred at about 65° C. for 78 hours. The reaction mixture was cooled to 0-5° C., quenched using ethyl acetate (300 mL), water (60 mL), 10% NaOH solution (60 mL), followed by water (60 mL), and the mixture was stirred at 20-25° C. for 30 minutes. The suspension was filtered through diatomaceous earth, and the filtrate was concentrated. This crude material was purified by column chromatography on silica gel using a gradient of 0-10% methanol-ethyl acetate to afford the title compound. $^1$H NMR (300 MHz, DMSO-$d_6$) δ ppm 1.46-1.49 (m, 2H), 1.68, (t, 1H, J=9.9 Hz), 1.91 (dd, 1H, J=5.4 Hz, J=8.9 Hz), 2.04-2.13 (m, 1H), 2.15-2.49 (m, 2H), 2.67 (d, 1H, J=10.3 Hz), 2.78 (d, 2H, J=5.4 Hz), 3.25 (dd, 1H, J=4.5 Hz, J=8.9 Hz), 3.47 (dd, 2H, J=4.5 Hz, J=17.4 Hz), 4.15-4.22 (m, 1H), 4.73 (bs, 1H), 7.23-7.318 (m, 5H); $^{13}$C NMR (75 MHz, DMSO-$d_6$) δ ppm 39.74, 51.34, 52.64, 57.61, 60.72, 62.56, 63.16, 68.46, 127.26, 128.54, 129.2, 138.84; MS (ESI) m/z 233 (M+H)$^+$.

Example 19E (7R,8aS)-2-{[3-(trifluoromethyl)phenyl]sulfonyl}octahydropyrrolo[1,2-a]-pyrazin-7-ol A mixture of (7R,8aS)-2-benzyloctahydropyrrolo[1,2-a]pyrazin-7-ol (Example 19D, 1 g, 4.30 mmol) and ethanol (10 mL) was added to 20% palladium hydroxide on carbon, wet (0.100 g) in a pressure bottle. The mixture was stirred at 50° C. for 16 hours under 30 psi of hydrogen. The mixture was filtered through a nylon membrane to give a crude intermediate (7R,8aS)-octahydropyrrolo[1,2-a]pyrazin-7-ol. The title compound was prepared according to the procedure described in Example 17E substituting (7R,8aS)-octahydropyrrolo[1,2-a]pyrazin-7-ol for (7S,8aR)-octahydropyrrolo[1,2-a]pyrazin-7-ol. $^1$H NMR (400 MHz, DMSO-$d_6$) δ ppm 1.43-1.58 (m, 2H), 1.97 (m, 2H), 2.10-2.35 (m, 3H), 2.90 (m, 1H), 3.20 (m, 1H), 3.62 (m, 1H), 3.77 (m, 1H), 4.14 (m, 1H), 4.80 (m, 1H), 7.92 (m, 2H), 8.10 (m, 2H); MS (ESI) m/z 351 (M+H)$^+$.

Example 20

(7R,8aS)-2-{[2-chloro-4-(trifluoromethyl)phenyl]sulfonyl}-7-{[6-(trifluoromethyl)pyridin-2-yl]oxy}octahydropyrrolo[1,2-a]pyrazine The title compound was prepared according to the procedure described in Example 17, substituting (7R,8aS)-octahydropyrrolo[1,2-a]pyrazin-7-ol for (7S,8aR)-octahydropyrrolo[1,2-a]pyrazin-7-ol and substituting 2-chloro-4-(trifluoromethyl)benzene-1-sulfonyl chloride for 3-(trifluoromethyl)benzene-1-sulfonyl chloride followed by the procedure for Example 18, substituting 2-chloro-6-(trifluoromethyl)pyridine for 2-bromo-5-cyclopropylpyrazine. $^1$H NMR (500 MHz, DMSO-$d_6$) δ ppm 1.88 (m, 2H), 2.22-2.32 (m, 3H), 2.60 (m, 1H), 2.92 (m, 1H), 3.00 (m, 1H), 3.67 (m, 2H), 3.88 (m, 1H), 5.28 (m, 1H), 7.03 (d, 1H, J=7 Hz), 7.15 (m, 2H), 7.48 (d, 1H, J=7 Hz), 7.74 (m 1H), 7.97 (m, 1H); MS (ESI) m/z 530 (M+H)$^+$.

Example 21

(7R,8aS)-7-[(5-cyclopropylpyrazin-2-yl)oxy]-2-{[3-(trifluoromethyl)phenyl]-sulfonyl}octahydropyrrolo[1,2-a]pyrazine To a solution of Example 19 (350 mg, 1 mmol) in tetrahydrofuran (10 mL) was added potassium tert-butoxide (1.6 mL, 1 M in tetrahydrofuran, 1.6 mmol) followed by a solution of 2-bromo-5-cyclopropylpyrazine (239 mg, 1.0 mmol) in tetrahydrofuran (1 mL). The mixture was stirred at room temperature for 2 days. The mixture was concentrated, and the residue was purified by chromatography on silica gel (dichloromethane/methanol=15:1) to give the title compound. $^1$H NMR (400 MHz, DMSO-$d_6$) δ ppm 0.80 (m, 2H), 0.92 (m, 2H), 1.70-1.95 (m, 2H), 2.08-2.40 (m, 6H), 2.98 (m, 1H), 3.57 (m, 1H), 3.69 (m, 1H), 3.82 (m, 1H), 5.20 (m, 1H), 7.92 (m, 2H), 8.15 (m, 4H); MS (ESI) m/z 469 (M+H)$^+$.

Example 22

(7R,8aS)-7-(pyrazin-2-yloxy)-2-{[3-(trifluoromethyl)phenyl]sulfonyl}-octahydropyrrolo[1,2-a]pyrazine The title compound was prepared according to the procedure described in Example 18, substituting Example 19 for Example 17 and substituting 2-chloropyrazine for 2-bromo-5-cyclopropylpyrazine. $^1$H NMR (400 MHz, DMSO-d$_6$) δ ppm 1.70-1.95 (m, 2H), 2.08-2.42 (m, 5H), 2.99 (m, 1H), 3.57 (m, 1H), 3.69 (m, 1H), 3.83 (m, 1H), 5.23 (m, 1H), 7.93 (m, 2H), 8.15 (m, 4H), 8.35 (s, 1H); MS (ESI) m/z 429 (M+H)$^+$.

Example 23

(7R,8aS)-7-[(6-cyclopropylpyrazin-2-yl)oxy]-2-{[3-(trifluoromethyl)phenyl]-sulfonyl}octahydropyrrolo[1,2-a]pyrazine The title compound was prepared according to the procedure described in Example 18, substituting Example 19 for Example 17 and substituting 2-bromo-6-cyclopropylpyrazine for 2-bromo-5-cyclopropylpyrazine. $^1$H NMR (400 MHz, DMSO-d$_6$) δ ppm 0.80 (m, 2H), 0.96 (m, 2H), 1.75 (m, 1H), 1.90 (m, 1H), 2.08-2.40 (m, 6H), 2.99 (m, 1H), 3.51 (m, 1H), 3.68 (m, 1H), 3.82 (m, 1H), 5.17 (m, 1H), 7.93 (m, 3H), 8.15 (m, 3H); MS (ESI) m/z 469 (M+H)$^+$.

Example 24

(7R,8aS)-2-{[4-(trifluoromethyl)phenyl]sulfonyl}octahydropyrrolo[1,2-a]-pyrazin-7-ol The title compound was prepared according to the procedure described in Example 17, substituting (7R,8aS)-octahydropyrrolo[1,2-a]pyrazin-7-ol for (7S,8aR)-octahydropyrrolo[1,2-a]pyrazin-7-ol and substituting 4-(trifluoromethyl)benzene-1-sulfonyl chloride for 3-(trifluoromethyl)benzene-1-sulfonyl chloride. $^1$H NMR (400 MHz, DMSO-d$_6$) δ ppm 1.46-1.58 (m, 2H), 1.97 (m, 2H), 2.12-2.36 (m, 3H), 2.90 (m, 1H), 3.21 (m, 1H), 3.61 (m, 1H), 3.76 (m, 1H), 4.14 (m, 1H), 4.81 (m, 1H), 7.96 (d, 2H, J=7 Hz), 8.04 (d, 2H, J=7 Hz); MS (ESI) m/z 351 (M+H)$^+$.

Example 25

(7R,8aS)-7-[(5-cyclopropylpyrazin-2-yl)oxy]-2-{[4-(trifluoromethyl)-phenyl]sulfonyl}octahydropyrrolo[1,2-a]pyrazine The title compound was prepared according to the procedure described in Example 18, substituting Example 24 for Example 17. $^1$H NMR (400 MHz, DMSO-d$_6$) δ ppm 0.80 (m, 2H), 0.92 (m, 2H), 1.73-1.92 (m, 2H), 2.08-2.40 (m, 6H), 2.98 (m, 1H), 3.57 (m, 1H), 3.65 (m, 1H), 3.80 (m, 1H), 5.20 (m, 1H), 7.96 (d, 2H, J=7 Hz), 8.03 (s, 1H), 8.06 (d, 2H, J=7 Hz); 8.14 (s, 1H); MS (ESI) m/z 469 (M+H)$^+$.

Example 26

(7R,8aS)-7-[(6-cyclopropylpyrazin-2-yl)oxy]-2-{[4-(trifluoromethyl)phenyl]-sulfonyl}octahydropyrrolo[1,2-a]pyrazine The title compound was prepared according to the procedure described in Example 18 substituting Example 24 for Example 17 and substituting 2-bromo-6-cyclopropylpyrazine for 2-bromo-5-cyclopropylpyrazine. $^1$H NMR (400 MHz, DMSO-d$_6$) δ ppm 0.89 (m, 2H), 0.98 (m, 2H), 1.75 (m, 1H), 1.90 (m, 1H), 2.08-2.40 (m, 6H), 2.99 (m, 1H), 3.52 (m, 1H), 3.62 (m, 1H), 3.80 (m, 1H), 5.17 (m, 1H), 8.00 (m, 5H), 8.18 (s, 1H); MS (ESI) m/z 469 (M+H)$^+$.

Example 27

(7R,8aS)-7-[(5-cyclopropylpyrazin-2-yl)oxy]-2-{[2-(trifluoromethyl)phenyl]-sulfonyl}octahydropyrrolo[1,2-a]pyrazine

Example 27A (7R,8aS)-2-benzyl-7-[(5-cyclopropylpyrazin-2-yl)oxy]octahydropyrrolo[1,2-a]pyrazine To (7R,8aS)-2-benzyloctahydropyrrolo[1,2-a]pyrazin-7-ol (Example 19D, 2.323 g, 10 mmol) in tetrahydrofuran (60 mL) at room temperature was added potassium tert-butoxide (14 mL, 1 M in tetrahydrofuran). After 10 minutes, 2-bromo-5-cyclopropylpyrazine (2.249 g, 11.3 mmol) in tetrahydrofuran (3 mL) was added. The mixture was stirred at room temperature for 2 days. The mixture was concentrated and diluted with dichloromethane (200 mL). This solution was washed with water (30 mL), dried over sodium sulfate, and filtered. The organic phase was concentrated. The residue was purified by chromatography on silica gel (dichloromethane/methanol=15:1) to give the title compound. $^1$H NMR (400 MHz, DMSO-d$_6$) δ ppm 0.80 (m, 2H), 0.92 (m, 2H), 1.78 (m, 3H), 2.08-2.38 (m, 5H), 2.70 (m, 1H), 2.83 (m, 2H), 3.53 (m, 3H), 5.24 (m, 1H), 7.28 (m, 5H), 8.12 (m, 2H); MS (ESI) m/z 351 (M+H)$^+$.

Example 27B (7R,8aS)-7-[(5-cyclopropylpyrazin-2-yl)oxy]octahydropyrrolo[1,2-a]pyrazine To a 100 mL pressure bottle was added Example 27A (2.78 g, 7.94 mmol) in tetrahydrofuran (20 mL) and 20% palladium hydroxide on carbon (0.22 g, 1.59 mmol). The mixture was stirred at 50° C. for 16 hours under 30 psi of hydrogen. The mixture was filtered through a nylon membrane to give the title compound. $^1$H NMR (400 MHz, DMSO-d$_6$) δ ppm 0.81 (m, 2H), 0.93 (m, 2H), 1.75 (m, 2H), 2.04-2.28 (m, 6H), 2.57 (m, 1H), 2.80 (m, 2H), 2.95 (1H), 3.53 (m, 3H), 5.20 (m, 1H), 8.16 (m, 2H); MS (ESI) m/z 261 (M+H)$^+$.

Example 27C (7R,8aS)-7-[(5-cyclopropylpyrazin-2-yl)oxy]-2-{[2-(trifluoromethyl)phenyl]-sulfonyl}octahydropyrrolo[1,2-a]pyrazine To a solution of Example 27B (50 mg, 0.192 mmol) and triethylamine (29.2 mg, 0.288 mmol) in dichloromethane (1 mL) was added 2-(trifluoromethyl)benzene-1-sulfonyl chloride (47 mg, 1.92 mmol). The mixture was stirred at room temperature for 16 hours. The mixture was purified by chromatography on silica gel (ethyl acetate/hexane=4:1) to give the title compound. $^1$H NMR (400 MHz, DMSO-d$_6$) δ ppm 0.80 (m, 2H), 0.92 (m, 2H), 1.84 (m, 2H), 2.09 (m, 1H), 2.22 (m, 2H), 2.33 (m, 1H), 2.52 (m, 1H), 2.78 (m, 1H), 2.99 (m, 1H), 3.64 (m, 2H), 3.82 (m, 1H), 5.25 (m, 1H), 7.92 (m, 2H), 8.15 (m, 4H); MS (ESI) m/z 469 (M+H)$^+$.

Example 28

(7R,8aS)-7-[(5-cyclopropylpyrazin-2-yl)oxy]-2-{[4-(trifluoromethoxy)-phenyl]sulfonyl}octahydropyrrolo[1,2-a]pyrazine The title compound was prepared using the procedure described in Example 27C substituting 4-(trifluoromethoxy)benzene-1-sulfonyl chloride for 2-(trifluoromethyl)-benzene-1-sulfonyl chloride. $^1$H NMR (400 MHz, DMSO-d$_6$) δ ppm 0.80 (m, 2H), 0.92 (m, 2H), 1.84 (m, 2H), 2.09 (m, 1H), 2.22 (m, 2H), 2.33 (m, 1H), 2.52 (m, 1H), 2.78 (m, 1H), 2.99 (m, 1H), 3.64 (m, 2H), 3.82 (m, 1H), 5.25 (m, 1H), 7.65 (d, J=7 Hz, 2H), 7.90 (d, J=7 Hz, 2H), 8.15 (s, 2H); MS (ESI) m/z 485 (M+H)$^+$.

Example 29

(7R,8aS)-7-[(5-cyclopropylpyrazin-2-yl)oxy]-2-{[4-(difluoromethoxy)-phenyl]sulfonyl}octahydropyrrolo[1,2-a]pyrazine The title compound was prepared using the procedure described in Example 27C substituting 4-(difluoromethoxy)benzene-1-sulfonyl chloride for 2-(trifluoromethyl)-benzene-1-sulfonyl chloride. $^1$H NMR (400 MHz, DMSO-d$_6$) δ ppm 0.80 (m, 2H), 0.92 (m, 2H), 1.84 (m, 2H), 2.09 (m, 1H), 2.22 (m, 2H), 2.33 (m, 1H), 2.52 (m, 1H), 2.78 (m, 1H), 2.99 (m, 1H), 3.64 (m, 2H), 3.82 (m, 1H), 5.25 (m, 1H), 7.42 (d, J=7 Hz, 2H), 7.82 (d, J=7 Hz, 2H), 8.15 (s, 2H); MS (ESI) m/z 467 (M+H)$^+$.

Example 30

(7R,8aS)-7-[(5-cyclopropylpyrazin-2-yl)oxy]-2-{[3-(difluoromethoxy)-phenyl]sulfonyl}octahydropyrrolo[1,2-a]pyrazine The title compound was prepared using the procedure described in Example 27C substituting 3-(difluoromethoxy)benzene-1-sulfonyl chloride for 2-(trifluoromethyl)-benzene-1-sulfonyl chloride. $^1$H NMR (400 MHz, DMSO-d$_6$) δ ppm 0.80 (m, 2H), 0.92 (m, 2H), 1.84 (m, 2H), 2.09 (m, 1H), 2.22 (m, 2H), 2.33 (m, 1H), 2.52 (m, 1H), 2.78 (m, 1H), 2.99 (m, 1H), 3.64 (m, 2H), 3.82 (m, 1H), 5.25 (m, 1H), 7.20-7.70 (m, 4H), 8.15 (s, 2H); MS (ESI) m/z 467 (M+H)$^+$.

Example 31

(7R,8aS)-7-[(5-cyclopropylpyrazin-2-yl)oxy]-2-[(2-fluorophenyl)sulfonyl]-octahydropyrrolo[1,2-a]pyrazine The title compound was prepared using the procedure described in Example 27C substituting 2-fluorobenzene-1-sulfonyl chloride for 2-(trifluoromethyl)benzene-1-sulfonyl chloride. $^1$H NMR (400 MHz, DMSO-d$_6$) δ ppm 0.82 (m, 2H), 0.92 (m, 2H), 1.84 (m, 2H), 2.09 (m, 1H), 2.22 (m, 2H), 2.33 (m, 1H), 2.52 (m, 1H), 2.78 (m, 1H), 2.99 (m, 1H), 3.64 (m, 2H), 3.82 (m, 1H), 5.25 (m, 1H), 7.47 (m, 2H), 7.80 (m, 2H), 8.15 (s, 2H); MS (ESI) m/z 419 (M+H)$^+$.

Example 32

(7R,8aS)-7-[(5-cyclopropylpyrazin-2-yl)oxy]-2-{[2-fluoro-5-(trifluoromethyl)phenyl]sulfonyl}octahydropyrrolo[1,2-a]pyrazine The title compound was prepared using the procedure described in Example 27C substituting 2-fluoro-5-(trifluoromethyl)benzene-1-sulfonyl chloride for 2-(trifluoromethyl)benzene-1-sulfonyl chloride. $^1$H NMR (400 MHz, DMSO-d$_6$) δ ppm 0.82 (m, 2H), 0.92 (m, 2H), 1.84 (m, 2H), 2.09 (m, 1H), 2.22 (m, 2H), 2.33 (m, 1H), 2.52 (m, 1H), 2.78 (m, 1H), 2.99 (m, 1H), 3.64 (m, 2H), 3.82 (m, 1H), 5.25 (m, 1H), 7.80 (m, 1H), 8.02 (m, 1H), 8.15 (s, 2H), 8.22 (m, 1H); MS (ESI) m/z 487 (M+H)$^+$.

Example 33

(7R,8aS)-7-[(5-cyclopropylpyrazin-2-yl)oxy]-2-(2-furylsulfonyl)octahydropyrrolo[1,2-a]pyrazine The title compound was prepared using the procedure described in Example 27C substituting furan-2-sulfonyl chloride for 2-(trifluoromethyl)benzene-1-sulfonyl chloride. $^1$H NMR (400 MHz, DMSO-d$_6$) δ ppm 0.82 (m, 2H), 0.92 (m, 2H), 1.84 (m, 2H), 2.09 (m, 1H), 2.22 (m, 2H), 2.33 (m, 1H), 2.52 (m, 1H), 2.78 (m, 1H), 2.99 (m, 1H), 3.64 (m, 2H), 3.82 (m, 1H), 5.25 (m, 1H), 6.76 (m, 1H), 7.22 (m, 1H), 8.05 (m, 1H), 8.10 (s, 2H); MS (ESI) m/z 391 (M+H)$^+$.

Example 34

(7R,8aS)-7-[(5-cyclopropylpyrazin-2-yl)oxy]-2-{[3-(trifluoromethoxy)-phenyl]sulfonyl}octahydropyrrolo[1,2-a]pyrazine The title compound was prepared using the procedure described in Example 27C substituting 3-(trifluoromethoxy)benzene-1-sulfonyl chloride for 2-(trifluoromethyl)-benzene-1-sulfonyl chloride. $^1$H NMR (400 MHz, DMSO-d$_6$) δ ppm 0.80 (m, 2H), 0.92 (m, 2H), 1.84 (m, 2H), 2.09 (m, 1H), 2.22 (m, 2H), 2.33 (m, 1H), 2.52 (m, 1H), 2.78 (m, 1H), 2.99 (m, 1H), 3.64 (m, 2H), 3.82 (m, 1H), 5.25 (m, 1H), 7.70 (m, 1H), 7.81 (m, 3H), 8.10 (s, 2H); MS (ESI) m/z 485 (M+H)$^+$.

Example 35

(8R*,8aS*)-8-[(5-chloropyridin-2-yl)oxy]-2-{[3-(trifluoromethyl)phenyl]-sulfonyl}octahydropyrrolo[1,2-a]pyrazine Example 35A 1-tert-butyl 3-methyl 4-(3-methoxy-3-oxopropyl)piperazine-1,3-dicarboxylate To a solution of 1-tert-butyl 3-methyl piperazine-1,3-dicarboxylate hydrochloride, (200 g, 0.82 mol) in methanol (1 L) was added methyl acrylate (214 g, 2.46 mol) with stirring at approximately 25° C. under N$_2$ atmosphere, and the reaction mixture was refluxed at 70° C. for 48 hours. The volatiles were removed under reduced pressure, and the residue was partitioned between ethyl acetate (1.2 L) and water (2 L). The organic layer was separated and washed with water (1 L×2)

and brine (500 mL), dried over Na$_2$SO$_4$, filtered and concentrated. The crude obtained was purified by column chromatography over silica gel using 30-40% ethyl acetate in petroleum ether to give the title compound. $^1$H NMR (300 MHz, CDCl$_3$) δ ppm 11.43 (s, 9H), 2.20-2.34 (m, 1H), 2.35-2.46 (m, 1H), 2.48 (t, 2H, J=7.2 Hz), 2.76-2.90 (m, 1H), 2.90-3.12 (m, 2H), 3.12-3.30 (m, 1H), 3.32 (t, 1H, J=4.5 Hz), 3.35-3.44 (m, 1H), 3.67 (s, 3H), 3.71 (s, 3H) 3.83-3.94 (m, 1H).

Example 35B 2-tert-butyl 7-methyl 8-oxohexahydropyrrolo[1,2-a]
pyrazine-2,7(111)-dicarboxylate To a solution of 1-tert-butyl 3-methyl 4-(3-methoxy-3-oxopropyl)piperazine-1,3-dicarboxylate (Example 35A, 180 g, 0.545 mol) in tetrahydrofuran (1.3 L) was added potassium t-butoxide (98 g, 0.872 mol) with stirring at 0-5° C. under N$_2$ atmosphere portion-wise over a period of 30 minutes. The reaction mixture was stirred at ambient temperature for 2 hours. The reaction was then quenched with saturated aqueous ammonium chloride solution (500 mL) and extracted with ethyl acetate (1 L). The organic layer was separated, washed with brine (500 mL), dried over Na$_2$SO$_4$, filtered and concentrated to afford the title compound. $^1$H NMR (300 MHz, CDCl$_3$) δ ppm 1.48 (s, 9H), 2.28-2.35 (m, 2H), 2.65-2.83 (m, 1H), 2.83-3.12 (m, 3H), 3.43 (t, 1H, J=8.4 Hz), 3.61 (t, 1H, J=8.4 Hz), 3.78 (s, 3H), 3.98-4.20 (bs, 1H), 4.20-4.45 (bs, 1H).

Example 35C tert-butyl 8-oxohexahydropyrrolo[1,2-a]pyrazine-2
(1H)-carboxylate

A mixture of 2-tert-butyl 7-methyl 8-oxohexahydropyrrolo[1,2-a]pyrazine-2,7(1H)-dicarboxylate (Example 35B, 131 g, 0.44 mol), dimethyl sulfoxide (530 mL), NaCl (25.6 g, 0.44 mol) and water (32 g, 1.75 mol) was heated to 130° C. and maintained at that temperature for 2 hours. The reaction mixture was cooled, diluted with water (1 L) and extracted with ethyl acetate (1 L×2). The combined organic layers were dried over Na$_2$SO$_4$, filtered and concentrated. The residue was chromatographed over silica gel eluting with 30-40% ethyl acetate in petroleum ether to afford the title compound. $^1$H NMR (300 MHz, CDCl$_3$) δ ppm 1.48 (s, 9H), 2.23-2.42 (m, 3H), 2.47-2.60 (m, 1H), 2.60-2.78 (m, 1H), 2.82-2.98 (m, 1H), 3.02-3.10 (m, 1H), 3.32-3.40 (m, 1H), 3.65-3.85 (m, 1H), 3.99-4.20 (bs, 1H), 4.20-4.45 (bs, 1H).

Example 35D (8R*,8aS*)-tert-Butyl 8-hydroxyhexahydropyrrolo
[1,2-a]pyrazine-2(1H)-carboxylate To a solution of Example 35C (46 g, 0.192 mol) in methanol (460 mL) was added NaBH$_4$ (13 g, 0.345 mol) at approximately 0° C., and the mixture was stirred at ambient temperature for 1 hour. The reaction mixture was quenched with saturated ammonium chloride solution (100 mL), and the volatiles were removed under reduced pressure. The residue obtained was partitioned between ethyl acetate (500 mL) and water (250 mL). The organic layer was separated, dried over Na$_2$SO$_4$, filtered and concentrated. The material obtained was purified by column chromatography over silica gel using 5-6% methanol in chloroform to get the first eluting product (Example 36A, 5.3 g) and second eluting product (Example 35D, 5.1 g) together with 20 g of a mixture of both diastereomers.

By repeating the chromatography procedure, more of Example 36A was collected. The mixture of diastereomers (enriched with Example 35D) was derivatized to benzoyl derivative and separated as described below.

Example 35E (8R*,8aS*)-tert-butyl 8-(benzoyloxy)hexahydropyrrolo[1,2-a]pyrazine-2(1H)-carboxylate To a solution of a mixture of diastereomers Example 35D and Example 36A (33 g, 0.136 mol) in dichloromethane and pyridine (1:1, 300 mL) was added 4-(dimethylamino)pyridine (4 g, 0.034 mol) and then benzoyl chloride (30 g, 0.163 mol) at 0° C. under a N$_2$ atmosphere. The reaction mixture was stirred at ambient temperature for 2 hours and then concentrated to remove the volatiles. The residue was taken into ethyl acetate (500 mL) and then washed with water (250 mL×2), 5% citric acid in water (250 mL×2), and brine (100 mL), dried over anhydrous Na$_2$SO$_4$, filtered and concentrated under reduced pressure. The residue was purified over silica gel using 20% ethyl acetate in petroleum ether to get the first eluting compound (Example 35E, found to be Example 35D after saponification, 13.5 g) and a mixture of Example 35E and its diastereomer (15 g). 1H NMR (300 MHz, CDCl$_3$) δ ppm 1.48 (s, 9H), 1.72-1.88 (m, 1H), 2.18-2.32 (m, 2H), 2.40-2.60 (m, 2H), 2.63-2.85 (m, 1H), 2.85-3.06 (m, 2H), 3.06-3.18 (m, 1H), 4.06 (bs, 1H), 3.38 (bs, 1H), 5.02-5.12 (m, 1H), 7.46 (t, 2H, J=7.5 Hz), 7.9 (t, 1H, J=7.5 Hz), 8.06 (d, 2H, J=7.5 Hz).

Mixtures of the diastereomeric esters were subjected to further chromatographic passes to obtain additional quantities of each diastereomer.

Example 35D

From Saponification of Example 35E (8R*,8aS*)-tert-Butyl 8-hydroxyhexahydropyrrolo
[1,2-a]pyrazine-2(1H)-carboxylate To a solution of Example 35E (8 g, 0.023 mol) in methanol (25 mL) was added potassium t-butoxide (14.5 g, 0.129 mol), and the reaction mixture was stirred at room temperature for 30 minutes. The reaction mixture was concentrated, the residue was diluted with 5% citric acid in water (100 mL), and the mixture was extracted with ethyl acetate (50 mL×2). The combined organic layers were discarded. The aqueous layer was basified using K$_2$CO$_3$ to pH 8-9 and extracted with ethyl acetate (50 mL×2). The combined organic layers were dried over Na$_2$SO$_4$ and concentrated to give the title compound. $^1$H NMR (300 MHz, CDCl$_3$) δ ppm 1.48 (s, 9H), 1.56-1.69 (m, 1H), 1.86-1.97 (m, 1H), 2.10-2.35 (m, 3H), 2.35-2.48 (m, 1H), 2.52-2.72 (m, 1H), 2.78-2.97 (m, 2H), 3.03 (dt, 1H, J=17.1, 2.4 Hz), 3.92-4.15 (m, 2H), 4.32 (bs, 1H).

The same procedure was applied to the diastereomer to provide additional Example 36A.

Example 35F (8R*,8aS*)-8-(5-chloropyridin-2-yloxy)octahydropyrrolo[1,2-a]pyrazine (8R*,8aS*)-tert-Butyl 8-hydroxyhexahydropyrrolo[1,2-a] pyrazine-2(1H)-carboxylate (Example 35D, 0.969 g, 4.0 mmol) and 2,5-dichloropyridine (0.651 g, 4.40 mmol) were treated with potassium tert-butoxide (0.987 g, 8.80 mmol) in dry tetrahydrofuran (5 mL). The mixture was heated to 80° C. and stirred for 16 hours. After the mixture cooled to room temperature, the mixture was purified via HPLC (Gilson®, Xbridge™ 30×100 mm column, eluted with pH=10 aqueous ammonium bicarbonate-ammonium hydroxide/methanol, UV=222 nm) to give the tert-butoxycarbonyl protected product, tert-butyl 8-(5-chloropyridin-2-yloxy)hexahydropyrrolo [1,2-a]pyrazine-2(1H)-carboxylate. This tert-butoxycarbonyl compound was dissolved in dichloromethane (5 mL) and trifluoroacetic acid (2 mL) was added. The reaction mixture was stirred at room temperature for 3 hours. The mixture was concentrated and then purified via HPLC (Gilson®, Xbridge™ 30×100 mm column, eluted with pH=10 aqueous ammonium bicarbonate-ammonium hydroxide/methanol, UV=220 nm) to give the title compound. $^1$H NMR (300 MHz, methanol-$d_4$) δ ppm 1.72-1.86 (m, 1H), 2.08-2.22 (m, 3H), 2.31-2.45 (m, 1H), 2.69-2.80 (m, 2H), 2.87-2.98 (m, 1H), 2.99-3.21 (m, 3H), 5.51 (ddd, 1H, J=7, 4, 2 Hz), 6.77 (d, 1H, J=9 Hz), 7.65 (dd, 1H, J=8, 2 Hz), 8.07 (d, 1H, J=2 Hz); MS (DCI) m/z 254 (M+H)$^+$.

Example 35G (8R*,8aS*)-8-[(5-chloropyridin-2-yl)oxy]-2-{[3-(trifluoromethyl)phenyl]-sulfonyl}octahydropyaolo [1,2-a]pyrazine To a mixture of Example 35F (120 mg, 0.473 mmol) in dry $CH_2Cl_2$ was added 3-(trifluoromethyl)benzene-1-sulfonyl chloride (139 mg, 0.568 mmol) followed by triethylamine (0.3 mL). The resultant mixture was stirred at room temperature for 16 hours and then purified by preparative HPLC (Gilson®, Xbridge™ 30×100 mm column, eluted with pH=10 aqueous ammonium bicarbonate-ammonium hydroxide/methanol, UV=222 nm) to give the title compound. $^1$H NMR (300 MHz, methanol-$d_4$) δ ppm 1.65-1.78 (m, 1H), 2.29-2.55 (m, 6H), 2.98-3.09 (m, 2H), 3.72-3.82 (m, 1H), 4.04 (ddd, 1H, J=17, 9, 1 Hz), 4.94-5.04 (m, 1H), 6.81 (d, 1H, J=8 Hz), 7.68 (dd, 1H, J=8, 2 Hz), 7.84 (t, 1H, J=8 Hz), 7.98-8.10 (m, 4H); MS (DCI) m/z 462 (M+H)$^+$.

Example 36

(8R*,8aR*)-8-[(5-chloropyridin-2-yl)oxy]-2-{[3-(trifluoromethyl)phenyl]-sulfonyl}octahydropyrrolo [1,2-a]pyrazine (8R*,8aR*)-tert-Butyl 8-hydroxyhexahydropyrrolo [1,2-a]pyrazine-2(1H)-carboxylate The title compound was prepared as described in Examples 35A through 35D. Example 36A was obtained as the faster eluting diastereomer in Example 35D. Additional quantities of Example 36A were obtained using the procedures described in Example 35E followed by the saponification procedure described for Example 35D. $^1$H NMR (300 MHz, $CDCl_3$) δ ppm 1.48 (s, 9H), 1.68-1.85 (m, 2H), 1.85-2.00 (bs, 1H), 2.00-2.17 (m, 2H), 2.18-2.30 (m, 1H), 2.78-2.98 (m, 2H), 3.03 (d, 1H, J=11.1 Hz), 3.20 (dt, 1H, J=17.7, 2.4 Hz), 4.07 (bs, 1H), 4.15-4.32 (m, 2H).

(8R*,8aR*)-8-(5-chloropyridin-2-yloxy)octahydropyrrolo[1,2-a]pyrazine (8R*,8aR*)-tert-Butyl 8-hydroxyhexahydropyrrolo[1,2-a]pyrazine-2(1H)-carboxylate (Example 36A, 0.969 g, 4.0 mmol) and 2,5-dichloropyridine (0.651 g, 4.40 mmol) were treated with potassium tert-butoxide (0.987 g, 8.80 mmol) in dry tetrahydrofuran (5 mL). The mixture was heated to 80° C. and stirred for 16 hours. After the mixture cooled to room temperature, the mixture was purified via HPLC (Gilson®, Xbridge™ 30×100 mm column, eluted with pH=10 aqueous ammonium bicarbonate-ammonium hydroxide/methanol, UV=222 nm) to give the tert-butoxycarbonyl protected product, (8R*,8aR*)-tert-butyl 8-(5-chloropyridin-2-yloxy) hexahydropyrrolo[1,2-a]pyrazine-2(1H)-carboxylate. This tert-butoxycarbonyl compound was dissolved in dichloromethane (5 mL) and trifluoroacetic acid (2 mL) was added. The reaction mixture was stirred at room temperature for 3 hours. The mixture was concentrated and then purified via HPLC (Gilson®, Xbridge™ 30×100 mm column, eluted with pH=10 aqueous ammonium bicarbonate-ammonium hydroxide/methanol, UV=220 nm) to give the title compound. $^1$H NMR (300 MHz, methanol-$d_4$) δ ppm 1.72-1.86 (m, 1H), 2.08-2.22 (m, 3H), 2.31-2.45 (m, 1H), 2.69-2.80 (m, 2H), 2.87-2.98 (m, 1H), 2.99-3.21 (m, 3H), 5.51 (ddd, 1H, J=7, 4, 2 Hz), 6.77 (d, 1H, J=9 Hz), 7.65 (dd, 1H, J=8, 2 Hz), 8.07 (d, 1H, J=2 Hz); MS (DCI) m/z 254 (M+H)$^+$.

Example 36C (8R*,8aR*)-8-[(5-chloropyridin-2-yl)oxy]-2-{[3-(trifluoromethyl)phenyl]-sulfonyl}octahydropyrrolo [1,2-a]pyrazine The title compound was prepared according to the procedure described in Example 35G substituting Example 36B for Example 35F. $^1$H NMR (300 MHz, methanol-$d_4$) δ ppm 1.74-1.88 (m, 1H), 2.12-2.49 (m, 6H), 3.09-3.18 (m, 2H), 3.76 (dd, 1H, J=11, 2 Hz), 3.89 (d, 1H, J=8 Hz), 5.54 (ddd, 1H, J=7, 4, 2 Hz), 6.65 (d, 1H, J=8 Hz), 7.65 (dd, 1H, J=8, 2 Hz), 7.82 (t, 1H, J=7 Hz), 7.90 (s, 1H), 7.95-8.02 (m, 2H), 8.12 (d, 1H, J=2 Hz); MS (DCI) m/z 462 (M+H)$^+$.

Example 37

(7S,8aS)—N-(diphenylmethyl)-2-{[3-(trifluoromethyl)phenyl]-sulfonyl}-octahydropyrrolo[1,2-a] pyrazine-7-carboxamide Example 37A (7S,8aS)-tert-butyl 7-(benzhydrylcarbamoyl)hexahydropyrrolo[1,2-a]-pyrazine-2(1H)-carboxylate To a solution of (7S,8aS)-2-(tert-butoxycarbonyl)octahydropyrrolo[1,2-a]pyrazine-7-carboxylic acid (80 mg, 0.296 mmol) in dichloromethane (2 mL) was added a solution of 1-ethyl-3-(3-dimethylaminopropyl) carbodiimide (68.9 mg, 0.444 mmol) and hydroxybenzotriazole hydrate (40.0 mg, 0.296 mmol) in dichloromethane (1 mL). The mixture was stirred at room temperature for 1 hour, and then diphenylmethanamine (54.2 mg, 0.296 mmol) was added. After stirring for three days the mixture was poured into water (10 mL). The mixture was extracted with dichloromethane (3×5 mL). The organic fractions were concentrated, and the residue was purified by flash chromatography (dichloromethane/methanol=25:1) to give the title compound. MS (ESI) m/z 436 (M+H)$^+$.

Example 37B (7S,8aS)—N-benzhydryloctahydropyrrolo[1,2-a] pyrazine-7-carboxamide

To Example 37A (109 mg, 0.25 mmol) in dichloromethane (0.5 mL) was added hydrochloric acid (0.5 mL, 4 N in dioxane). The mixture was stirred at room temperature overnight and concentrated to give the title compound as a hydrochloric acid salt. MS (ESI) m/z 336 (M+H)$^+$.

Example 37C (7S,8aS)—N-(diphenylmethyl)-2-{[3-(trifluoromethyl)phenyl]sulfonyl}-octahydropyrrolo[1,2-a]pyrazine-7-carboxamide To a solution of Example 37B (50 mg, 0.134 mmol) in dichloromethane (1 mL) was added 3-(trifluoromethyl)benzene-1-sulfonyl chloride (32.9 mg, 0.134 mmol) followed by triethylamine (0.2 mL). The mixture was stirred at room temperature overnight and then concentrated. The residue was purified by flash chromatography (dichloromethane/methanol=50:1) to give the title compound. $^1$H NMR (500 MHz, DMSO-d$_6$) δ ppm 1.58 (m, 1H), 2.03 (m, 1H), 2.27-2.41 (m, 5H), 2.86 (m, 1H), 3.06 (m, 1H), 3.22 (m, 1H), 3.78 (m, 1H), 3.90 (m, 1H), 6.10 (m, 1H), 7.08 (m, 2H), 7.15 (m, 4H), 7.26 (m, 4H), 7.70 (m, 1H), 7.90 (m, 3H), 8.00 (s, 1H); MS (ESI) m/z 544 (M+H)$^+$.

Example 38

(7S,8aS)—N-(diphenylmethyl)-2-{[4-(trifluoromethyl)phenyl]sulfonyl}-octahydropyrrolo[1,2-a]pyrazine-7-carboxamide The title compound was prepared according to the procedure described in Example 37C substituting 4-(trifluoromethyl)benzene-1-sulfonyl chloride for 3-(trifluoromethyl)benzene-1-sulfonyl chloride. $^1$H NMR (500 MHz, DMSO-d$_6$) δ ppm 1.25 (m, 1H), 2.03 (m, 1H), 2.27-2.41 (m, 5H), 2.86 (m, 1H), 3.06 (m, 1H), 3.22 (m, 1H), 3.78 (m, 1H), 3.90 (m, 1H), 6.10 (m, 1H), 7.10 (m, 5H), 7.26 (m, 5H), 7.84 (m, 2H), 7.87 (m, 2H); MS (ESI) m/z 544 (M+H)$^+$.

Example 39

(7S,8aS)—N-(diphenylmethyl)-2-{[4-fluoro-3-(trifluoromethyl)phenyl]-sulfonyl}octahydropyrrolo[1,2-a]pyrazine-7-carboxamide The title compound was prepared according to the procedure described in Example 37C substituting 4-fluoro-3-(trifluoromethyl)benzene-1-sulfonyl chloride for 3-(trifluoromethyl)benzene-1-sulfonyl chloride. $^1$H NMR (500 MHz, DMSO-d$_6$) δ ppm 1.25 (m, 1H), 2.03 (m, 1H), 2.27-2.41 (m, 5H), 2.86 (m, 1H), 3.06 (m, 1H), 3.22 (m, 1H), 3.78 (m, 1H), 3.90 (m, 1H), 6.10 (m, 1H), 7.10 (m, 5H), 7.26 (m, 5H), 7.97 (m, 3H); MS (ESI) m/z 562 (M+H)$^+$.

Example 40

(7S,8aS)—N-(4,4,4-trifluorobutyl)-2-{[3-(trifluoromethyl)phenyl]-sulfonyl}octahydropyrrolo[1,2-a]pyrazine-7-carboxamide The title compound was prepared according to the procedure described in Example 37 substituting 4,4,4-trifluorobutan-1-amine for diphenylmethanamine $^1$H NMR (500 MHz, DMSO-d$_6$) δ ppm 1.50-2.50 (m, 11H), 3.18 (m, 5H), 3.85 (m, 2H), 7.71 (m, 1H), 7.88 (m, 1H), 7.96 (m, 1H), 8.03 (s, 1H); MS (ESI) m/z 488 (M+H)$^+$.

Example 41

(7S,8aS)-7-[4-(trifluoromethoxy)phenoxy]-2-{[3-(trifluoromethyl)phenyl]-sulfonyl}octahydropyrrolo[1,2-a]pyrazine To a solution of Example 19 (92 mg, 0.26 mmol), 4-(trifluoromethoxy)phenol (47 mg, 0.26 mmol), and triphenylphosphine (104 mg, 0.396 mmol) in anhydrous tetrahydrofuran (1.2 mL) at ambient temperature was added diisopropyl azodicarboxylate (0.080 mL, 0.39 mmol) dropwise. The reaction was allowed to stir for 16 hours and then the mixture was concentrated. The residue was purified via flash chromatography (0% to 70% ethyl acetate/hexanes). This material was triturated with diethyl ether and the solvent was decanted. The resulting solid was dried to afford the title compound. $^1$H NMR (300 MHz, DMSO-d$_6$) δ ppm 1.40-1.27 (m, 1H), 2.23-2.02 (m, 3H), 2.47-2.35 (m, 3H), 3.08-2.95 (m, 2H), 3.67 (d, 1H, J=11 Hz), 3.82 (d, 1H, J=10 Hz), 4.90-4.79 (m, 1H), 6.90 (d, 2H, J=9 Hz), 7.24 (d, 2H, J=8 Hz), 7.91 (t, 1H, J=8 Hz), 7.98 (s, 1H), 8.08 (d, 1H, J=8.0), 8.14 (d, 1H, J=8 Hz); MS (ESI+) m/z 511 (M+H)$^+$.

Example 42

(7S,8aS)-7-(4-tert-butylphenoxy)-2-{[3-(trifluoromethyl)phenyl]-sulfonyl}octahydropyrrolo[1,2-a]pyrazine The title compound was prepared according to the procedure described in Example 41 substituting 4-tert-butylphenol for 4-(trifluoromethoxy)phenol. $^1$H NMR (300 MHz, DMSO-d$_6$) δ ppm 1.22 (s, 9H), 1.38-1.26 (m, 1H), 2.22-2.01 (m, 3H), 2.48-2.33 (m, 3H), 3.06-2.93 (m, 2H), 3.66 (d, 1H, J=11 Hz), 3.81 (d, 1H, J=10 Hz), 4.83-4.72 (m, 1H), 6.72 (d, 2H, J=9 Hz), 7.24 (d, 2H, J=9 Hz), 7.91 (t, 1H, J=8 Hz), 7.97 (s, 1H), 8.08 (d, 1H, J=8 Hz), 8.14 (d, 1H, J=8 Hz); MS (ESI+) m/z 483 (M+H)$^+$.

Example 43

(7S,8aS)-7-[4-(1H-imidazol-1-yl)phenoxy]-2-{[3-(trifluoromethyl)phenyl]-sulfonyl}octahydropyrrolo[1,2-a]pyrazine The title compound was prepared according to the procedure described in Example 41 substituting 4-(1H-imidazol-1-yl)phenol for 4-(trifluoromethoxy)phenol. $^1$H NMR (300 MHz, DMSO-d$_6$) δ ppm 1.42-1.29 (m, 1H), 2.24-2.02 (m, 3H), 2.48-2.36 (m, 3H), 3.09-2.94 (m, 2H), 3.73-3.62 (m, 1H), 3.89-3.78 (m, 1H), 4.94-4.83 (m, 1H), 6.98-6.89 (m, 2H), 7.08-7.03 (m, 1H), 7.54-7.45 (m, 2H), 7.65-7.57 (m, 1H), 7.96-7.87 (m, 1H), 7.98 (s, 1H), 8.18-8.04 (m, 3H); MS (ESI+) m/z 493 (M+H).

Example 44

(7R,8aS)-7-[(6-cyclopropylpyridazin-3-yl)oxy]-2-{[3-(trifluoromethyl)-phenyl]sulfonyl}octahydropyrrolo[1,2-a]pyrazine To a solution of Example 19 (220 mg, 0.628 mmol) in tetrahydrofuran (5 mL) was added potassium tert-butoxide (1 mL, 1 M in tetrahydrofuran, 1 mmol) followed by a solution of 3-chloro-6-cyclopropylpyridazine (121 mg, 0.785 mmol) in tetrahydrofuran (1 mL). The mixture was stirred at room temperature for 18 hours. The mixture was concentrated, and the residue was purified by chromatography on silica gel (ethyl acetate) to give the title compound. $^1$H NMR (400 MHz, DMSO-d$_6$) δ ppm 0.90-1.02 (m, 4H), 1.78-1.92 (m, 2H), 2.08-2.42 (m, 6H), 2.99 (m, 1H), 3.60 (m, 1H), 3.65 (m, 1H), 3.82 (m, 1H), 5.35 (m, 1H), 7.05 (d, 1H, J=5 Hz), 7.42 (d, 1H, J=5 Hz), 7.92 (m, 2H), 8.12 (m, 2H); MS (ESI) m/z 469 (M+H)$^+$.

Example 45

(7R,8aS)-7-[(6-cyclopropylpyridazin-3-yl)oxy]-2-{ [4-(trifluoromethyl)-phenyl] sulfonyl}octahydropyrrolo[1,2-a]pyrazine The title compound was prepared according to the procedure described in Example 17E substituting (7R,8aS)-octahydropyrrolo[1,2-a]pyrazin-7-ol for (7S,8aR)-octahydropyrrolo[1,2-a]pyrazin-7-ol and substituting 4-(trifluoromethyl)benzene-1-sulfonyl chloride for 3-(trifluoromethyl)benzene-1-sulfonyl chloride followed by the procedure described in Example 18 substituting 3-chloro-6-cyclopropylpyridazine for 2-bromo-5-cyclopropylpyrazine. $^1$H NMR (400 MHz, DMSO-d$_6$) δ ppm 0.93-1.03 (m, 4H), 1.80 (m, 1H), 1.92 (m, 1H), 2.08-2.43 (m, 6H), 2.99 (m, 1H), 3.61 (m, 2H), 3.81 (m, 1H), 5.18 (m, 1H), 7.05 (d, 1H, J=5 Hz), 7.42 (d, 1H, J=5 Hz), 7.96 (d, 2H, J=7 Hz), 8.04 (d, 2H, J=7 Hz); MS (ESI) m/z 469 (M+H)$^+$.

Example 46

(7R,8aS)-7-[(4-cyclopropylpyrimidin-2-yl)oxy]-2-{ [3-(trifluoromethyl)-phenyl] sulfonyl}octahydropyrrolo[1,2-a]pyrazine The title compound was prepared according to the procedure described in Example 17E substituting (7R,8aS)-octahydropyrrolo[1,2-a]pyrazin-7-ol for (7S,8aR)-octahydropyrrolo[1,2-a]pyrazin-7-ol followed by the procedure described in Example 18 substituting 2-chloro-4-cyclopropylpyrimidine for 2-bromo-5-cyclopropylpyrazine. $^1$H NMR (400 MHz, DMSO-d$_6$) δ ppm 1.00 (m, 4H), 1.76 (m, 1H), 1.88 (m, 1H), 2.08-2.42 (m, 6H), 2.99 (m, 1H), 3.51 (m, 1H), 3.68 (m, 1H), 3.82 (m, 1H), 5.16 (m, 1H), 7.05 (d, 1H, J=5 Hz), 7.93 (m, 2H), 8.11 (m, 2H), 8.32 (d, 1H, J=5 Hz); MS (ESI) m/z 469 (M+H)$^+$.

Example 47

(7R,8aS)-7-[(4-cyclopropylpyrimidin-2-yl)oxy]-2-{ [4-(trifluoromethyl)-phenyl] sulfonyl}octahydropyrrolo[1,2-a]pyrazine The title compound was prepared according to the procedure described in Example 17E substituting (7R,8aS)-octahydropyrrolo[1,2-a]pyrazin-7-ol for (7S,8aR)-octahydropyrrolo[1,2-a]pyrazin-7-ol and substituting 4-(trifluoromethyl)benzene-1-sulfonyl chloride for 3-(trifluoromethyl)benzene-1-sulfonyl chloride followed by the procedure described in Example 18 substituting 2-chloro-4-cyclopropylpyrimidine for 2-bromo-5-cyclopropylpyrazine. $^1$H NMR (400 MHz, DMSO-d$_6$) δ ppm 1.02 (m, 4H), 1.75 (m, 1H), 1.90 (m, 1H), 2.05-2.43 (m, 6H), 2.98 (m, 1H), 3.51 (m, 1H), 3.62 (m, 1H), 3.81 (m, 1H), 5.17 (m, 1H), 7.05 (d, 1H, J=5 Hz), 7.96 (d, 2H, J=7 Hz), 8.04 (d, 2H, J=7 Hz); MS (ESI) m/z 469 (M+H)$^+$.

Example 48

1-(4-{[(7R,8aS)-7-[(5-cyclopropylpyrazin-2-yl)oxy] hexahydropyrrolo[1,2-a]-pyrazin-2(1H)-yl] sulfonyl}phenyl)ethanone The title compound was prepared according to the procedure described in Example 27C substituting 4-acetylbenzene-1-sulfonyl chloride for 2-(trifluoromethyl)-benzene-1-sulfonyl chloride. $^1$H NMR (400 MHz, DMSO-d$_6$) δ ppm 0.80 (m, 2H), 0.92 (m, 2H), 1.72 (m, 1H), 1.90 (m, 1H), 2.05-2.40 (m, 6H), 2.64 (s, 3H), 2.98 (m, 1H), 3.55 (m, 1H), 3.62 (m, 1H), 3.80 (m, 1H), 5.20 (m, 1H), 7.88 (d, 2H, J=7 Hz), 8.11 (s, 2H), 8.38 (d, 2H, J=7 Hz); MS (ESI) m/z 443 (M+H)$^+$.

Example 49

(7S,8aS)-7-[(5-cyclopropylpyrazin-2-yl)oxy]-2-{[3-(trifluoromethyl)-phenyl]sulfonyl}octahydropyrrolo [1,2-a]pyrazine

Example 49A (7S,8aS)-tert-butyl 7-(5-cyclopropylpyrazin-2-yloxy) hexahydropyrrolo[1,2-a]pyrazine-2(1H)-carboxylate To a solution of (7S,8aS)-tert-butyl 7-hydroxyhexahydropyrrolo[1,2-a]pyrazine-2(1H)-carboxylate (Wuxi Pharma, 0.485 g, 2 mmol) in tetrahydrofuran (0.3 mL) was added potassium tert-butoxide (2.8 mL, 1 M in tetrahydrofuran, 2.8 mmol) followed by a solution of 2-bromo-5-cyclopropylpyrazine (446 mg, 2.24 mmol) in tetrahydrofuran (1 mL). The mixture was stirred at room temperature for 16 hours. The mixture was concentrated, and the residue was purified by chromatography on silica gel (ethyl acetate) to give the titled compound. $^1$H NMR (400 MHz, DMSO-d$_6$) δ ppm 0.80 (m, 2H), 0.92 (m, 2H), 1.39 (s, 9H), 1.90 (m, 2H), 2.09 (m, 1H), 2.40 (m, 3H), 2.90 (m, 2H), 3.08 (m, 1H), 3.28 (m, 1H), 3.86-4.08 (m, 2H), 5.27 (m, 1H), 8.11 (m, 2H); MS (ESI) m/z 361 (M+H)$^+$.

Example 49B (7S,8aS)-7-[(5-cyclopropylpyrazin-2-yl)oxy]octahydropyrrolo[1,2-a]pyrazine To Example 49A (640 mg, 1.776 mmol) in dichloromethane (2 mL) was added hydrochloric acid (3 mL, 4 N in dioxane). The mixture was stirred at room temperature overnight and concentrated to give the compound as a hydrochloric acid salt. MS (ESI) m/z 261 (M+H)$^+$.

Example 49C (7S,8aS)-7-[(5-cyclopropylpyrazin-2-yl)oxy]-2-{[3-(trifluoromethyl)-phenyl]sulfonyl}octahydropyrrolo [1,2-a]pyrazine To a solution of Example 49B (200 mg, 0.674 mmol)) in dichloromethane (3 mL) was added 3-(trifluoromethyl)benzene-1-sulfonyl chloride (198 mg, 0.809 mmol) followed by triethylamine (0.3 mL). The mixture was stirred at room temperature overnight and then concentrated. The residue was purified by flash chromatography (ethyl acetate/hexane=1:1) to give the title compound. $^1$H NMR (400 MHz, DMSO-d$_6$) δ ppm 0.80 (m, 2H), 0.92 (m, 2H), 1.38 (m, 1H), 2.04-2.20 (m, 4H), 2.42 (m, 3H), 3.00 (m, 2H), 3.66 (m, 1H), 3.82 (m, 1H), 5.20 (m, 1H), 7.92 (m, 1H), 7.98 (m, 1H), 8.03 (m, 1H), 8.11 (m, 3H); MS (ESI) m/z 469 (M+H)+.

Example 50

(7S,8aS)-7-[(5-cyclopropylpyrazin-2-yl)oxy]-2-{[4-(trifluoromethyl)phenyl]-sulfonyl}octahydropyrrolo[1,2-a]pyrazine The title compound was prepared according to the procedure described in Example 49C substituting 4-(trifluoromethyl)benzene-1-sulfonyl chloride for 3-(trifluoromethyl)benzene-1-sulfonyl chloride $^1$H NMR (400 MHz, DMSO-$d_6$) δ ppm 0.80 (m, 2H), 0.92 (m, 2H), 1.38 (m, 1H), 2.04-2.20 (m, 4H), 2.42 (m, 3H), 3.00 (m, 1H), 3.57 (m, 1H), 3.66 (m, 1H), 3.82 (m, 1H), 5.20 (m, 1H), 7.80 (m, 2H), 8.02 (m, 3H), 8.11 (s, 1H); MS (ESI) m/z 469 (M+H)+.

Example 51

(7R,8aS)-7-[(5-cyclopropylpyrazin-2-yl)oxy]-2-{[3-fluoro-5-(trifluoromethyl)phenyl]sulfonyl}octahydropyrrolo[1,2-a]pyrazine The title compound was prepared according to the procedure described in Example 27C substituting 3-fluoro-5-(trifluoromethyl)benzene-1-sulfonyl chloride for 2-(trifluoromethyl)benzene-1-sulfonyl chloride. $^1$H NMR (400 MHz, DMSO-$d_6$) δ ppm 0.80 (m, 2H), 0.92 (m, 2H), 1.78-1.88 (m, 2H), 2.08-2.48 (m, 6H), 3.00 (m, 1H), 3.56 (m, 1H), 3.68 (m, 1H), 3.84 (m, 1H), 5.20 (m, 1H), 7.85 (m, 1H), 8.00 (m, 1H), 8.12 (s, 2H), 8.17 (m, 1H); MS (ESI) m/z 487 (M+H)+.

Example 52

(7R,8aS)-7-[(5-cyclopropylpyrazin-2-yl)oxy]-2-{[4-fluoro-3-(trifluoromethyl)phenyl]sulfonyl}octahydropyrrolo[1,2-a]pyrazine The title compound was prepared according to the procedure described in Example 27C substituting 4-fluoro-3-(trifluoromethyl)benzene-1-sulfonyl chloride for 2-(trifluoromethyl)benzene-1-sulfonyl chloride. $^1$H NMR (400 MHz, DMSO-$d_6$) δ ppm 0.80 (m, 2H), 0.90 (m, 2H), 1.78-1.88 (m, 2H), 2.06-2.48 (m, 6H), 3.00 (m, 1H), 3.56 (m, 1H), 3.68 (m, 1H), 3.84 (m, 1H), 5.20 (m, 1H), 7.85 (m, 1H), 8.00 (m, 1H), 8.11 (s, 2H), 8.17 (m, 1H); MS (ESI) m/z 487 (M+H)+.

Example 53

(7R,8aS)-2-[(3-tert-butylphenyl)sulfonyl]-7-[(5-cyclopropylpyrazin-2-yl)-oxy]octahydropyrrolo[1,2-a]pyrazine The title compound was prepared according to the procedure described in Example 27C substituting 3-tert-butylbenzene-1-sulfonyl chloride for 2-(trifluoromethyl)benzene-1-sulfonyl chloride. $^1$H NMR (400 MHz, DMSO-$d_6$) δ ppm 0.80 (m, 2H), 0.90 (m, 2H), 1.32 (s, 9H), 1.75 (m, 1H), 1.88 (m, 1H), 1.98-2.30 (m, 6H), 3.00 (m, 1H), 3.56 (m, 1H), 3.68 (m, 1H), 3.84 (m, 1H), 5.20 (m, 1H), 7.58 (m, 2H), 7.67 (s, 1H), 7.78 (m, 1H), 8.11 (s, 2H); MS (ESI) m/z 457 (M+H)+.

Example 54

(7S,8aR)-7-[(5-cyclopropylpyrazin-2-yl)oxy]-2-{[4-(trifluoromethyl)phenyl]-sulfonyl}octahydropyrrolo[1,2-a]pyrazine The title compound was prepared according to the procedure described in Example 17 substituting 4-(trifluoromethyl)benzene-1-sulfonyl chloride for 3-(trifluoromethyl)benzene-1-sulfonyl chloride followed by the procedure described in Example 18. $^1$H NMR (400 MHz, DMSO-$d_6$) δ ppm 0.80 (m, 2H), 0.92 (m, 2H), 1.38 (m, 1H), 2.04-2.20 (m, 4H), 2.42 (m, 3H), 3.57 (m, 1H), 3.00 (m, 1H), 3.66 (m, 1H), 3.82 (m, 1H), 5.20 (m, 1H), 7.98 (d, 2H, J=7 Hz), 8.03 (d, 2H, J=7 Hz), 8.15 (s, 2H); MS (ESI) m/z 469 (M+H)+.

Example 55

(7R,8aS)-2-[(3-chlorophenyl)sulfonyl]-7-[(5-cyclopropylpyrazin-2-yl)oxy]-octahydropyrrolo[1,2-a]pyrazine The title compound was prepared according to the procedure described in Example 27C substituting 3-chlorobenzene-1-sulfonyl chloride for 2-(trifluoromethyl)benzene-1-sulfonyl chloride. $^1$H NMR (400 MHz, DMSO-$d_6$) δ ppm 0.80 (m, 2H), 0.90 (m, 2H), 1.75 (m, 1H), 1.88 (m, 1H), 1.98-2.30 (m, 6H), 3.00 (m, 1H), 3.56 (m, 1H), 3.68 (m, 1H), 3.84 (m, 1H), 5.20 (m, 1H), 7.65 (m, 2H), 7.67 (s, 1H), 7.82 (m, 1H), 8.11 (s, 2H); MS (ESI) m/z 435 (M+H)+.

Example 56

(7R,8aS)-2-[(4-tert-butylphenyl)sulfonyl]-7-[(5-cyclopropylpyrazin-2-yl)-oxy]octahydropyrrolo[1,2-a]pyrazine The title compound was prepared according to the procedure described in Example 27C substituting 4-tert-butylbenzene-1-sulfonyl chloride for 2-(trifluoromethyl)benzene-1-sulfonyl chloride. $^1$H NMR (400 MHz, DMSO-$d_6$) δ ppm 0.80 (m, 2H), 0.90 (m, 2H), 1.32 (s, 9H), 1.75 (m, 1H), 1.88 (m, 1H), 1.98-2.35 (m, 6H), 2.97 (m, 1H), 3.56 (m, 2H), 3.77 (m, 1H), 5.20 (m, 1H), 7.62 (s, 4H), 8.12 (s, 2H); MS (ESI) m/z 457 (M+H)+.

Example 57

(7R,8aS)-2-[(3-tert-butyl-4-methoxyphenyl)sulfonyl]-7-[(5-cyclopropylpyrazin-2-yl)oxy]octahydropyrrolo[1,2-a]pyrazine To a solution of the product from Example 27B (30 mg, 0.115 mmol) in dichloromethane (1 mL) was added 3-tert-butyl-4-methoxybenzene-1-sulfonyl chloride (36 mg, 0.138 mmol) and diisopropylethylamine (0.040 mL, 0.23 mmol). The resulting mixture was stirred at room temperature for 90 minutes. Water (2 mL) was added, and the mixture was extracted with dichloromethane (2×2 mL). The combined organic layers were dried over Na$_2$SO$_4$, filtered and concentrated in vacuo to give a crude product. Purification by column chromatography on silica gel eluting with a solvent gradient of 0-60% ethyl acetate in hexanes gave the titled compound. $^1$H NMR (300 MHz, CDCl$_3$) δ ppm 0.87-1.00 (m, 4H), 1.38 (s, 9H), 1.73-1.87 (m, 1H), 1.91-2.03 (m, 2H), 2.08 (t, J=10.51 Hz, 1H), 2.31 (dd, J=10.17, 5.09 Hz, 1H), 2.37-2.48 (m, 2H), 2.48-2.60 (m, 1H), 2.91-3.05 (m, 1H), 3.63 (dd, J=10.17, 6.78 Hz, 1H), 3.68-3.76 (m, 1H), 3.83-3.90 (m, 1H), 3.90 (s, 3H), 5.23-5.35 (m, 1H), 6.94 (d, J=9.16 Hz, 1H), 7.57-7.66 (m, 2H), 7.91 (d, J=1.36 Hz, 1H), 8.02 (d, J=1.70 Hz, 1H); MS (ESI) m/z 487.1 (M+H)$^+$.

Example 58

(7R,8aS)-2-[(6-tert-butylpyridin-2-yl)sulfonyl]-7-[(5-cyclopropylpyrazin-2-yl)oxy]octahydropyrrolo[1,2-a]pyrazine

Example 58A 2-(benzylthio)-6-tert-butylpyridine

To a solution of benzyl mercaptan (0.22 mL, 1.87 mmol) in anhydrous N,N-dimethylformamide (10 mL) was added a 1.0 M solution of potassium tert-butoxide in tetrahydrofuran (1.87 mL, 1.87 mmol) dropwise over 2 minutes. To the resulting suspension was added 2-bromo-6-tert-butylpyridine (0.20 g, 0.93 mmol), and the resulting mixture was stirred at 50° C. for 16 hours. The cooled mixture was poured into water (50 mL) and extracted with ethyl acetate (50 mL), and the ethyl acetate layer was dried over Na$_2$SO$_4$, filtered and concentrated in vacuo to give a crude product. Purification by column chromatography on silica gel using hexanes gave the titled compound. $^1$H NMR (300 MHz, CDCl$_3$) δ ppm 1.35 (s, 9H), 4.50 (s, 2H), 6.93-7.03 (m, 2H), 7.17-7.45 (m, 6H); MS (APCI) m/z 258.3 (M+H)$^+$.

Example 58B 6-tert-butylpyridine-2-sulfonyl chloride

To a solution of the product from Example 58A (0.10 g, 0.389 mmol) in acetic acid (1 mL) was added water (0.5 mL) and N-chlorosuccinimide (0.21 g, 1.55 mmol), and the resulting mixture was stirred at room temperature for 90 minutes. Volatiles were removed by evaporation with dry N$_2$ and the residue was partitioned between water and ethyl acetate (2×). The combined ethyl acetate extracts were dried over Na$_2$SO$_4$, filtered and concentrated in vacuo to give a semisolid that was triturated with hexanes. The hexane layer was removed, and the resulting solids were rinsed with hexanes (2×). The combined hexane layers were combined and concentrated in vacuo to give the title compound. $^1$H NMR (300 MHz, CDCl$_3$) δ ppm 1.43 (s, 9H), 7.68 (d, J=7.54 Hz, 1H), 7.82-8.01 (m, 2H); MS (APCI) m/z 234.3 (M+H)$^+$.

Example 58C (7R,8aS)-2-[(6-tert-butylpyridin-2-yl)sulfonyl]-7-[(5-cyclopropylpyrazin-2-yl)oxy]octahydropyrrolo[1,2-a]pyrazine The title compound was prepared using the procedure described in Example 57, substituting the product from Example 58B for 3-tert-butyl-4-methoxybenzene-1-sulfonyl chloride. $^1$H NMR (300 MHz, CDCl$_3$) δ ppm 0.89-0.98 (m, 4H), 1.39 (s, 9H), 1.74-1.90 (m, 1H), 1.90-2.03 (m, 2H), 2.27-2.60 (m, 3H), 2.60-2.73 (m, 1H), 2.90-3.06 (m, 2H), 3.67 (dd, J=9.92, 6.74 Hz, 1H), 3.90 (d, J=13.49 Hz, 1H), 4.06 (d, J=10.71 Hz, 1H), 5.31 (q, J=5.82 Hz, 1H), 7.50 (dd, J=7.54, 1.19 Hz, 1H), 7.71-7.84 (m, 2H), 7.92 (d, J=1.59 Hz, 1H), 8.03 (d, J=1.19 Hz, 1H); MS (ESI) m/z 458.0 (M+H)$^+$.

Example 59

(7R,8aS)-7-[(5-cyclopropylpyrazin-2-yl)oxy]-2-{[6-(morpholin-4-yl)pyridin-2-yl]sulfonyl}octahydropyrrolo[1,2-a]pyrazine The title compound was prepared using the procedure described for Example 58, substituting 4-(6-bromopyridin-2-yl)morpholine for 2-bromo-6-tert-butylpyridine. $^1$H NMR (300 MHz, CDCl$_3$) δ ppm 0.86-1.01 (m, 4H), 1.72-1.89 (m, 1H), 1.91-2.03 (m, 2H), 2.28-2.61 (m, 4H), 2.84-3.04 (m, 2H), 3.50-3.59 (m, 4H), 3.67 (dd, J=9.92, 6.74 Hz, 1H), 3.77-3.92 (m, 5H), 3.93-4.06 (m, J=7.14 Hz, 1H), 5.25-5.37 (m, 1H), 6.76 (d, J=8.73 Hz, 1H), 7.17-7.25 (m, 1H), 7.63 (dd, J=8.53, 7.34 Hz, 1H), 7.92 (d, J=1.59 Hz, 1H), 8.03 (d, J=1.19 Hz, 1H); MS (ESI) m/z 487.1 (M+H)$^+$.

Example 60

(7R,8aS)-7-[(5-cyclopropylpyrazin-2-yl)oxy]-2-{[6-(piperidin-1-yl)pyridin-2-yl]sulfonyl}octahydropyrrolo[1,2-a]pyrazine The title compound was prepared using the procedure described for Example 58, substituting 2-bromo-6-(piperidin-1-yl)pyridine for 2-bromo-6-tert-butylpyridine. $^1$H NMR (300 MHz, CDCl$_3$) δ ppm 0.89-0.99 (m, 4H), 1.59-1.70 (m, 6H), 1.74-1.90 (m, 1H), 1.90-2.03 (m, 2H), 2.27-2.65 (m, 4H), 2.83-3.07 (m, 2H), 3.50-3.61 (m, 4H), 3.66 (dd, J=9.83, 6.78 Hz, 1H), 3.78-3.91 (m, 1H), 3.96-4.07 (m, 1H), 5.22-5.41 (m, 1H), 6.74 (d, J=8.48 Hz, 1H), 7.13 (d, J=6.78 Hz, 1H), 7.54 (dd, J=8.65, 7.29 Hz, 1H), 7.92 (d, J=1.36 Hz, 1H), 8.03 (d, J=1.36 Hz, 1H); MS (ESI) m/z 485.1 (M+H)$^+$.

Example 61

(7R,8aS)-7-[(5-cyclopropylpyrazin-2-yl)oxy]-2-{[6-(pyrrolidin-1-yl)pyridin-2-yl]sulfonyl}octahydropyrrolo[1,2-a]pyrazine The title compound was prepared using the procedure described for Example 58, substituting 2-bromo-6-(pyrrolidin-1-yl)pyridine for 2-bromo-6-tert-butylpyridine. $^1$H NMR (300 MHz, CDCl$_3$) δ ppm 0.89-0.99 (m, 4H), 1.75-1.91 (m, 1H), 1.90-2.08 (m, 6H), 2.34 (dd, J=9.91, 5.16 Hz, 1H), 2.38-2.61 (m, 2H), 2.61-2.74 (m, 1H), 2.92-3.10 (m, 2H), 3.39-3.55 (m, J=6.54, 6.54 Hz, 4H), 3.67 (dd, J=10.11, 6.94 Hz, 1H), 3.87 (d, J=13.09 Hz, 1H), 4.01 (d, J=10.71 Hz, 1H), 5.25-5.38 (m, 1H), 6.46 (d, J=8.33 Hz, 1H), 7.11 (d, J=7.14 Hz, 1H), 7.53 (dd, J=8.53, 7.34 Hz, 1H), 7.92 (d, J=1.59 Hz, 1H), 8.03 (d, J=1.19 Hz, 1H); MS (ESI) m/z 471.1 (M+H)$^+$.

Example 62

(7R,8aS)-7-[(5-cyclopropylpyrazin-2-yl)oxy]-2-[(2,4-difluorophenyl)-sulfonyl]octahydropyrrolo[1,2-a]pyrazine The title compound was prepared using the procedure described for Example 110, substituting 2,4-difluorobenzene-1-sulfonyl chloride for 4-methylbenzene-1-sulfonyl chloride. $^1$H NMR (300 MHz, CDCl$_3$) δ ppm 0.89-0.98 (m, 4H), 1.75-1.89 (m, 1H), 1.91-2.03 (m, 2H), 2.28-2.60 (m, 4H), 2.68-2.82 (m, 1H), 2.95-3.05 (m, 1H), 3.67 (dd, J=10.17, 6.78 Hz, 1H), 3.80 (dd, J=10.51, 1.36 Hz, 1H), 3.94 (d, J=10.85 Hz, 1H), 5.24-5.37 (m, 1H), 6.90-7.05 (m, 2H), 7.82-7.92 (m, 1H), 7.92 (d, J=1.36 Hz, 1H), 8.02 (d, J=1.36 Hz, 1H); MS (ESI) m/z 437.0 (M+H)+.

Example 63

(7R,8aS)-7-[(5-cyclopropylpyrazin-2-yl)oxy]-2-{[4-(trifluoromethyl)pyridin-2-yl]sulfonyl}octahydropyrrolo[1,2-a]pyrazine The title compound was prepared using the procedure described for Example 58, substituting 2-bromo-4-(trifluoromethyl)pyridine for 2-bromo-6-tert-butylpyridine. $^1$H NMR (300 MHz, CDCl$_3$) δ ppm 0.87-0.99 (m, 4H), 1.76-1.91 (m, 1H), 1.92-2.04 (m, 2H), 2.35 (dd, J=10.17, 5.09 Hz, 1H), 2.39-2.60 (m, 2H), 2.59-2.69 (m, 1H), 2.90-3.07 (m, 2H), 3.68 (dd, J=10.17, 6.78 Hz, 1H), 3.87-3.95 (m, 1H), 4.01-4.11 (m, 1H), 5.25-5.37 (m, 1H), 7.71 (dd, J=4.92, 0.85 Hz, 1H), 7.92 (d, J=1.36 Hz, 1H), 8.03 (d, J=1.36 Hz, 1H), 8.14-8.18 (m, J=0.68 Hz, 1H), 8.90 (d, J=4.75 Hz, 1H); MS (ESI) m/z 470.0 (M+H)+.

Example 64

3-{[(7R,8aS)-7-[(5-cyclopropylpyrazin-2-yl)oxy]hexahydropyrrolo[1,2-a]-pyrazin-2(1H)-yl]sulfonyl}-5-(trifluoromethyl)benzonitrile

Example 64A (7R,8aS)-2-{[3-bromo-5-(trifluoromethyl)phenyl]sulfonyl}-7-[(5-cyclopropylpyrazin-2-yl)oxy]octahydropyrrolo[1,2-a]pyrazine The title compound was prepared using the procedure described for Example 57, substituting 3-bromo-5-(trifluoromethyl)benzene-1-sulfonyl chloride for 3-tert-butyl-4-methoxybenzene-1-sulfonyl chloride. $^1$H NMR (300 MHz, CDCl$_3$) δ ppm 0.89-1.00 (m, 4H), 1.75-1.90 (m, 1H), 1.91-2.05 (m, 2H), 2.16 (t, J=10.51 Hz, 1H), 2.34 (dd, J=10.31, 5.16 Hz, 1H), 2.39-2.64 (m, 3H), 2.98-3.08 (m, 1H), 3.66 (dd, J=10.31, 6.74 Hz, 1H), 3.74-3.81 (m, 1H), 3.86-3.98 (m, J=9.52 Hz, 1H), 5.23-5.36 (m, 1H), 7.92 (d, J=1.59 Hz, 1H), 7.93 (s, 1H), 7.98 (s, 1H), 8.03 (d, J=1.59 Hz, 1H), 8.08 (s, 1H).

Example 64B

3-{[(7R,8aS)-7-[(5-cyclopropylpyrazin-2-yl)oxy]hexahydropyrrolo[1,2-a]-pyrazin-2(1H)-yl]sulfonyl}-5-(trifluoromethyl)benzonitrile To a solution of the product from Example 64A (30 mg, 0.055 mmol) in N,N-dimethylformamide (0.3 mL) was added copper(I) cyanide (10 mg, 0.11 mmol), and the resulting mixture was stirred at 130° C. for 16 hours. The cooled mixture was partitioned between water and ethyl acetate (3×), and the combined organic layers were dried over Na$_2$SO$_4$, filtered and concentrated in vacuo. The crude product was purified by column chromatography on silica gel using a solvent gradient of 0-60% ethyl acetate in hexanes to give the title compound. $^1$H NMR (300 MHz, CDCl$_3$) δ ppm 0.87-1.00 (m, 4H), 1.74-1.90 (m, 1H), 1.91-2.07 (m, 2H), 2.19 (t, J=10.34 Hz, 1H), 2.34 (dd, J=10.17, 5.09 Hz, 1H), 2.39-2.63 (m, 3H), 2.98-3.10 (m, 1H), 3.66 (dd, J=10.17, 6.78 Hz, 1H), 3.80 (dd, J=10.17, 1.70 Hz, 1H), 3.88-3.99 (m, 1H), 5.24-5.36 (m, 1H), 7.92 (d, J=1.36 Hz, 1H), 8.03 (d, J=1.36 Hz, 1H), 8.11-8.14 (m, J=1.02 Hz, 1H), 8.17-8.26 (m, J=4.07, 1.02 Hz, 2H); MS (ESI) m/z 494.0 (M+H)+.

Example 65

4-{[(7R,8aS)-7-[(5-cyclopropylpyrazin-2-yl)oxy]hexahydropyrrolo[1,2-a]-pyrazin-2(1H)-yl]sulfonyl}-2-(trifluoromethyl)benzonitrile The title compound was prepared using the procedure described for Example 64, substituting 4-bromo-3-(trifluoromethyl)benzene-1-sulfonyl chloride for 3-bromo-5-(trifluoromethyl)benzene-1-sulfonyl chloride. $^1$H NMR (300 MHz, CDCl$_3$) δ ppm 0.87-1.00 (m, 4H), 1.72-1.90 (m, 1H), 1.91-2.07 (m, 2H), 2.18 (t, J=10.31 Hz, 1H), 2.34 (dd, J=9.92, 5.16 Hz, 1H), 2.39-2.63 (m, 3H), 2.97-3.08 (m, 1H), 3.66 (dd, J=10.31, 6.74 Hz, 1H), 3.76-3.83 (m, 1H), 3.89-3.99 (m, 1H), 5.22-5.36 (m, 1H), 7.91 (d, J=1.59 Hz, 1H), 8.01-8.10 (m, 3H), 8.13-8.17 (m, J=0.79 Hz, 1H); MS (ESI) m/z 494.0 (M+H)+.

Example 66

(7R,8aS)-7-[(5-cyclopropylpyrazin-2-yl)oxy]-2-{[6-(trifluoromethyl)pyridin-2-yl]sulfonyl}octahydropyrrolo[1,2-a]pyrazine The title compound was prepared using the procedure described for Example 57, substituting 6-(trifluoromethyl)pyridine-2-sulfonyl chloride for 3-tert-butyl-4-methoxybenzene-1-sulfonyl chloride. $^1$H NMR (300 MHz, CDCl$_3$) δ ppm 0.90-0.98 (m, 4H), 1.76-2.07 (m, 3H), 2.25-2.85 (m, 4H), 2.94-3.19 (m, 2H), 3.58-3.80 (m, 1H), 3.93 (d, J=12.7 Hz, 1H), 4.07 (d, J=11.5 Hz, 1H), 5.34 (q, J=5.9 Hz, 1H), 7.82-7.90 (m, 1H), 7.93 (d, J=1.2 Hz, 1H), 8.03 (d, J=1.2 Hz, 1H), 8.10-8.14 (m, 2H); MS (ESI) m/z 470.1 (M+H)+.

Example 67

(7R,8aS)-7-[(5-cyclopropylpyrazin-2-yl)oxy]-2-{[5-(trifluoromethyl)pyridin-2-yl]sulfonyl}octahydropyrrolo[1,2-a]pyrazine The title compound was prepared using the procedure described for Example 57, substituting 5-(trifluoromethyl)pyridine-2-sulfonyl chloride for 3-tert-butyl-4-methoxybenzene-1-sulfonyl chloride. $^1$H NMR (300 MHz, CDCl$_3$) δ ppm 0.83-1.03 (m, 4H), 1.75-1.91 (m, 1H), 1.92-2.05 (m, 2H), 2.29-2.73 (m, 4H), 2.88-3.10 (m, 2H), 3.68 (dd, J=9.8, 6.8 Hz, 1H), 3.84-3.96 (m, 1H), 4.00-4.11 (m, J=8.8, 2.0 Hz, 1H), 5.24-5.38 (m, 1H), 7.92 (d, J=1.4 Hz, 1H), 8.03 (d, J=1.4 Hz, 1H), 8.05-8.11 (m, 1H), 8.14-8.20 (m, 1H), 8.96 (d, J=1.4 Hz, 1H); MS (ESI) m/z 470.0 (M+H)+.

Example 68

2-chloro-5-{[(7R,8aS)-7-[(5-cyclopropylpyrazin-2-yl)oxy]hexahydropyrrolo[1,2-a]pyrazin-2(1H)-yl]sulfonyl}benzonitrile The title compound was prepared using the procedure described for Example 57, substituting 4-chloro-3-cyanobenzene-1-sulfonyl chloride for 3-tert-butyl-4-methoxybenzene-1-sulfonyl chloride. $^1$H NMR (300 MHz, CDCl$_3$) δ ppm 0.90-0.98 (m, 4H), 1.70-1.88 (m, 1H), 1.91-2.04 (m, 2H), 2.17 (t, J=10.5 Hz, 1H), 2.33 (dd, J=9.9, 5.2 Hz, 1H), 2.38-2.63 (m, 3H), 3.01 (d, J=10.3 Hz, 1H), 3.65 (dd, J=9.9, 6.7 Hz, 1H), 3.76 (d, J=10.3 Hz, 1H), 3.91 (d, J=9.9 Hz, 1H), 5.18-5.43 (m, 1H), 7.51 (d, J=8.3 Hz, 1H), 7.92 (d, J=1.2 Hz, 1H), 7.99 (dd, J=8.3, 2.8 Hz, 1H), 8.03 (d, J=1.6 Hz, 1H), 8.77 (d, J=2.4 Hz, 1H); MS (ESI) m/z 436.0 (M+H)$^+$.

Example 69

(7R,8aS)-7-{[6-(trifluoromethyl)pyridin-3-yl]oxy}-2-{[6-(trifluoromethyl)-pyridin-2-yl]sulfonyl}octahydropyrrolo[1,2-a]pyrazine Example 69A (7R,8aS)-2-benzyl-7-{[6-(trifluoromethyl)pyridin-3-yl]oxy}octahydropyrrolo[1,2-a]pyrazine To a solution of (7R,8aS)-2-benzyloctahydropyrrolo[1,2-a]pyrazin-7-ol (Example 19D, 0.103 g, 0.443 mmol) in dimethyl sulfoxide (4 mL) was added a 1.0 M solution of potassium tert-butoxide in tetrahydrofuran (0.665 mL, 0.665 mmol), and the resulting suspension was stirred at room temperature for 5 minutes. 5-Fluoro-2-(trifluoromethyl)pyridine (0.137 g, 0.829 mmol) was added, and the reaction mixture was stirred at room temperature for 48 hours. The mixture was partitioned between ethyl acetate and water, and the organic extract was dried over anhydrous sodium sulfate, filtered, and concentrated in vacuo. Purification by column chromatography on silica gel using a solvent gradient of 0-95% ethyl acetate in hexane gave the titled compound. MS (APCI) m/z 378.4 (M+H)$^+$.

Example 69B (7R,8aS)-7-{[6-(trifluoromethyl)pyridin-3-yl]oxy}octahydropyrrolo[1,2-a]-pyrazine The product from Example 69A (92 mg, 0.244 mmol) was subject to the procedure described for Example 27B to give the title compound. MS (APCI) m/z 288.3 (M+H)$^+$.

Example 69C (7R,8aS)-7-{[6-(trifluoromethyl)pyridin-3-yl]oxy}-2-{[6-(trifluoromethyl)-pyridin-2-yl]sulfonyl}octahydropyrrolo[1,2-a]pyrazine The product from Example 69B (48 mg, 0.167 mmol) was subjected to the procedure described in Example 27C, substituting 6-(trifluoromethyl)pyridine-2-sulfonyl chloride for 2-(trifluoromethyl)benzene-1-sulfonyl chloride to give the titled compound. $^1$H NMR (300 MHz, CDCl$_3$) δ ppm 1.78-1.94 (m, 1H), 1.95-2.07 (m, 1H), 2.41-2.68 (m, 3H), 2.75 (t, J=10.9 Hz, 1H), 2.97-3.17 (m, 2H), 3.69 (dd, J=9.7, 6.5 Hz, 1H), 3.89-4.00 (m, 1H), 4.09 (dd, J=11.5, 2.0 Hz, 1H), 4.80-5.01 (m, 1H), 7.21 (dd, J=8.7, 2.4 Hz, 1H), 7.56-7.64 (m, 1H), 7.81-7.91 (m, 1H), 8.09-8.16 (m, 2H), 8.32 (d, J=2.8 Hz, 1H); MS (ESI) m/z 497.0 (M+H)$^+$.

Example 70

(7R,8aS)-7-[(5-cyclopropylpyrazin-2-yl)oxy]-2-{[6-(morpholin-4-yl)pyridin-3-yl]sulfonyl}octahydropyrrolo[1,2-a]pyrazine To a solution of the product from Example 27B (28 mg, 0.11 mmol) in dichloromethane (1 mL) was added triethylamine (0.023 mL, 0.164 mmol) and 6-morpholinopyridine-3-sulfonyl chloride (32 mg, 0.120 mmol), and the resulting mixture was stirred at room temperature for 4 hours. The mixture was partitioned between water and dichloromethane (3×), and the combined organic layers were concentrated in vacuo The crude product was purified by column chromatography on C-18 silica gel using a solvent gradient of 0-100% acetonitrile in water (0.1% trifluoroacetic acid). Fractions containing the pure product were pooled and concentrated by evaporation to give the title compound as a trifluoroacetic acid salt. $^1$H NMR (300 MHz, CDCl$_3$) δ ppm 0.86-1.09 (m, 4H), 1.91-2.10 (m, 1H), 2.31-3.49 (m, 11H), 3.64-3.73 (m, 4H), 3.79-3.87 (m, 4H), 5.44-5.65 (m, 1H), 6.63 (d, J=9.2 Hz, 1H), 7.70 (dd, J=9.2, 2.7 Hz, 1H), 7.94 (d, J=1.4 Hz, 1H), 8.10 (d, J=1.4 Hz, 1H), 8.51 (d, J=2.7 Hz, 1H); MS (ESI) m/z 487.1 (M+H)$^+$.

Example 71

(7R,8aS)-2-[(5-tert-butyl-2-methoxyphenyl)sulfonyl]-7-[(5-cyclopropylpyrazin-2-yl)oxy]octahydropyrrolo[1,2-a]pyrazine The title compound was prepared as a trifluoroacetic acid salt using the procedure described in Example 70, substituting 5-tert-butyl-2-methoxybenzene-1-sulfonyl chloride for 6-morpholinopyridine-3-sulfonyl chloride. $^1$H NMR (300 MHz, CDCl$_3$) δ ppm 0.92-1.01 (m, 4H), 1.31 (s, 9H), 1.91-2.08 (m, 2H), 2.25-2.57 (m, 2H), 2.75-3.81 (m, 7H), 3.92 (s, 3H), 3.94-4.60 (m, 3H), 5.46-5.64 (m, 1H), 6.97 (d, J=8.7 Hz, 1H), 7.57 (dd, J=8.7, 2.8 Hz, 1H), 7.87 (d, J=2.4 Hz, 1H), 7.93 (d, J=1.6 Hz, 1H), 8.08 (d, J=1.2 Hz, 1H); MS (ESI) m/z 487.1 (M+H)$^+$.

Example 72

(7R,8aS)-7-[(5-cyclopropylpyrazin-2-yl)oxy]-2-[(5-methyl-2-thienyl)-sulfonyl]octahydropyrrolo[1,2-a]pyrazine The title compound was prepared as a trifluoroacetic acid salt using the procedure described in Example 70, substituting 5-methylthiophene-2-sulfonyl chloride for 6-morpholinopyridine-3-sulfonyl chloride. $^1$H NMR (300 MHz, CDCl$_3$) δ ppm 0.92-1.02 (m, 4H), 1.93-2.06 (m, 2H), 2.30-2.51 (m, 3H), 2.55 (s, 3H), 2.79-4.55 (m, 7H), 5.46-5.59 (m, 1H), 6.84 (dd, J=3.8, 1.0 Hz, 1H), 7.39 (d, J=4.0 Hz, 1H), 7.93 (d, J=1.6 Hz, 1H), 8.08 (d, J=1.6 Hz, 1H); MS (ESI) m/z 421.0 (M+H)$^+$.

Example 73

(7R,8aS)-2-[(5-bromopyridin-3-yl)sulfonyl]-7-[(5-cyclopropylpyrazin-2-yl)-oxy]octahydropyrrolo[1,2-a]pyrazine The title compound was prepared using the procedure described for Example 27C, substituting 5-bromopyridine-3-sulfonyl chloride for 2-(trifluoromethyl)benzene-1-sulfonyl chloride. $^1$H NMR (300 MHz, CDCl$_3$) δ ppm 0.87-1.02 (m, 4H), 1.74-2.67 (m, H), 3.03 (d, J=11.1 Hz, 1H), 3.66 (dd, J=9.9, 6.7 Hz, 1H), 3.78 (d, J=10.7 Hz, 1H), 3.93 (d, J=10.3 Hz, 1H), 5.30 (q, J=6.1 Hz, 1H), 7.92 (d, J=1.2 Hz, 1H), 8.03 (d, J=1.2 Hz, 1H), 8.18 (t, J=2.2 Hz, 1H), 8.89 (t, J=2.2 Hz, 2H); MS (ESI) m/z 479.9 (M+H)$^+$.

Example 74

(7R,8aS)-7-[(5-cyclopropylpyrazin-2-yl)oxy]-2-[(5-cyclopropylpyridin-3-yl)sulfonyl]octahydropyrrolo[1,2-a]pyrazine

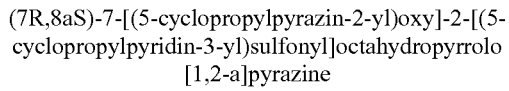

A suspension of the product from Example 73 (21 mg, 0.044 mmol), cyclopropylboronic acid (4.9 mg, 0.057 mmol), tricyclohexylphosphine (1.2 mg, 4.39 μmol) and tribasic potassium phosphate (33 mg, 0.154 mmol) in toluene (0.5 mL) and water (0.100 mL) was degassed by bubbling with $N_2$ for 10 minutes. Palladium(II) acetate (0.49 mg, 2.2 μmol) was added and the mixture was further degassed with $N_2$ for 15 minutes, and the reaction vessel was sealed and the mixture was stirred at 100° C. for 3.5 hours. The cooled mixture was diluted with ethyl acetate and washed with water. The organic extract was dried over anhydrous sodium sulfate, filtered and concentrated in vacuo to give a crude product that was purified by column chromatography on C-18 silica gel using a solvent gradient of 0-100% acetonitrile in water (0.1% trifluoroacetic acid). Fractions containing the pure product were pooled and concentrated by evaporation to give the title compound as a trifluoroacetic acid salt. $^1$H NMR (300 MHz, $CDCl_3$) δ ppm 0.80-0.89 (m, 2H), 0.92-1.02 (m, 4H), 1.14-1.23 (m, 2H), 1.91-2.09 (m, 3H), 2.91-3.38 (m, J=10.3 Hz, 4H), 3.49-3.73 (m, 2H), 3.71-3.94 (m, 1H), 3.93-4.14 (m, 1H), 4.14-4.38 (m, 1H), 5.45-5.63 (m, 1H), 7.66 (t, J=2.2 Hz, 1H), 7.93 (d, J=1.2 Hz, 1H), 8.09 (d, J=1.2 Hz, 1H), 8.65 (d, J=2.0 Hz, 1H), 8.78 (d, J=2.0 Hz, 1H); MS (ESI) m/z 442.0 $(M+H)^+$.

Example 75

(7R,8aS)-2-[(6-chloropyridin-3-yl)sulfonyl]-7-[(5-cyclopropylpyrazin-2-yl)-oxy]octahydropyrrolo[1,2-a]pyrazine The title compound was prepared using the procedure described for Example 27C, substituting 6-chloropyridine-3-sulfonyl chloride for 2-(trifluoromethyl)benzene-1-sulfonyl chloride. $^1$H NMR (300 MHz, $CDCl_3$) δ ppm 0.90-0.98 (m, 4H), 1.70-1.88 (m, 1H), 1.91-2.04 (m, 2H), 2.17 (t, J=10.5 Hz, 1H), 2.33 (dd, J=9.9, 5.2 Hz, 1H), 2.38-2.63 (m, 3H), 3.01 (d, J=10.3 Hz, 1H), 3.65 (dd, J=9.9, 6.7 Hz, 1H), 3.76 (d, J=10.3 Hz, 1H), 3.91 (d, J=9.9 Hz, 1H), 5.18-5.43 (m, 1H), 7.51 (d, J=8.3 Hz, 1H), 7.92 (d, J=1.2 Hz, 1H), 7.99 (dd, J=8.3, 2.8 Hz, 1H), 8.03 (d, J=1.6 Hz, 1H), 8.77 (d, J=2.4 Hz, 1H); MS (ESI) m/z 436.0 $(M+H)^+$.

Example 76

5-{[(7S,8aS)-2-{[3-(trifluoromethyl)phenyl]sulfonyl}octahydropyrrolo[1,2-a]pyrazin-7-yl]oxy}-1,3-benzoxazole

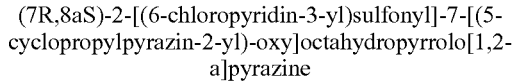

The title compound was prepared according to the procedure described in Example 41, substituting benzo[d]oxazol-5-ol for 4-(trifluoromethoxy)phenol. Purification by chromatography on silica gel (first with 4% $CH_3OH/CH_2Cl_2$, then a second time with 40% to 100% ethyl acetate/hexanes) afforded the title compound. $^1$H NMR (300 MHz, DMSO-$d_6$) δ ppm 8.65 (s, 1H), 8.18-8.03 (m, 2H), 7.98 (s, 1H), 7.92 (t, J=7.8, 1H), 7.62 (d, J=8.9, 1H), 7.22 (d, J=2.5, 1H), 6.90 (dd, J=8.9, 2.5, 1H), 4.95-4.84 (m, 1H), 3.88-3.78 (m, 1H), 3.73-3.60 (m, 1H), 3.11-2.94 (m, 2H), 2.59-2.38 (m, 3H), 2.24-2.03 (m, 3H), 1.46-1.29 (m, 1H); MS (ESI+) m/z 468 $(M+H)^+$.

Example 77

(7S,8aS)-2-{[3-(trifluoromethyl)phenyl]sulfonyl}-7-{[6-(trifluoromethyl)-pyridin-3-yl]oxy}octahydropyrrolo[1,2-a]pyrazine

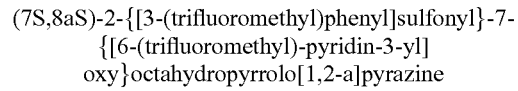

Diisopropyl azodicarboxylate (0.085 mL, 0.440 mmol) was added dropwise to a mixture of Example 19 (140 mg, 0.400 mmol), 6-(trifluoromethyl)pyridin-3-ol (71 mg, 0.44 mmol), and polymer supported triphenylphosphine (3 mmol/g, 147 mg, 0.440 mmol) in anhydrous tetrahydrofuran (1.5 mL) at ambient temperature. The reaction mixture was stirred for 18 hours and then filtered into a mixture of ethyl acetate and $H_2O$. The separated organic phase was washed with brine, dried ($Na_2SO_4$), filtered, and concentrated in vacuo. Chromatography on silica gel (50% ethyl acetate/hexanes) afforded the title compound. $^1$H NMR (300 MHz, DMSO-$d_6$) δ ppm 8.33 (d, J=2.8, 1H), 8.14 (d, J=7.9, 1H), 8.08 (d, J=7.9, 1H), 7.98 (s, 1H), 7.91 (t, J=7.8, 1H), 7.80 (d, J=8.7, 1H), 7.49 (dd, J=8.7, 2.7, 1H), 5.07-4.98 (m, 1H), 3.88-3.79 (m, 1H), 3.73-3.63 (m, 1H), 3.12-2.96 (m, 2H), 2.61-2.38 (m, 3H), 2.25-2.04 (m, 3H), 1.44-1.31 (m, 1H); MS (ESI+) m/z 496 $(M+H)^+$.

Example 78

2-methyl-6-{[(7S,8aS)-2-{[3-(trifluoromethyl)phenyl]sulfonyl}octahydropyrrolo[1,2-a]pyrazin-7-yl]oxy}-1,3-benzoxazole

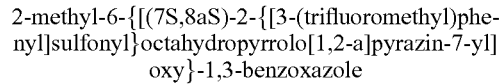

To a mixture of Example 19 (138 mg, 0.394 mmol), 2-methylbenzo[d]oxazol-6-ol (88 mg, 0.59 mmol), and polymer supported triphenylphosphine (3 mmol/g, 197 mg, 0.591 mmol) in anhydrous tetrahydrofuran (1.5 mL) was added diisopropyl azodicarboxylate (0.11 mL, 0.59 mmol) dropwise via syringe. The reaction mixture was stirred for 18 hours, then filtered through glass wool, and the filtrate was concentrated in vacuo. The residue was chromatographed on silica gel (50% ethyl acetate/hexanes) to afford the title compound. $^1$H NMR (300 MHz, DMSO-$d_6$) δ ppm 8.14 (d, J=8.6, 1H), 8.12-8.05 (m, 1H), 7.98 (bs, 1H), 7.92 (t, J=7.8, 1H), 7.47 (d, J=8.6, 1H), 7.15 (d, J=2.3, 1H), 6.79 (dd, J=8.6, 2.4, 1H), 4.93-4.83 (m, 1H), 3.83 (bd, J=10.3, 1H), 3.67 (bd, J=11.2, 1H), 3.09-2.97 (m, 2H), 2.81-2.60 (m, 1H), 2.54 (s, 3H), 2.47-2.38 (m, 2H), 2.24-2.01 (m, 3H), 1.42-1.29 (m, 1H); MS (ESI+) m/z 482 $(M+H)^+$.

Example 79

(7S,8aS)-7-(4-fluoro-3-methylphenoxy)-2-{[3-(trifluoromethyl)phenyl]-sulfonyl}octahydropyrrolo[1,2-a]pyrazine

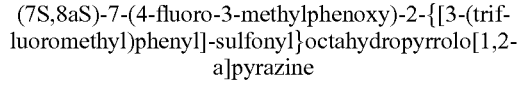

The title compound was prepared according to the procedure described in Example 78 substituting 4-fluoro-3-methylphenol for 2-methylbenzo[d]oxazol-6-ol. Purification by chromatography (first by silica gel; 15% to 50% ethyl acetate/hexanes and 0% to 5% $CH_3OH/CH_2Cl_2$, and then by reverse phase HPLC; Phenomenex® Luna® C8(2) 5 μm 100 Å AXIA column (30×75 mm) with gradient of acetonitrile (A) and 0.1% trifluoroacetic acid in water (B) at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A)) afforded the title compound as a trifluoroacetic acid salt. $^1$H NMR (300 MHz, DMSO-$d_6$) δ ppm 8.23-8.09 (m, J=16.8, 7.9, 2H), 8.04 (s, 1H), 7.97 (t, J=7.8, 1H), 7.05 (t, J=9.1, 1H), 6.79 (dd, J=6.3, 3.0, 1H), 6.75-6.65 (m, J=8.8, 1H), 5.10-4.94 (m, 1H), 4.57-2.58 (m, 14H), 1.85-1.39 (m, 1H); MS (ESI+) m/z 459 (M+H)+.

Example 80

(7R,8aS)-7-[(5-methylpyrazin-2-yl)oxy]-2-{[3-(trifluoromethyl)phenyl]-sulfonyl}octahydropyrrolo[1,2-a]pyrazine The title compound was prepared according to the procedure described in Example 18, substituting Example 19 for Example 17 and 2-bromo-5-methylpyrazine for 2-bromo-5-cyclopropylpyrazine. $^1$H NMR (300 MHz, DMSO-$d_6$) δ ppm 8.18-8.06 (m, 3H), 8.03 (d, J=0.8, 1H), 7.99 (s, 1H), 7.92 (t, J=7.9, 1H), 5.25-5.15 (m, 1H), 3.88-3.79 (m, 1H), 3.72-3.62 (m, 1H), 3.55 (dd, J=9.8, 6.8, 1H), 3.02-2.93 (m, 1H), 2.45-2.30 (m, 5H), 2.30-2.23 (m, 1H), 2.19 (dd, J=9.8, 5.2, 1H), 2.08 (t, J=10.6, 1H), 1.87 (ddd, J=13.6, 5.9, 1.6, 1H), 1.84-1.70 (m, 1H); MS (ESI+) m/z 443 (M+H)+.

Example 81

(7R,8aS)-7-[(6-methylpyrazin-2-yl)oxy]-2-{[3-(trifluoromethyl)phenyl]-sulfonyl}octahydropyrrolo[1,2-a]pyrazine The title compound was prepared according to the procedure described in Example 18, substituting Example 19 for Example 17 and 2-bromo-6-methylpyrazine for 2-bromo-5-cyclopropylpyrazine. $^1$H NMR (300 MHz, DMSO-$d_6$) δ ppm 8.18-8.04 (m, 4H), 7.99 (bs, 1H), 7.93 (t, J=7.9, 1H), 5.29-5.18 (m, 1H), 3.88-3.79 (m, 1H), 3.71-3.62 (m, 1H), 3.57 (dd, J=9.9, 6.7, 1H), 3.06-2.95 (m, 1H), 2.42-2.15 (m, 7H), 2.09 (t, J=10.5, 1H), 1.91 (ddd, J=13.6, 5.9, 1.9, 1H), 1.85-1.71 (m, 1H); MS (ESI+) m/z 443 (M+H)+.

Example 82

(7R,8aS)-7-{[6-chloro-5-(trifluoromethyl)pyridin-3-yl]oxy}-2-{[3-(trifluoromethyl)phenyl]sulfonyl}octahydropyrrolo[1,2-a]pyrazine A solution of potassium t-butoxide, 1.0 M in tetrahydrofuran (0.57 mL, 0.57 mmol) was added dropwise via syringe to a solution of Example 19 (143 mg, 0.408 mmol) in anhydrous dimethyl sulfoxide (1.5 mL) at ambient temperature. After stirring for 5 minutes, a solution of 2-chloro-5-fluoro-3-(trifluoromethyl)pyridine (98 mg, 0.49 mmol) in dimethyl sulfoxide (1 mL) was added. The reaction was allowed to proceed for 6 days, and then the mixture was poured into H$_2$O. The product was extracted with ethyl acetate, and the organic extract was washed with brine, dried over Na$_2$SO$_4$, filtered, and concentrated in vacuo. Chromatography on silica gel (50% to 100% ethyl acetate/hexanes) afforded the title compound. $^1$H NMR (300 MHz, DMSO-$d_6$) δ ppm 8.41-8.36 (m, 1H), 8.19-8.11 (m, 1H), 8.13-8.06 (m, 1H), 7.99 (d, J=1.8, 1H), 7.93 (t, J=7.8, 1H), 7.81 (d, J=3.0, 1H), 5.12-5.01 (m, 1H), 3.88-3.80 (m, 1H), 3.72-3.63 (m, 1H), 3.59 (dd, J=9.8, 6.6, 1H), 3.03-2.95 (m, 1H), 2.44-2.16 (m, 4H), 2.08 (t, J=10.5, 1H), 2.01-1.74 (m, 2H); MS (ESI+) m/z 530 (M+H)+.

Example 83

(7R,8aS)-2-{[3-(trifluoromethyl)phenyl]sulfonyl}-7-{[5-(trifluoromethyl)-pyridin-2-yl]oxy}octahydropyrrolo[1,2-a]pyrazine The title compound was prepared according to the procedure described in Example 18, substituting Example 19 for Example 17 and 2-bromo-5-(trifluoromethyl)-pyridine for 2-bromo-5-cyclopropylpyrazine. $^1$H NMR (300 MHz, DMSO-$d_6$) δ ppm 8.58-8.53 (m, 1H), 8.18-8.02 (m, 3H), 7.99 (bs, 1H), 7.92 (t, J=7.9, 1H), 7.00 (d, J=8.7, 1H), 5.38-5.27 (m, 1H), 3.89-3.80 (m, 1H), 3.72-3.63 (m, 1H), 3.58 (dd, J=9.9, 6.7, 1H), 3.06-2.95 (m, 1H), 2.45-2.16 (m, 4H), 2.09 (t, J=10.6, 1H), 1.97-1.87 (m, 1H), 1.79 (ddd, J=13.7, 10.4, 8.2, 1H); MS (ESI+) m/z 496 (M+H)+.

Example 84

(7R,8aS)-2-{[3-(trifluoromethyl)phenyl]sulfonyl}-7-{[6-(trifluoromethyl)-pyridin-3-yl]oxy}octahydropyrrolo[1,2-a]pyrazine The title compound was prepared according to the procedure described in Example 82, substituting 5-fluoro-2-(trifluoromethyl)pyridine for 2-chloro-5-fluoro-3-(trifluoromethyl)pyridine. $^1$H NMR (300 MHz, DMSO-$d_6$) δ ppm 8.40 (d, J=2.8, 1H), 8.18-8.06 (m, 2H), 7.99 (bs, 1H), 7.93 (t, J=7.9, 1H), 7.82 (d, J=8.7, 1H), 7.55 (dd, J=8.7, 2.9, 1H), 5.06-4.95 (m, 1H), 3.90-3.80 (m, 1H), 3.71-3.56 (m, 2H), 3.06-2.95 (m, 1H), 2.46-2.19 (m, 4H), 2.08 (t, J=10.6, 1H), 1.96-1.75 (m, 2H); MS (ESI+) m/z 496 (M+H)+.

Example 85

6-{[(7R,8aS)-2-{[3-(trifluoromethyl)phenyl]sulfonyl}octahydropyrrolo[1,2-a]pyrazin-7-yl]oxy}nicotinonitrile The title compound was prepared according to the procedure described in Example 18, substituting Example 19 for Example 17 and 6-bromonicotinonitrile for 2-bromo-5-cyclopropylpyrazine. $^1$H NMR (300 MHz, DMSO-$d_6$) δ ppm 8.66 (dd, J=2.3, 0.6, 1H), 8.18-8.11 (m, 2H), 8.09 (d, J=7.9, 1H), 7.99 (bs, 1H), 7.92 (t, J=7.8, 1H), 6.99 (dd, J=8.7, 0.8, 1H), 5.36-5.26 (m, 1H), 3.88-3.79 (m, 1H), 3.71-3.62 (m, 1H), 3.57 (dd, J=9.9, 6.7, 1H), 3.07-2.94 (m, 1H), 2.45-2.16 (m, 4H), 2.13-2.04 (m, 1H), 1.91 (ddd, J=13.6, 5.8, 1.8, 1H), 1.79 (ddd, J=13.6, 10.4, 8.0, 1H); MS (ESI+) m/z 453 (M+H)+.

Example 86

5-{[(7R,8aS)-2-{[3-(trifluoromethyl)phenyl]sulfonyl}octahydropyrrolo[1,2-a]pyrazin-7-yl]oxy}pyridine-2-carbonitrile The title compound was prepared according to the procedure described in Example 82, substituting 5-fluoropicolinonitrile for 2-chloro-5-fluoro-3-(trifluoromethyl)pyridine. $^1$H NMR (300 MHz, DMSO-$d_6$) δ ppm 8.41-8.37 (m, 1H), 8.14 (d, J=7.8, 1H), 8.09 (d, J=8.1, 1H), 8.01-7.89 (m, 3H), 7.53 (dd, J=8.7, 2.9, 1H), 5.06-4.95 (m, 1H), 3.89-3.80 (m, 1H), 3.71-3.64 (m, 1H), 3.60 (dd, J=9.8, 6.7, 1H), 3.02-2.94 (m, 1H), 2.45-2.19 (m, 5H), 1.94-1.75 (m, 2H); MS (ESI+) m/z 453 (M+H)+.

Example 87

(7R,8aS)-7-[(6-bromopyridin-3-yl)oxy]-2-{[3-(trifluoromethyl)phenyl]-sulfonyl}octahydropyaolo[1,2-a]pyrazine The title compound was prepared according to the procedure described in Example 82, substituting 2-bromo-5-fluoropyridine for 2-chloro-5-fluoro-3-(trifluoromethyl)pyridine. ¹H NMR (300 MHz, DMSO-d₆) δ ppm 8.18-8.04 (m, 3H), 7.99 (bs, 1H), 7.93 (t, J=7.9, 1H), 7.53 (d, J=8.7, 1H), 7.34 (dd, J=8.7, 3.2, 1H), 4.94-4.83 (m, 1H), 3.89-3.80 (m, 1H), 3.71-3.63 (m, 1H), 3.56 (dd, J=9.7, 6.7, 1H), 3.02-2.94 (m, 1H), 2.43-2.16 (m, 4H), 2.07 (t, J=10.5, 1H), 1.92-1.70 (m, 2H); MS (ESI+) m/z 506/508 (M+H)⁺.

Example 88

(7R,8aS)-7-[(6-cyclopropylpyridin-3-yl)oxy]-2-{[3-(trifluoromethyl)phenyl]-sulfonyl}octahydropyrrolo[1,2-a]pyrazine A solution of Example 87 (150 mg, 0.296 mmol) and [1,3-bis(2,6-diisopropylphenyl)imidazol-2-ylidene](3-chloropyridyl)palladium(II) dichloride (2.0 mg, 2.9 μmol) in anhydrous tetrahydrofuran (0.3 mL) was stirred at ambient temperature for 30 minutes. A solution of cyclopropylzinc(II) bromide, 0.5 M in tetrahydrofuran (0.90 mL, 0.44 mmol) was then added. The reaction was allowed to proceed for 20 hours and then quenched by addition of 3 M HCl (0.5 mL). The crude product mixture was partitioned between ethyl acetate and 2 N NaOH solution. The separated organic phase was washed with brine, dried over Na₂SO₄, filtered, and concentrated in vacuo. Chromatography on silica gel (50% to 100% ethyl acetate/hexanes) yielded the title compound. ¹H NMR (300 MHz, DMSO-d₆) δ ppm 8.18-8.02 (m, 3H), 7.99 (bs, 1H), 7.92 (t, J=7.9, 1H), 7.23-7.13 (m, 2H), 4.86-4.76 (m, 1H), 3.90-3.78 (m, 1H), 3.73-3.61 (m, 1H), 3.53 (dd, J=9.6, 6.7, 1H), 3.02-2.91 (m, 1H), 2.42-2.13 (m, 4H), 2.11-1.94 (m, 2H), 1.89-1.67 (m, 2H), 0.90-0.73 (m, 4H). MS (ESI+) m/z 468 (M+H)⁺.

Example 89

(7R,8aS)-7-[(5-bromopyridin-2-yl)oxy]-2-{[3-(trifluoromethyl)phenyl]-sulfonyl}octahydropyrrolo[1,2-a]pyrazine The title compound was prepared according to the procedure described in Example 18, substituting Example 19 for Example 17 and 2,5-dibromopyridine for 2-bromo-5-cyclopropylpyrazine. ¹H NMR (300 MHz, DMSO-d₆) δ ppm 8.24 (dd, J=2.7, 0.6, 1H), 8.17-8.12 (m, 1H), 8.11-8.06 (m, 1H), 7.98 (bs, 1H), 7.93 (d, J=7.9, 1H), 7.88 (dd, J=8.8, 2.5, 1H), 6.80 (d, J=8.8, 1H), 5.25-5.15 (m, 1H), 3.87-3.79 (m, 1H), 3.71-3.62 (m, 1H), 3.54 (dd, J=9.8, 6.7, 1H), 3.02-2.93 (m, 1H), 2.44-2.13 (m, 4H), 2.08 (t, J=10.6, 1H), 1.87 (ddd, J=6.5, 5.9, 1.9, 1H), 1.75 (ddd, J=13.5, 10.3, 8.1, 1H). MS (ESI+) m/z 506/508 (M+H)⁺.

Example 90

(7R,8aS)-7-[(5-cyclopropylpyridin-2-yl)oxy]-2-{[3-(trifluoromethyl)phenyl]-sulfonyl}octahydropyaolo[1,2-a]pyrazine The title compound was prepared according to the procedure described in Example 88, substituting Example 89 for Example 87. ¹H NMR (300 MHz, DMSO-d₆) δ ppm 8.18-8.11 (m, 1H), 8.13-8.05 (m, 1H), 7.98 (bs, 1H), 7.96-7.87 (m, 2H), 7.34 (dd, J=8.5, 2.5, 1H), 6.67 (d, J=8.5, 1H), 5.25-5.13 (m, 1H), 3.87-3.78 (m, 1H), 3.72-3.62 (m, 1H), 3.53 (dd, J=9.8, 6.7, 1H), 3.00-2.93 (m, 1H), 2.45-2.01 (m, 5H), 1.92- 1.79 (m, 2H), 1.80-1.66 (m, 1H), 0.94-0.84 (m, 2H), 0.65-0.57 (m, 2H); MS (ESI+) m/z 468 (M+H)⁺.

Example 91

(7R,8aS)-7-[(6-bromopyridin-2-yl)oxy]-2-{[3-(trifluoromethyl)phenyl]-sulfonyl}octahydropyaolo[1,2-a]pyrazine The title compound was prepared according to the procedure described in Example 82, substituting 2-bromo-6-fluoropyridine for 2-chloro-5-fluoro-3-(trifluoromethyl)pyridine. ¹H NMR (300 MHz, DMSO-d₆) δ ppm 8.14 (dd, J=7.9, 1.7, 1H), 8.13-8.05 (m, 1H), 7.99 (s, 1H), 7.92 (t, J=7.8, 1H), 7.65 (dd, J=8.2, 7.5, 1H), 7.21 (dd, J=7.5, 0.6, 1H), 6.84 (dd, J=8.2, 0.6, 1H), 5.22-5.11 (m, 1H), 3.88-3.80 (m, 1H), 3.71-3.62 (m, 1H), 3.55 (dd, J=9.8, 6.7, 1H), 3.07-2.95 (m, 1H), 2.45-2.14 (m, 4H), 2.09 (t, J=10.6, 1H), 1.89 (ddd, J=13.5, 5.9, 1.7, 1H), 1.77 (ddd, J=13.6, 10.3, 8.1, 1H); MS (ESI+) m/z 506/508 (M+H)⁺.

Example 92

(7R,8aS)-7-[(6-cyclopropylpyridin-2-yl)oxy]-2-{[3-(trifluoromethyl)-phenyl]sulfonyl}octahydropyrrolo[1,2-a]pyrazine The title compound was prepared according to the procedure described in Example 88, substituting Example 91 for Example 87. ¹H NMR (300 MHz, DMSO-d₆) δ ppm 8.18-8.06 (m, 2H), 7.99 (d, J=1.7, 1H), 7.93 (t, J=7.9, 1H), 7.51 (dd, J=8.2, 7.3, 1H), 6.88 (dd, J=7.3, 0.8, 1H), 6.49 (dd, J=8.1, 0.8, 1H), 5.19-5.07 (m, 1H), 3.88-3.79 (m, 1H), 3.71-3.62 (m, 1H), 3.49 (dd, J=9.7, 6.7, 1H), 3.02-2.94 (m, 1H), 2.43-1.94 (m, 6H), 1.85 (ddd, J=13.5, 6.0, 1.9, 1H), 1.80-1.65 (m, 1H), 0.92-0.83 (m, 4H); MS (ESI+) m/z 468 (M+H)⁺.

Example 91

(7R,8aS)-7-[(5-bromo-1,3-thiazol-2-yl)oxy]-2-{[3-(trifluoromethyl)-phenyl]sulfonyl}octahydropyrrolo[1,2-a]pyrazine The title compound was prepared according to the procedure described in Example 18, substituting Example 19 for Example 17 and 2,5-dibromothiazole for 2-bromo-5-cyclopropylpyrazine. ¹H NMR (300 MHz, DMSO-d₆) δ ppm 8.14 (bd, J=7.9, 1H), 8.08 (bd, J=8.0, 1H), 7.98 (bs, 1H), 7.92 (t, J=7.9, 1H), 7.30 (s, 1H), 5.28-5.16 (m, 1H), 3.88-3.78 (m, 1H), 3.71-3.61 (m, 1H), 3.55 (dd, J=10.2, 6.8, 1H), 3.02-2.92 (m, 1H), 2.44-2.20 (m, 4H), 2.13-1.93 (m, 2H), 1.83-1.68 (m, 1H); MS (ESI+) m/z 512/514 (M+H)⁺.

Example 94

(7R,8aS)-7-[(5-cyclopropyl-1,3-thiazol-2-yl)oxy]-2-{[3-(trifluoromethyl)-phenyl]sulfonyl}octahydropyrrolo[1,2-a]pyrazine The title compound was prepared according to the procedure described in Example 88, substituting Example 93 for Example 87. ¹H NMR (300 MHz, DMSO-d₆) δ ppm 8.18-8.10 (m, 1H), 8.12-8.05 (m, 1H), 7.98 (bs, 1H), 7.92 (t, J=7.9, 1H), 6.86 (d, J=1.1, 1H), 5.21-5.10 (m, 1H), 3.87-3.78 (m, 1H), 3.70-3.62 (m, 1H), 3.53 (dd, J=10.1, 6.7, 1H), 3.01-2.92 (m, 1H), 2.43-2.16 (m, 4H), 2.06 (t, J=10.6, 1H), 1.99-1.87

(m, 2H), 1.80-1.65 (m, 1H), 0.95-0.84 (m, 2H), 0.64-0.55 (m, 2H); MS (ESI+) m/z 474 (M+H)$^+$.

Example 95

(7R,8aS)-7-[(5-cyclopropylpyrazin-2-yl)oxy]-2-[(2,3-difluorophenyl)-sulfonyl]octahydropyrrolo[1,2-a]pyrazine The title compound was prepared according to the procedure described in Example 27C, substituting 2,3-difluorobenzene-1-sulfonyl chloride for 2-(trifluoromethyl)benzene-1-sulfonyl chloride. $^1$H NMR (300 MHz, DMSO-d$_6$) δ ppm 8.11 (s, 2H), 7.90-7.76 (m, 1H), 7.65-7.55 (m, 1H), 7.46 (tdd, J=8.2, 4.6, 1.4, 1H), 5.22 (dd, J=12.5, 5.8, 1H), 3.90-3.73 (m, 1H), 3.71-3.50 (m, 2H), 3.06-2.94 (m, 1H), 2.71-2.58 (m, 1H), 2.41-2.16 (m, 4H), 2.10 (tt, J=8.2, 4.9, 1H), 1.97-1.72 (m, 2H), 0.99-0.74 (m, 4H); MS (ESI+) m/z 437 (M+H)$^+$.

Example 96

(7R,8aS)-7-[(5-cyclopropylpyrazin-2-yl)oxy]-2-{[3-fluoro-2-(piperidin-1-yl)-phenyl]sulfonyl}octahydropyrrolo[1,2-a]pyrazine A reaction vial charged with Example 95 (98 mg, 0.22 mmol), piperidine (0.044 mL, 0.449 mmol), and anhydrous dimethyl sulfoxide (1 mL) was placed in a heating block at 105° C. for 3.5 hours. The reaction mixture was cooled to ambient temperature and poured into H$_2$O. The product was extracted with ethyl acetate, and the organic extract was washed with brine, dried over Na$_2$SO$_4$, filtered, and concentrated in vacuo. Chromatography on silica gel (50% ethyl acetate/hexanes) yielded the title compound. $^1$H NMR (300 MHz, DMSO-d$_6$) δ ppm 8.13-8.10 (m, 2H), 7.71-7.63 (m, 1H), 7.54 (ddd, J=12.6, 8.2, 1.6, 1H), 7.40 (td, J=8.1, 5.0, 1H), 5.30-5.18 (m, 1H), 3.91-3.83 (m, 1H), 3.75-3.65 (m, 1H), 3.59 (dd, J=9.8, 6.8, 1H), 3.05-2.96 (m, 5H), 2.75-2.62 (m, 1H), 2.44-2.16 (m, 4H), 2.15-2.04 (m, 1H), 1.96-1.50 (m, 8H), 0.98-0.87 (m, 2H), 0.87-0.77 (m, 2H); MS (ESI+) m/z 502 (M+H)$^+$.

Example 97

(7R,8aS)-7-[(4-tert-butylbenzyl)oxy]-2-{[3-(trifluoromethyl)phenyl]-sulfonyl}octahydropyrrolo[1,2-a]pyrazine To a solution of Example 19 (0.033 g, 0.094 mmol) in tetrahydrofuran (1 mL) was added a 1.0 M solution of potassium tert-butoxide in tetrahydrofuran (0.118 mL, 0.118 mmol). The resulting mixture was stirred for 10 minutes, and 1-(bromomethyl)-4-tert-butylbenzene (0.019 ml, 0.104 mmol) was added. The resulting mixture was stirred at room temperature for 16 hours. The mixture was partitioned between water and ethyl acetate. The organic extract was dried over Na$_2$SO$_4$, filtered and concentrated in vacuo. The crude product was purified by column chromatography on C18 reversed-phase chromatography using a solvent gradient of 0-100% acetonitrile in water (0.1% trifluoroacetic acid). The title compound was obtained as a trifluoroacetic acid salt. $^1$H NMR (300 MHz, DMSO-d$_6$) δ ppm 1.27 (s, 9H), 2.15 (s, 2H), 2.84-3.23 (m, 2H), 3.76-4.32 (m, 3H), 4.34-4.46 (m, 2H), 7.20-7.29 (m, 2H), 7.33-7.39 (m, 2H), 7.95 (t, J=7.9 Hz, 1H), 8.04 (s, 1H), 8.15 (dd, J=14.1, 8.1 Hz, 2H); MS (ESI+) m/z 497 (M+H)$^+$.

Example 98

(7R,8aS)-7-{[4-(trifluoromethoxy)benzyl]oxy}-2-{[3-(trifluoromethyl)-phenyl]sulfonyl}octahydropyrrolo[1,2-a]pyrazine The title compound was prepared as a trifluoroacetic acid salt according to the procedure described in Example 97, substituting 1-(bromomethyl)-4-(trifluoromethoxy)benzene for 1-(bromomethyl)-4-tert-butylbenzene. $^1$H NMR (300 MHz, DMSO-d$_6$) δ ppm 1.42-2.24 (m, 2H), 3.65-4.36 (m, J=73.8 Hz, 4H), 4.40-4.55 (m, 2H), 7.29-7.39 (m, 2H), 7.41-7.51 (m, 2H), 7.95 (t, J=7.7 Hz, 1H), 8.03 (s, 1H), 8.15 (dd, J=13.9, 7.9 Hz, 2H); MS (ESI+) m/z 525 (M+H)$^+$.

Example 99

(7R,8aS)-7-{[4-(trifluoromethyl)benzyl]oxy}-2-{[3-(trifluoromethyl)-phenyl]sulfonyl}octahydropyrrolo[1,2-a]pyrazine The title compound was prepared as a trifluoroacetic acid salt according to the procedure described in Example 97, substituting 1-(bromomethyl)-4-(trifluoromethyl)benzene for 1-(bromomethyl)-4-tert-butylbenzene. $^1$H NMR (300 MHz, DMSO-d$_6$) δ ppm 1.51-2.22 (m, 3H), 3.56-4.41 (m, 5H), 4.46-4.63 (m, 2H), 7.55 (d, J=7.8 Hz, 2H), 7.72 (d, J=8.1 Hz, 2H), 7.95 (t, J=7.8 Hz, 1H), 8.03 (s, 1H), 8.15 (dd, J=13.2, 7.8 Hz, 2H); MS (ESI+) m/z 509 (M+H)$^+$.

Example 100

(7R,8aS)-7-[(5-cyclopropylpyrazin-2-yl)oxy]-2-{[4-(1,1-difluoroethyl)-phenyl]sulfonyl}octahydropyrrolo[1,2-a]pyrazine To 1-(4-{[(7R,8aS)-7-[(5-cyclopropylpyrazin-2-yl)oxy]hexahydropyrrolo[1,2-a]pyrazin-2(1H)-yl]sulfonyl}phenyl)ethanone (Example 48, 120 mg, 0.271 mmol) in dichloromethane (0.5 mL) was added bis(2-methoxyethyl)aminosulfur trifluoride (300 mg, 1.356 mmol). The mixture was heated at 80° C. for 18 hours, and then 1 N Na$_2$CO$_3$ (15 mL) was added. The mixture was extracted with dichloromethane (2×30 mL), and the combined organic phases were concentrated. The residue was purified by chromatography on silica gel (hexane/ethyl acetate=1:1) to give the title compound (25 mg, 20% yield) as a gummy solid. $^1$H NMR (400 MHz, DMSO-d$_6$) δ ppm 0.86-1.25 (m, 4H), 1.82-2.15 (m, 7H), 2.92 (m, 1H), 2.32 (m, 1H), 3.45-3.73 (m, 4H), 5.21 (m, 1H), 7.84 (m, 4H), 8.11 (s, 2H); MS (ESI) m/z 467 (M+H)$^+$.

Example 101

(7R,8aS)-7-[(5-cyclobutylpyrazin-2-yl)oxy]-2-{[3-(trifluoromethyl)phenyl]-sulfonyl}octahydropyrrolo[1,2-a]pyrazine The procedures for Example 17E and Example 18 were used substituting (7R,8aS)-octahydropyrrolo[1,2-a]pyrazin-7-ol for (7S,8aR)-octahydropyrrolo[1,2-a]pyrazin-7-ol and substituting 2-bromo-5-cyclobutylpyrazine for 2-bromo-5-cyclopropylpyrazine to give the title compound 64% yield) as a solid. $^1$H NMR (400 MHz, DMSO-d$_6$) δ ppm 1.87 (m, 3H), 2.05 (m, 3H), 2.23 (m, 5H), 2.38 (m, 2H), 2.99 (m, 1H), 3.58 (m, 3H), 3.84 (m, 1H), 5.21 (m, 1H), 7.95 (m, 2H), 8.05 (m, 2H), 8.15 (s, 2H); MS (ESI) m/z 484 (M+H)$^+$.

Example 102

(7R,8aS)-7-[(5-cyclobutylpyrazin-2-yl)oxy]-2-{[4-(trifluoromethyl)phenyl]-sulfonyl}octahydropyrrolo[1,2-a]pyrazine The procedures for Example 17E and Example 18 were used substituting (7R,8aS)-octahydropyrrolo[1,2-a]pyrazin-7-ol for (7S,8aR)-octahydropyrrolo[1,2-a]pyrazin-7-ol, substituting 2-bromo-5-cyclobutylpyrazine for 2-bromo-5-cyclopropylpyrazine, and substituting 4-(trifluoromethyl)benzene-1-sulfonyl chloride for 3-(trifluoromethyl)benzene-1-sulfonyl chloride to give the title compound (64% yield) as a solid. $^1$H NMR (400 MHz, DMSO-d$_6$) δ ppm 1.87 (m, 3H), 2.05 (m, 3H), 2.23 (m, 5H), 2.38 (m, 2H), 2.99 (m, 1H), 3.58 (m, 3H), 3.84 (m, 1H), 5.21 (m, 1H), 8.03 (m, 5H), 8.24 (s, 1H); MS (ESI) m/z 484 (M+H)$^+$.

Example 103

(7R,8aS)-2-(biphenyl-3-ylsulfonyl)-7-[(5-cyclopropylpyrazin-2-yl)oxy]-octahydropyrrolo[1,2-a]pyrazine The title compound was prepared as a trifluoroacetic acid salt using the procedure described in Example 70, substituting biphenyl-3-sulfonyl chloride for 6-morpholinopyridine-3-sulfonyl chloride. $^1$H NMR (300 MHz, DMSO-d$_6$) δ ppm 0.77-0.86 (m, 2H), 0.90-1.00 (m, 2H), 1.88-2.35 (m, 3H), 3.12-3.44 (m, 4H), 3.69-4.28 (m, 5H), 5.33 (s, 1H), 7.41-7.60 (m, 3H), 7.71-7.85 (m, 4H), 7.95 (s, 1H), 8.03-8.11 (m, 1H), 8.12-8.18 (m, 2H); MS (ESI) m/z 477 (M+H)$^+$.

Example 104

(7R,8aS)-7-[(5-cyclopropylpyrazin-2-yl)oxy]-2-[(4-isopropylphenyl)-sulfonyl]octahydropyrrolo[1,2-a]pyrazine The title compound was prepared as a trifluoroacetic acid salt using the procedure described in Example 70, substituting 4-isopropylbenzene-1-sulfonyl chloride for 6-morpholinopyridine-3-sulfonyl chloride. $^1$H NMR (300 MHz, DMSO-d$_6$) δ ppm 0.77-0.87 (m, 2H), 0.90-1.01 (m, 2H), 1.24 (d, J=6.7 Hz, 6H), 2.02-2.33 (m, 3H), 2.91-3.17 (m, 2H), 3.63-4.64 (m, J=3.2 Hz, 8H), 5.39 (d, J=6.7 Hz, 1H), 7.56 (d, J=8.3 Hz, 2H), 7.68-7.76 (m, 2H), 8.16 (d, J=4.0 Hz, 2H); MS (ESI) m/z 443 (M+H)$^+$.

Example 105

(7R,8aS)-7-[(5-cyclopropylpyrazin-2-yl)oxy]-2-[(3-methoxyphenyl)sulfonyl]-octahydropyrrolo[1,2-a]pyrazine The title compound was prepared as a trifluoroacetic acid salt using the procedure described in Example 70, substituting 3-methoxybenzene-1-sulfonyl chloride for 6-morpholinopyridine-3-sulfonyl chloride. $^1$H NMR (300 MHz, DMSO-d$_6$) δ ppm 0.75-0.86 (m, 2H), 0.89-1.03 (m, 2H), 2.02-2.35 (m, 3H), 3.57-4.49 (m, 12H), 5.39 (s, 1H), 7.20-7.26 (m, 1H), 7.31-7.39 (m, 2H), 7.62 (t, J=8.1 Hz, 1H), 8.09-8.20 (m, 2H); MS (ESI) m/z 431 (M+H)$^+$.

Example 106

(7R,8aS)-7-[(5-cyclopropylpyrazin-2-yl)oxy]-2-{[4-methoxy-3-(trifluoromethyl)phenyl]sulfonyl}octahydropyrrolo[1,2-a]pyrazine The title compound was prepared as a trifluoroacetic acid salt using the procedure described in Example 70, substituting 4-methoxy-3-(trifluoromethyl)benzene-1-sulfonyl chloride for 6-morpholinopyridine-3-sulfonyl chloride. $^1$H NMR (300 MHz, DMSO-d$_6$) δ ppm 0.77-0.86 (m, 2H), 0.90-1.00 (m, 2H), 1.99-2.33 (m, 3H), 3.24-3.43 (m, 4H), 3.80-3.96 (m, J=7.5 Hz, 2H), 4.03 (s, 3H), 5.35 (s, 1H), 7.56 (d, J=8.8 Hz, 1H), 7.88 (d, J=2.0 Hz, 1H), 8.07 (dd, J=8.8, 2.4 Hz, 1H), 8.12-8.19 (m, 2H); MS (ESI) m/z 499 (M+H)$^+$.

Example 107

(7R,8aS)-2-[(3-tert-butylphenyl)sulfonyl]octahydropyrrolo[1,2-a]pyrazin-7-ol

The procedure for making Example 19 was used substituting 3-(tert-butyl)benzene-1-sulfonyl chloride for 3-(trifluoromethyl)benzene-1-sulfonyl chloride to give the title compound (93% yield). MS (ESI) m/z 338 (M+H)$^+$.

Example 108

1-(3-{[(7R,8aS)-7-[(5-cyclopropylpyrazin-2-yl)oxy]hexahydropyrrolo[1,2-a]-pyrazin-2(1H)-yl]sulfonyl}phenyl)ethanone To (7R,8aS)-7-[(5-cyclopropylpyrazin-2-yl)oxy]octahydropyrrolo[1,2-a]pyrazine (1 mmol, Example 27B) and triethylamine (1.5 mmol) in dichloromethane (6 mL) was added 3-acetylbenzene-1-sulfonyl chloride (1.1 mmol) in dichloromethane (2 mL). The mixture was stirred at room temperature for 18 hours. The mixture was concentrated, and the residue was purified by chromatography on silica gel (ethyl acetate) to give the title compound (370 mg) as a solid. $^1$H NMR (400 MHz, DMSO-d$_6$) δ ppm 0.81 (m, 2H), 0.91 (m, 2H), 1.75 (m, 1H), 1.89 (m, 1H), 2.06 (m, 2H), 2.19 (m, 2H), 2.30 (m, 3H), 3.67 (s, 2H), 2.97 (m, 1H), 3.54 (m, 1H), 3.65 (m, 1H), 3.80 (m, 1H), 5.19 (m, 1H), 7.83 (m, 1H), 8.00 (m, 1H), 8.15 (m, 3H), 8.30 (m, 1H); MS (ESI) m/z 444 (M+H)$^+$.

Example 109

(7R,8aS)-7-[(5-cyclopropylpyrazin-2-yl)oxy]-2-{[3-(1,1-difluoroethyl)-phenyl]sulfonyl}octahydropyrrolo[1,2-a]pyrazine To 1-(3-{[(7R,8aS)-7-[(5-cyclopropylpyrazin-2-yl)oxy]hexahydropyrrolo[1,2-a]pyrazin-2(1H)-yl]sulfonyl}phenyl)ethanone (221 mg, 0.5 mmol, Example 108) in dichloromethane (0.5 mL) was added bis(2-methoxyethyl)aminosulfur trifluoride (498 mg, 2.25 mmol). The mixture was heated at 60° C. for 18 hours. Then 1 N Na$_2$CO$_3$ (25 mL) was added. The mixture was extracted with dichloromethane (2×30 mL). The organic phase was concentrated, and the residue was purified by chromatography on silica gel (hexane/ethyl acetate=1:1) to give the title compound (18 mg, 8% yield) as a gummy solid. $^1$H NMR (400 MHz, DMSO-d$_6$) δ ppm 0.85 (m, 3H), 1.82 (m, 2H), 2.02 (m, 4H), 2.16 (m, 2H), 2.35 (m, 2H), 3.11 (m, 2H), 3.54 (m, 2H), 5.21 (m, 1H), 7.92 (m, 2H), 7.81 (m, 2H), 8.11 (m, 2H); MS (ESI) m/z 467 (M+H)$^+$.

Example 110

(7R,8aS)-7-[(5-cyclopropylpyrazin-2-yl)oxy]-2-[(4-methylphenyl)sulfonyl]-octahydropyrrolo[1,2-a]pyrazine To a solution of the product from Example 27B (20 mg, 0.077 M) in pyridine (1.0 mL) was added 4-methylbenzene-1-sulfonyl chloride (18 mg, 0.092 mmol), and the resulting mixture was shaken at room temperature overnight. The reaction mixture was concentrated to dryness, and the residue was purified by C18 reversed-phase chromatography using a solvent gradient of 0-100% acetonitrile in water (0.1% trifluoroacetic acid) to give the title compound as a trifluoroacetic acid salt (18.5 mg, 46%). $^1$H NMR (500 MHz, DMSO-$d_6$/D$_2$O, temperature=90° C.) δ ppm 8.09 (dd, J=12.82, 1.53 Hz, 2H) 7.69 (d, J=8.24 Hz, 2H) 7.48 (d, J=7.93 Hz, 2H) 5.39-5.53 (m, 1H) 3.89 (dd, J=12.66, 6.26 Hz, 1H) 3.75 (dd, J=13.12, 3.36 Hz, 1H) 3.59-3.69 (m, 1H) 3.55 (d, J=12.82 Hz, 1H) 3.39-3.47 (m, 1H) 3.17-3.27 (m, 2H) 2.94-3.07 (m, 1H) 2.86 (dd, J=12.82, 9.16 Hz, 1H) 2.43 (s, 3H) 2.07-2.34 (m, 3H) 0.91-1.02 (m, 2H) 0.77-0.87 (m, 2H); MS (ESI) m/z 415 (M+H)$^+$.

Example 111

(7R,8aR)-7-[(5-cyclopropylpyrazin-2-yl)oxy]-2-{[3-(trifluoromethyl)phenyl]-sulfonyl}octahydropyrrolo[1,2-a]pyrazine A mixture of (7S,8aR)-2-{[3-(trifluoromethyl)phenyl]sulfonyl}octahydropyrrolo[1,2-a]pyrazin-7-ol (Example 17, 103 mg, 0.294 mmol), 5-cyclopropylpyrazin-2-ol (40 mg, 0.294 mmol) and triphenylphosphine (154 mg, 0.588 mmol) in tetrahydrofuran (1 mL) was stirred at room temperature for 1 hour. Then (E)-diisopropyl diazene-1,2-dicarboxylate (119 mg, 0.588 mmol) was added, and the reaction was continued at room temperature overnight. The solution was concentrated, and the residue was purified by chromatography on silica gel (ethyl acetate/hexane=3:2) to give the title compound (68 mg, 48% yield) as a solid. $^1$H NMR (400 MHz, DMSO-$d_6$) δ ppm 0.86 (m, 4H), 1.22 (m, 2H), 2.12 (m, 4H), 2.41 (m, 2H), 3.01 (m, 2H), 3.67 (m, 1H), 3.83 (m, 1H), 5.25 (m, 1H), 7.94 (m, 1H), 8.03 (m, 1H), 8.15 (m, 4H); MS (ESI) m/z 469 (M+H)$^+$.

Example 112

(7R,8aS)-2-{[3-bromo-5-(trifluoromethyl)phenyl]sulfonyl}-7-[(5-cyclopropylpyrazin-2-yl)oxy]octahydropyrrolo[1,2-a]pyrazine The procedures for Example 17E and Example 18 were used substituting (7R,8aS)-octahydropyrrolo[1,2-a]pyrazin-7-ol for (7S,8aR)-octahydropyrrolo[1,2-a]pyrazin-7-ol and substituting 3-bromo-5-(trifluoromethyl)benzene-1-sulfonyl chloride for 3-(trifluoromethyl)benzene-1-sulfonyl chloride to give the title compound (67% yield) as a solid. $^1$H NMR (400 MHz, DMSO-$d_6$) δ ppm 0.87 (m, 4H), 1.89 (m, 3H), 2.21 (m, 5H), 2.99 (m, 1H), 3.56 (m, 1H), 3.69 (m, 1H), 3.85 (m, 1H), 5.21 (m, 1H), 7.99 (m, 1H), 8.11 (s, 1H), 8.23 (s, 2H), 8.42 (m, 1H); MS (ESI) m/z 548 (M+H)$^+$.

Example 113

(7R,8aS)-2-[(3-tert-butylphenyl)sulfonyl]-7-{[5-(prop-1-en-2-yl)pyrazin-2-yl]oxy}octahydropyrrolo[1,2-a]pyrazine The procedures for Example 17E and Example 18 were used substituting (7R,8aS)-octahydropyrrolo[1,2-a]pyrazin-7-ol for (7S,8aR)-octahydropyrrolo[1,2-a]pyrazin-7-ol and substituting 2-bromo-5-(prop-1-en-2-yl)pyrazine for 2-bromo-5-cyclopropylpyrazine to give the title compound (45% yield) as a solid. $^1$H NMR (400 MHz, DMSO-$d_6$) δ ppm 1.76 (s, 9H), 1.95 (m, 1H), 2.12 (m, 2H), 2.28 (m, 7H), 2.96 (m, 1H), 3.59 (m, 2H), 3.80 (m, 1H), 5.24 (m, 2H), 5.85 (m, 1H), 7.63 (m, 3H), 7.78 (m, 1H), 8.25 (s, 1H), 8.38 (m, 1H); MS (ESI) m/z 457 (M+H)$^+$.

Example 114

(7R,8aS)-7-[(5-cyclopropylpyrazin-2-yl)oxy]-2-(2,3-dihydro-1-benzofuran-5-ylsulfonyl)octahydropyrrolo[1,2-a]pyrazine The title compound was prepared as a trifluoroacetic acid salt using the procedure described in Example 70, substituting 2,3-dihydrobenzofuran-5-sulfonyl chloride for 6-morpholinopyridine-3-sulfonyl chloride. $^1$H NMR (300 MHz, CDCl$_3$) δ ppm 0.87-1.06 (m, 4H) 1.93-2.08 (m, 2H) 2.38 (dd, J=13.68, 4.96 Hz, 2H) 2.76-3.22 (m, 3H) 3.29 (t, J=8.72 Hz, 2H) 3.40-4.53 (m, 5H) 4.71 (t, J=8.92 Hz, 2H) 5.53 (s, 1H) 6.89 (d, J=9.12 Hz, 1H) 7.50-7.59 (m, 2H) 7.93 (d, J=1.19 Hz, 1H) 8.09 (d, J=1.19 Hz, 1H); MS (ESI) m/z 443 (M+H)$^+$.

Example 115

(7R,8aS)-7-{[5-(prop-1-en-2-yl)pyrazin-2-yl]oxy}-2-{[3-(trifluoromethyl)-phenyl]sulfonyl}octahydropyrrolo[1,2-a]pyrazine The procedures for Example 17E and Example 18 were used substituting (7R,8aS)-octahydropyrrolo[1,2-a]pyrazin-7-ol for (7S,8aR)-octahydropyrrolo[1,2-a]pyrazin-7-ol and substituting 2-bromo-5-(prop-1-en-2-yl)pyrazine for 2-bromo-5-cyclopropylpyrazine to give the title compound (77% yield) as a solid. $^1$H NMR (400 MHz, DMSO-$d_6$) δ ppm 1.93 (m, 1H), 2.11 (m, 4H), 2.24 (m, 2H), 2.38 (m, 2H), 2.99 (m, 1H), 3.58 (m, 2H), 3.66 (m, 1H), 3.84 (m, 1H), 5.26 (m, 2H), 5.85 (m, 1H), 7.95 (m, 2H), 8.10 (m, 2H), 8.26 (m, 1H), 8.38 (m, 1H); MS (ESI) m/z 469 (M+H)$^+$.

Example 116

(7R,8aS)-7-{[5-(prop-1-en-2-yl)pyrazin-2-yl]oxy}-2-{[4-(trifluoromethyl)-phenyl]sulfonyl}octahydropyrrolo[1,2-a]pyrazine The procedures for Example 17E and Example 18 were used substituting (7R,8aS)-octahydropyrrolo[1,2-a]pyrazin-7-ol for (7S,8aR)-octahydropyrrolo[1,2-a]pyrazin-7-ol, substituting 2-bromo-5-(prop-1-en-2-yl)pyrazine for 2-bromo-5-cyclopropylpyrazine, and substituting 4-(trifluoromethyl)benzene-1-sulfonyl chloride for 3-(trifluoromethyl)benzene-1-sulfonyl chloride to give the title compound (85% yield) as a solid. $^1$H NMR (400 MHz, DMSO-$d_6$) δ ppm 1.93 (m, 1H), 2.11 (m, 4H), 2.24 (m, 2H), 2.38 (m, 2H), 2.99 (m, 1H), 3.58 (m, 2H), 3.66 (m, 1H), 3.84 (m, 1H), 5.26 (m, 2H), 5.85 (m, 1H), 7.98 (m, 2H), 8.05 (m, 2H), 8.26 (m, 1H), 8.39 (m, 1H); MS (ESI) m/z 469 (M+H)$^+$.

Example 117

(7R,8aS)-2-[(3-tert-butylphenyl)sulfonyl]-7-[(5-isopropylpyrazin-2-yl)-oxy]octahydropyrrolo[1,2-a]pyrazine (7R,8aS)-2-[(3-tert-Butylphenyl)sulfonyl]-7-{[5-(prop-1-en-2-yl)pyrazin-2-yl]oxy}octahydropyrrolo[1,2-a]pyrazine (164.3 mg, 0.360 mmol, Example 113) in ethanol (5 mL) was added to Raney® nickel 2800 water slurry (202.9 mg, 1.556 mmol) in a 20 mL pressure bottle. The mixture was stirred under 30 psi of hydrogen at ambient temperature for 15 hours. The mixture was filtered through a polypropylene membrane, the filtrate was concentrated, and the residue was purified by column chromatography on silica gel eluted with ethyl acetate/hexane (3:7) to give the title compound (56% yield). $^1$H NMR (400 MHz, DMSO-$d_6$) δ ppm 1.20 (m, 6H), 1.33 (s, 9H), 1.62 (m, 1H), 1.94 (m, 2H), 2.26 (m, 4H), 2.99 (m, 2H), 3.54 (m, 1H), 3.62 (m, 1H), 3.79 (m, 1H), 5.20 (m, 1H), 7.59 (m, 2H), 7.67 (m, 1H), 7.78 (s, 1H), 8.06 (m, 1H), 8.20 (m, 1H); MS (ESI) m/z 459 (M+H)$^+$.

Example 118

(7R,8aS)-7-[(5-isopropylpyrazin-2-yl)oxy]-2-{[3-(trifluoromethyl)-phenyl]sulfonyl}octahydropyrrolo[1,2-a]pyrazine (7R,8aS)-7-{[5-(Prop-1-en-2-yl)pyrazin-2-yl]oxy}-2-{[3-(trifluoromethyl)-phenyl]sulfonyl}octahydropyrrolo[1,2-a]pyrazine (196 mg, 0.418 mmol, Example 115) in ethanol (10 mL) was added to 20% palladium hydroxide on carbon (12 mg, 0.084 mmol). The mixture was stirred at room temperature for 16 hours under 30 psi of hydrogen. The mixture was filtered through a nylon membrane and concentrated. The residue was purified by chromatography on silica gel (hexane/ethyl acetate=1:1) to give the title compound (170 mg, 86%) as a solid. $^1$H NMR (400 MHz, DMSO-$d_6$) δ ppm 1.21 (s, 6H), 1.77 (m, 1H), 1.91 (m, 1H), 2.09 (m, 1H), 2.20-2.30 (m, 2H), 2.39 (m, 2H), 3.01 (m, 2H), 3.56 (m, 1H), 3.66 (m, 1H), 3.84 (m, 1H), 5.21 (m, 1H), 7.95 (m, 2H), 8.10 (m, 2H), 8.26 (m, 1H), 8.38 (m, 1H); MS (ESI) m/z 471 (M+H)$^+$.

Example 119

(7R,8aS)-7-[(5-cyclopropylpyrazin-2-yl)oxy]-2-[(3,4,5-trifluorophenyl)-sulfonyl]octahydropyrrolo[1,2-a]pyrazine The title compound was prepared as a trifluoroacetic acid salt according to the procedure described in Example 110, substituting 3,4,5-trifluorobenzene-1-sulfonyl chloride for 4-methylbenzene-1-sulfonyl chloride. $^1$H NMR (500 MHz, DMSO-$d_6$/$D_2O$, temperature=90° C.) δ ppm 8.06-8.12 (m, 2H) 7.71-7.77 (m, 2H) 5.41-5.48 (m, 1H) 3.84 (dd, J=12.21, 6.10 Hz, 2H) 3.60-3.69 (m, 1H) 3.44-3.54 (m, 1H) 3.34-3.42 (m, 1H) 3.01-3.17 (m, 3H) 2.87 (dd, J=12.97, 9.61 Hz, 1H) 2.05-2.28 (m, 3H) 0.92-0.99 (m, 2H) 0.80-0.87 (m, 2H); MS (ESI) m/z 455 (M+H)$^+$.

Example 120

(7R,8aS)-2-[(3-chloro-2-fluorophenyl)sulfonyl]-7-[(5-cyclopropylpyrazin-2-yl)oxy]octahydropyrrolo[1,2-a]pyrazine The title compound was prepared as a trifluoroacetic acid salt according to the procedure described in Example 110, substituting 3-chloro-2-fluorobenzene-1-sulfonyl chloride for 4-methylbenzene-1-sulfonyl chloride. $^1$H NMR (500 MHz, DMSO-$d_6$/$D_2O$, temperature=90° C.) δ ppm 8.06-8.11 (m, 2H) 7.89-7.95 (m, 1H) 7.77-7.82 (m, 1H) 7.44-7.50 (m, 1H) 5.43-5.50 (m, 1H) 3.84-3.92 (m, 2H) 3.69 (d, J=13.12 Hz, 1H) 3.51 (d, 1H) 3.37-3.44 (m, 1H) 2.97-3.25 (m, 4H) 2.06-2.31 (m, 3H) 0.93-0.99 (m, 2H) 0.81-0.87 (m, 2H); MS (ESI) m/z 453 (M+H)$^+$.

Example 121

(7R,8aS)-7-[(5-cyclopropylpyrazin-2-yl)oxy]-2-[(2-fluoro-5-methylphenyl)-sulfonyl]octahydropyrrolo[1,2-a]pyrazine The title compound was prepared as a trifluoroacetic acid salt according to the procedure described in Example 110, substituting 2-fluoro-5-methylbenzene-1-sulfonyl chloride for 4-methylbenzene-1-sulfonyl chloride. $^1$H NMR (500 MHz, DMSO-$d_6$/$D_2O$, temperature=90° C.) δ ppm 8.06-8.12 (m, 2H) 7.54-7.63 (m, 2H) 7.34 (dd, J=10.53, 8.39 Hz, 1H) 5.42-5.51 (m, 1H) 3.81-3.94 (m, 2H) 3.51-3.71 (m, 2H) 3.37-3.45 (m, 1H) 3.12-3.25 (m, 3H) 3.02 (dd, J=13.12, 9.46 Hz, 1H) 2.38 (s, 3H) 2.07-2.32 (m, 3H) 0.93-1.00 (m, 2H) 0.80-0.86 (m, 2H); MS (ESI) m/z 433 (M+H)$^+$.

Example 122

(7R,8aS)-7-[(5-cyclopropylpyrazin-2-yl)oxy]-2-[(2,6-difluorophenyl)-sulfonyl]octahydropyrrolo[1,2-a]pyrazine The title compound was prepared as a trifluoroacetic acid salt according to the procedure described in Example 110, substituting 2,6-difluorobenzene-1-sulfonyl chloride for 4-methylbenzene-1-sulfonyl chloride. $^1$H NMR (500 MHz, DMSO-$d_6$/$D_2O$, temperature=90° C.) δ ppm 8.06-8.12 (m, 2H) 7.72-7.83 (m, 1H) 7.30 (t, J=9.00 Hz, 2H) 5.44-5.51 (m, 1H) 3.85-3.95 (m, 2H) 3.72 (d, J=13.12 Hz, 1H) 3.56 (s, 1H) 3.39-3.46 (m, 1H) 3.04-3.26 (m, 4H) 2.07-2.34 (m, 3H) 0.91-1.01 (m, 2H) 0.79-0.87 (m, 2H); MS (ESI) m/z 437 (M+H)$^+$.

Example 123

(7R,8aS)-7-[(5-cyclopropylpyrazin-2-yl)oxy]-2-[(2,3,4-trifluorophenyl)-sulfonyl]octahydropyrrolo[1,2-a]pyrazine The title compound was prepared as a trifluoroacetic acid salt according to the procedure described in Example 110, substituting 2,3,4-trifluorobenzene-1-sulfonyl chloride for 4-methylbenzene-1-sulfonyl chloride. $^1$H NMR (500 MHz, DMSO-$d_6$/$D_2O$, temperature=90° C.) δ ppm 8.05-8.11 (m, 2H) 7.64-7.74 (m, 1H) 7.45-7.54 (m, 1H) 5.41-5.49 (m, 1H) 3.81-3.89 (m, 2H) 3.63-3.72 (m, 1H) 3.34-3.51 (m, 2H) 2.93-3.21 (m, 4H) 2.06-2.28 (m, 3H) 0.92-0.99 (m, 2H) 0.81-0.86 (m, 2H); MS (ESI) m/z 455 (M+H)$^+$.

Example 124

(7R,8aS)-2-[(5-chloro-2-fluorophenyl)sulfonyl]-7-[(5-cyclopropylpyrazin-2-yl)oxy]octahydropyrrolo[1,2-a]pyrazine The title compound was prepared as a trifluoroacetic acid salt according to the procedure described in Example 110, substituting 2-fluoro-5-chlorobenzene-1-sulfonyl chloride for 4-methylbenzene-1-sulfonyl chloride. $^1$H NMR (500 MHz, DMSO-$d_6$/$D_2O$, temperature=90° C.) δ ppm 8.05-8.12 (m, 2H) 7.76-7.84 (m, 2H) 7.49-7.56 (m, 1H) 5.42-5.50 (m, 1H) 3.83-3.92 (m, 2H) 3.65-3.75 (m, 1H) 3.43-3.53 (m, 1H)

3.35-3.41 (m, 1H) 2.96-3.24 (m, 4H) 2.06-2.31 (m, 3H) 0.92-0.99 (m, 2H) 0.79-0.87 (m, 2H); MS (ESI) m/z 453 (M+H)$^+$.

Example 125

(7R,8aS)-7-[(5-cyclopropylpyrazin-2-yl)oxy]-2-[(3-fluoro-4-methylphenyl)-sulfonyl]octahydropyrrolo[1,2-a]pyrazine The title compound was prepared as a trifluoroacetic acid salt according to the procedure described in Example 110, substituting 3-fluoro-4-methylbenzene-1-sulfonyl chloride for 4-methylbenzene-1-sulfonyl chloride. $^1$H NMR (500 MHz, DMSO-d$_6$/D$_2$O, temperature=90° C.) δ ppm 8.08 (dd, J=11.60, 1.22 Hz, 2H) 7.48-7.63 (m, 3H) 5.40-5.50 (m, 1H) 3.74-3.90 (m, 2H) 3.48-3.63 (m, J=13.12 Hz, 2H) 3.35-3.44 (m, 1H) 3.09-3.22 (m, 2H) 2.93-3.05 (m, J=10.07 Hz, 1H) 2.83 (dd, J=12.66, 9.92 Hz, 1H) 2.35 (d, J=1.83 Hz, 3H) 2.07-2.29 (m, 3H) 0.92-0.99 (m, 2H) 0.80-0.86 (m, 2H); MS (ESI) m/z 433 (M+H)$^+$.

Example 126

(7R,8aS)-7-[(5-cyclopropylpyrazin-2-yl)oxy]-2-[(3,5-difluorophenyl)-sulfonyl]octahydropyrrolo[1,2-a]pyrazine The title compound was prepared as a trifluoroacetic acid salt according to the procedure described in Example 110, substituting 3,5-difluorobenzene-1-sulfonyl chloride for 4-methylbenzene-1-sulfonyl chloride. $^1$H NMR (500 MHz, DMSO-d$_6$/D$_2$O, temperature=90° C.) δ ppm 8.05-8.11 (m, 2H) 7.47-7.60 (m, 3H) 5.38-5.47 (m, 1H) 3.78-3.88 (m, 2H) 3.61-3.68 (m, 1H) 3.32-3.48 (m, 2H) 2.96-3.13 (m, J=3.66 Hz, 3H) 2.77-2.87 (m, 1H) 2.07-2.27 (m, 3H) 0.92-0.99 (m, 2H) 0.80-0.86 (m, 2H); MS (ESI) m/z 437 (M+H)$^+$.

Example 127

(7R,8aS)-7-[(5-cyclopropylpyrazin-2-yl)oxy]-2-[(3,5-dimethylphenyl)-sulfonyl]octahydropyrrolo[1,2-a]pyrazine The title compound was prepared as a trifluoroacetic acid salt according to the procedure described in Example 110, substituting 3,5-dimethylbenzene-1-sulfonyl chloride for 4-methylbenzene-1-sulfonyl chloride. $^1$H NMR (500 MHz, DMSO-d$_6$/D$_2$O, temperature=90° C.) δ ppm 8.10 (d, J=1.22 Hz, 1H) 8.07-8.08 (m, 1H) 7.36-7.41 (m, 3H) 5.41-5.51 (m, 1H) 3.88 (dd, J=12.36, 6.26 Hz, 1H) 3.76 (dd, J=12.66, 2.90 Hz, 1H) 3.50-3.65 (m, 2H) 3.35-3.46 (m, 1H) 3.12-3.25 (m, 2H) 2.99 (t, J=9.92 Hz, 1H) 2.84 (dd, J=12.66, 9.31 Hz, 1H) 2.39 (s, 6H) 2.08-2.31 (m, 3H) 0.92-0.99 (m, 2H) 0.81-0.86 (m, 2H); MS (ESI) m/z 429 (M+H)$^+$.

Example 128

(7R,8aS)-2-{[4-bromo-3-(trifluoromethyl)phenyl]sulfonyl}-7-[(5-cyclopropylpyrazin-2-yl)oxy]octahydropyaolo[1,2-a]pyrazine The title compound was prepared as a trifluoroacetic acid salt according to the procedure described in Example 110, substituting 4-bromo-3-trifluoromethylbenzene-1-sulfonyl chloride for 4-methylbenzene-1-sulfonyl chloride. $^1$H NMR (500 MHz, DMSO-d$_6$/D$_2$O, temperature=90° C.) δ ppm 8.18 (d, J=8.55 Hz, 1H) 7.95-8.10 (m, 4H) 5.37-5.47 (m, 1H) 3.78-3.89 (m, 2H) 3.62-3.69 (m, 1H) 3.32-3.48 (m, 2H) 2.94-3.13 (m, J=7.02 Hz, 3H) 2.75-2.91 (m, 1H) 2.06-2.27 (m, 3H) 0.92-1.00 (m, 2H) 0.80-0.86 (m, 2H); MS (ESI) m/z 547 (M+H)$^+$.

Example 129

(7R,8aS)-7-[(5-cyclopropylpyrazin-2-yl)oxy]-2-[(4-fluoro-2-methylphenyl)-sulfonyl]octahydropyrrolo[1,2-a]pyrazine The title compound was prepared as a trifluoroacetic acid salt according to the procedure described in Example 110, substituting 4-fluoro-2-methylbenzene-1-sulfonyl chloride for 4-methylbenzene-1-sulfonyl chloride. $^1$H NMR (500 MHz, DMSO-d$_6$/D$_2$O, temperature=90° C.) δ ppm 8.09 (dd, J=11.14, 1.37 Hz, 2H) 7.92 (dd, J=8.85, 5.80 Hz, 1H) 7.18-7.34 (m, 2H) 5.43-5.51 (m, 1H) 3.92 (dd, J=12.51, 6.41 Hz, 1H) 3.79 (dd, J=13.12, 3.36 Hz, 1H) 3.52-3.65 (m, 2H) 3.37-3.46 (m, 1H) 3.11-3.27 (m, 3H) 3.06 (dd, J=13.28, 9.61 Hz, 1H) 2.59 (s, 3H) 2.04-2.35 (m, 3H) 0.93-1.00 (m, 2H) 0.81-0.86 (m, 2H); MS (ESI) m/z 433 (M+H)$^+$.

Example 130

(7R,8aS)-2-[(4-chloro-2-fluorophenyl)sulfonyl]-7-[(5-cyclopropylpyrazin-2-yl)oxy]octahydropyrrolo[1,2-a]pyrazine The title compound was prepared as a trifluoroacetic acid salt according to the procedure described in Example 110, substituting 4-chloro-2-fluorobenzene-1-sulfonyl chloride for 4-methylbenzene-1-sulfonyl chloride. $^1$H NMR (500 MHz, DMSO-d$_6$/D$_2$O, temperature=90° C.) δ ppm 8.05-8.12 (m, 2H) 7.84 (t, J=8.09 Hz, 1H) 7.67 (dd, J=10.22, 1.98 Hz, 1H) 7.52 (dd, J=8.54, 1.83 Hz, 1H) 5.44-5.52 (m, 1H) 3.82-3.94 (m, 2H) 3.56-3.71 (m, 2H) 3.39-3.51 (m, 1H) 3.16-3.27 (m, 3H) 3.06 (dd, J=13.12, 9.46 Hz, 1H) 2.06-2.36 (m, 3H) 0.92-1.00 (m, 2H) 0.81-0.88 (m, 2H); MS (ESI) m/z 453 (M+H)$^+$.

Example 131

(7R,8aS)-7-[(5-cyclopropylpyrazin-2-yl)oxy]-2-[(2,5-difluorophenyl)-sulfonyl]octahydropyrrolo[1,2-a]pyrazine The title compound was prepared as a trifluoroacetic acid salt according to the procedure described in Example 110, substituting 2,5-difluorobenzene-1-sulfonyl chloride for 4-methylbenzene-1-sulfonyl chloride. $^1$H NMR (500 MHz, DMSO-d$_6$/D$_2$O, temperature=90° C.) δ ppm 8.06-8.13 (m, 2H) 7.49-7.65 (m, 3H) 5.42-5.55 (m, 1H) 3.85-3.96 (m, 2H) 3.60-3.75 (m, 2H) 3.42-3.52 (m, 1H) 3.18-3.28 (m, 3H) 3.11 (dd, J=13.12, 9.46 Hz, 1H) 2.07-2.35 (m, 3H) 0.93-1.01 (m, 2H) 0.81-0.87 (m, 2H); MS (ESI) m/z 437 (M+H)$^+$.

Example 132

(7R,8aS)-2-[(3-chloro-4-methylphenyl)sulfonyl]-7-[(5-cyclopropylpyrazin-2-yl)oxy]octahydropyrrolo[1,2-a]pyrazine The title compound was prepared as a trifluoroacetic acid salt according to the procedure described in Example 110, substituting 3-chloro-4-methylbenzene-1-sulfonyl chloride for 4-methylbenzene-1-sulfonyl chloride. $^1$H NMR (500

MHz, DMSO-d$_6$/D$_2$O, temperature=90° C.) δ ppm 8.02-8.13 (m, 2H) 7.77 (d, J=1.53 Hz, 1H) 7.58-7.70 (m, 2H) 5.35-5.52 (m, 1H) 3.70-3.91 (m, 2H) 3.41-3.65 (m, J=12.82 Hz, 2H) 3.35-3.43 (m, 1H) 3.05-3.19 (m, 2H) 2.93-3.04 (m, 1H) 2.82 (dd, J=12.51, 9.46 Hz, 1H) 2.45 (s, 3H) 2.04-2.30 (m, 3H) 0.90-1.00 (m, 2H) 0.79-0.87 (m, 2H); MS (ESI) m/z 449 (M+H)$^+$.

Example 133

(7R,8aS)-2-[(4-bromo-3-methylphenyl)sulfonyl]-7-[(5-cyclopropylpyrazin-2-yl)oxy]octahydropyrrolo[1,2-a]pyrazine The title compound was prepared as a trifluoroacetic acid salt according to the procedure described in Example 110, substituting 4-bromo-3-methylbenzene-1-sulfonyl chloride for 4-methylbenzene-1-sulfonyl chloride. $^1$H NMR (500 MHz, DMSO-d$_6$/D$_2$O, temperature=90° C.) δ ppm 8.08 (dd, J=10.99, 1.53 Hz, 2H) 7.86 (d, J=8.24 Hz, 1H) 7.73 (d, J=2.14 Hz, 1H) 7.53 (dd, J=8.54, 2.14 Hz, 1H) 5.40-5.47 (m, 1H) 3.73-3.89 (m, 2H) 3.59 (d, J=12.82 Hz, 1H) 3.40-3.51 (m, 1H) 3.33-3.39 (m, 1H) 3.02-3.15 (m, 2H) 2.90-3.00 (m, 1H) 2.78 (dd, J=12.36, 9.61 Hz, 1H) 2.47 (s, 3H) 2.04-2.29 (m, 3H) 0.92-1.00 (m, 2H) 0.80-0.86 (m, 2H); MS (ESI) m/z 493 (M+H)$^+$.

Example 134

(7R,8aS)-2-{[2-bromo-5-(trifluoromethyl)phenyl]sulfonyl}-7-[(5-cyclopropylpyrazin-2-yl)oxy]octahydropyraolo[1,2-a]pyrazine The title compound was prepared as a trifluoroacetic acid salt according to the procedure described in Example 110, substituting 2-bromo-5-trifluoromethylbenzene-1-sulfonyl chloride for 4-methylbenzene-1-sulfonyl chloride. $^1$H NMR (500 MHz, DMSO-d$_6$/D$_2$O, temperature=90° C.) δ ppm 8.23 (d, J=1.83 Hz, 1H) 8.14 (d, J=8.24 Hz, 1H) 8.05-8.10 (m, 2H) 7.93 (dd, J=8.09, 1.98 Hz, 1H) 5.36-5.50 (m, J=6.71 Hz, 1H) 3.90-3.97 (m, 1H) 3.84 (dd, J=11.90, 6.41 Hz, 1H) 3.75 (d, J=10.68 Hz, 1H) 3.28-3.37 (m, 3H) 2.85-3.13 (m, 3H) 2.04-2.23 (m, 3H) 0.92-1.00 (m, 2H) 0.80-0.86 (m, 2H).

Example 135

(7R,8aS)-7-[(5-cyclopropylpyrazin-2-yl)oxy]-2-(mesitylsulfonyl)-octahydropyrrolo[1,2-a]pyrazine The title compound was prepared as a trifluoroacetic acid salt according to the procedure described in Example 110, substituting mesitylsulfonyl chloride for 4-methylbenzene-1-sulfonyl chloride. $^1$H NMR (500 MHz, DMSO-d$_6$/D$_2$O, temperature=90° C.) δ ppm 8.06-8.11 (m, 2H) 7.08 (s, 2H) 5.43-5.50 (m, 1H) 3.90 (dd, J=12.21, 6.41 Hz, 1H) 3.68 (dd, J=13.12, 3.05 Hz, 1H) 3.32-3.52 (m, 3H) 3.11-3.21 (m, 2H) 2.98-3.09 (m, 2H) 2.56 (s, 6H) 2.29 (s, 3H) 2.05-2.24 (m, 3H) 0.91-0.99 (m, 2H) 0.78-0.87 (m, 2H); MS (ESI) m/z 443 (M+H)$^+$.

Example 136

(7R,8aS)-2-(biphenyl-4-ylsulfonyl)-7-[(5-cyclopropylpyrazin-2-yl)oxy]-octahydropyrrolo[1,2-a]pyrazine The title compound was prepared as a trifluoroacetic acid salt according to the procedure described in Example 110, substituting biphenyl-4-sulfonyl chloride for 4-methylbenzene-1-sulfonyl chloride. $^1$H NMR (500 MHz, DMSO-d$_6$/D$_2$O, temperature=90° C.) δ ppm 8.05-8.10 (m, 2H) 7.84-7.96 (m, 4H) 7.70-7.76 (m, 2H) 7.43-7.56 (m, 3H) 5.36-5.45 (m, 1H) 3.81 (dd, J=11.90, 6.41 Hz, 2H) 3.58-3.67 (m, 1H) 3.31-3.42 (m, 2H) 2.90-3.10 (m, 3H) 2.68-2.83 (m, 1H) 2.05-2.30 (m, 3H) 0.92-0.99 (m, 2H) 0.79-0.87 (m, 2H); MS (ESI) m/z 477 (M+H)$^+$.

Example 137

(7R,8aS)-2-[(3-bromophenyl)sulfonyl]-7-[(5-cyclopropylpyrazin-2-yl)oxy]-octahydropyrrolo[1,2-a]pyrazine The title compound was prepared as a trifluoroacetic acid salt according to the procedure described in Example 110, substituting 3-bromobenzene-1-sulfonyl chloride for 4-methylbenzene-1-sulfonyl chloride. $^1$H NMR (500 MHz, DMSO-d$_6$/D$_2$O, temperature=90° C.) δ ppm 8.06-8.12 (m, 2H) 7.90-7.95 (m, 2H) 7.78-7.82 (m, 1H) 7.63 (t, J=8.09 Hz, 1H) 5.36-5.49 (m, 1H) 3.78-3.87 (m, 2H) 3.62 (d, J=12.51 Hz, 1H) 3.33-3.47 (m, 2H) 2.92-3.12 (m, 3H) 2.74-2.86 (m, 1H) 2.04-2.28 (m, 3H) 0.92-0.99 (m, 2H) 0.80-0.86 (m, 2H); MS (ESI) m/z 479 (M+H)$^+$.

Example 138

(7R,8aS)-2-{[2,5-bis(trifluoromethyl)phenyl]sulfonyl}-7-[(5-cyclopropylpyrazin-2-yl)oxy]octahydropyrrolo[1,2-a]pyrazine The title compound was prepared as a trifluoroacetic acid salt according to the procedure described in Example 110, substituting 2,5-bis(trifluoromethyl)benzene-1-sulfonyl chloride for 4-methylbenzene-1-sulfonyl chloride. $^1$H NMR (500 MHz, DMSO-d$_6$/D$_2$O, temperature=90° C.) δ ppm 8.27-8.32 (m, 3H) 8.06-8.12 (m, 2H) 5.44-5.50 (m, 1H) 3.87-4.00 (m, 2H) 3.74 (d, J=13.73 Hz, 1H) 3.35-3.55 (m, 2H) 3.05-3.22 (m, 4H) 2.07-2.33 (m, 3H) 0.92-1.00 (m, 2H) 0.80-0.87 (m, 2H); MS (ESI) m/z 537 (M+H)$^+$.

Example 139

(7R,8aS)-7-[(5-cyclopropylpyrazin-2-yl)oxy]-2-[(5-fluoro-2-methylphenyl)-sulfonyl]octahydropyrrolo[1,2-a]pyrazine The title compound was prepared as a trifluoroacetic acid salt according to the procedure described in Example 110, substituting 5-fluoro-2-methylbenzene-1-sulfonyl chloride for 4-methylbenzene-1-sulfonyl chloride. $^1$H NMR (500 MHz, DMSO-d$_6$/D$_2$O, temperature=90° C.) δ ppm 8.06-8.12 (m, 2H) 7.37-7.66 (m, 3H) 5.44-5.52 (m, 1H) 3.92 (dd, J=12.51, 6.41 Hz, 1H) 3.83 (dd, J=13.12, 3.36 Hz, 1H) 3.50-3.73 (m, 2H) 3.39-3.46 (m, 1H) 3.04-3.27 (m, 4H) 2.55 (s, 3H) 2.07-2.31 (m, 3H) 0.92-0.99 (m, 2H) 0.80-0.87 (m, 2H); MS (ESI) m/z 433 (M+H)$^+$.

Example 140

(7R,8aS)-7-[(5-cyclopropylpyrazin-2-yl)oxy]-2-[(2,5-dichloro-3-thienyl)-sulfonyl]octahydropyrrolo[1,2-a]pyrazine The title compound was prepared as a trifluoroacetic acid salt according to the procedure described in Example 110, substituting 2,5-dichlorothiophene-3-sulfonyl chloride for 4-methylbenzene-1-sulfonyl chloride. $^1$H NMR (500 MHz, DMSO-d$_6$/D$_2$O, temperature=90° C.) δ ppm 8.06-8.11 (m, 2H) 7.31 (s, 1H) 5.43-5.50 (m, 1H) 3.84-3.92 (m, 2H) 3.66-3.74 (m, 1H) 3.36-3.52 (m, 2H) 2.98-3.24 (m, 4H) 2.05-2.29 (m, 3H) 0.93-0.98 (m, 2H) 0.81-0.88 (m, 2H); MS (ESI) m/z 475 (M+H)$^+$.

Example 141

(7R,8aS)-2-[(5-chloro-2-thienyl)sulfonyl]-7-[(5-cyclopropylpyrazin-2-yl)-oxy]octahydropyrrolo[1,2-a]pyrazine The title compound was prepared as a trifluoroacetic acid salt according to the procedure described in Example 110, substituting 5-chlorothiophene-2-sulfonyl chloride for 4-methylbenzene-1-sulfonyl chloride. $^1$H NMR (500 MHz, DMSO-d$_6$/D$_2$O, temperature=90° C.) δ ppm 8.05-8.12 (m, 2H) 7.57 (d, J=4.27 Hz, 1H) 7.31 (d, J=3.97 Hz, 1H) 5.42-5.49 (m, 1H) 3.76-3.92 (m, 2H) 3.57-3.65 (m, 1H) 3.45-3.55 (m, 1H) 3.37-3.44 (m, 1H) 2.99-3.17 (m, 3H) 2.87 (dd, J=12.66, 9.61 Hz, 1H) 2.06-2.30 (m, 3H) 0.92-1.00 (m, 2H) 0.81-0.87 (m, 2H); MS (ESI) m/z 441 (M+H)$^+$.

Example 142

(7R,8aS)-2-[(4-chlorophenyl)sulfonyl]-7-[(5-cyclopropylpyrazin-2-yl)oxy]-octahydropyrrolo[1,2-a]pyrazine The title compound was prepared as a trifluoroacetic acid salt according to the procedure described in Example 110, substituting 4-chlorobenzene-1-sulfonyl chloride for 4-methylbenzene-1-sulfonyl chloride. $^1$H NMR (500 MHz, DMSO-d$_6$/D$_2$O, temperature=90° C.) δ ppm 8.05-8.10 (m, 2H) 7.78-7.84 (m, 2H) 7.69-7.74 (m, 2H) 5.37-5.47 (m, 1H) 3.75-3.86 (m, 2H) 3.59 (d, J=12.21 Hz, 1H) 3.30-3.45 (m, 2H) 2.89-3.10 (m, 3H) 2.70-2.79 (m, 1H) 2.07-2.25 (m, 3H) 0.92-1.00 (m, 2H) 0.80-0.86 (m, 2H); MS (ESI) m/z 435 (M+H)$^+$.

Example 143

(7R,8aS)-7-[(5-cyclopropylpyrazin-2-yl)oxy]-2-[(4-fluorophenyl)-sulfonyl]octahydropyrrolo[1,2-a]pyrazine The title compound was prepared as a trifluoroacetic acid salt according to the procedure described in Example 110, substituting 4-fluorobenzene-1-sulfonyl chloride for 4-methylbenzene-1-sulfonyl chloride. $^1$H NMR (500 MHz, DMSO-d$_6$/D$_2$O, temperature=90° C.) δ ppm 8.06-8.11 (m, 2H) 7.84-7.93 (m, 2H) 7.43-7.51 (m, 2H) 5.40-5.52 (m, 1H) 3.87 (dd, J=12.51, 6.41 Hz, 1H) 3.78 (dd, J=12.97, 3.51 Hz, 1H) 3.58 (d, J=12.51 Hz, 2H) 3.37-3.45 (m, 1H) 3.12-3.25 (m, 2H) 3.02 (t, 1H) 2.85 (dd, J=12.51, 9.46 Hz, 1H) 2.08-2.31 (m, 3H) 0.91-0.99 (m, 2H) 0.79-0.88 (m, 2H); MS (ESI) m/z 419 (M+H)$^+$.

Example 144

(7R,8aS)-7-[(5-cyclopropylpyrazin-2-yl)oxy]-2-[(3-fluorophenyl)sulfonyl]-octahydropyrrolo[1,2-a]pyrazine The title compound was prepared as a trifluoroacetic acid salt according to the procedure described in Example 110, substituting 3-fluorobenzene-1-sulfonyl chloride for 4-methylbenzene-1-sulfonyl chloride. $^1$H NMR (500 MHz, DMSO-d$_6$/D$_2$O, temperature=90° C.) δ ppm 8.06-8.11 (m, 2H) 7.71-7.80 (m, 1H) 7.63-7.69 (m, 1H) 7.54-7.63 (m, 2H) 5.42-5.51 (m, 1H) 3.78-3.93 (m, 2H) 3.55-3.66 (m, 2H) 3.37-3.46 (m, 1H) 3.13-3.26 (m, 2H) 3.00-3.10 (m, 1H) 2.90 (dd, J=13.12, 9.46 Hz, 1H) 2.07-2.34 (m, 3H) 0.92-1.00 (m, 2H) 0.80-0.87 (m, 2H); MS (ESI) m/z 419 (M+H)$^+$.

Example 145

(7R,8aS)-7-[(5-cyclopropylpyrazin-2-yl)oxy]-2-[(3-methylphenyl)-sulfonyl]octahydropyrrolo[1,2-a]pyrazine The title compound was prepared as a trifluoroacetic acid salt according to the procedure described in Example 110, substituting 3-methylbenzene-1-sulfonyl chloride for 4-methylbenzene-1-sulfonyl chloride. $^1$H NMR (500 MHz, DMSO-d$_6$/D$_2$O, temperature=90° C.) δ ppm 8.04-8.11 (m, 2H) 7.51-7.63 (m, 4H) 5.39-5.50 (m, 1H) 3.86 (dd, J=12.21, 6.41 Hz, 1H) 3.77 (dd, J=12.82, 3.05 Hz, 1H) 3.46-3.63 (m, J=12.82 Hz, 2H) 3.35-3.43 (m, 1H) 3.06-3.21 (m, 2H) 2.91-3.03 (m, 1H) 2.81 (dd, J=12.66, 9.61 Hz, 1H) 2.43 (s, 3H) 2.06-2.31 (m, 3H) 0.92-1.01 (m, 2H) 0.79-0.85 (m, 2H); MS (ESI) m/z 415 (M+H)$^+$.

Example 146

2-{[(7R,8aS)-7-[(5-cyclopropylpyrazin-2-yl)oxy]hexahydropyrrolo[1,2-a]-pyrazin-2(1H)-yl]sulfonyl}benzonitrile The title compound was prepared as a trifluoroacetic acid salt according to the procedure described in Example 110, substituting 2-cyanobenzene-1-sulfonyl chloride for 4-methylbenzene-1-sulfonyl chloride. $^1$H NMR (500 MHz, DMSO-d$_6$/D$_2$O, temperature=90° C.) δ ppm 8.05-8.19 (m, 4H) 7.87-8.00 (m, 2H) 5.40-5.50 (m, 1H) 3.83-3.95 (m, 2H) 3.72 (d, J=13.43 Hz, 1H) 3.47-3.58 (m, 1H) 3.38-3.47 (m, 1H) 2.99-3.27 (m, 4H) 2.05-2.31 (m, 3H) 0.92-1.08 (m, 2H) 0.78-0.87 (m, 2H); MS (ESI) m/z 426 (M+H)$^+$.

Example 147

(7R,8aS)-7-[(5-cyclopropylpyrazin-2-yl)oxy]-2-[(4-methoxyphenyl)-sulfonyl]octahydropyrrolo[1,2-a]pyrazine The title compound was prepared as a trifluoroacetic acid salt according to the procedure described in Example 110, substituting 4-methoxybenzene-1-sulfonyl chloride for 4-methylbenzene-1-sulfonyl chloride. $^1$H NMR (500 MHz, DMSO-d$_6$/D$_2$O, temperature=90° C.) δ ppm 8.09 (d, J=11.29 Hz, 2H) 7.71-7.80 (m, 2H) 7.13-7.21 (m, 2H) 5.41-5.49 (m, 1H) 3.83-3.91 (m, 4H) 3.68-3.78 (m, 1H) 3.47-3.64 (m, J=13.12 Hz, 2H) 3.37-3.46 (m, 1H) 3.13-3.25 (m, 2H) 2.98 (t, J=9.77 Hz, 1H) 2.82 (dd, J=12.51, 9.46 Hz, 1H) 2.03-2.33 (m, 3H) 0.90-1.03 (m, 2H) 0.79-0.90 (m, 2H); MS (ESI) m/z 431 (M+H)$^+$.

Example 148

(7R,8aS)-7-[(5-cyclopropylpyrazin-2-yl)oxy]-2-[(3,5-dichlorophenyl)-sulfonyl]octahydropyrrolo[1,2-a]pyrazine The title compound was prepared as a trifluoroacetic acid salt according to the procedure described in Example 110, substituting 3,5-dichlorobenzene-1-sulfonyl chloride for 4-methylbenzene-1-sulfonyl chloride. $^1$H NMR (500 MHz, DMSO-$d_6$/D$_2$O, temperature=90° C.) δ ppm 8.05-8.12 (m, 2H) 7.93 (t, J=1.83 Hz, 1H) 7.78 (d, J=1.83 Hz, 2H) 5.41-5.50 (m, 1H) 3.82-3.92 (m, 2H) 3.63-3.69 (m, 1H) 3.46-3.58 (m, 1H) 3.36-3.44 (m, 1H) 3.01-3.22 (m, 3H) 2.90 (dd, J=12.82, 9.46 Hz, 1H) 2.07-2.28 (m, 3H) 0.91-1.00 (m, 2H) 0.80-0.86 (m, 2H); MS (ESI) m/z 469 (M+H)$^+$.

Example 149

(7R,8aS)-7-[(5-cyclopropylpyrazin-2-yl)oxy]-2-[(2, 3-dichlorophenyl)-sulfonyl]octahydropyrrolo[1,2-a] pyrazine The title compound was prepared as a trifluoroacetic acid salt according to the procedure described in Example 110, substituting 2,3-dichlorobenzene-1-sulfonyl chloride for 4-methylbenzene-1-sulfonyl chloride. $^1$H NMR (500 MHz, DMSO-$d_6$/D$_2$O, temperature=90° C.) δ ppm 8.05-8.12 (m, 2H) 8.01 (dd, J=8.09, 1.37 Hz, 1H) 7.90-7.96 (m, 1H) 7.59 (t, J=8.09 Hz, 1H) 5.43-5.52 (m, 1H) 3.84-3.96 (m, 2H) 3.67-3.76 (m, 1H) 3.44-3.54 (m, 1H) 3.30-3.42 (m, 2H) 3.05-3.23 (m, 3H) 2.05-2.30 (m, 3H) 0.91-1.04 (m, 2H) 0.80-0.86 (m, 2H); MS (ESI) m/z 469 (M+H)$^+$.

Example 150

(7R,8aS)-2-[(4-bromophenyl)sulfonyl]-7-[(5-cyclopropylpyrazin-2-yl)oxy]-octahydropyrrolo[1,2-a] pyrazine The title compound was prepared as a trifluoroacetic acid salt according to the procedure described in Example 110, substituting 4-bromobenzene-1-sulfonyl chloride for 4-methylbenzene-1-sulfonyl chloride. $^1$H NMR (500 MHz, DMSO-$d_6$/D$_2$O, temperature=90° C.) δ ppm 8.05-8.10 (m, 2H) 7.83-7.89 (m, 2H) 7.70-7.76 (m, 2H) 5.36-5.44 (m, 1H) 3.74-3.85 (m, 2H) 3.54-3.65 (m, 1H) 3.28-3.38 (m, 2H) 2.83-3.13 (m, 3H) 2.65-2.77 (m, 1H) 2.05-2.24 (m, 3H) 0.91-0.99 (m, 2H) 0.80-0.87 (m, 2H); MS (ESI) m/z 479 (M+H)$^+$.

Example 151

(7R,8aS)-7-[(5-cyclopropylpyrazin-2-yl)oxy]-2-[(3, 4-dichlorophenyl)-sulfonyl]octahydropyrrolo[1,2-a] pyrazine The title compound was prepared as a trifluoroacetic acid salt according to the procedure described in Example 110, substituting 3,4-dichlorobenzene-1-sulfonyl chloride for 4-methylbenzene-1-sulfonyl chloride. $^1$H NMR (500 MHz, DMSO-$d_6$/D$_2$O, temperature=90° C.) δ ppm 8.05-8.12 (m, 2H) 7.97 (d, J=2.14 Hz, 1H) 7.90 (d, J=8.54 Hz, 1H) 7.77 (dd, J=8.54, 2.14 Hz, 1H) 5.37-5.46 (m, 1H) 3.77-3.88 (m, 2H) 3.58-3.66 (m, 1H) 3.32-3.48 (m, 2H) 2.91-3.14 (m, 3H) 2.81 (dd, J=12.36, 9.92 Hz, 1H) 2.05-2.27 (m, 3H) 0.91-0.99 (m, 2H) 0.79-0.87 (m, 2H); MS (ESI) m/z 469 (M+H)$^+$.

Example 152

(7R,8aS)-7-[(5-cyclopropylpyrazin-2-yl)oxy]-2-[(2, 5-dichlorophenyl)-sulfonyl]octahydropyrrolo[1,2-a] pyrazine The title compound was prepared as a trifluoroacetic acid salt according to the procedure described in Example 110, substituting 2,5-dichlorobenzene-1-sulfonyl chloride for 4-methylbenzene-1-sulfonyl chloride. $^1$H NMR (500 MHz, DMSO-$d_6$/D$_2$O, temperature=90° C.) δ ppm 8.07-8.12 (m, 2H) 7.98 (d, J=2.44 Hz, 1H) 7.71-7.77 (m, 2H) 5.45-5.53 (m, 1H) 3.88-3.98 (m, J=12.36, 6.26 Hz, 2H) 3.70-3.78 (m, 1H) 3.54-3.65 (m, 1H) 3.33-3.47 (m, 2H) 3.14-3.27 (m, 3H) 2.08-2.34 (m, 3H) 0.93-1.03 (m, 2H) 0.81-0.88 (m, 2H); MS (ESI) m/z 469 (M+H)$^+$.

Example 153

4-{[(7R,8aS)-7-[(5-cyclopropylpyrazin-2-yl)oxy] hexahydropyrrolo[1,2-a]-pyrazin-2(1H)-yl] sulfonyl}benzonitrile The title compound was prepared as a trifluoroacetic acid salt according to the procedure described in Example 110, substituting 4-cyanobenzene-1-sulfonyl chloride for 4-methylbenzene-1-sulfonyl chloride. $^1$H NMR (500 MHz, DMSO-$d_6$/D$_2$O, temperature=90° C.) δ ppm 8.10 (d, J=1.83 Hz, 2H) 8.06-8.09 (m, 2H) 7.98 (d, J=8.54 Hz, 2H) 5.41-5.47 (m, 1H) 3.78-3.90 (m, 2H) 3.63 (d, J=12.51 Hz, 1H) 3.45-3.56 (m, 1H) 3.34-3.41 (m, 1H) 2.97-3.19 (m, 3H) 2.86 (dd, J=12.97, 9.61 Hz, 1H) 2.03-2.32 (m, 3H) 0.90-1.02 (m, 2H) 0.77-0.88 (m, 2H); MS (ESI) m/z 426 (M+H)$^+$.

Example 154

(7R,8aS)-7-[(5-cyclopropylpyrazin-2-yl)oxy]-2-[(2, 4-dichlorophenyl)-sulfonyl]octahydropyrrolo[1,2-a] pyrazine The title compound was prepared as a trifluoroacetic acid salt according to the procedure described in Example 110, substituting 2,4-dichlorobenzene-1-sulfonyl chloride for 4-methylbenzene-1-sulfonyl chloride. $^1$H NMR (500 MHz, DMSO-$d_6$/D$_2$O, temperature=90° C.) δ ppm 8.07-8.11 (m, 2H) 8.01 (d, J=8.54 Hz, 1H) 7.83 (d, J=2.14 Hz, 1H) 7.64 (dd, J=8.54, 2.14 Hz, 1H) 5.44-5.51 (m, 1H) 3.90 (dd, J=12.21, 6.10 Hz, 2H) 3.65-3.75 (m, 1H) 3.45-3.59 (m, 1H) 3.37-3.44 (m, 1H) 3.31-3.35 (m, J=3.05 Hz, 1H) 3.06-3.24 (m, 3H) 2.06-2.31 (m, 3H) 0.92-1.01 (m, 2H) 0.80-0.86 (m, 2H); MS (ESI) m/z 469 (M+H)$^+$.

Example 155

(7R,8aS)-7-[(5-cyclopropylpyrazin-2-yl)oxy]-2-(1-naphthylsulfonyl)-octahydropyrrolo[1,2-a]pyrazine The title compound was prepared as a trifluoroacetic acid salt according to the procedure described in Example 110, substituting naphthalene-1-sulfonyl chloride for 4-methylbenzene-1-sulfonyl chloride. $^1$H NMR (500 MHz, DMSO-$d_6$/D$_2$O, temperature=90° C.) δ ppm 8.61 (d, J=8.54 Hz, 1H) 8.29 (d, J=8.24 Hz, 1H) 8.17-8.22 (m, 1H) 8.11 (d, J=7.32 Hz, 1H) 8.02-8.09 (m, 2H) 7.65-7.79 (m, 3H) 5.37-5.48 (m, 1H) 3.80-3.93 (m, 2H) 3.64-3.72 (m, 1H) 3.40-3.53 (m, 1H) 3.33-3.40 (m, 1H) 2.95-3.23 (m, 4H) 2.06-2.26 (m, 3H) 0.92-0.99 (m, 2H) 0.80-0.86 (m, 2H); MS (ESI) m/z 451 (M+H)$^+$.

Example 156

(7R,8aS)-7-[(5-cyclopropylpyrazin-2-yl)oxy]-2-(2-naphthylsulfonyl)-octahydropyrrolo[1,2-a]pyrazine The title compound was prepared as a trifluoroacetic acid salt according to the procedure described in Example 110, substituting naphthalene-2-sulfonyl chloride for 4-methylbenzene-1-sulfonyl chloride. $^1$H NMR (500 MHz, DMSO-d$_6$/D$_2$O, temperature=90° C.) δ ppm 8.46 (d, J=1.83 Hz, 1H) 8.14-8.21 (m, 2H) 8.03-8.11 (m, 3H) 7.67-7.89 (m, 3H) 5.36-5.51 (m, 1H) 3.77-3.91 (m, 2H) 3.53-3.73 (m, 2H) 3.35-3.47 (m, 1H) 3.12-3.23 (m, 2H) 3.00-3.10 (m, 1H) 2.90 (dd, J=12.66, 9.31 Hz, 1H) 2.05-2.34 (m, 3H) 0.91-1.01 (m, 2H) 0.79-0.86 (m, 2H); MS (ESI) m/z 451 (M+H)$^+$.

Example 157

(7R,8aS)-7-[(5-cyclopropylpyrazin-2-yl)oxy]-2-[(4-propylphenyl)-sulfonyl]octahydropyrrolo[1,2-a]pyrazine The title compound was prepared as a trifluoroacetic acid salt according to the procedure described in Example 110, substituting 4-propylbenzene-1-sulfonyl chloride for 4-methylbenzene-1-sulfonyl chloride. $^1$H NMR (500 MHz, DMSO-d$_6$/D$_2$O, temperature=90° C.) δ ppm 8.04-8.12 (m, 2H) 7.71 (d, J=8.54 Hz, 2H) 7.48 (d, J=8.24 Hz, 2H) 5.39-5.49 (m, 1H) 3.87 (dd, J=12.51, 6.41 Hz, 1H) 3.76 (dd, J=12.97, 3.20 Hz, 1H) 3.50-3.64 (m, J=12.82 Hz, 2H) 3.36-3.45 (m, 1H) 3.10-3.25 (m, 2H) 2.92-3.04 (m, J=10.07 Hz, 1H) 2.84 (dd, J=12.51, 9.46 Hz, 1H) 2.68 (t, J=7.48 Hz, 2H) 1.98-2.33 (m, 3H) 1.57-1.73 (m, 2H) 0.88-1.01 (m, 5H) 0.79-0.87 (m, 2H); MS (ESI) m/z 443 (M+H)$^+$.

Example 158

(7R,8aS)-7-[(5-cyclopropylpyrazin-2-yl)oxy]-2-[(2-methylphenyl)-sulfonyl]octahydropyrrolo[1,2-a]pyrazine The title compound was prepared as a trifluoroacetic acid salt according to the procedure described in Example 110, substituting 2-methylbenzene-1-sulfonyl chloride for 4-methylbenzene-1-sulfonyl chloride. $^1$H NMR (500 MHz, DMSO-d$_6$/D$_2$O, temperature=90° C.) δ ppm 8.05-8.13 (m, 2H) 7.64-7.88 (m, 1H) 7.57-7.65 (m, J=7.48, 7.48 Hz, 1H) 7.42-7.50 (m, 2H) 5.41-5.55 (m, 1H) 3.87-3.97 (m, 1H) 3.74-3.83 (m, J=13.73, 3.36 Hz, 1H) 3.52-3.68 (m, 2H) 3.38-3.50 (m, 1H) 3.14-3.26 (m, 2H) 3.02-3.13 (m, J=13.12, 9.46 Hz, 2H) 2.58 (s, 3H) 2.04-2.33 (m, 3H) 0.91-0.97 (m, 2H) 0.77-0.86 (m, 2H); MS (ESI) m/z 415 (M+H)$^+$.

Example 159

3-{[(7R,8aS)-7-[(5-cyclopropylpyrazin-2-yl)oxy]hexahydropyrrolo[1,2-a]-pyrazin-2(1H)-yl]sulfonyl}benzonitrile The title compound was prepared as a trifluoroacetic acid salt according to the procedure described in Example 110, substituting 3-cyanobenzene-1-sulfonyl chloride for 4-methylbenzene-1-sulfonyl chloride. $^1$H NMR (500 MHz, DMSO-d$_6$/D$_2$O, temperature=90° C.) δ ppm 8.17-8.23 (m, 1H) 8.09-8.17 (m, 2H) 8.06-8.09 (m, J=10.53, 1.37 Hz, 2H) 7.87 (t, J=7.93 Hz, 1H) 5.37-5.45 (m, 1H) 3.76-3.88 (m, 2H) 3.57-3.69 (m, J=7.93 Hz, 1H) 3.30-3.45 (m, 1H) 2.94-3.10 (m, 4H) 2.79 (t, 1H) 2.05-2.27 (m, 3H) 0.90-0.99 (m, 2H) 0.81-0.85 (m, 2H); MS (ESI) m/z 426 (M+H)$^+$.

Example 160

(7R,8aS)-7-[(5-cyclopropylpyrazin-2-yl)oxy]-2-[(2,5-dimethoxyphenyl)-sulfonyl]octahydropyrrolo[1,2-a]pyrazine The title compound was prepared as a trifluoroacetic acid salt according to the procedure described in Example 110, substituting 2,5-dimethoxybenzene-1-sulfonyl chloride for 4-methylbenzene-1-sulfonyl chloride. $^1$H NMR (500 MHz, DMSO-d$_6$/D$_2$O, temperature=90° C.) δ ppm 8.07-8.12 (m, 2H) 7.19-7.32 (m, 3H) 5.44-5.55 (m, 1H) 3.88-3.97 (m, 1H) 3.87 (s, 3H) 3.80-3.86 (m, 1H) 3.78 (s, 3H) 3.58-3.70 (m, 2H) 3.39-3.46 (m, 1H) 3.33-3.36 (m, J=2.44 Hz, 1H) 3.16-3.26 (m, 2H) 3.12 (dd, J=13.73, 9.16 Hz, 1H) 2.05-2.37 (m, 3H) 0.92-1.01 (m, 2H) 0.81-0.86 (m, 2H); MS (ESI) m/z 461 (M+H)$^+$.

Example 161

(7R,8aS)-2-[(3-chloro-4-fluorophenyl)sulfonyl]-7-[(5-cyclopropylpyrazin-2-yl)oxy]octahydropyrrolo[1,2-a]pyrazine The title compound was prepared as a trifluoroacetic acid salt according to the procedure described in Example 110, substituting 3-chloro-4-fluorobenzene-1-sulfonyl chloride for 4-methylbenzene-1-sulfonyl chloride. $^1$H NMR (500 MHz, DMSO-d$_6$/D$_2$O, temperature=90° C.) δ ppm 8.08 (dd, J=11.29, 1.53 Hz, 2H) 7.98 (dd, J=6.71, 2.14 Hz, 1H) 7.81-7.87 (m, 1H) 7.65 (t, J=8.85 Hz, 1H) 5.37-5.51 (m, 1H) 3.77-3.90 (m, 2H) 3.63 (d, J=12.82 Hz, 1H) 3.46-3.58 (m, 1H) 3.35-3.43 (m, 1H) 2.97-3.21 (m, 3H) 2.86 (dd, J=12.82, 9.77 Hz, 1H) 1.98-2.34 (m, 3H) 0.91-1.00 (m, 2H) 0.78-0.87 (m, 2H); MS (ESI) m/z 453 (M+H)$^+$.

Example 162

(7R,8aS)-7-[(5-isopropylpyrazin-2-yl)oxy]-2-{[4-(trifluoromethyl)-phenyl]sulfonyl}octahydropyrrolo[1,2-a]pyrazine (7R,8aS)-7-{[5-(Prop-1-en-2-yl)pyrazin-2-yl]oxy}-2-{[4-(trifluoromethyl)phenyl]sulfonyl}octahydropyrrolo[1,2-a]pyrazine (240 mg, 0.512 mmol, Example 116) in ethanol (10 mL) was added to 20% palladium hydroxide on carbon (15 mg, 0.11 mmol). The mixture was stirred at room temperature for 16 hours under 30 psi of hydrogen. The mixture was filtered through a nylon membrane and concentrated. The residue was purified by chromatography on silica gel (hexane/ethyl acetate=3:2) to give the title compound (217 mg, 90% yield) as a solid. $^1$H NMR (400 MHz, DMSO-d$_6$) δ ppm 1.21 (s, 6H), 1.77 (m, 1H), 1.91 (m, 1H), 2.09 (m, 1H), 2.21-2.42 (m, 4H), 3.01 (m, 2H), 3.56 (m, 1H), 3.66 (m, 1H), 3.84 (m, 1H), 5.22 (m, 1H), 8.02 (m, 5H), 8.20 (m, 1H); MS (ESI) m/z 471 (M+H)$^+$.

Example 163

5-{[(7R,8aS)-7-[(5-cyclopropylpyrazin-2-yl)oxy]hexahydropyrrolo[1,2-a]-pyrazin-2(1H)-yl]sulfonyl}-1-methyl-1,3-dihydro-2H-indol-2-one The title compound was prepared as a trifluoroacetic acid salt using the procedure described in Example 70, substituting 1-methyl-2-oxoindoline-5-sulfonyl chloride for 6-morpholinopyridine-3-sulfonyl chloride. $^1$H NMR (300 MHz, CDCl$_3$) δ ppm 0.89-1.07 (m, 4H) 1.91-2.08 (m, 2H) 2.40 (dd, J=13.49, 5.55 Hz, 4H) 2.77-3.20 (m, 4H) 3.27 (s, 3H) 3.62 (s, 2H) 5.44-5.61 (m, J=3.17 Hz, 1H) 6.95 (d, J=8.33 Hz, 1H) 7.61 (s, 1H) 7.73 (dd, J=8.33, 1.59 Hz, 1H) 7.93 (d, J=1.59 Hz, 1H) 8.09 (d, J=1.19 Hz, 1H); MS (ESI) m/z 470 (M+H)$^+$.

Example 164

(7R,8aS)-7-[(5-cyclopropylpyrazin-2-yl)oxy]-2-[(5-ethyl-2-thienyl)sulfonyl]-octahydropyrrolo[1,2-a]pyrazine The title compound was prepared as a trifluoroacetic acid salt using the procedure described in Example 70, substituting 5-ethylthiophene-2-sulfonyl chloride for 6-morpholinopyridine-3-sulfonyl chloride. $^1$H NMR (300 MHz, CDCl$_3$) δ ppm 0.90-1.03 (m, 4H) 1.35 (t, J=7.54 Hz, 3H) 1.92-2.07 (m, 2H) 2.28-2.41 (m, 2H) 2.40-2.57 (m, 1H) 2.90 (q, J=7.54 Hz, 2H) 2.96-3.27 (m, 3H) 3.39-3.73 (m, J=21.42 Hz, 2H) 3.88-4.43 (m, 2H) 5.44-5.62 (m, 1H) 6.83-6.89 (m, J=3.57 Hz, 1H) 7.41 (d, J=3.97 Hz, 1H) 7.93 (d, J=1.59 Hz, 1H) 8.08 (d, J=1.19 Hz, 1H); MS (ESI) m/z 435 (M+H)$^+$.

Example 165

(7R,8aS)-7-[(5-cyclopropylpyrazin-2-yl)oxy]-2-[(1-ethyl-1H-pyrazol-4-yl)-sulfonyl]octahydropyrrolo[1,2-a]pyrazine The title compound was prepared as a trifluoroacetic acid salt using the procedure described in Example 70, substituting 1-ethyl-1H-pyrazole-4-sulfonyl chloride for 6-morpholinopyridine-3-sulfonyl chloride. $^1$H NMR (300 MHz, CDCl$_3$) δ ppm 0.87-1.07 (m, 4H) 1.54 (t, J=7.34 Hz, 3H) 1.93-2.07 (m, 2H) 2.34-2.43 (m, 2H) 2.43-2.64 (m, 2H) 2.74-3.34 (m, 4H) 3.43-3.77 (m, 2H) 4.24 (q, J=7.14 Hz, 2H) 5.46-5.62 (m, 1H) 7.76 (s, 1H) 7.80 (s, 1H) 7.93 (d, J=1.19 Hz, 1H) 8.08 (d, J=1.59 Hz, 1H); MS (ESI) m/z 419 (M+H)$^+$.

Example 166

(7R,8aS)-7-[(2-cyclopropylpyrimidin-4-yl)oxy]-2-{[3-(trifluoromethyl)-phenyl]sulfonyl}octahydropyrrolo[1,2-a]pyrazine The procedures for Examples 17E and Example 18 were used substituting (7R,8aS)-octahydropyrrolo[1,2-a]pyrazin-7-ol for (7S,8aR)-octahydropyrrolo[1,2-a]pyrazin-7-ol and substituting 4-chloro-2-cyclopropylpyrimidine for 2-bromo-5-cyclopropylpyrazine to give the title compound (26% yield) as a solid. $^1$H NMR (400 MHz, DMSO-d$_6$) δ ppm 0.99 (m, 3H), 1.90 (m, 2H), 2.07 (m, 3H), 2.27 (m, 3H), 2.97 (m, 1H), 3.52 (m, 1H), 3.64 (m, 1H), 3.85 (m, 1H), 5.21 (m, 1H), 6.64 (m, 1H), 7.95 (m, 2H), 8.12 (s, 2H), 8.31 (m, 2H); MS (ESI) m/z 469 (M+H)$^+$.

Example 167

(7R,8aS)-7-[(2-cyclopropylpyrimidin-4-yl)oxy]-2-{[4-(trifluoromethyl)-phenyl]sulfonyl}octahydropyrrolo[1,2-a]pyrazine The procedures for Examples 17E and Example 18 were used substituting (7R,8aS)-octahydropyrrolo[1,2-a]pyrazin-7-ol for (7S,8aR)-octahydropyrrolo[1,2-a]pyrazin-7-ol, substituting 4-chloro-2-cyclopropylpyrimidine for 2-bromo-5-cyclopropylpyrazine, and substituting 4-(trifluoromethyl)benzene-1-sulfonyl chloride for 3-(trifluoromethyl)benzene-1-sulfonyl chloride to give the title compound (26% yield) as a solid. $^1$H NMR (400 MHz, DMSO-d$_6$) δ ppm 0.99 (m, 3H), 1.90 (m, 2H), 2.07 (m, 3H), 2.27 (m, 3H), 2.97 (m, 1H), 3.52 (m, 1H), 3.64 (m, 1H), 3.85 (m, 1H), 5.21 (m, 1H), 6.64 (m, 1H), 7.98 (m, 2H), 8.04 (s, 2H), 8.31 (m, 2H); MS (ESI) m/z 469 (M+H)$^+$.

Example 168

(7R,8aS)-2-[(5-tert-butyl-2-methylphenyl)sulfonyl]-7-[(5-cyclopropylpyrazin-2-yl)oxy]octahydropyrrolo[1,2-a]pyrazine The title compound was prepared as a trifluoroacetic acid salt according to the procedure described in Example 110, substituting 5-tert-butyl-2-methylbenzene-1-sulfonyl chloride for 4-methylbenzene-1-sulfonyl chloride. $^1$H NMR (500 MHz, DMSO-d$_6$/D$_2$O, temperature=90° C.) δ ppm 8.05-8.12 (m, 2H) 7.77-7.82 (m, 1H) 7.61 (dd, J=7.93, 2.14 Hz, 1H) 7.39 (d, J=8.24 Hz, 1H) 5.40-5.49 (m, 1H) 3.87 (dd, J=11.90, 6.41 Hz, 1H) 3.78 (dd, J=13.12, 3.05 Hz, 1H) 3.57 (d, J=12.51 Hz, 1H) 3.31-3.44 (m, 2H) 2.85-3.17 (m, 4H) 2.54 (s, 3H) 2.05-2.30 (m, 3H) 1.31 (s, 9H) 0.90-1.00 (m, 2H) 0.79-0.88 (m, 2H); MS (ESI) m/z 471 (M+H)$^+$.

Example 169

(7R,8aS)-7-[(5-cyclopropylpyrazin-2-yl)oxy]-2-(5,6,7,8-tetrahydronaphthalen-2-ylsulfonyl)octahydropyrrolo[1,2-a]pyrazine The title compound was prepared as a trifluoroacetic acid salt according to the procedure described in Example 110, substituting 5,6,7,8-tetrahydronaphthalene-2-sulfonyl chloride for 4-methylbenzene-1-sulfonyl chloride. $^1$H NMR (500 MHz, DMSO-d$_6$/D$_2$O, temperature=90° C.) δ ppm 8.04-8.11 (m, 2H) 7.45-7.51 (m, 2H) 7.29-7.37 (m, 1H) 5.43 (dd, J=4.12, 1.98 Hz, 1H) 3.84 (dd, J=12.21, 6.41 Hz, 1H) 3.71-3.78 (m, 1H) 3.41-3.61 (m, J=12.51 Hz, 2H) 3.33-3.40 (m, 1H) 3.02-3.16 (m, 2H) 2.92 (t, 1H) 2.66-2.86 (m, 5H) 2.04-2.29 (m, 3H) 1.71-1.84 (m, 4H) 0.91-1.03 (m, 2H) 0.81-0.86 (m, 2H); MS (ESI) m/z 455 (M+H)$^+$.

Example 170

(7R,8aS)-7-[(5-cyclopropylpyrazin-2-yl)oxy]-2-[(4-methoxy-3-methylphenyl)sulfonyl]octahydropyrrolo[1,2-a]pyrazine The title compound was prepared as a trifluoroacetic acid salt according to the procedure described in Example 110, substituting 4-methoxy-3-methylbenzene-1-sulfonyl chloride for 4-methylbenzene-1-sulfonyl chloride. $^1$H NMR (500 MHz, DMSO-d$_6$/D$_2$O, temperature=90° C.) δ ppm 8.05-8.11 (m, 2H) 7.63 (dd, J=8.70, 2.29 Hz, 1H) 7.56 (d, J=1.53 Hz, 1H) 7.17 (d, J=8.54 Hz, 1H) 5.41-5.50 (m, 1H) 3.83-3.93 (m, 4H) 3.73 (dd, J=12.66, 2.90 Hz, 1H) 3.48-3.64 (m, J=13.12 Hz, 1H) 3.36-3.45 (m, 1H) 3.12-3.24 (m, 2H) 2.95 (t, J=9.92 Hz, 1H) 2.80 (dd, J=12.51, 9.77 Hz, 1H) 2.16-2.36 (m, 5H) 2.07-2.16 (m, 3H) 0.92-1.02 (m, 2H) 0.80-0.87 (m, 2H); MS (ESI) m/z 445 (M+H)$^+$.

Example 171

(7R,8aS)-2-{[4-chloro-3-(trifluoromethyl)phenyl]sulfonyl}-7-[(5-cyclopropylpyrazin-2-yl)oxy]octahydropyaolo[1,2-a]pyrazine The title compound was prepared as a trifluoroacetic acid salt according to the procedure described in Example 110, substituting 4-chloro-3-trifluoromethylbenzene-1-sulfonyl chloride for 4-methylbenzene-1-sulfonyl chloride. $^1$H NMR (500 MHz, DMSO-d$_6$/D$_2$O, temperature=90° C.) δ ppm 8.05-8.13 (m, 4H) 7.98-8.03 (m, 1H) 5.39-5.49 (m, 1H) 3.81-3.90 (m, J=12.21, 6.41 Hz, 2H) 3.61-3.71 (m, 1H) 3.49-3.60 (m, 1H) 3.37-3.45 (m, 1H) 3.02-3.22 (m, 3H) 2.90 (dd, J=12.82, 9.77 Hz, 1H) 2.04-2.32 (m, 3H) 0.90-1.01 (m, 2H) 0.80-0.88 (m, 2H); MS (ESI) m/z 503 (M+H)$^+$.

Example 172

(7R,8aS)-2-{[2-chloro-5-(trifluoromethyl)phenyl]sulfonyl}-7-[(5-cyclopropylpyrazin-2-yl)oxy]octahydropyaolo[1,2-a]pyrazine The title compound was prepared as a trifluoroacetic acid salt according to the procedure described in Example 110, substituting 2-chloro-5-trifluoromethylbenzene-1-sulfonyl chloride for 4-methylbenzene-1-sulfonyl chloride. $^1$H NMR (500 MHz, DMSO-d$_6$/D$_2$O, temperature=90° C.) δ ppm 8.22 (d, J=1.83 Hz, 1H) 8.01-8.11 (m, 3H) 7.94-7.98 (m, 1H) 5.42-5.50 (m, 1H) 3.84-3.98 (m, 2H) 3.68-3.80 (m, 1H) 3.31-3.46 (m, 2H) 3.00-3.21 (m, 4H) 2.05-2.31 (m, 3H) 0.92-1.00 (m, 2H) 0.78-0.88 (m, 2H); MS (ESI) m/z 503 (M+H)$^+$.

Example 173

(7R,8aS)-7-[(5-cyclopropylpyrazin-2-yl)oxy]-2-{[2-methoxy-5-(trifluoromethyl)phenyl]sulfonyl}octahydropyrrolo[1,2-a]pyrazine The title compound was prepared as a trifluoroacetic acid salt according to the procedure described in Example 110, substituting 2-methoxy-5-trifluoromethylbenzene-1-sulfonyl chloride for 4-methylbenzene-1-sulfonyl chloride. $^1$H NMR (500 MHz, DMSO-d$_6$/D$_2$O, temperature=90° C.) δ ppm 8.06-8.12 (m, 2H) 7.97-8.03 (m, 2H) 7.49 (d, J=9.46 Hz, 1H) 5.42-5.51 (m, 1H) 4.03 (s, 3H) 3.88 (dd, J=12.36, 6.26 Hz, 2H) 3.62-3.74 (m, 1H) 3.44-3.60 (m, 1H) 3.33-3.44 (m, 1H) 3.16-3.25 (m, 2H) 3.04-3.15 (m, 2H) 2.07-2.30 (m, 3H) 0.93-1.00 (m, 2H) 0.80-0.86 (m, 2H); MS (ESI) m/z 499 (M+H)$^+$.

Example 174

(7R,8aS)-7-[(5-cyclopropylpyrazin-2-yl)oxy]-2-(2,3-dihydro-1H-inden-5-yl-sulfonyl)octahydropyrrolo[1,2-a]pyrazine The title compound was prepared as a trifluoroacetic acid salt according to the procedure described in Example 110, substituting 2,3-dihydro-1H-indene-5-sulfonyl chloride for 4-methylbenzene-1-sulfonyl chloride. $^1$H NMR (500 MHz, DMSO-d$_6$/D$_2$O, temperature=90° C.) δ ppm 8.06-8.14 (m, 2H) 7.62 (s, 1H) 7.52-7.60 (m, 1H) 7.46-7.52 (m, 1H) 5.41-5.49 (m, 1H) 3.88 (dd, J=12.51, 6.41 Hz, 1H) 3.75 (dd, J=12.66, 3.20 Hz, 1H) 3.49-3.66 (m, J=13.12 Hz, 2H) 3.37-3.46 (m, 1H) 3.14-3.25 (m, 2H) 2.91-3.04 (m, 5H) 2.84 (dd, J=12.66, 9.00 Hz, 1H) 2.15-2.35 (m, 2H) 2.04-2.15 (m, 3H) 0.92-1.01 (m, 2H) 0.79-0.87 (m, 2H); MS (ESI) m/z 441 (M+H)$^+$.

Example 175

(7R,8aS)-7-[(5-cyclopropylpyrazin-2-yl)oxy]-2-[(3,4-dimethylphenyl)-sulfonyl]octahydropyrrolo[1,2-a]pyrazine The title compound was prepared as a trifluoroacetic acid salt according to the procedure described in Example 110, substituting 3,4-dimethylbenzene-1-sulfonyl chloride for 4-methylbenzene-1-sulfonyl chloride. $^1$H NMR (500 MHz, DMSO-d$_6$/D$_2$O, temperature=90° C.) δ ppm 8.05-8.12 (m, 2H) 7.48-7.58 (m, 2H) 7.39-7.45 (m, 1H) 5.40-5.50 (m, 1H) 3.88 (dd, J=12.51, 6.41 Hz, 1H) 3.75 (dd, J=12.97, 3.20 Hz, 1H) 3.49-3.65 (m, J=13.73 Hz, 2H) 3.37-3.46 (m, 1H) 3.11-3.26 (m, 2H) 2.99 (t, J=10.68 Hz, 1H) 2.83 (dd, J=12.36, 9.31 Hz, 1H) 2.34 (s, 6H) 2.05-2.30 (m, 3H) 0.92-0.98 (m, 2H) 0.78-0.88 (m, 2H); MS (ESI) m/z 429 (M+H)$^+$.

Example 176

(7R,8aS)-7-[(5-cyclopropylpyrazin-2-yl)oxy]-2-{[3-(1-methyl-1H-pyrazol-5-yl)phenyl]sulfonyl}octahydropyrrolo[1,2-a]pyrazine The title compound was prepared as a trifluoroacetic acid salt according to the procedure described in Example 110, substituting 3-(1-methyl-1H-pyrazol-5-yl)benzene-1-sulfonyl chloride for 4-methylbenzene-1-sulfonyl chloride. $^1$H NMR (500 MHz, DMSO-d$_6$/D$_2$O, temperature=90° C.) δ ppm 8.05-8.12 (m, 2H) 7.77-7.91 (m, 4H) 7.51 (d, J=1.83 Hz, 1H) 6.50 (d, J=2.44 Hz, 1H) 5.43-5.51 (m, 1H) 3.80-3.95 (m, 5H) 3.60-3.71 (m, 2H) 3.41-3.52 (m, 1H) 3.17-3.29 (m, 2H) 3.10 (t, 1H) 2.95 (dd, J=12.97, 9.31 Hz, 1H) 2.17-2.38 (m, 2H) 2.06-2.16 (m, 1H) 0.91-1.04 (m, 2H) 0.81-0.87 (m, 2H); MS (ESI) m/z 481 (M+H)$^+$.

Example 177

(7R,8aS)-7-[(5-cyclopropylpyrazin-2-yl)oxy]-2-{[2-methyl-6-(trifluoromethyl)pyridin-3-yl]sulfonyl}octahydropyrrolo[1,2-a]pyrazine The title compound was prepared as a trifluoroacetic acid salt according to the procedure described in Example 110, substituting 2-methyl-6-(trifluoromethyl)pyridine-3-sulfonyl chloride for 4-methylbenzene-1-sulfonyl chloride. $^1$H NMR (500 MHz, DMSO-d$_6$/D$_2$O, temperature=90° C.) δ ppm 8.47 (d, J=8.24 Hz, 1H) 8.06-8.11 (m, 2H) 7.94 (d, J=8.24 Hz, 1H) 5.43-5.51 (m, 1H) 3.83-3.95 (m, 2H) 3.65-3.77 (m, 1H) 3.48-3.61 (m, 1H) 3.38-3.47 (m, 1H) 3.05-3.27 (m, 4H) 2.84 (s, 3H) 2.06-2.30 (m, 3H) 0.91-1.01 (m, 2H) 0.81-0.87 (m, 2H); MS (ESI) m/z 484 (M+H)$^+$.

Example 178

(7R,8aS)-7-[(5-cyclopropylpyrazin-2-yl)oxy]-2-{[2-(morpholin-4-yl)-5-(trifluoromethyl)phenyl]sulfonyl}octahydropyrrolo[1,2-a]pyrazine The title compound was prepared as a trifluoroacetic acid salt according to the procedure described in Example 110, substituting 2-morpholino-5-(trifluoromethyl)-benzene-1-sulfonyl chloride for 4-methylbenzene-1-sulfonyl chloride.

¹H NMR (500 MHz, DMSO-d₆/D₂O, temperature=90° C.) δ ppm 8.05-8.10 (m, J=8.24, 1.53 Hz, 3H) 8.01 (dd, J=8.85, 2.14 Hz, 1H) 7.71 (d, J=8.54 Hz, 1H) 5.36-5.43 (m, J=7.02 Hz, 1H) 3.85-3.93 (m, 1H) 3.74-3.82 (m, 5H) 3.64-3.72 (m, 1H) 3.09-3.22 (m, 1H) 3.03-3.11 (m, 5H) 2.65-3.04 (m, 4H) 1.97-2.22 (m, 3H) 0.91-1.00 (m, 2H) 0.77-0.86 (m, 2H); MS (ESI) m/z 554 (M+H)⁺.

Example 179

(7R,8aS)-7-[(5-cyclopropylpyrazin-2-yl)oxy]-2-{[3-(methoxymethyl)-phenyl]sulfonyl}octahydropyrrolo[1,2-a]pyrazine The title compound was prepared as a trifluoroacetic acid salt according to the procedure described in Example 110, substituting 3-methoxymethylbenzene-1-sulfonyl chloride for 4-methylbenzene-1-sulfonyl chloride. ¹H NMR (500 MHz, DMSO-d₆/D₂O, temperature=90° C.) δ ppm 8.05-8.11 (m, 2H) 7.70-7.77 (m, 2H) 7.62-7.69 (m, 2H) 5.39-5.50 (m, 1H) 4.54 (s, 2H) 3.86 (dd, J=12.21, 6.41 Hz, 1H) 3.78 (dd, J=12.97, 3.20 Hz, 1H) 3.49-3.63 (m, 2H) 3.34-3.45 (m, 4H) 3.11-3.23 (m, 2H) 2.99 (t, 1H) 2.79-2.88 (m, 1H) 2.04-2.32 (m, 3H) 0.92-1.00 (m, 2H) 0.80-0.87 (m, 2H); MS (ESI) m/z 445 (M+H)⁺.

Example 180

(7R,8aS)-7-[(5-cyclopropylpyrazin-2-yl)oxy]-2-{[4-methyl-3-(trifluoromethyl)phenyl]sulfonyl}octahydropyrrolo[1,2-a]pyrazine The title compound was prepared as a trifluoroacetic acid salt according to the procedure described in Example 110, substituting 4-methyl-3-trifluoromethylbenzene-1-sulfonyl chloride for 4-methylbenzene-1-sulfonyl chloride. ¹H NMR (500 MHz, DMSO-d₆/D₂O, temperature=90° C.) δ ppm 8.03-8.12 (m, 2H) 7.92-8.00 (m, 2H) 7.75 (d, J=7.93 Hz, 1H) 5.38-5.51 (m, 1H) 3.70-3.93 (m, 2H) 3.62 (d, J=12.51 Hz, 1H) 3.42-3.51 (m, 1H) 3.33-3.41 (m, 1H) 2.91-3.18 (m, 3H) 2.81 (dd, J=12.51, 9.77 Hz, 1H) 2.57 (d, J=1.53 Hz, 3H) 2.05-2.29 (m, 3H) 0.91-0.99 (m, 2H) 0.79-0.87 (m, 2H); MS (ESI) m/z 483 (M+H)⁺.

Example 181

5-{[(7R,8aS)-7-[(5-cyclopropylpyrazin-2-yl)oxy]hexahydropyrrolo[1,2-a]-pyrazin-2(1H)-yl]sulfonyl}-2-fluorobenzonitrile The title compound was prepared using the procedure described in Example 27C substituting 3-cyano-4-fluorobenzene-1-sulfonyl chloride for 2-(trifluoromethyl)-benzene-1-sulfonyl chloride. ¹H NMR (300 MHz, DMSO-d₆) δ ppm 0.74-0.87 (m, 2H), 0.87-0.99 (m, 2H), 1.68-1.96 (m, 2H), 2.03-2.46 (m, 6H), 2.97 (d, J=10.9 Hz, 1H), 3.50-3.70 (m, 2H), 3.79 (d, J=10.2 Hz, 1H), 5.10-5.35 (m, 1H), 7.79 (t, J=9.0 Hz, 1H), 8.06-8.19 (m, 3H), 8.37 (dd, J=6.1, 2.4 Hz, 1H); MS (ESI) m/z 444 (M+H)⁺.

Example 182

2-{[(7R,8aS)-7-[(5-cyclopropylpyrazin-2-yl)oxy]hexahydropyrrolo[1,2-a]-pyrazin-2(1H)-yl]sulfonyl}-4-methylbenzonitrile The title compound was prepared as a trifluoroacetic acid salt using the procedure described in Example 70, substituting 2-cyano-5-methylbenzene-1-sulfonyl chloride for 6-morpholinopyridine-3-sulfonyl chloride. ¹H NMR (300 MHz, CDCl₃) δ ppm 0.91-1.05 (m, 4H) 1.94-2.07 (m, 1H) 2.32-2.50 (m, 2H) 2.53 (s, 3H) 2.85-3.24 (m, 3H) 3.29-3.78 (m, 4H) 3.78-4.48 (m, 2H) 5.42-5.63 (m, 1H) 7.54 (dd, J=7.93, 0.79 Hz, 1H) 7.80 (d, J=7.93 Hz, 1H) 7.85 (s, 1H) 7.93 (d, J=1.19 Hz, 1H) 8.09 (d, J=1.19 Hz, 1H); MS (ESI) m/z 440 (M+H)⁺.

Example 183

(7R,8aS)-7-[(5-cyclopropylpyrazin-2-yl)oxy]-2-[(1-isopropyl-3-methyl-1H-pyrazol-4-yl)sulfonyl]octahydropyrrolo[1,2-a]pyrazine The title compound was prepared as a trifluoroacetic acid salt using the procedure described in Example 70, substituting 1-isopropyl-3-methyl-1H-pyrazole-4-sulfonyl chloride for 6-morpholinopyridine-3-sulfonyl chloride. ¹H NMR (300 MHz, CDCl₃) δ ppm 0.88-1.05 (m, 4H) 1.51 (d, J=6.78 Hz, 6H) 1.93-2.07 (m, 1H) 2.32-2.38 (m, 1H) 2.40 (s, 3H) 2.76-3.40 (m, J=32.89 Hz, 5H) 3.42-4.10 (m, 4H) 4.14-4.35 (m, 1H) 4.35-4.54 (m, 1H) 5.42-5.64 (m, 1H) 7.74 (s, 1H) 7.93 (d, J=1.36 Hz, 1H) 8.08 (d, J=1.36 Hz, 1H); MS (ESI) m/z 447 (M+H)⁺.

Example 184

(7R,8aS)-2-{[4-fluoro-3-(trifluoromethyl)phenyl]sulfonyl}octahydropyrrolo[1,2-a]pyrazin-7-ol The procedure for making Example 19 was used substituting 4-fluoro-3-(trifluoromethyl)benzene-1-sulfonyl chloride for 3-(trifluoromethyl)benzene-1-sulfonyl chloride to give the title compound (81% yield). MS (ESI) m/z 369 (M+H)⁺.

Example 185

(7R,8aS)-2-{[3-fluoro-5-(trifluoromethyl)phenyl]sulfonyl}octahydropyrrolo[1,2-a]pyrazin-7-ol The procedure for making Example 19 was used substituting 3-fluoro-5-(trifluoromethyl)benzene-1-sulfonyl chloride for 3-(trifluoromethyl)benzene-1-sulfonyl chloride to give the title compound (80% yield). MS (ESI) m/z 369 (M+H)⁺.

Example 186

(7R,8aS)-2-{[2-fluoro-5-(trifluoromethyl)phenyl]sulfonyl}octahydropyrrolo[1,2-a]pyrazin-7-ol The procedure for making Example 19 was used substituting 2-fluoro-5-(trifluoromethyl)benzene-1-sulfonyl chloride for 3-(trifluoromethyl)benzene-1-sulfonyl chloride to give the title compound (80%). MS (ESI) m/z 369 (M+H)⁺.

Example 187

(7R,8aS)-2-{[4-chloro-3-(trifluoromethyl)phenyl]sulfonyl}octahydropyrrolo[1,2-a]pyrazin-7-ol The procedure for making Example 19 was used substituting 4-chloro-3-(trifluoromethyl)benzene-1-sulfonyl chloride for 3-(trifluoromethyl)benzene-1-sulfonyl chloride to give the title compound (81°/0 yield). MS (ESI) m/z 386 (M+H)⁺.

Example 188

(7R,8aS)-2-{[4-chloro-3-(trifluoromethyl)phenyl]sulfonyl}-7-ethoxy-octahydropyrrolo[1,2-a]pyrazine To (7R,8aS)-2-{[4-chloro-3-(trifluoromethyl)phenyl]sulfonyl}octahydropyrrolo[1,2-a]pyrazin-7-ol (0.3 mmol, Example 187) in tetrahydrofuran (1 mL) at room temperature was added NaH (20 mg, 60% in mineral oil). After 15 minutes, iodoethane (0.39 mmol) was added. The mixture was stirred at 60° C. for 2 days. The mixture was partially purified by chromatography on silica gel ($CH_2Cl_2/CH_3OH$=10:1) to give the title compound as an impure solid (77 mg). The product was purified by HPLC (Gilson®, Xbridge™ 30×100 mm column, eluted with pH=10 aqueous ammonium bicarbonate-ammonium hydroxide/methanol (70:30 to 0:100 gradient over 16 minutes), flow rate 36 mL/minute, UV=220 nm) to give the title compound (20 mg, 16% yield) as a solid. $^1$H NMR (400 MHz, DMSO-$d_6$) δ ppm 1.07 (m, 3H), 1.47 (m, 1H), 1.73 (m, 1H), 2.00 (m, 1H), 2.08 (m, 1H), 2.19 (m, 1H), 2.39 (m, 6H), 2.93 (m, 1H), 3.63 (m, 1H), 3.76 (m, 1H), 3.92 (m, 1H), 8.04 (m, 3H); MS (ESI) m/z 469 (M+H)$^+$.

Example 189

(7R,8aS)-7-[(5-cyclopropylpyrazin-2-yl)oxy]-2-[(3,3,3-trifluoropropyl)-sulfonyl]octahydropyrrolo[1,2-a]pyrazine The procedures for Example 17E and Example 18 were used substituting (7R,8aS)-octahydropyrrolo[1,2-a]pyrazin-7-ol for (7S,8aR)-octahydropyrrolo[1,2-a]-pyrazin-7-ol and substituting 3,3,3-trifluoropropane-1-sulfonyl chloride for 3-(trifluoromethyl)benzene-1-sulfonyl chloride to give the title compound (96% yield) as a solid. $^1$H NMR (400 MHz, DMSO-$d_6$) δ ppm 0.82 (m, 2H), 0.91 (m, 2H), 1.81 (m, 2H), 2.11 (m, 1H), 2.24 (m, 2H), 2.33 (m, 2H), 2.69 (m, 4H), 2.98 (m, 2H), 3.56 (m, 2H), 3.63 (m, 1H), 5.27 (m, 1H), 8.13 (s, 2H); MS (ESI) m/z 421 (M+H)$^+$.

Example 190

(7S,8aR)-2-{[4-(trifluoromethyl)phenyl]sulfonyl}octahydropyrrolo[1,2-a]-pyrazin-7-ol To (7S,8aR)-octahydropyrrolo[1,2-a]pyrazin-7-ol (0.208 g, 1.463 mmol) and 4-(trifluoromethyl)benzene-1-sulfonyl chloride (0.358 g, 1.463 mmol) in dichloromethane (3 mL) was added triethylamine (303 mg, 3 mmol). The mixture was stirred at room temperature overnight. The mixture was concentrated and the residue was purified by chromatography on silica gel ($CH_2Cl_2/CH_3OH$=10:1) to give the title compound (0.4 g, 78% yield). MS (ESI) m/z 421 (M+H)$^+$.

Example 191

(7R,8aS)-2-(butylsulfonyl)-7-[(5-cyclopropylpyrazin-2-yl)oxy]-octahydropyrrolo[1,2-a]pyrazine The title compound was prepared as a trifluoroacetic acid salt according to the procedure described in Example 110, substituting butane-1-sulfonyl chloride for 4-methylbenzene-1-sulfonyl chloride. $^1$H NMR (500 MHz, DMSO-$d_6$/$D_2O$, temperature=90° C.) δ ppm 8.08-8.15 (m, 2H) 5.47-5.56 (m, 1H) 3.91-4.01 (m, 1H) 3.81 (dd, J=13.58, 3.20 Hz, 1H) 3.63 (dd, J=9.92, 3.20 Hz, 1H) 3.39-3.48 (m, 1H) 3.30-3.37 (m, 2H) 3.07-3.25 (m, 4H) 2.20-2.36 (m, 2H) 2.07-2.18 (m, 1H) 1.63-1.75 (m, 2H) 1.37-1.51 (m, 2H) 0.87-1.03 (m, 5H) 0.80-0.87 (m, 2H); MS (ESI) m/z 381 (M+H)$^+$.

Example 192

(7R,8aS)-7-[(5-cyclopropylpyrazin-2-yl)oxy]-2-(2-thienylsulfonyl)-octahydropyrrolo[1,2-a]pyrazine The title compound was prepared as a trifluoroacetic acid salt according to the procedure described in Example 110, substituting thiophene-2-sulfonyl chloride for 4-methylbenzene-1-sulfonyl chloride. $^1$H NMR (500 MHz, DMSO-$d_6$/$D_2O$, temperature=90° C.) δ ppm 8.06-8.16 (m, 2H) 8.03 (dd, J=4.88, 1.22 Hz, 1H) 7.70 (dd, J=3.81, 1.37 Hz, 1H) 7.24-7.35 (m, 1H) 5.40-5.50 (m, 1H) 3.90 (dd, J=12.51, 6.41 Hz, 1H) 3.79 (dd, J=12.82, 3.36 Hz, 1H) 3.53-3.69 (m, 2H) 3.41-3.49 (m, 1H) 3.17-3.28 (m, 2H) 3.00-3.13 (m, 1H) 2.92 (dd, J=12.82, 9.16 Hz, 1H) 2.04-2.36 (m, 3H) 0.91-1.04 (m, 2H) 0.78-0.90 (m, 2H); MS (ESI) m/z 407 (M+H)$^+$.

Example 193

(7R,8aS)-2-(benzylsulfonyl)-7-[(5-cyclopropylpyrazin-2-yl)oxy]octahydropyrrolo[1,2-a]pyrazine The title compound was prepared as a trifluoroacetic acid salt according to the procedure described in Example 110, substituting phenylmethanesulfonyl chloride for 4-methylbenzene-1-sulfonyl chloride. $^1$H NMR (500 MHz, DMSO-$d_6$/$D_2O$, temperature=90° C.) δ ppm 8.08 (d, J=5.80 Hz, 2H) 7.36-7.46 (m, 5H) 5.33-5.45 (m, 1H) 4.43 (s, 2H) 3.78 (dd, J=11.44, 6.26 Hz, 1H) 3.65-3.73 (m, 1H) 3.45-3.56 (m, 1H) 3.16-3.22 (m, 1H) 2.99-3.14 (m, 2H) 2.77 (d, J=71.11 Hz, 3H) 1.96-2.18 (m, 3H) 0.89-1.00 (m, 2H) 0.83 (dd, J=5.04, 2.59 Hz, 2H); MS (ESI) m/z 415 (M+H)$^+$.

Example 194

(7R,8aS)-7-[(5-cyclopropylpyrazin-2-yl)oxy]-2-(isopropylsulfonyl)octahydropyrrolo[1,2-a]pyrazine The title compound was prepared as a trifluoroacetic acid salt according to the procedure described in Example 110, substituting propane-2-sulfonyl chloride for 4-methylbenzene-1-sulfonyl chloride. $^1$H NMR (500 MHz, DMSO-$d_6$/$D_2O$, temperature=90° C.) δ ppm 8.04-8.15 (m, 2H) 5.46-5.55 (m, 1H) 3.90-3.99 (m, 1H) 3.86 (d, 1H) 3.50-3.72 (m, 2H) 3.32-3.47 (m, 3H) 3.10-3.25 (m, 3H) 2.19-2.36 (m, 2H) 2.07-2.17 (m, 1H) 1.27 (d, J=6.71 Hz, 6H) 0.90-1.01 (m, 2H) 0.79-0.88 (m, 2H); MS (ESI) m/z 367 (M+H)$^+$.

Example 195

(7R,8aS)-7-[(5-cyclopropylpyrazin-2-yl)oxy]-2-{[6-(trifluoromethyl)pyridin-3-yl]sulfonyl}octahydropyrrolo[1,2-a]pyrazine The title compound was prepared as a trifluoroacetic acid salt according to the procedure described in Example 110, substituting 6-(trifluoromethyl)pyridine-3-sulfonyl chloride for 4-methylbenzene-1-sulfonyl chloride. $^1$H NMR (500 MHz, DMSO-$d_6$/$D_2O$, temperature=90° C.) δ ppm 9.13 (d, J=2.14 Hz, 1H) 8.49 (dd, J=8.24, 2.14 Hz, 1H) 8.16 (d, J=8.24 Hz, 1H) 8.08 (d, J=8.85 Hz, 2H) 5.38-5.48 (m, 1H) 3.78-3.97 (m, 2H) 3.66-3.76 (m, 1H) 3.33-3.51 (m, 2H) 3.02-3.16 (m, J=8.85 Hz, 3H) 2.90 (dd, J=12.21, 10.07 Hz, 1H) 2.05-2.29 (m, 3H) 0.91-1.00 (m, 2H) 0.78-0.88 (m, 2H); MS (ESI) m/z 470 (M+H)+.

Example 196

(7R,8aS)-7-[(5-cyclopropylpyrazin-2-yl)oxy]-2-[(4-methylpyridin-2-yl)-sulfonyl]octahydropyrrolo[1,2-a]pyrazine The title compound was prepared as a trifluoroacetic acid salt according to the procedure described in Example 110, substituting 4-methylpyridine-2-sulfonyl chloride for 4-methylbenzene-1-sulfonyl chloride. $^1$H NMR (500 MHz, DMSO-d$_6$/D$_2$O, temperature=90° C.) δ ppm 8.59 (d, J=4.88 Hz, 1H) 8.04-8.12 (m, 2H) 7.78 (s, 1H) 7.53 (d, J=4.88 Hz, 1H) 5.39-5.51 (m, 1H) 3.81-3.95 (m, 2H) 3.70 (m, 1H) 3.43-3.60 (m, 1H) 3.35-3.42 (m, 2H) 3.03-3.19 (m, 3H) 2.46 (s, 3H) 2.04-2.32 (m, 3H) 0.91-1.00 (m, 2H) 0.80-0.87 (m, 2H); MS (ESI) m/z 416 (M+H)+.

Example 197

(7R,8aS)-7-[(5-cyclopropylpyrazin-2-yl)oxy]-2-[(6-methoxypyridin-3-yl)-sulfonyl]octahydropyrrolo[1,2-a]pyrazine The title compound was prepared as a trifluoroacetic acid salt according to the procedure described in Example 110, substituting 6-methoxypyridine-3-sulfonyl chloride for 4-methylbenzene-1-sulfonyl chloride. $^1$H NMR (500 MHz, DMSO-d$_6$/D$_2$O, temperature=90° C.) δ ppm 8.59 (d, J=2.44 Hz, 1H) 8.00-8.15 (m, 3H) 7.04 (d, J=8.85 Hz, 1H) 5.39-5.50 (m, 1H) 3.99 (s, 3H) 3.74-3.89 (m, 2H) 3.49-3.64 (m, J=13.43 Hz, 2H) 3.34-3.45 (m, 1H) 3.08-3.22 (m, 2H) 3.02 (t, J=12.51 Hz, 1H) 2.84 (dd, J=12.51, 9.77 Hz, 1H) 2.01-2.33 (m, 3H) 0.92-1.00 (m, 2H) 0.80-0.88 (m, 2H); MS (ESI) m/z 432 (M+H)+.

Example 198

3-{[(7R,8aS)-7-[(5-cyclopropylpyrazin-2-yl)oxy] hexahydropyrrolo[1,2-a]pyrazin-2(1H)-yl]sulfonyl}-N,N-dimethylbenzamide The title compound was prepared as a trifluoroacetic acid salt according to the procedure described in Example 110 substituting 3-(dimethylcarbamoyl)benzene-1-sulfonyl chloride for 4-methylbenzene-1-sulfonyl chloride. $^1$H NMR (500 MHz, DMSO-d$_6$/D$_2$O, 90° C.) δ ppm 8.04-8.11 (m, 2H) 7.84-7.90 (m, 1H) 7.72-7.78 (m, 3H) 5.39-5.49 (m, 1H) 3.78-3.90 (m, J=12.21, 6.41 Hz, 2H) 3.56-3.65 (m, 1H) 3.44-3.56 (m, 1H) 3.35-3.43 (m, 1H) 3.07-3.21 (m, 2H) 2.92-3.06 (m, 7H) 2.85 (t, J=11.60 Hz, 1H) 2.06-2.31 (m, 3H) 0.92-0.99 (m, 2H) 0.80-0.87 (m, 2H); (ESI) m/z 472 (M+H)+.

Example 199

(7R,8aS)-7-[(5-cyclopropylpyrazin-2-yl)oxy]-2-[(5-fluoropyridin-3-yl)-sulfonyl]octahydropyrrolo[1,2-a] pyrazine The title compound was prepared as a trifluoroacetic acid salt according to the procedure described in Example 110 substituting 5-fluoropyridine-3-sulfonyl chloride for 4-methylbenzene-1-sulfonyl chloride. $^1$H NMR (500 MHz, DMSO-d$_6$/D$_2$O, 90° C.) δ ppm 0.79-0.87 (m, 2H) 0.92-1.01 (m, 2H) 2.06-2.16 (m, 1H) 2.17-2.34 (m, 2H) 2.99 (dd, J=13.12, 9.46 Hz, 1H) 3.09-3.29 (m, 3H) 3.39-3.48 (m, 1H) 3.58-3.74 (m, 2H) 3.83-3.94 (m, 2H) 5.42-5.51 (m, 1H) 8.07 (d, J=1.53 Hz, 1H) 8.09-8.15 (m, 2H) 8.85 (s, 1H) 8.89 (d, J=2.75 Hz, 1H); (ESI) m/z 420 (M+H)+.

Example 200

5-{[(7R,8aS)-7-[(5-cyclopropylpyrazin-2-yl)oxy] hexahydropyrrolo[1,2-a]-pyrazin-2(1H)-yl]sulfonyl}-3,3-dimethyl-1,3-dihydro-2H-indol-2-one The title compound was prepared as a trifluoroacetic acid salt according to the procedure described in Example 110, substituting 3,3-dimethyl-2-oxoindoline-5-sulfonyl chloride for 4-methylbenzene-1-sulfonyl chloride. $^1$H NMR (500 MHz, DMSO-d$_6$/D$_2$O, temperature=90° C.) δ ppm 8.04-8.08 (m, 2H) 7.62-7.68 (m, 2H) 7.11 (d, J=7.93 Hz, 1H) 5.34-5.44 (m, J=6.41 Hz, 1H) 3.71-3.84 (m, J=11.90, 6.41 Hz, 2H) 3.49-3.60 (m, 1H) 3.28-3.38 (m, 2H) 2.81-3.06 (m, 3H) 2.69 (t, J=1.83 Hz, 1H) 2.62-2.77 (m, J=1.83 Hz, 1H) 2.04-2.26 (m, 3H) 1.33 (d, J=1.53 Hz, 6H) 0.91-0.98 (m, 2H) 0.80-0.86 (m, 2H); MS (ESI) m/z 484 (M+H)+.

Example 201

2-{[(7R,8aS)-7-[(5-cyclopropylpyrazin-2-yl)oxy] hexahydropyrrolo[1,2-a]-pyrazin-2(1H)-yl]sulfonyl}-4-(trifluoromethyl)benzonitrile Example 201A (7R,8aS)-2-{[2-bromo-5-(trifluoromethyl)phenyl] sulfonyl}-7-[(5-cyclopropylpyrazin-2-yl)oxy]octahydropyrrolo[1,2-a]pyrazine The title compound was prepared according to the procedure described in Example 57, substituting 2-bromo-5-(trifluoromethyl)benzene-1-sulfonyl chloride for 3-tert-butyl-4-methoxybenzene-1-sulfonyl chloride.

Example 201B

2-{[(7R,8aS)-7-[(5-cyclopropylpyrazin-2-yl)oxy] hexahydropyrrolo[1,2-a]-pyrazin-2(1H)-yl]sulfonyl}-4-(trifluoromethyl)benzonitrile To a solution of Example 201A (105 mg, 0.192 mmol) in N,N-dimethylformamide (1 mL) was added copper(I) cyanide (52 mg, 0.58 mmol), and the resulting mixture was heated at 120° C. and stirred for 24 hours. The cooled mixture was partitioned between water and ethyl acetate, and the organic layer was dried over Na$_2$SO$_4$. The drying agent was removed by filtration, the filtrate was concentrated in vacuo, and the residue was purified on silica gel using a solvent gradient of 0-60% ethyl acetate in hexanes. The title compound was obtained as a colorless solid (70 mg, 74%). $^1$H NMR (300 MHz, CDCl$_3$) δ ppm 0.88-0.99 (m, 4H), 1.77-1.91 (m, 1H), 1.93-2.06 (m, 2H), 2.35 (dd, J=10.00, 5.26 Hz, 1H), 2.39-2.61 (m, 3H), 2.81-2.96 (m, 1H), 3.03 (dd, J=8.82, 2.37 Hz, 1H), 3.68 (dd, J=10.17, 6.78 Hz, 1H), 3.89 (dd, J=10.51, 1.70 Hz, 1H), 3.96-4.08 (m, 1H), 5.23-5.39 (m, 1H), 7.90-7.98 (m, 2H), 7.99-8.06 (m, 2H), 8.30 (s, 1H); MS (ESI) m/z 494 (M+H)+.

Example 202

(7R,8aS)-2-[(6-tert-butylpyridin-2-yl)sulfonyl]-7-{
[5-(prop-1-en-2-yl)-pyrazin-2-yl]
oxy}octahydropyrrolo[1,2-a]pyrazine

Example 202A tert-butyl (7R,8aS)-7-hydroxyhexahydropyrrolo[1,2-a]pyrazine-2(1H)-carboxylate To a solution of (7R,8aS)-octahydropyrrolo[1,2-a]pyrazin-7-ol (1.0 g, 7.03 mmol) in anhydrous dichloromethane (35 mL) was added di-tert-butyl-dicarbonate (1.714 mL, 7.38 mmol), and the resulting mixture was stirred at room temperature for 16 hours. The mixture was washed with 1 N NaOH (20 mL) and water, and the organic extract was dried over $Na_2SO_4$. The drying agent was removed by filtration, and the crude product was purified by column chromatography on silica gel using a solvent gradient of 0-10% methanol in dichloromethane. The title compound was obtained as a colorless oil (0.88 g, 52%).

Example 202B tert-butyl (7R,8aS)-7-{[5-(prop-1-en-2-yl)pyrazin-2-yl]oxy}hexahydropyrrolo[1,2-a]pyrazine-2(1H)-carboxylate To a solution of the product from Example 202A (0.88 g, 3.63 mmol)) in anhydrous tetrahydrofuran (20 mL) was added a 1.0 M solution of potassium tert-butoxide in tetrahydrofuran (4.36 mL, 4.36 mmol). The resulting mixture was stirred at room temperature for 20 minutes, and then 2-bromo-5-(prop-1-en-2-yl)pyrazine (0.867 g, 4.36 mmol) was added. The resulting dark mixture was stirred at room temperature for 16 hours, and the mixture was then poured into water (50 mL) and extracted with ethyl acetate (3×50 mL). The combined organic layers were dried over $Na_2SO_4$. The drying agent was removed by filtration, and the crude product was purified by column chromatography on silica gel using a solvent gradient of 0-60% ethyl acetate in hexanes. The title compound was obtained as a light tan oil that crystallized on standing (0.67 g, 51.2%).

Example 202C (7R,8aS)-7-{[5-(prop-1-en-2-yl)pyrazin-2-yl]
oxy}octahydropyrrolo[1,2-a]-pyrazine hydrochloride To a solution of the product from Example 202B (100 mg, 0.277 mmol) in 1,4-dioxane (1 mL) was added 4 N HCl in 1,4-dioxane (1 mL, 4.00 mmol). The resulting mixture was stirred at ambient temperature for 3 hours, and the mixture was then concentrated to give the title compound as an off-white solid (82 mg, quantitative).

Example 202D (7R,8aS)-2-[(6-tert-butylpyridin-2-yl)sulfonyl]-7-{
[5-(prop-1-en-2-yl)-pyrazin-2-yl]
oxy}octahydropyrrolo[1,2-a]pyrazine The title compound was prepared according to the procedure described in Example 57, substituting the product from Example 202C (82 mg, 0.28 mmol) for the product from Example 27B, and substituting the product from Example 58B for 3-tert-butyl-4-methoxybenzene-1-sulfonyl chloride. The title compound was obtained as a colorless solid (79 mg, 62%). $^1$H NMR (300 MHz, $CDCl_3$) δ ppm 1.39 (s, 9H), 1.78-2.06 (m, 2H), 2.17 (s, 3H), 2.31-2.49 (m, 2H), 2.50-2.62 (m, 1H), 2.61-2.74 (m, 1H), 2.91-3.06 (m, 2H), 3.69 (dd, J=9.92, 6.74 Hz, 1H), 3.85-3.96 (m, 1H), 4.02-4.13 (m, 1H), 5.22 (t, J=1.59 Hz, 1H), 5.32-5.42 (m, 1H), 5.77-5.81 (m, J=1.59 Hz, 1H), 7.51 (dd, J=7.54, 1.19 Hz, 1H), 7.71-7.84 (m, 2H), 8.15 (d, J=1.59 Hz, 1H), 8.20 (d, J=1.19 Hz, 1H).

Example 203

(7R,8aS)-2-[(6-tert-butylpyridin-2-yl)sulfonyl]-7-
[(5-isopropylpyrazin-2-yl)-oxy]octahydropyrrolo[1,
2-a]pyrazine To a solution of the product from Example 202D (21 mg, 0.046 mmol) in tetrahydrofuran (10 mL) in a 50 mL pressure bottle was added 5% palladium on carbon, wet (4.20 mg, 0.039 mmol). The resulting mixture was placed under $H_2$ gas (30 psi) and stirred for 15 minutes at room temperature. The mixture was filtered and concentrated in vacuo, and the crude product was purified by column chromatography on silica gel using a solvent gradient of 0-60% ethyl acetate in hexanes to give the title compound (18 mg, 85%). $^1$H NMR (300 MHz, $CDCl_3$) δ ppm 1.29 (d, J=6.78 Hz, 6H), 1.39 (s, 9H), 1.76-1.91 (m, 1H), 1.92-2.03 (m, 1H), 2.30-2.61 (m, 3H), 2.67 (t, J=10.68 Hz, 1H), 2.92-3.08 (m, 3H), 3.68 (dd, J=9.83, 6.78 Hz, 1H), 3.85-3.96 (m, 1H), 4.02-4.12 (m, 1H), 5.26-5.40 (m, 1H), 7.51 (dd, J=7.80, 1.02 Hz, 1H), 7.71-7.84 (m, 2H), 7.91 (d, J=1.36 Hz, 1H), 8.13 (d, J=1.36 Hz, 1H); MS (ESI) m/z 460 (M+H)$^+$.

Example 204

(7R,8aS)-7-{[5-(prop-1-en-2-yl)pyrazin-2-yl]oxy}-
2-{[6-(trifluoromethyl)-pyridin-2-yl]
sulfonyl}octahydropyrrolo[1,2-a]pyrazine A solution of the product from Example 202B (100 mg, 0.277 mmol) in $CH_2Cl_2$ (2 mL) was treated dropwise with trifluoroacetic acid (1 mL, 12.98 mmol), and the resulting mixture was stirred at room temperature for 30 minutes. The mixture was concentrated with a stream of dry $N_2$, and the residue was dried in vacuo. To this residue was added $CH_2Cl_2$ (2.5 mL), (6-(trifluoromethyl)pyridine-2-sulfonyl chloride (102 mg, 0.416 mmol)), and diisopropylethylamine (0.242 mL, 1.385 mmol), and the resulting mixture was stirred at room temperature for 3 hours. The mixture was partitioned between water and $CH_2Cl_2$, and the organic layer was dried over $Na_2SO_4$. The drying agent was removed by filtration, and the solution was concentrated in vacuo. The crude product was purified by column chromatography on silica gel using a solvent gradient of 0-40% ethyl acetate in hexanes. The title compound was obtained as a colorless solid (102 mg, 78%). $^1$H NMR (300 MHz, $CDCl_3$) δ ppm 1.79-1.94 (m, 1H), 1.94-2.06 (m, 1H), 2.18 (s, 3H), 2.37 (dd, J=9.83, 5.09 Hz, 1H), 2.40-2.64 (m, 2H), 2.72 (t, J=10.85 Hz, 1H), 2.96-3.13 (m, 2H), 3.71 (dd, J=9.83, 6.78 Hz, 1H), 3.93 (d, J=12.89 Hz, 1H), 4.08 (d, J=11.19 Hz, 1H), 5.22 (t, J=1.53 Hz, 1H), 5.33-5.43 (m, 1H), 5.77-5.81 (m, 1H), 7.82-7.90 (m, 1H), 8.08-8.14 (m, 2H), 8.15 (d, J=1.36 Hz, 1H), 8.20 (d, J=1.36 Hz, 1H); MS (ESI) m/z 470 (M+H)$^+$.

Example 205

(7R,8aS)-7-[(5-isopropylpyrazin-2-yl)oxy]-2-{[6-
(trifluoromethyl)pyridin-2-yl]
sulfonyl}octahydropyrrolo[1,2-a]pyrazine The title compound was prepared according to the procedure described in Example 203, substituting the product from Example 204 (30 mg, 0.064 mmol) for the product from Example 202D. The title compound was obtained as a colorless solid (23 mg, 76%). $^1$H NMR (300 MHz, CDCl$_3$) δ ppm 1.28 (s, 3H), 1.30 (s, 3H), 1.78-1.93 (m, 1H), 1.93-2.03 (m, 1H), 2.36 (dd, J=10.00, 5.26 Hz, 1H), 2.40-2.62 (m, 2H), 2.64-2.77 (m, 1H), 2.95-3.14 (m, 3H), 3.70 (dd, J=10.00, 6.61 Hz, 1H), 3.86-3.99 (m, 1H), 4.02-4.13 (m, 1H), 5.28-5.41 (m, 1H), 7.82-7.89 (m, J=5.76, 3.05 Hz, 1H), 7.91 (d, J=1.36 Hz, 1H), 8.08-8.17 (m, 3H); MS (ESI) m/z 472 (M+H)$^+$.

Example 206

(7R,8aS)-7-{[5-(1-methylcyclopropyl)pyrazin-2-yl]oxy}-2-{[3-(trifluoromethyl)phenyl]sulfonyl}octahydropyrrolo[1,2-a]pyrazine Example 206A tert-butyl (7R,8aS)-7-{[5-(1-methylcyclopropyl)pyrazin-2-yl]oxy}-hexahydropyrrolo[1,2-a]pyrazine-2(1H)-carboxylate To a solution of the product from Example 202B (40 mg, 0.111 mmol) in anhydrous tetrahydrofuran (1 mL) was added a 0.67 M solution of diazomethane in diethyl ether. The yellow solution was cooled to 0° C., and palladium(II) acetate (1 mg, 4.45 µmol) was added resulting in rapid gas evolution. More diazomethane solution (1 mL) was added dropwise, and the mixture was stirred at 0° C. for 30 minutes. The addition of 1 mL diazomethane solution was repeated several more times at 0° C. while monitoring reaction progress by LCMS (C18 silica gel using a 3 minute gradient of 0-100% acetonitrile in water (0.1% trifluoroacetic acid)). The reaction mixture was concentrated in vacuo and purified by column chromatography on silica gel using a solvent gradient of 0-50% ethyl acetate in hexanes. The title compound was obtained as a colorless oil that crystallized on standing (30 mg, 72%).

Example 206B (7R,8aS)-7-{[5-(1-methylcyclopropyl)pyrazin-2-yl]oxy}-2-{[3-(trifluoromethyl)phenyl]sulfonyl}octahydropyrrolo[1,2-a]pyrazine To a solution of the product from Example 206A (28 mg, 0.075 mmol) in 1,4-dioxane (1 mL) was added a 4 M solution of hydrogen chloride in 1,4-dioxane (0.5 mL, 2.0 mmol). The resulting mixture was stirred at room temperature for 90 minutes, and the mixture was then concentrated and dried in vacuo. To the resulting colorless solid was added CH$_2$Cl$_2$ (0.75 mL), diisopropylethylamine (0.065 mL, 0.375 mmol) and 3-(trifluoromethyl)benzene-1-sulfonyl chloride (22.02 mg, 0.090 mmol). The resulting mixture was stirred at room temperature for 3 hours. The mixture was partitioned between water and CH$_2$Cl$_2$, and the organic layer was dried over Na$_2$SO$_4$. The drying agent was removed by filtration, and the filtrate was concentrated in vacuo. The crude product was purified by column chromatography on silica gel using a solvent gradient of 0-40% ethyl acetate in hexanes. The title compound was obtained as a colorless solid (10 mg, 28%). $^1$H NMR (300 MHz, CDCl$_3$) δ ppm 0.72-0.81 (m, 2H), 1.07-1.17 (m, 2H), 1.48 (s, 3H), 1.72-1.88 (m, 1H), 1.92-2.05 (m, 1H), 2.12 (t, J=10.51 Hz, 1H), 2.33 (dd, J=9.92, 5.16 Hz, 1H), 2.38-2.63 (m, 3H), 2.94-3.07 (m, 1H), 3.65 (dd, J=10.31, 6.74 Hz, 1H), 3.72-3.82 (m, 1H), 3.86-3.98 (m, 1H), 5.23-5.35 (m, 1H), 7.70 (t, J=7.93 Hz, 1H), 7.87 (d, J=7.93 Hz, 1H), 7.96 (d, J=7.93 Hz, 1H), 8.00 (d, J=1.19 Hz, 1H), 8.01-8.04 (m, 1H), 8.05 (d, J=1.19 Hz, 1H); MS (ESI) m/z 483 (M+H)$^+$.

Example 207

7-[(5-cyclopropylpyrazin-2-yl)oxy]-2-{[3-(trifluoromethyl)phenyl]-sulfonyl}hexahydropyrrolo[1,2-a]pyrazin-6(2H)-one Example 207A tert-butyl 6-oxohexahydropyrrolo[1,2-a]pyrazine-2(1H)-carboxylate To a suspension of hexahydropyrrolo[1,2-a]pyrazin-6(2H)-one hydrochloride (0.50 g, 2.83 mmol) in CH$_2$Cl$_2$ (25 mL) was added di-tert-butyl-dicarbonate (0.741 g, 3.41 mmol) and triethylamine (0.79 mL, 5.66 mmol). The resulting mixture was stirred at room temperature for 3 hours. The mixture was partitioned between water and CH$_2$Cl$_2$, and the organic layer was dried over Na$_2$SO$_4$. The drying agent was removed by filtration, and the filtrate was concentrated in vacuo. The crude product was purified by column chromatography on silica gel using a solvent gradient of 0-5% methanol in CH$_2$Cl$_2$ to give the title compound (0.58 g, 85%).

Example 207B tert-butyl 7-hydroxy-6-oxohexahydropyrrolo[1,2-a]pyrazine-2(1H)-carboxylate To a solution of the product from Example 207A (0.20 g, 0.832 mmol) in anhydrous tetrahydrofuran (6 mL) at −78° C. under N$_2$ was added a 1 M solution of lithium bis(trimethylsilyl)amide in tetrahydrofuran (1.25 mL, 1.25 mmol). The resulting mixture was stirred at −78° C. for 20 minutes, and then a solution of 3-phenyl-2-(phenylsulfonyl)-1,2-oxaziridine (0.326 g, 1.248 mmol) in anhydrous tetrahydrofuran (3 mL) was added dropwise. The mixture was stirred at −78° C. for 20 minutes and then warmed to −40° C. and stirred for 2 hours. A solution of NH$_4$Cl (10% in water, 2 mL) was added, and the mixture was allowed to warm to room temperature and partitioned between water and ethyl acetate (5×). The combined organic layers were dried over Na$_2$SO$_4$. The drying agent was removed by filtration, and the filtrate was concentrated in vacuo. The crude product was purified by column chromatography on silica gel using a solvent gradient of 0-10% CH$_3$OH in CH$_2$Cl$_2$ to give the title compound (89 mg, 42%).

Example 207C tert-butyl 7-[(5-cyclopropylpyrazin-2-yl)oxy]-6-oxo-hexahydropyrrolo[1,2-a]-pyrazine-2(1H)-carboxylate To a solution of the product from Example 207B (89 mg, 0.347 mmol) in anhydrous acetonitrile (3.5 mL) was added cesium carbonate (226 mg, 0.695 mmol) and 2-bromo-5-cyclopropylpyrazine (104 mg, 0.521 mmol). The resulting mixture was stirred under N$_2$ at 50° C. for 48 hours. The mixture was allowed to cool to room temperature and partitioned between water and ethyl acetate (3×). The combined organic layers were dried over Na$_2$SO$_4$. The drying agent was removed by filtration, and the filtrate was concentrated in vacuo. The crude product was purified by column chromatography on silica gel using a solvent gradient of 0-10% $CH_3OH$ in $CH_2Cl_2$ to give the title compound (82 mg, 63%).

Example 207D

7-[(5-cyclopropylpyrazin-2-yl)oxy]-2-{[3-(trifluoromethyl)phenyl]-sulfonyl}hexahydropyrrolo[1,2-a]pyrazin-6(2H)-one To a solution of the product from Example 207C (40 mg, 0.107 mmol) in 1,4-dioxane (0.5 mL) was added a 4 M solution of hydrogen chloride in 1,4-dioxane (0.5 mL, 2.0 mmol). The resulting mixture was stirred at room temperature for 90 minutes and then concentrated in vacuo. To the residue was added $CH_2Cl_2$ (1 mL), 3-(trifluoromethyl)-benzene-1-sulfonyl chloride (0.021 mL, 0.130 mmol) and triethylamine (0.045 mL, 0.324 mmol), and the resulting mixture was stirred at room temperature for 90 minutes. The mixture was partitioned between water and $CH_2Cl_2$, and the organic layer was dried over $Na_2SO_4$. The drying agent was removed by filtration, and the filtrate was concentrated in vacuo. The crude product was purified by column chromatography on silica gel using a solvent gradient of 0-5% $CH_3OH$ in $CH_2Cl_2$ to give the title compound (47 mg, 90%). 1H NMR (300 MHz, $CDCl_3$) δ ppm 0.84-1.04 (m, 4H) 1.55-1.65 (m, 0.6H) 1.89-2.50 (m, 4H) 2.85-2.98 (m, 0.4H) 3.00-3.20 (m, 1H) 3.69-3.84 (m, 0.4H) 3.83-3.96 (m, 1.6H) 3.95-4.07 (m, 1H) 4.20 (dd, J=13.22, 2.37 Hz, 1H) 5.43 (dd, J=8.14, 5.09 Hz, 0.6H) 5.57 (t, J=7.63 Hz, 0.4H) 7.74 (t, J=7.80 Hz, 1H) 7.86-7.99 (m, 3H) 8.00-8.04 (m, 1H) 8.07-8.13 (m, 1H); MS (ESI) m/z 483 $(M+H)^+$.

Example 208

(7S,8aR)-7-[(5-cyclopropylpyrazin-2-yl)oxy]-2-{[3-(trifluoromethyl)-phenyl]sulfonyl}hexahydropyrrolo[1,2-a]pyrazin-6(2H)-one The product from Example 207D was subjected to chiral chromatography (Chiracel® OJ-H column), eluted with 10-50% $CH_3OH$ in supercritical $CO_2$. The title compound was the first of four stereoisomers to elute. $^1$H NMR (300 MHz, $CDCl_3$) δ ppm 0.89-1.01 (m, 4H) 1.92-2.39 (m, 5H) 3.06-3.21 (m, 1H) 3.82-3.97 (m, 2H) 3.97-4.05 (m, 1H) 4.20 (dd, J=13.56, 2.37 Hz, 1H) 5.43 (dd, J=8.14, 4.75 Hz, 1H) 7.74 (t, J=7.97 Hz, 1H) 7.88-7.98 (m, 3H) 8.02 (s, 1H) 8.12 (d, J=1.36 Hz, 1H).

Example 209

(7S,8aS)-7-[(5-cyclopropylpyrazin-2-yl)oxy]-2-{[3-(trifluoromethyl)-phenyl]sulfonyl}hexahydropyrrolo[1,2-a]pyrazin-6(2H)-one The product from Example 207D was subjected to chiral chromatography (Chiracel® OJ-H column), eluted with 10-50% $CH_3OH$ in supercritical $CO_2$. The title compound was the second of four stereoisomers to elute. $^1$H NMR (500 MHz, $CDCl_3$) δ ppm 0.89-1.00 (m, 4H) 1.57-1.64 (m, 1H) 1.93-2.02 (m, 1H) 2.15 (t, J=10.99 Hz, 1H) 2.37-2.47 (m, 1H) 2.87-2.97 (m, 1H) 3.03-3.12 (m, 1H) 3.73-3.84 (m, 1H) 3.87-3.94 (m, 1H) 3.97-4.05 (m, 1H) 4.20 (dd, J=13.43, 2.44 Hz, 1H) 5.57 (t, J=8.24 Hz, 1H) 7.74 (t, J=7.93 Hz, 1H) 7.88 (d, J=1.22 Hz, 1H) 7.92 (d, J=7.63 Hz, 1H) 7.95 (d, J=7.93 Hz, 1H) 8.02 (s, 1H) 8.09 (d, J=1.53 Hz, 1H).

Example 210

(7R,8aR)-7-[(5-cyclopropylpyrazin-2-yl)oxy]-2-{[3-(trifluoromethyl)-phenyl]sulfonyl}hexahydropyrrolo[1,2-a]pyrazin-6(2H)-one The product from Example 207D was subjected to chiral chromatography (Chiracel® OJ-H column), eluted with 10-50% $CH_3OH$ in supercritical $CO_2$. The title compound was the third of four stereoisomers to elute. $^1$H NMR (500 MHz, $CDCl_3$) δ ppm 0.88-1.01 (m, 4H) 1.56-1.63 (m, 2H) 1.94-2.02 (m, 1H) 2.15 (t, J=11.14 Hz, 1H) 2.37-2.47 (m, 1H) 2.87-2.97 (m, 1H) 3.74-3.82 (m, 1H) 3.87-3.93 (m, 1H) 4.00 (dd, J=11.60, 2.44 Hz, 1H) 4.20 (dd, J=13.43, 2.75 Hz, 1H) 5.57 (t, J=8.24 Hz, 1H) 7.74 (t, J=7.78 Hz, 1H) 7.88 (s, 1H) 7.91 (d, J=7.93 Hz, 1H) 7.95 (d, J=7.93 Hz, 1H) 8.02 (s, 1H) 8.09 (s, 1H).

Example 211

(7R,8aS)-7-[(5-cyclopropylpyrazin-2-yl)oxy]-2-{[3-(trifluoromethyl)-phenyl]sulfonyl}hexahydropyrrolo[1,2-a]pyrazin-6(2H)-one The product from Example 207D was subjected to chiral chromatography (Chiracel® OJ-H column), eluted with 10-50% $CH_3OH$ in supercritical $CO_2$. The title compound was the fourth of four stereoisomers to elute. $^1$H NMR (500 MHz, $CDCl_3$) δ ppm 0.90-1.02 (m, 4H) 1.94-2.03 (m, 1H) 2.07 (t, J=10.99 Hz, 1H) 2.15-2.40 (m, 3H) 3.08-3.20 (m, 1H) 3.84-3.96 (m, 2H) 3.97-4.06 (m, 1H) 4.20 (d, J=12.82 Hz, 1H) 5.43 (dd, J=8.24, 4.58 Hz, 1H) 7.74 (t, J=7.78 Hz, 1H) 7.89-7.94 (m, 2H) 7.96 (d, J=7.63 Hz, 1H) 8.02 (s, 1H) 8.12 (s, 1H).

Example 212

7-[(5-cyclopropylpyrazin-2-yl)oxy]-2-{[4-(trifluoromethyl)phenyl]-sulfonyl}hexahydropyrrolo[1,2-a]pyrazin-6(2H)-one The title compound was prepared according to the procedure described in Example 207D, substituting 4-(trifluoromethyl)benzene-1-sulfonyl chloride for 3-(trifluoromethyl)benzene-1-sulfonyl chloride. $^1$H NMR (300 MHz, $CDCl_3$) δ ppm 0.87-1.02 (m, 4H) 1.54-1.65 (m, 0.6H) 1.90-2.48 (m, 4H) 2.84-2.98 (m, 0.4H) 2.99-3.20 (m, 1H) 3.70-3.82 (m, 0.4H) 3.82-3.96 (m, 1.6H) 3.96-4.05 (m, 1H) 4.19 (dd, J=13.22, 2.37 Hz, 1H) 5.43 (dd, J=8.31, 4.92 Hz, 0.6H) 5.51-5.62 (m, 0.4H) 7.80-7.94 (m, 5H) 8.07-8.14 (m, 1H); MS (ESI) m/z 483 $(M+H)^+$.

Example 213

(8aS)-7-(3-fluorobenzyl)-2-{[4-(trifluoromethyl)phenyl]-sulfonyl}-hexahydropyrrolo[1,2-a]pyrazin-6(2H)-one

Example 213A tert-butyl (8aS)-7-(3-fluorobenzyl)-6-oxohexahydropyrrolo[1,2-a]pyrazine-2(1H)-carboxylate To a solution of the product from Example 207A (0.10 g, 0.416 mmol) in anhydrous tetrahydrofuran (4 mL) at −78° C. under $N_2$ was added a 1 M solution of lithium bis(trimethylsilyl)amide in tetrahydrofuran (0.458 mL, 0.458 mmol) dropwise over 2 minutes. To the resulting solution was added 1-(bromomethyl)-3-fluorobenzene (0.056 mL, 0.458 mmol), and the resulting mixture was stirred at −40° C. for 3 hours. A solution of NH$_4$Cl (10% in water, 1 mL) was added, and the mixture was allowed to warm to room temperature and partitioned between water and ethyl acetate (3×). The combined organic layers were dried over Na$_2$SO$_4$. The drying agent was removed by filtration, and the filtrate was concentrated in vacuo. The crude product was purified by column chromatography on silica gel using a solvent gradient of 0-10% CH$_3$OH in CH$_2$Cl$_2$ to give the title compound (75 mg, 52%).

Example 213B (8aS)-7-(3-fluorobenzyl)hexahydropyrrolo[1,2-a]pyrazin-6(2H)-one hydrochloride To a solution of the product from Example 213A (72 mg, 0.207 mmol) in 1,4-dioxane (1 mL) was added a 4 M solution of hydrogen chloride in 1,4-dioxane (1 mL, 4.0 mmol). The resulting mixture was stirred at room temperature for 90 minutes and concentrated and dried in vacuo to give the title compound (59 mg, quantitative).

Example 213C (8aS)-7-(3-fluorobenzyl)-2-{[4-(trifluoromethyl)phenyl]sulfonyl}-hexahydropyrrolo[1,2-a]pyrazin-6(2H)-one The product from Example 213B (20 mg, 0.070 mmol) was suspended in CH$_2$Cl$_2$ (0.5 mL), 4-(trifluoromethyl)benzene-1-sulfonyl chloride (21 mg, 0.084 mmol) and triethylamine (0.049 mL, 0.35 mmol) were added, and the resulting mixture was stirred at room temperature for 90 minutes. The mixture was partitioned between water and CH$_2$Cl$_2$, and the organic layer was dried over Na$_2$SO$_4$. The drying agent was removed by filtration, and the filtrate was concentrated in vacuo. The crude product was purified by column chromatography on silica gel using a solvent gradient of 0-5% CH$_3$OH in CH$_2$Cl$_2$ to give the title compound (30 mg, 94%). $^1$H NMR (300 MHz, CDCl$_3$) δ ppm 1.16-1.51 (m, 1H) 1.59-1.72 (m, 1H) 1.88-2.03 (m, 1H) 2.09-2.32 (m, 1H) 2.64-3.12 (m, 4H) 3.27-3.64 (m, 1H) 3.73-3.86 (m, 2H) 4.11 (dd, J=13.22, 2.37 Hz, 1H) 6.68-6.98 (m, 3H) 7.08-7.29 (m, 1H) 7.77-7.89 (m, 4H); MS (ESI) m/z 457 (M+H)$^+$.

Example 214

(8aS)-7-(3-fluorobenzyl)-2-{[3-(trifluoromethyl)phenyl]sulfonyl}-hexahydropyrrolo[1,2-a]pyrazin-6(2H)-one The product from Example 213B (38 mg, 0.133 mmol) was subjected to the procedure described for Example 213C, substituting 3-(trifluoromethyl)benzene-1-sulfonyl chloride for 4-(trifluoromethyl)benzene-1-sulfonyl chloride. The title compound was obtained as a colorless solid (45 mg, 74%). $^1$H NMR (300 MHz, CDCl$_3$) δ ppm 1.16-1.51 (m, 1H) 1.59-1.74 (m, 1H) 1.88-2.03 (m, 1H) 2.10-2.32 (m, 1H) 2.65-3.13 (m, 4H) 3.26-3.65 (m, 1H) 3.74-3.87 (m, 2H) 4.12 (dd, J=13.39, 2.20 Hz, 1H) 6.65-6.99 (m, 3H) 7.09-7.30 (m, 1H) 7.66-7.77 (m, 1H) 7.85-8.01 (m, 3H); MS (ESI) m/z 457 (M+H)$^+$.

Example 215

(7S,8aS)-7-[(3-fluorophenyl)(hydroxy)methyl]-2-{[3-(trifluoromethyl)-phenyl]sulfonyl}hexahydropyrrolo[1,2-a]pyrazin-6(2H)-one Example 215A tert-butyl (7S,8aS)-7-[(3-fluorophenyl)(hydroxy)methyl]-6-oxohexahydropyrrolo[1,2-a]pyrazine-2(1H)-carboxylate The title compound was prepared according to the procedure described in Example 213A substituting 3-fluorobenzaldehyde for 1-(bromomethyl)-3-fluorobenzene. The title compound was the first of two stereoisomers to elute during chromatography.

Example 215B (7S,8aS)-7-[(3-fluorophenyl)(hydroxy)methyl]-2-{[3-(trifluoromethyl)-phenyl]sulfonyl}hexahydropyrrolo[1,2-a]pyrazin-6(2H)-one The product from Example 215A (64 mg, 0.176 mmol) was subjected to the procedures described for Example 213B and Example 213C substituting 3-(trifluoromethyl)benzene-1-sulfonyl chloride for 4-(trifluoromethyl)benzene-1-sulfonyl chloride. The title compound was obtained as a colorless solid (33 mg, 40%). $^1$H NMR (300 MHz, CDCl$_3$) δ ppm 1.36-1.66 (m, 1H) 1.76-2.03 (m, 2H) 2.13-2.36 (m, 1.5H) 2.64-2.83 (m, 1H) 2.85-3.07 (m, 1.5H) 3.46-3.70 (m, 1H) 3.75-3.92 (m, 2H) 4.08-4.21 (m, 1H) 5.28 (dd, J=5.09, 3.05 Hz, 1H) 6.79-7.16 (m, 3H) 7.17-7.37 (m, 1H) 7.64-7.80 (m, 1H) 7.83-8.02 (m, 3H); MS (ESI) m/z 473 (M+H)$^+$.

Example 216

(7R,8aS)-7-[(3-fluorophenyl)(hydroxy)methyl]-2-{[3-(trifluoromethyl)-phenyl]sulfonyl}hexahydropyrrolo[1,2-a]pyrazin-6(2H)-one Example 216A tert-butyl (7R,8aS)-7-[(3-fluorophenyl)(hydroxy)methyl]-6-oxohexahydropyrrolo[1,2-a]pyrazine-2(1H)-carboxylate The title compound was prepared according to the procedure described in Example 213A, substituting 3-fluorobenzaldehyde for 1-(bromomethyl)-3-fluorobenzene. The title compound was the second of two stereoisomers to elute during chromatography.

Example 216B (7R,8aS)-7-[(3-fluorophenyl)(hydroxy)methyl]-2-{[3-(trifluoromethyl)-phenyl]sulfonyl}hexahydropyrrolo[1,2-a]pyrazin-6(2H)-one The product from Example 216A (24 mg, 0.066 mmol) was subjected to the procedures described for Example 213B and Example 213C substituting 3-(trifluoromethyl)benzene-1-sulfonyl chloride for 4-(trifluoromethyl)benzene-1-sulfonyl chloride. The title compound was obtained as a colorless solid (7 mg, 22%). $^1$H NMR (300 MHz, CDCl$_3$) δ ppm 1.43-1.52 (m, 1H) 1.85-2.04 (m, 2H) 2.21-2.32 (m, 1H) 2.63-2.75 (m, 1H) 2.94-3.07 (m, 1H) 3.47-3.59 (m, 1H) 3.75-3.86 (m, 2H) 4.09-4.19 (m, 1H) 4.58 (s, 1H) 4.73 (d, J=8.82 Hz, 1H)

6.95-7.05 (m, 1H) 7.05-7.12 (m, 2H) 7.26-7.36 (m, 1H) 7.71 (t, J=7.80 Hz, 1H) 7.90 (d, J=7.80 Hz, 2H) 7.97 (s, 1H); MS (ESI) m/z 473 (M+H)⁺.

Example 217

2-{[3-(trifluoromethyl)phenyl]sulfonyl}-7-{[5-(trifluoromethyl)pyridin-2-yl]-oxy}hexahydropyrrolo[1,2-a]pyrazin-6(2H)-one Example 217A 2-{[3-(trifluoromethyl)phenyl]sulfonyl}hexahydropyrrolo[1,2-a]pyrazin-6(2H)-one To a solution of hexahydropyrrolo[1,2-a]pyrazin-6(2H)-one hydrochloride (0.1 g, 0.566 mmol) in $CH_2Cl_2$ (5 mL) was added triethylamine (0.237 mL, 1.698 mmol) and 3-(trifluoromethyl)benzene-1-sulfonyl chloride (0.109 mL, 0.679 mmol). The resulting mixture was stirred at room temperature for 90 minutes, after which time it was partitioned between water (10 mL) and $CH_2Cl_2$ (2×10 mL). The combined organic layer was dried over $Na_2SO_4$. The crude product was purified by column chromatography on silica gel using a solvent gradient of 0-5% $CH_3OH$ in $CH_2Cl_2$ to give the title compound as a colorless solid (0.169 mg, 86%).

Example 217B 7-hydroxy-2-{[3-(trifluoromethyl)phenyl]sulfonyl}hexahydropyrrolo[1,2-a]-pyrazin-6(2H)-one To a solution of the product from Example 217A (98 mg, 0.281 mmol) in anhydrous tetrahydrofuran (2 mL) at −78° C. under $N_2$ was added lithium bis(trimethylsilyl)amide (1 M in tetrahydrofuran) (0.422 mL, 0.422 mmol). The resulting mixture was stirred at −78° C. for 20 minutes, and then a solution of 3-phenyl-2-(phenylsulfonyl)-1,2-oxaziridine (147 mg, 0.563 mmol) in anhydrous tetrahydrofuran (1 mL) was added dropwise. Once the addition was complete, the mixture was warmed to −40° C. and stirred for 2 hours. A solution of $NH_4Cl$ (10% in water, 2 mL) was added, and the mixture was allowed to warm to room temperature and partitioned between water and ethyl acetate (5×). The combined organic layers were dried over $Na_2SO_4$. The drying agent was removed by filtration, and the filtrate was concentrated in vacuo. The crude product was purified by column chromatography on silica gel using a solvent gradient of 0-5% $CH_3OH$ in $CH_2Cl_2$ to give the title compound (24 mg, 23%).

Example 217C

2-{[3-(trifluoromethyl)phenyl]sulfonyl}-7-{[5-(trifluoromethyl)pyridin-2-yl]-oxy}hexahydropyrrolo[1,2-a]pyrazin-6(2H)-one To a solution of the product from Example 217B (23 mg, 0.063 mmol) in anhydrous N,N-dimethylformamide (0.6 mL) at 0° C. was added sodium hydride (60% suspension in mineral oil, 2.78 mg, 0.069 mmol). The resulting mixture was stirred at 0° C. for 10 minutes, and 2-bromo-5-(trifluoromethyl)pyridine (21 mg, 0.095 mmol) was added. The resulting mixture was allowed to warm to room temperature and stirred for 3 hours. The mixture was partitioned between water and ethyl acetate (3×), and the combined organic layers were concentrated in vacuo and purified on C18 silica gel using a solvent gradient of 0-100% acetonitrile in water (0.1% trifluoroacetic acid). The title compound was obtained as a colorless solid (22 mg, 68%). ¹H NMR (300 MHz, $CDCl_3$) δ ppm 1.58-1.68 (m, 0.5H) 2.03-2.49 (m, 3H) 2.88-3.21 (m, 1.5H) 3.72-4.08 (m, 3H) 4.21 (dd, J=13.39, 3.22 Hz, 1H) 5.50-5.74 (m, 1H) 6.88 (t, J=8.82 Hz, 1H) 7.69-7.85 (m, 2H) 7.88-8.00 (m, 2H) 8.02 (s, 1H) 8.26-8.43 (m, 1H); MS (ESI) m/z 510 (M+H)⁺.

Example 218

(7R,8aS)-7-[(5-cyclopropylpyrazin-2-yl)oxy]-2-{[3-(trifluoromethyl)-benzyl]sulfonyl}octahydropyrrolo[1,2-a]pyrazine The title compound was prepared according to the procedure described in Example 57, substituting (3-(trifluoromethyl)phenyl)methanesulfonyl chloride for 3-tert-butyl-4-methoxybenzene-1-sulfonyl chloride. ¹H NMR (300 MHz, $CDCl_3$) δ ppm 0.85-1.04 (m, 4H) 1.75-1.90 (m, 3H) 2.20-2.60 (m, 4H) 2.76-3.11 (m, 2H) 3.54-3.87 (m, 3H) 4.26 (s, 2H) 5.24-5.43 (m, 1H) 7.48-7.70 (m, 4H) 7.92 (d, J=1.36 Hz, 1H) 8.03 (d, J=1.36 Hz, 1H); MS (ESI) m/z 483 (M+H)⁺.

Example 219

(7R,8aS)-7-[(5-cyclopropylpyrazin-2-yl)oxy]-2-[(4,4,4-trifluorobutyl)-sulfonyl]octahydropyrrolo[1,2-a]pyrazine The procedures for Example 17E and Example 18 were used substituting (7R,8aS)-octahydropyrrolo[1,2-a]pyrazin-7-ol for (7S,8aR)-octahydropyrrolo[1,2-a]pyrazin-7-ol and substituting 4,4,4-trifluorobutane-1-sulfonyl chloride for 3-(trifluoromethyl)benzene-1-sulfonyl chloride to give the title compound (53% yield) as a solid. ¹H NMR (400 MHz, DMSO-$d_6$) δ ppm 0.87 (m, 4H), 1.86 (m, 4H), 2.36 (m, 4H), 2.60 (m, 2H), 2.90 (m, 1H), 3.10 (m, 4H), 3.54 (m, 1H), 3.63 (m, 1H), 3.70 (m, 1H), 5.27 (m, 1H), 8.13 (s, 2H); MS (ESI) m/z 435 (M+H)⁺.

Example 220

(7R,8aS)-7-[(5-cyclopropylpyrazin-2-yl)oxy]-2-{[3-(trifluoromethyl)-phenyl]sulfonyl}hexahydropyrrolo[1,2-a]pyrazin-4(1H)-one Example 220A tert-butyl (2S,4R)-4-hydroxy-2-({[(4-methylphenyl)sulfonyl]oxy}methyl)-pyrrolidine-1-carboxylate tert-Butyl (2S,4R)-4-hydroxy-2-(hydroxymethyl)pyrrolidine-1-carboxylate (500 mg; 2.3 mmol) in pyridine (20 mL) was cooled to 0° C. To this cooled solution was added a solution of p-toluenesulfonyl chloride (483 mg, 2.53 mmol) in pyridine (5 mL) over a period of 1 hour. The reaction mixture was allowed to slowly warm to ambient temperature and stirring was continued at ambient for 48 hours. The volatiles were removed in vacuo, and the residue was redissolved in toluene and concentrated again in vacuo. The crude material was triturated with ethyl acetate. This was further purified by chromatography on a 12 g silica gel column eluted with 5% ethyl acetate/hexanes for 3 minutes and then eluted with a gradient to 100% ethyl acetate over 20 minutes. The title compound was isolated as an oil (397 mg; 64% yield). ¹H NMR (300 MHz, DMSO-$d_6$) δ ppm 7.82-7.69 (m, 2H), 7.48

(d, J=7.9 Hz, 2H), 4.92 (d, J=2.8 Hz, 1H), 4.23-3.82 (m, 4H), 3.12 (dd, J=25.5, 13.9 Hz, 2H), 2.42 (d, J=3.6 Hz, 3H), 1.87 (d, J=20.3 Hz, 2H), 1.35 (dd, J=23.0, 13.0 Hz, 9H).

Example 220B tert-butyl (2S,4R)-2-(azidomethyl)-4-hydroxypyrrolidine-1-carboxylate To a solution of Example 220A (365 mg, 1.021 mmol) in N,N-dimethylformamide (5 mL) was added sodium azide (531 mg, 8.17 mmol). The reaction mixture was stirred at 55° C. for 8 hours. Chromatography on a 12 g silica gel column eluted with 5% ethyl acetate/hexanes for 3 minutes followed by a gradient to 100% ethyl acetate over 20 minutes provided the title compound (135 mg, 0.557 mmol, 54.6% yield) as an oil. $^1$H NMR (400 MHz, DMSO-d$_6$) δ ppm 4.65 (d, J=3.5 Hz, 1H), 4.24 (d, J=3.5 Hz, 1H), 3.97 (ddd, J=10.2, 7.6, 3.1 Hz, 1H), 3.64 (dd, J=12.3, 5.5 Hz, 1H), 3.39-3.22 (m, 3H), 2.01-1.80 (m, 2H), 1.42 (s, 9H); MS (DCI) m/z 243 (M+H)$^+$.

Example 220C tert-butyl (2S,4R)-2-(azidomethyl)-4-[(5-cyclopropylpyrazin-2-yl)oxy]-pyrrolidine-1-carboxylate To a solution of Example 220B (98 mg, 0.404 mmol) in tetrahydrofuran (1 mL) was added potassium t-butoxide (63.5 mg, 0.566 mmol) followed by addition of 2-bromo-5-cyclopropylpyrazine (Combi-Phos Inc) (89 mg, 0.445 mmol). The reaction mixture was stirred at room temperature for 24 hours. The mixture was diluted with water and extracted with ethyl acetate (2×20 mL). Volatiles were removed with a stream of nitrogen. The residue was chromatographed on a 12 g SiO$_2$ column eluted with 5% ethyl acetate/hexanes for 3 minutes and then with a gradient to 100% ethyl acetate over 20 minutes. The title compound (87 mg, 0.241 mmol, 59.7% yield) was isolated as a colorless oil. $^1$H NMR (400 MHz, DMSO-d$_6$) δ ppm 8.09 (d, J=1.3 Hz, 1H), 8.06 (d, J=1.3 Hz, 1H), 5.44-5.39 (m, 1H), 4.12-4.04 (m, 1H), 3.71 (dd, J=12.4, 5.3 Hz, 1H), 3.64 (d, J=12.3 Hz, 1H), 3.57 (dd, J=12.4, 4.6 Hz, 1H), 3.39 (dd, J=12.4, 3.2 Hz, 1H), 2.30-2.06 (m, 3H), 1.41 (s, 9H), 0.97-0.90 (m, 2H), 0.87-0.81 (m, 2H).

Example 220D tert-butyl (2S,4R)-2-(aminomethyl)-4-[(5-cyclopropylpyrazin-2-yl)oxy]-pyrrolidine-1-carboxylate Example 220C (2.54 g, 7.05 mmol) was dissolved in methanol containing 7 M ammonia (30 mL). The resulting solution was added to Raney®-nickel 2800/water, that had been washed once with methanol to remove excess water, in a stainless steel container (250 mL). The mixture was shaken for 4 hours under hydrogen (30 psi). The resulting slurry was filtered through a 0.45 μm nylon membrane, and the solvents were removed in vacuo. The resulting green viscous oil was carried on without additional purification.

Example 220E tert-butyl (2S,4R)-4-[(5-cyclopropylpyrazin-2-yl)oxy]-2-{[(2-methoxy-2-oxoethyl)amino]methyl}pyrrolidine-1-carboxylate Example 220E (361 mg, 1.080 mmol) was dissolved in methanol (2 mL). Triethylamine (331 μL, 2.375 mmol) was added followed by addition of methyl 2-bromoacetate (110 μL, 1.187 mmol). The mixture was stirred at 65° C. for 3 hours. Chromatography on a 24 g SiO$_2$ column eluted with 5% ethyl acetate/hexanes for 3 minutes and then with a gradient to 100% ethyl acetate over 20 minutes provided the title compound (185 mg, 0.455 mmol, 42.2% yield) as a colorless oil. $^1$H NMR (300 MHz, DMSO-d$_6$) δ ppm 8.13 (dd, J=11.8, 1.3 Hz, 2H), 5.36 (s, 1H), 3.90 (s, 1H), 3.63-3.48 (m, 6H), 2.72 (s, 2H), 2.14 (ddd, J=23.5, 13.0, 12.5 Hz, 4H), 1.37 (s, 10H), 1.00-0.87 (m, 2H), 0.85-0.76 (m, 2H); MS (ESI) m/z 407 (M+H)$^+$.

Example 220F tert-butyl (2S,4R)-4-[(5-cyclopropylpyrazin-2-yl)oxy]-2-{[(2-methoxy-2-oxoethyl){[3-(trifluoromethyl)phenyl]sulfonyl}amino]methyl}pyrrolidine-1-carboxylate Example 220E (92 mg, 0.226 mmol) was dissolved in methylene chloride (1 mL). Triethylamine (63.1 μL, 0.453 mmol) and 3(trifluoromethyl)benzenesulfonyl chloride (39.9 μL, 0.249 mmol) were sequentially added. The reaction mixture was stirred at ambient temperature for 2 hours. Chromatography on a 12 g SiO$_2$ column eluted with 5% ethyl acetate/hexanes for 3 minutes and then with a gradient to 100% ethyl acetate over 20 minutes afforded the title compound (101 mg, 0.164 mmol, 72.6% yield) as a viscous oil. $^1$H NMR (400 MHz, DMSO-d$_6$) δ ppm 8.22-8.01 (m, 5H), 7.85 (t, J=7.8 Hz, 1H), 5.36 (s, 1H), 4.39-4.15 (m, 2H), 4.15-4.04 (m, 1H), 3.56 (dd, J=46.9, 17.5 Hz, 6H), 3.38 (s, 1H), 2.30-2.08 (m, 3H), 1.33 (d, J=6.0 Hz, 9H), 0.97-0.92 (m, 2H), 0.86-0.80 (m, 2H); MS (ESI) m/z 515 (M-t-Bu+H)$^+$.

Example 220G methyl N-({(2S,4R)-4-[(5-cyclopropylpyrazin-2-yl)oxy]pyrrolidin-2-yl}-methyl)-N-{[3-(trifluoromethyl)phenyl]sulfonyl}glycinate hydrochloride Example 220F (99 mg, 0.161 mmol) was dissolved in methylene chloride (25 mL). 4 N HCl (1 mL) in dioxane was added, and the reaction mixture was stirred at ambient temperature for 1 hour. Removal of solvents in vacuo afforded the title compound as a white foam that was used without further purification.

Example 220H (7R,8aS)-7-[(5-cyclopropylpyrazin-2-yl)oxy]-2-{[3-(trifluoromethyl)phenyl]-sulfonyl}hexahydropyrrolo[1,2-a]pyrazin-4(1H)-one Example 220G (89 mg, 0.162 mmol) was dissolved in methanol (1 mL) and treated with triethylamine (90 μL, 0.646 mmol). The mixture was heated to reflux for 48 hours, cooled to ambient temperature and purified by chromatography on a 12 g SiO$_2$ column eluted with 5% ethyl acetate/hexanes for 3 minutes and then with a gradient to 100% ethyl acetate over 20 minutes. The title compound (28.4 mg, 0.059 mmol, 36.4% yield) was isolated as a white solid. $^1$H NMR (300 MHz, DMSO-d$_6$) δ ppm 8.24-8.04 (m, 5H), 7.98-7.86 (m, 1H), 5.52-5.41 (m, 1H), 4.20-3.98 (m, 2H), 3.95-3.73 (m, 2H), 3.40-3.33 (m, 1H), 3.29-3.22 (m, 1H), 2.76-2.59 (m, 1H), 2.32-2.04 (m, 2H), 1.86-1.70 (m, 1H), 1.01-0.88 (m, 2H), 0.86-0.74 (m, 2H); MS (ESI) m/z 483 (M+H)$^+$.

Example 221

(7R,8aS)-7-[(5-cyclopropylpyrazin-2-yl)oxy]-2-{[4-(trifluoromethyl)-phenyl]sulfonyl}hexahydropyrrolo[1,2-a]pyrazin-4(1H)-one

Example 221A methyl N-({(2S,4R)-4-[(5-cyclopropylpyrazin-2-yl)oxy]pyrrolidin-2-yl}-methyl)glycinate hydrochloride Example 220E (1.10 g, 2.71 mmol) was dissolved in methylene chloride (3 mL). 4 M HCl in dioxane (3 mL) was added, and the mixture was stirred for 30 minutes. The volatiles were removed in vacuo to supply the title compound which was used in the next step without further purification.

Example 221B (7R,8aS)-7-[(5-cyclopropylpyrazin-2-yl)oxy]hexahydropyrrolo[1,2-a]pyrazin-4(1H)-one Example 221A (0.958 g, 2.79 mmol) was dissolved in methanol (10 mL), and triethylamine was added until the mixture was found to be basic by pH paper. The mixture was allowed to reflux overnight after which the solvents were removed in vacuo. Chromatography on a 12 g SiO$_2$ column eluted with 2.5% methanol (containing 2 N ammonia) in methylene chloride for 3 minutes and then with a gradient from 0-10% methanol (containing 2 N ammonia) in methylene chloride provided the title compound. $^1$H NMR (300 MHz, DMSO-d$_6$) δ ppm 8.15 (dd, J=9.2, 1.4 Hz, 2H), 5.47 (t, J=5.0 Hz, 1H), 4.05-3.88 (m, 1H), 3.87-3.69 (m, 1H), 3.26-3.01 (m, 4H), 2.67 (s, 1H), 2.34 (dd, J=12.7, 10.2 Hz, 1H), 2.24-2.03 (m, 2H), 1.73 (ddd, J=13.3, 11.9, 4.8 Hz, 1H), 1.03-0.88 (m, 2H), 0.82 (ddd, J=6.8, 4.7, 2.4 Hz, 2H); MS (ESI) m/z 275 (M+H)$^+$.

Example 221C (7R,8aS)-7-[(5-cyclopropylpyrazin-2-yl)oxy]-2-{[4-(trifluoromethyl)-phenyl]sulfonyl}hexahydropyrrolo[1,2-a]pyrazin-4(1H)-one Example 221B (86 mg, 0.314 mmol) in CH$_2$Cl$_2$ (2 mL) was treated with triethylamine(43.7 µL, 0.314 mmol) and 4-(trifluoromethyl)benzene-1-sulfonyl chloride (84 mg, 0.345 mmol). The mixture was stirred at ambient temperature for 18 hours. Chromatography on a 12 g SiO$_2$ column eluted with 5% ethyl acetate/hexanes for 3 minutes and then with a gradient to 100% ethyl acetate over 20 minutes furnished the title compound (31 mg, 0.064 mmol, 20.49% yield) as a white solid. $^1$H NMR (300 MHz, DMSO-d$_6$) δ ppm 8.31 (s, 1H), 8.21-7.96 (m, 5H), 5.47 (t, J=4.7 Hz, 1H), 4.17-3.96 (m, 4H), 3.93-3.75 (m, 2H), 2.66 (dd, J=24.2, 12.4 Hz, 1H), 2.25 (dd, J=13.5, 4.5 Hz, 1H), 2.11 (td, J=8.2, 4.1 Hz, 1H), 1.84-1.70 (m, 1H), 1.02-0.76 (m, 4H); MS (ESI) m/z 483 (M+H)$^+$.

Example 222

(8aR)-7-[(5-cyclopropylpyrazin-2-yl)oxy]-2-{[3-(trifluoromethyl)-phenyl]sulfonyl}hexahydropyrrolo[1,2-a]pyrazin-6(2H)-one The title compound was prepared according to the procedures for Example 207, substituting (R)-hexahydropyrrolo[1,2-a]pyrazin-6(7H)-one hydrochloride for hexahydropyrrolo[1,2-a]pyrazin-6(2H)-one hydrochloride. $^1$H NMR (300 MHz, CDCl$_3$) δ ppm 0.84-1.04 (m, 4H) 1.54-1.65 (m, 0.65H) 1.89-2.50 (m, 4H) 2.85-2.99 (m, 0.35H) 3.00-3.20 (m, 1H) 3.68-3.84 (m, 0.35H) 3.83-3.96 (m, 1.65H) 3.95-4.07 (m, 1H) 4.20 (dd, J=13.22, 2.37 Hz, 1H) 5.43 (dd, J=8.14, 4.75 Hz, 0.65H) 5.53-5.61 (m, 0.35H) 7.74 (t, J=7.80 Hz, 1H) 7.86-7.99 (m, 3H) 8.00-8.05 (m, 1H) 8.07-8.14 (m, 1H); MS (ESI) m/z 483 (M+H)$^+$.

Example 223

(8aS)-7-[3-(trifluoromethyl)benzyl]-2-{[3-(trifluoromethyl)phenyl]-sulfonyl}hexahydropyrrolo[1,2-a]pyrazin-6(2H)-one The title compound was prepared according to the procedures described for Example 213, substituting 1-(bromomethyl)-3-(trifluoromethyl)benzene for 1-(bromomethyl)-3-fluorobenzene and substituting 3-(trifluoromethyl)benzene-1-sulfonyl chloride for 4-(trifluoromethyl)benzene-1-sulfonyl chloride. NMR indicates a 4:1 ratio of trans:cis isomers. $^1$H NMR (300 MHz, CDCl$_3$) δ ppm 1.59-1.76 (m, 1H) 1.89-2.01 (m, 1.8H) 2.06-2.19 (m, 0.2H) 2.20-2.32 (m, 1H) 2.67-2.99 (m, 3H) 3.07-3.17 (m, 1H) 3.26-3.39 (m, 0.8H) 3.51-3.65 (m, 0.2H) 3.74-3.87 (m, 2H) 4.06-4.18 (m, 1H) 7.29-7.54 (m, 4H) 7.66-7.76 (m, 1H) 7.85-7.99 (m, 3H); MS (ESI) m/z 507 (M+H)$^+$.

Example 224

(8aS)-7-[3-(trifluoromethyl)benzyl]-2-{[4-(trifluoromethyl)phenyl]-sulfonyl}hexahydropyrrolo[1,2-a]pyrazin-6(2H)-one The title compound was prepared according to the procedures described for Example 213, substituting 1-(bromomethyl)-3-(trifluoromethyl)benzene for 1-(bromomethyl)-3-fluorobenzene. NMR indicates a 4:1 ratio of trans:cis isomers. $^1$H NMR (300 MHz, CDCl$_3$) δ ppm 1.59-1.75 (m, 1H) 1.87-2.02 (m, 1.8H) 2.04-2.18 (m, 0.2H) 2.19-2.34 (m, 1H) 2.68-2.98 (m, 3H) 3.12 (dd, J=13.56, 4.07 Hz, 1H) 3.25-3.40 (m, 0.8H) 3.52-3.67 (m, 0.2H) 3.72-3.87 (m, 2H) 4.05-4.19 (m, 1H) 7.28-7.55 (m, 4H) 7.76-7.89 (m, 4H); MS (ESI) m/z 507 (M+H)$^+$.

Example 225

3-{[(8aS)-6-oxo-7-[3-(trifluoromethyl)benzyl]hexahydropyrrolo[1,2-a]-pyrazin-2(1H)-yl]sulfonyl}benzonitrile The title compound was prepared according to the procedures described for Example 213, substituting 1-(bromomethyl)-3-(trifluoromethyl)benzene for 1-(bromomethyl)-3-fluorobenzene and substituting 3-cyanobenzene-1-sulfonyl chloride for 4-(trifluoromethyl)benzene-1-sulfonyl chloride. NMR indicates a 4:1 ratio of trans:cis isomers. $^1$H NMR (300 MHz, CDCl$_3$) δ ppm 1.63-1.77 (m, 1H) 1.88-2.04 (m, 1.8H) 2.07-2.19 (m, 0.2H) 2.21-2.33 (m, 1H) 2.68-3.01 (m, 3H) 3.08-3.17 (m, 1H) 3.26-3.39 (m, 0.8H) 3.53-3.66 (m, 0.2H)

3.73-3.86 (m, 2H) 4.06-4.19 (m, 1H) 7.32-7.55 (m, 4H) 7.65-7.75 (m, 1H) 7.87-8.02 (m, 3H); MS (ESI) m/z 464 (M+H)$^+$.

Example 226

(7R,8aS)-2-{[4-(trifluoromethyl)phenyl]sulfonyl}-7-{[5-(trifluoromethyl)-pyridin-2-yl]oxy}octahydropyrrolo[1,2-a]pyrazine

Example 226A tert-butyl (7R,8aS)-7-{[5-(trifluoromethyl)pyridin-2-yl]oxy}hexahydropyrrolo[1,2-a]pyrazine-2(1H)-carboxylate To a solution of the product from Example 202A (0.20 g, 0.825 mmol) in anhydrous tetrahydrofuran (8 mL) was added a 1.0 M solution of potassium tert-butoxide in tetrahydrofuran (0.825 mL, 0.825 mmol), followed by 2-bromo-5-(trifluoromethyl)pyridine. The resulting mixture was stirred at room temperature for 3 hours, and then it was partitioned between water and ethyl acetate (3×). The organic extracts were combined and dried over Na$_2$SO$_4$. The crude product was purified by column chromatography on silica gel using a solvent gradient of 0-5% CH$_3$OH in CH$_2$Cl$_2$ to give the title compound as a colorless solid (0.28 g, 88%).

Example 226B (7R,8aS)-2-{[4-(trifluoromethyl)phenyl]sulfonyl}-7-{[5-(trifluoromethyl)-pyridin-2-yl]oxy}octahydropyrrolo[1,2-a]pyrazine A solution of the product from Example 226A (0.14 g, 0.361 mmol) in dichloromethane (2.5 mL) and trifluoroacetic acid (2.5 mL) was stirred at room temperature for 2 hours and then concentrated in vacuo. The residue was dissolved in a mixture of dichloromethane (3 mL) and triethylamine (0.30 mL, 2.17 mmol), and 4-(trifluoromethyl)benzene-1-sulfonyl chloride (0.097 g, 0.398 mmol) was added. The resulting mixture was stirred at room temperature for 16 hours, and then it was partitioned between water and dichloromethane. The organic extract was dried over Na$_2$SO$_4$. The crude product was purified by column chromatography on silica gel using a solvent gradient of 0-3% ethyl acetate in heptane to give the title compound as a colorless solid (0.132 g, 74%). $^1$H NMR (300 MHz, CDCl$_3$) δ ppm 1.72-1.90 (m, 1H) 1.91-2.06 (m, 1H) 2.06-2.20 (m, 1H) 2.33 (dd, J=9.49, 4.75 Hz, 1H) 2.37-2.70 (m, 3H) 3.00 (d, J=7.80 Hz, 1H) 3.58-3.73 (m, 1H) 3.77 (d, J=8.82 Hz, 1H) 3.92 (d, J=10.17 Hz, 1H) 5.41 (q, J=6.22 Hz, 1H) 6.79 (d, J=8.82 Hz, 1H) 7.76 (dd, J=8.65, 2.54 Hz, 1H) 7.79-7.94 (m, 4H) 8.39 (d, J=2.37 Hz, 1H); MS (ESI) m/z 496 (M+H)$^+$.

Example 227

3-{[(7R,8aS)-7-{[5-(trifluoromethyl)pyridin-2-yl]oxy}hexahydropyrrolo[1,2-a]pyrazin-2(1H)-yl]sulfonyl}benzonitrile The title compound was obtained following the procedure described in Example 226B, substituting 3-cyanobenzene-1-sulfonyl chloride for 4-(trifluoromethyl)benzene-1-sulfonyl chloride. $^1$H NMR (300 MHz, CDCl$_3$) δ ppm 1.74-1.92 (m, 1H) 1.94-2.07 (m, 1H) 2.15 (t, J=10.34 Hz, 1H) 2.33 (dd, J=9.83, 5.09 Hz, 1H) 2.38-2.65 (m, 3H) 3.02 (d, J=9.16 Hz, 1H) 3.68 (dd, J=10.00, 6.95 Hz, 1H) 3.77 (d, J=9.16 Hz, 1H) 3.92 (d, J=10.17 Hz, 1H) 5.42 (q, J=6.10 Hz, 1H) 6.79 (d, J=8.82 Hz, 1H) 7.69 (t, J=7.80 Hz, 1H) 7.77 (dd, J=8.65, 2.20 Hz, 1H) 7.85-7.92 (m, 1H) 7.94-8.03 (m, 1H) 8.03-8.10 (m, 1H) 8.39 (d, J=2.37 Hz, 1H); MS (ESI) m/z 453 (M+H)$^+$.

Example 228

(7R,8aS)-2-{[4-(trifluoromethyl)phenyl]sulfonyl}-7-{[6-(trifluoromethyl)-pyridin-3-yl]oxy}octahydropyrrolo[1,2-a]pyrazine The title compound was obtained according to the procedures described for Example 226, substituting 5-fluoro-2-(trifluoromethyl)pyridine for 2-bromo-5-(trifluoromethyl)pyridine. $^1$H NMR (300 MHz, CDCl$_3$) δ ppm 1.73-1.88 (m, 1H) 2.02 (dd, J=13.43, 5.80 Hz, 1H) 2.14 (t, J=10.38 Hz, 1H) 2.37-2.51 (m, 3H) 2.54-2.66 (m, 1H) 2.93-3.09 (m, 1H) 3.63 (dd, J=10.07, 6.71 Hz, 1H) 3.70-3.85 (m, 1H) 3.93 (d, J=10.68 Hz, 1H) 4.87 (q, J=6.41 Hz, 1H) 7.20 (dd, J=8.85, 2.75 Hz, 1H) 7.60 (d, J=8.85 Hz, 1H) 7.77-7.86 (m, 2H) 7.87-7.95 (m, 2H) 8.30 (d, J=2.75 Hz, 1H); MS (ESI) m/z 496 (M+H)$^+$.

Example 229

3-{[(7R,8aS)-7-{[6-(trifluoromethyl)pyridin-3-yl]oxy}hexahydropyrrolo[1,2-a]pyrazin-2(1H)-yl]sulfonyl}benzonitrile The title compound was obtained according to the procedures described for Example 226 substituting 5-fluoro-2-(trifluoromethyl)pyridine for 2-bromo-5-(trifluoromethyl)pyridine and substituting 3-cyanobenzene-1-sulfonyl chloride for 4-(trifluoromethyl)benzene-1-sulfonyl chloride. $^1$H NMR (300 MHz, CDCl$_3$) δ ppm 1.73-1.90 (m, 1H) 2.01-2.10 (m, 1H) 2.16 (t, J=10.51 Hz, 1H) 2.37-2.53 (m, 3H) 2.53-2.67 (m, 1H) 2.93-3.13 (m, 1H) 3.64 (dd, J=9.83, 6.78 Hz, 1H) 3.71-3.86 (m, 1H) 3.94 (d, J=10.17 Hz, 1H) 4.88 (q, J=6.22 Hz, 1H) 7.20 (dd, J=8.65, 2.88 Hz, 1H) 7.60 (d, J=8.82 Hz, 1H) 7.70 (t, J=7.63 Hz, 1H) 7.85-7.92 (m, 1H) 7.96-8.02 (m, 1H) 8.06 (t, J=1.36 Hz, 1H) 8.30 (d, J=2.71 Hz, 1H); MS (ESI) m/z 453 (M+H)$^+$.

Example 230

(7R,8aS)-2-{[3-(trifluoromethyl)phenyl]sulfonyl}-7-{[6-(trifluoromethyl)-pyridin-2-yl]oxy}octahydropyrrolo[1,2-a]pyrazine The title compound was obtained according to the procedures described for Example 226 substituting 2-fluoro-6-(trifluoromethyl)pyridine for 2-bromo-5-(trifluoromethyl)pyridine and substituting 3-(trifluoromethyl)benzene-1-sulfonyl chloride for 4-(trifluoromethyl)benzene-1-sulfonyl chloride. $^1$H NMR (300 MHz, CDCl$_3$) δ ppm 1.74-1.92 (m, 1H) 1.94-2.06 (m, 1H) 2.13 (t, J=10.51 Hz, 1H) 2.32 (dd, J=9.83, 5.09 Hz, 1H) 2.38-2.64 (m, 3H) 3.02 (d, J=7.80 Hz, 1H) 3.69 (dd, J=9.49, 7.12 Hz, 1H) 3.78 (d, J=8.14 Hz, 1H) 3.92 (d, J=10.51 Hz, 1H) 5.28-5.47 (m, 1H) 6.88 (d, J=8.48 Hz, 1H) 7.18-7.24 (m, 1H) 7.70 (t, J=7.97 Hz, 2H) 7.87 (d, J=8.14 Hz, 1H) 7.96 (d, J=7.80 Hz, 1H) 8.03 (s, 1H); MS (ESI) m/z 496 (M+H)$^+$.

Example 231

(7R,8aS)-2-{[3-(trifluoromethyl)phenyl]sulfonyl}-7-{[5-(trifluoromethyl)-pyridin-3-yl]oxy}octahydropyrrolo[1,2-a]pyrazine The title compound was obtained according to the procedures described for Example 226 substituting 3-fluoro-5-

(trifluoromethyl)pyridine for 2-bromo-5-(trifluoromethyl)pyridine and substituting 3-(trifluoromethyl)benzene-1-sulfonyl chloride for 4-(trifluoromethyl)benzene-1-sulfonyl chloride. $^1$H NMR (300 MHz, CDCl$_3$) δ ppm 1.72-1.90 (m, 1H) 1.97-2.07 (m, 1H) 2.14 (t, J=10.34 Hz, 1H) 2.37-2.53 (m, 3H) 2.53-2.69 (m, 1H) 2.92-3.12 (m, 1H) 3.64 (dd, J=9.83, 6.78 Hz, 1H) 3.72-3.87 (m, J=8.14 Hz, 1H) 3.94 (d, J=9.83 Hz, 1H) 4.86 (q, J=6.44 Hz, 1H) 7.28 (t, J=2.03 Hz, 1H) 7.71 (t, J=7.80 Hz, 1H) 7.88 (d, J=8.14 Hz, 1H) 7.97 (d, J=8.14 Hz, 1H) 8.03 (s, 1H) 8.40 (d, J=2.03 Hz, 1H) 8.50 (s, 1H); MS (ESI) m/z 496 (M+H)$^+$.

Many variations in the invention can suggest themselves to those skilled in the art in light of the foregoing detailed description. All such obvious variations are within the full intended scope of the appended claims.

We claim:

1. A compound of Formula (I):

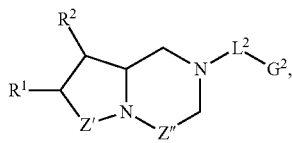

or a salt thereof, wherein:
Z' is CH$_2$ or C(O);
Z'' is CH$_2$;
one of R$^1$ and R$^2$ is hydrogen and the other of R$^1$ and R$^2$ is G$^1$-L$^1$-;
L$^1$ is —C(R$^c$)(R$^d$)—, —C(O)NR$^a$—, —NR$^a$C(O)—, —S(O)$_2$NR$^a$—, —NR$^a$S(O)$_2$—; —NR$^a$—, or —O—;
G$^1$ is C$_1$-C$_8$-alkyl, C$_1$-C$_8$-haloalkyl, Ar$^1$, —(CR$^a$R$^b$)$_j$—Ar$^1$, —CH(Ar$^1$)$_2$, or —Ar$^1$-G$^a$;
R$^a$ and R$^b$, at each occurrence, are each independently hydrogen, C$_1$-C$_4$-alkyl, or C$_1$-C$_4$-haloalkyl;
R$^c$ and R$^d$ are each independently hydrogen, hydroxy, C$_1$-C$_4$-alkyl, or C$_1$-C$_4$-haloalkyl;
j is 1, 2, 3, 4, or 5;
Ar$^1$ is, at each occurrence, independently aryl or heteroaryl, wherein Ar$^1$ is unsubstituted or substituted with 1, 2, 3, 4, or 5 substituents selected from the group consisting of C$_1$-C$_4$-alkyl, C$_2$-C$_4$-alkenyl, C$_2$-C$_4$-alkynyl, halogen, cyano, —NO$_2$, —OR$^s$, —OC(O)R$^s$, —OC(O)N(R$^s$)(R$^t$), —SR$^s$, —S(O)R$^s$, —S(O)$_2$R$^s$, —S(O)$_2$N(R$^s$)(R$^t$), —C(O)R$^s$, —C(O)OR$^s$, —C(O)N(R$^s$)(R$^t$), —N(R$^s$)(R$^t$), —N(R$^s$)C(O)R$^t$, —N(R$^s$)C(O)O(R$^t$), —N(R$^s$)S(O)$_2$(R$^t$), C$_1$-C$_4$-cyanoalkyl, and C$_1$-C$_4$-haloalkyl;
R$^s$ and R$^t$ are, at each occurrence, independently hydrogen, C$_1$-C$_4$-alkyl, C$_2$-C$_4$-alkenyl, C$_2$-C$_4$-alkynyl, or C$_1$-C$_4$-haloalkyl;
G$^a$ is C$_3$-C$_7$-cycloalkyl, C$_3$-C$_7$-cycloalkenyl, heterocyclyl, or heteroaryl, wherein the C$_3$-C$_7$-cycloalkyl, C$_3$-C$_7$-cycloalkenyl, heterocyclyl, or heteroaryl are unsubstituted or substituted with 1, 2, or 3 C$_1$-C$_4$-alkyl, C$_1$-C$_4$-haloalkyl, or halogen;
L$^2$ is —S(O)$_2$—, —S(O)$_2$CH$_2$—, or —S(O)—;
G$^2$ is C$_1$-C$_8$-alkyl, C$_1$-C$_8$-haloalkyl, C$_3$-C$_8$-cycloalkyl, Ar$^2$ or Ar$^3$;
Ar$^2$ is aryl or heteroaryl, wherein Ar$^2$ is unsubstituted or substituted with 1, 2, 3, 4, or 5 substituents selected from the group consisting of C$_1$-C$_4$-alkyl, C$_2$-C$_4$-alkenyl, C$_2$-C$_4$-alkynyl, halogen, cyano, —NO$_2$, -alkyl-OR$^u$, —OC(O)R$^u$, —OC(O)N(R$^u$)(R$^v$), —SR$^u$, —S(O)R$^u$, —S(O)$_2$R$^u$, —S(O)$_2$N(R$^u$)(R$^v$), —C(O)R$^u$, —C(O)OR$^u$, —C(O)N(R$^u$)(R$^v$), —N(R$^u$)(R$^v$), —N(R$^u$)C(O)R$^v$, —N(R$^u$)C(O)O(R$^v$), —N(R$^u$)S(O)$_2$(R$^v$), C$_1$-C$_4$-cyanoalkyl, C$_1$-C$_4$-haloalkyl, and -G$^b$;
G$^b$ is C$_3$-C$_7$-cycloalkyl, C$_3$-C$_7$-cycloalkenyl, heterocyclyl, aryl, or heteroaryl, wherein the C$_3$-C$_7$-cycloalkyl, C$_3$-C$_7$-cycloalkenyl, heterocyclyl, aryl, or heteroaryl are unsubstituted or substituted with 1, 2, or 3 C$_1$-C$_4$-alkyl, C$_1$-C$_4$-haloalkyl, or halogen;
R$^u$ and R$^v$ are, at each occurrence, independently hydrogen, C$_1$-C$_4$-alkyl, C$_2$-C$_4$-alkenyl, C$_2$-C$_4$-alkynyl, or C$_1$-C$_4$-haloalkyl;
Ar$^3$ is (i), wherein:

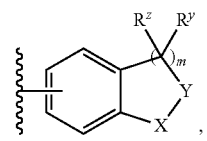

X is O, S, NR$^w$, or CH$_2$; wherein R$^w$ is hydrogen or alkyl;
Y is C(O) or CH$_2$;
R$^z$ and R$^y$ are independently, at each occurrence, hydrogen or C$_1$-C$_4$-alkyl; and
m is 1, 2 or 3.

2. The compound of claim 1, or a salt thereof, wherein:
Z' is CH$_2$;
R$^1$ is G$^1$-L$^1$-; and
R$^2$ is hydrogen.

3. The compound of claim 1, or a salt thereof, wherein:
Z' is C(O);
R$^1$ is G$^1$-L$^1$-; and
R$^2$ is hydrogen.

4. The compound of claim 1, or a salt thereof, wherein L$^1$ is —C(O)NR$^a$—, —NR$^a$C(O)—, —NR$^a$—, or —O—.

5. The compound of claim 1, or a salt thereof, wherein:
G$^1$ is —Ar$^1$-G$^a$;
Ar$^1$ is pyridinyl or pyrazinyl; and
G$^a$ is cyclopropyl.

6. The compound of claim 1, or a salt thereof, wherein:
G$^2$ is Ar$^2$; and
Ar$^2$ is phenyl or pyridinyl; wherein Ar$^2$ is unsubstituted or substituted with 1 or 2 substituents selected from the group consisting of halogen, cyano, C$_1$-C$_4$-alkyl, halomethyl, methoxy, and halomethoxy.

7. The compound of claim 1, or a salt thereof, wherein:
L' is —C(R$^c$)(R$^d$)—, —C(O)NR$^a$—, —NR$^a$C(O)—, —NR$^a$—, or —O—;
R$^a$ and R$^b$, at each occurrence, are each hydrogen;
R$^c$ and R$^d$ are each independently hydrogen or hydroxy;
Ar$^1$ is, at each occurrence, independently selected from the group consisting of phenyl, thiazolyl, pyridinyl, pyrimidinyl, pyrazinyl, pyridazinyl, and benzoxazolyl; wherein Ar$^1$ is unsubstituted or substituted with 1, 2, 3, 4, or 5 substituents selected from the group consisting of halogen, cyano, C$_1$-C$_4$-alkyl, C$_2$-C$_4$-alkenyl, C$_1$-C$_4$-haloalkyl, and C$_1$-C$_4$-haloalkoxy;
G$^a$ is cyclopropyl, cyclobutyl, or imidazolyl;
L$^2$ is —S(O)$_2$— or —S(O)$_2$CH$_2$—;
Ar$^2$ is aryl or heteroaryl; wherein the Ar$^2$ aryl is selected from the group consisting of phenyl, naphthyl, and tetrahydronaphthylenyl; the Ar$^2$ heteroaryl is selected from the group consisting of furyl, thienyl, pyrazolyl, and pyridinyl; and Ar$^2$ is unsubstituted or substituted with 1, 2, 3, 4, or 5 substituents selected from the group consisting of halogen, cyano, $C_1$-$C_4$-alkyl, $C_1$-$C_4$-haloalkyl, —$OR^u$, —$C(O)R^u$, —$C(O)OR^u$, —$C(O)N(R^u)(R^v)$, and -$G^b$;

$G^b$ is selected from the group consisting of cyclopropyl, phenyl, pyrrolidinyl, piperidinyl, morpholinyl, and pyrazolyl; wherein the cyclopropyl, phenyl, pyrrolidinyl, piperidinyl, morpholinyl, and pyrazolyl are unsubstituted or substituted with 1, 2, or 3 $C_1$-$C_4$-alkyl;

$R^u$ and $R^v$ are, at each occurrence, independently hydrogen, $C_1$-$C_4$-alkyl, or $C_1$-$C_4$-haloalkyl; and $Ar^3$ is dihydroindenyl or dihydrobenzofuranyl, wherein the dihydroindenyl and dihydrobenzofuranyl are unsubstituted or substituted with 1, 2, or 3 $C_1$-$C_4$-alkyl.

8. The compound of claim 1, or a salt thereof, wherein:
$G^1$ is —$Ar^1$ or —$Ar^1$-$G^a$;
$R^a$, at each occurrence, is hydrogen;
$R^c$ and $R^d$ are each independently hydrogen or hydroxy;
$Ar^1$ is, at each occurrence, independently selected from the group consisting of phenyl, thiazolyl, pyridinyl, pyrimidinyl, pyrazinyl, pyridazinyl, and benzoxazolyl; wherein $Ar^1$ is unsubstituted or substituted with 1, 2, or 3 substituents selected from the group consisting of halogen, cyano, $C_1$-$C_4$-alkyl, $C_2$-$C_4$-alkenyl, $C_1$-$C_4$-haloalkyl, and $C_1$-$C_4$-haloalkoxy;
$G^a$ is cyclopropyl, cyclobutyl, or imidazolyl; and
$L^2$ is —$S(O)_2$— or —$S(O)_2CH_2$—.

9. The compound of claim 1, or a salt thereof, wherein:
$R^a$ and $R^b$, at each occurrence, are each hydrogen;
$R^c$ and $R^d$ are each independently hydrogen or hydroxy;
$L^2$ is —$S(O)_2$— or —$S(O)_2CH_2$—;
$G^2$ is $Ar^2$;
$Ar^2$ is aryl or heteroaryl; wherein the $Ar^2$ aryl is selected from the group consisting of phenyl, naphthyl, and tetrahydronaphthylenyl; the $Ar^2$ heteroaryl is selected from the group consisting of furyl, thienyl, pyrazolyl, and pyridinyl; and $Ar^2$ is unsubstituted or substituted with 1, 2, 3, 4, or 5 substituents selected from the group consisting of halogen, cyano, $C_1$-$C_4$-alkyl, $C_1$-$C_4$-haloalkyl, —$OR^u$, —$C(O)R^u$, —$C(O)OR^u$, —$C(O)N(R^u)(R^v)$, and -$G^b$;

$G^b$ is selected from the group consisting of cyclopropyl, phenyl, pyrrolidinyl, piperidinyl, morpholinyl, and pyrazolyl; wherein the cyclopropyl, phenyl, pyrrolidinyl, piperidinyl, morpholinyl, and pyrazolyl are unsubstituted or substituted with 1, 2, or 3 $C_1$-$C_4$-alkyl; and $R^u$ and $R^v$ are, at each occurrence, independently hydrogen, $C_1$-$C_4$-alkyl, or $C_1$-$C_4$-haloalkyl.

10. The compound of claim 1, or a salt thereof, wherein:
$L^1$ is —$C(O)NR^a$—, —$NR^aC(O)$—, or —O—;
$G^1$ is $Ar^1$ or —$Ar^1$-$G^a$;
$R^a$, at each occurrence, is hydrogen;
$Ar^1$ is, at each occurrence, independently phenyl, pyridinyl, or pyrazinyl; wherein $Ar^1$ is unsubstituted or substituted with 1, 2, or 3 substituents selected from the group consisting of halogen, cyano, $C_1$-$C_4$-alkyl, $C_2$-$C_4$-alkenyl, $C_1$-$C_4$-haloalkyl, and $C_1$-$C_4$-haloalkoxy;
$G^a$ is cyclopropyl, cyclobutyl, or imidazolyl;
$L^2$ is —$S(O)_2$—;
$G^2$ is $Ar^2$;
$Ar^2$ is phenyl or pyridinyl; wherein $Ar^2$ is unsubstituted or substituted with 1, 2, or 3 substituents selected from the group consisting of halogen, cyano, $C_1$-$C_4$-alkyl, $C_1$-$C_4$-haloalkyl, —$OR^u$, —$C(O)R^u$, —$C(O)OR^u$, —$C(O)N(R^u)(R^v)$, and -$G^b$;
$G^b$ is selected from the group consisting of cyclopropyl, phenyl, pyrrolidinyl, piperidinyl, morpholinyl, and pyrazolyl; wherein the cyclopropyl, phenyl, pyrrolidinyl, piperidinyl, morpholinyl, and pyrazolyl are unsubstituted or substituted with 1, 2, or 3 $C_1$-$C_4$-alkyl; and $R^u$ and $R^v$ are, at each occurrence, independently hydrogen, $C_1$-$C_4$-alkyl, or $C_1$-$C_4$-haloalkyl.

11. The compound of claim 1, or a salt thereof, wherein:
$L^1$ is —$C(O)NR^a$—, —$NR^aC(O)$—, or —O—;
$G^1$ is $Ar^1$ or —$Ar^1$-$G^a$;
$R^a$, at each occurrence, is hydrogen;
$Ar^1$ is, at each occurrence, independently phenyl, pyridin-2-yl, or pyrazin-2-yl; wherein $Ar^1$ is unsubstituted or substituted with 1 or 2 substituents selected from the group consisting of halogen, $C_1$-$C_4$-alkyl, halomethyl, and halomethoxy;
$G^a$ is cyclopropyl;
$L^2$ is —$S(O)_2$—;
$G^2$ is $Ar^2$; and
$Ar^2$ is phenyl or pyridinyl; wherein $Ar^2$ is unsubstituted or substituted with 1 or 2 substituents selected from the group consisting of halogen, cyano, $C_1$-$C_4$-alkyl, halomethyl, methoxy, and halomethoxy.

12. The compound of claim 1, or a salt thereof, wherein:
$L^1$ is —$C(O)NR^a$—, —$NR^aC(O)$—, or —O—;
$G^1$ is —$Ar^1$-$G^a$;
$R^a$, at each occurrence, is hydrogen;
$Ar^1$ is pyrazin-2-yl; wherein $Ar^1$ is unsubstituted or substituted with 1 or 2 substituents selected from the group consisting of halogen, $C_1$-$C_4$-alkyl, halomethyl, and halomethoxy;
$G^a$ is cyclopropyl;
$L^2$ is —$S(O)_2$—;
$G^2$ is $Ar^2$; and
$Ar^2$ is phenyl or pyridinyl; wherein $Ar^2$ is substituted with 1 or 2 substituents selected from the group consisting of chloro, fluoro, trifluoromethyl, and trifluoromethoxy.

13. The compound of claim 1, or a salt thereof, wherein:
$L^1$ is —$C(O)NR^a$—, —$NR^aC(O)$—, or —O—;
$G^1$ is $Ar^1$ or —$Ar^1$-$G^a$;
$R^a$, at each occurrence, is hydrogen;
$Ar^1$ is phenyl, pyridin-2-yl, or pyrazin-2-yl; wherein $Ar^1$ substituted with 1 or 2 substituents selected from the group consisting of chloro, fluoro, trifluoromethyl, and trifluoromethoxy;
$G^a$ is cyclopropyl;
$L^2$ is —$S(O)_2$—; and
$Ar^2$ is phenyl; wherein $Ar^2$ is substituted with 1 or 2 substituents selected from the group consisting of chloro, fluoro, trifluoromethyl, and trifluoromethoxy.

14. The compound of claim 1, or a salt thereof, wherein:
$L^1$ is —$C(O)NR^a$—, —$NR^aC(O)$—, or —O—;
$G^1$ is $Ar^1$ or —$Ar^1$-$G^a$;
$R^a$, at each occurrence, is hydrogen;
$Ar^1$ is phenyl, pyridin-2-yl, or pyrazin-2-yl; wherein $Ar^1$ substituted with 1 or 2 substituents selected from the group consisting of chloro, fluoro, trifluoromethyl, and trifluoromethoxy;
$G^a$ is cyclopropyl;
$L^2$ is —$S(O)_2$—; and
$Ar^2$ is pyridinyl; wherein $Ar^2$ is substituted with 1 or 2 substituents selected from the group consisting of chloro, fluoro, trifluoromethyl, and trifluoromethoxy.

15. The compound of claim 1, or a salt thereof, wherein $L^1$ is —O—.

16. The compound, or a salt thereof, of claim 1, wherein the salt is a pharmaceutically acceptable salt.

17. The compound of claim 1, or a salt thereof, wherein the compound is selected from the group consisting of:

4-fluoro-N-[(7S,8aS)-2-{[3-(trifluoromethyl)phenyl]sulfonyl}octahydropyrrolo[1,2-a]pyrazin-7-yl]benzamide;

4-fluoro-N-[(7S,8aS)-2-{[4-(trifluoromethyl)phenyl]sulfonyl}octahydropyrrolo[1,2-a]pyrazin-7-yl]benzamide;

N-[(7S,8aS)-2-{[2-chloro-4-(trifluoromethyl)phenyl]sulfonyl}octahydropyrrolo[1,2-a]pyrazin-7-yl]-4-fluorobenzamide;

N-[(7S,8aS)-2-{[2-chloro-5-(trifluoromethyl)phenyl]sulfonyl}octahydropyrrolo[1,2-a]pyrazin-7-yl]-4-fluorobenzamide;

4-chloro-N-[(7S,8aS)-2-{[3-(trifluoromethyl)phenyl]sulfonyl}octahydropyrrolo[1,2-a]pyrazin-7-yl]benzamide;

4-chloro-N-[(7S,8aS)-2-{[4-(trifluoromethyl)phenyl]sulfonyl}octahydropyrrolo[1,2-a]pyrazin-7-yl]benzamide;

4-chloro-N-[(7S,8aS)-2-{[2-chloro-4-(trifluoromethyl)phenyl]sulfonyl}octahydropyrrolo[1,2-a]pyrazin-7-yl]benzamide;

4-chloro-N-[(7S,8aS)-2-{[4-fluoro-2-(trifluoromethyl)phenyl]sulfonyl}octahydropyrrolo[1,2-a]pyrazin-7-yl]benzamide;

4-chloro-N-[(7S,8aS)-2-{[2-(trifluoromethyl)phenyl]sulfonyl}octahydropyrrolo[1,2-a]pyrazin-7-yl]benzamide;

N-[(7S,8aS)-2-{[2-chloro-4-(trifluoromethyl)phenyl]sulfonyl}octahydropyrrolo[1,2-a]pyrazin-7-yl]-2,4-difluorobenzamide;

2,4-difluoro-N-[(7S,8aS)-2-{[4-(trifluoromethyl)phenyl]sulfonyl}octahydropyrrolo[1,2-a]pyrazin-7-yl]benzamide;

N-{(7S,8aS)-2-[(2,4-dichlorophenyl)sulfonyl]octahydropyrrolo[1,2-a]pyrazin-7-yl}-2,4-difluorobenzamide;

N-[(7S,8aS)-2-{[2-chloro-4-(trifluoromethyl)phenyl]sulfonyl}octahydropyrrolo[1,2-a]pyrazin-7-yl]-3,4-difluorobenzamide;

3,4-difluoro-N-[(7S,8aS)-2-{[4-(trifluoromethyl)phenyl]sulfonyl}octahydropyrrolo[1,2-a]pyrazin-7-yl]benzamide;

(7S,8aS)-2-[(3,5-dichlorophenyl)sulfonyl]-N-[6-(trifluoromethyl)pyridin-2-yl]octahydropyrrolo[1,2-a]pyrazin-7-amine;

(7S,8aS)-2-{[2-chloro-4-(trifluoromethyl)phenyl]sulfonyl}-N-[6-(trifluoromethyl)-pyridin-2-yl]octahydropyrrolo[1,2-a]pyrazin-7-amine;

(7R,8aR)-7-[(5-cyclopropylpyrazin-2-yl)oxy]-2-{[3-(trifluoromethyl)phenyl]-sulfonyl}octahydropyrrolo[1,2-a]pyrazine;

(7R,8aS)-2-{[2-chloro-4-(trifluoromethyl)phenyl]sulfonyl}-7-{[6-(trifluoromethyl)-pyridin-2-yl]oxy}octahydropyrrolo[1,2-a]pyrazine;

(7R,8aS)-7-[(5-cyclopropylpyrazin-2-yl)oxy]-2-{[3-(trifluoromethyl)phenyl]-sulfonyl}octahydropyrrolo[1,2-a]pyrazine;

(7R,8aS)-7-(pyrazin-2-yloxy)-2-{[3-(trifluoromethyl)phenyl]-sulfonyl}-octahydropyrrolo[1,2-a]pyrazine;

(7R,8aS)-7-[(6-cyclopropylpyrazin-2-yl)oxy]-2-{[3-(trifluoromethyl)phenyl]-sulfonyl}octahydropyrrolo[1,2-a]pyrazine;

(7R,8aS)-7-[(5-cyclopropylpyrazin-2-yl)oxy]-2-{[4-(trifluoromethyl)phenyl]-sulfonyl}octahydropyrrolo[1,2-a]pyrazine;

(7R,8aS)-7-[(6-cyclopropylpyrazin-2-yl)oxy]-2-{[4-(trifluoromethyl)phenyl]-sulfonyl}octahydropyrrolo[1,2-a]pyrazine;

(7R,8aS)-7-[(5-cyclopropylpyrazin-2-yl)oxy]-2-{[2-(trifluoromethyl)phenyl]-sulfonyl}octahydropyrrolo[1,2-a]pyrazine;

(7R,8aS)-7-[(5-cyclopropylpyrazin-2-yl)oxy]-2-{[4-(trifluoromethoxy)phenyl]-sulfonyl}octahydropyrrolo[1,2-a]pyrazine;

(7R,8aS)-7-[(5-cyclopropylpyrazin-2-yl)oxy]-2-{[4-(difluoromethoxy)phenyl]-sulfonyl}octahydropyrrolo[1,2-a]pyrazine;

(7R,8aS)-7-[(5-cyclopropylpyrazin-2-yl)oxy]-2-{[3-(difluoromethoxy)phenyl]-sulfonyl}octahydropyrrolo[1,2-a]pyrazine;

(7R,8aS)-7-[(5-cyclopropylpyrazin-2-yl)oxy]-2-[(2-fluorophenyl)sulfonyl]-octahydropyrrolo[1,2-a]pyrazine;

(7R,8aS)-7-[(5-cyclopropylpyrazin-2-yl)oxy]-2-{[2-fluoro-5-(trifluoromethyl)-phenyl]-sulfonyl}octahydropyrrolo[1,2-a]pyrazine;

(7R,8aS)-7-[(5-cyclopropylpyrazin-2-yl)oxy]-2-(2-furylsulfonyl)octahydropyrrolo-[1,2-a]pyrazine;

(7R,8aS)-7-[(5-cyclopropylpyrazin-2-yl)oxy]-2-{[3-(trifluoromethoxy)phenyl]-sulfonyl}octahydropyrrolo[1,2-a]pyrazine;

(8R*,8aS*)-8-[(5-chloropyridin-2-yl)oxy]-2-{[3-(trifluoromethyl)phenyl]-sulfonyl}octahydropyrrolo[1,2-a]pyrazine;

(8R*,8aR*)-8-[(5-chloropyridin-2-yl)oxy]-2-{[3-(trifluoromethyl)phenyl]-sulfonyl}octahydropyrrolo[1,2-a]pyrazine;

(7S,8aS)—N-(diphenylmethyl)-2-{[3-(trifluoromethyl)phenyl]sulfonyl}-octahydropyrrolo[1,2-a]pyrazine-7-carboxamide;

(7S,8aS)—N-(diphenylmethyl)-2-{[4-(trifluoromethyl)phenyl]sulfonyl}-octahydropyrrolo[1,2-a]pyrazine-7-carboxamide;

(7S,8aS)—N-(diphenylmethyl)-2-{[4-fluoro-3-(trifluoromethyl)phenyl]sulfonyl}-octahydropyrrolo[1,2-a]pyrazine-7-carboxamide;

(7S,8aS)—N-(4,4,4-trifluorobutyl)-2-{[3-(trifluoromethyl)phenyl]sulfonyl}-octahydropyrrolo[1,2-a]pyrazine-7-carboxamide;

(7S,8aS)-7-[4-(trifluoromethoxy)phenoxy]-2-{[3-(trifluoromethyl)phenyl]sulfonyl}-octahydropyrrolo[1,2-a]pyrazine;

(7S,8aS)-7-(4-tert-butylphenoxy)-2-{[3-(trifluoromethyl)phenyl]sulfonyl}-octahydropyrrolo[1,2-a]pyrazine;

(7S,8aS)-7-[4-(1H-imidazol-1-yl)phenoxy]-2-{[3-(trifluoromethyl)phenyl]-sulfonyl}-octahydropyrrolo[1,2-a]pyrazine;

(7S,8aS)-7-[(6-cyclopropylpyridazin-3-yl)oxy]-2-{[3-(trifluoromethyl)phenyl]-sulfonyl}octahydropyrrolo[1,2-a]pyrazine;

(7S,8aS)-7-[(6-cyclopropylpyridazin-3-yl)oxy]-2-{[4-(trifluoromethyl)phenyl]-sulfonyl}octahydropyrrolo[1,2-a]pyrazine;

(7S,8aS)-7-[(4-cyclopropylpyrimidin-2-yl)oxy]-2-{[3-(trifluoromethyl)phenyl]-sulfonyl}octahydropyrrolo[1,2-a]pyrazine;

(7S,8aS)-7-[(4-cyclopropylpyrimidin-2-yl)oxy]-2-{[4-(trifluoromethyl)phenyl]-sulfonyl}octahydropyrrolo[1,2-a]pyrazine;

1-(4-{[(7R,8aS)-7-[(5-cyclopropylpyrazin-2-yl)oxy]hexahydropyrrolo[1,2-a]pyrazin-2(1H)-yl]sulfonyl}phenyl)ethanone;

(7S,8aS)-7-[(5-cyclopropylpyrazin-2-yl)oxy]-2-{[3-(trifluoromethyl)phenyl]-sulfonyl}octahydropyrrolo[1,2-a]pyrazine;

(7S,8aS)-7-[(5-cyclopropylpyrazin-2-yl)oxy]-2-{[4-(trifluoromethyl)phenyl]-sulfonyl}octahydropyrrolo[1,2-a]pyrazine;

(7R,8aS)-7-[(5-cyclopropylpyrazin-2-yl)oxy]-2-{[3-fluoro-5-(trifluoromethyl)-phenyl]-sulfonyl}octahydropyrrolo[1,2-a]pyrazine;

(7R,8aS)-7-[(5-cyclopropylpyrazin-2-yl)oxy]-2-{[4-fluoro-3-(trifluoromethyl)-phenyl]-sulfonyl}octahydropyrrolo[1,2-a]pyrazine;

(7S,8aS)-2-[(3-tert-butylphenyl)sulfonyl]-7-[(5-cyclopropylpyrazin-2-yl)oxy]-octahydropyrrolo[1,2-a]pyrazine;

(7S,8aR)-7-[(5-cyclopropylpyrazin-2-yl)oxy]-2-{[4-(trifluoromethyl)phenyl]-sulfonyl}octahydropyrrolo[1,2-a]pyrazine;

(7S,8aS)-2-[(3-chlorophenyl)sulfonyl]-7-[(5-cyclopropylpyrazin-2-yl)oxy]-octahydropyrrolo[1,2-a]pyrazine;

(7S,8aS)-2-[(4-tert-butylphenyl)sulfonyl]-7-[(5-cyclopropylpyrazin-2-yl)oxy]-octahydropyrrolo[1,2-a]pyrazine;

(7S,8aS)-2-[(3-tert-butyl-4-methoxyphenyl)sulfonyl]-7-[(5-cyclopropylpyrazin-2-yl)oxy]octahydropyrrolo[1,2-a]pyrazine;

(7S,8aS)-2-[(6-tert-butylpyridin-2-yl)sulfonyl]-7-[(5-cyclopropylpyrazin-2-yl)oxy]octahydropyrrolo[1,2-a]pyrazine;

(7S,8aS)-7-[(5-cyclopropylpyrazin-2-yl)oxy]-2-{[6-(morpholin-4-yl)pyridin-2-yl]sulfonyl}octahydropyrrolo[1,2-a]pyrazine;

(7S,8aS)-7-[(5-cyclopropylpyrazin-2-yl)oxy]-2-{[6-(piperidin-1-yl)pyridin-2-yl]sulfonyl}octahydropyrrolo[1,2-a]pyrazine;

(7S,8aS)-7-[(5-cyclopropylpyrazin-2-yl)oxy]-2-{[6-(pyrrolidin-1-yl)pyridin-2-yl]sulfonyl}octahydropyrrolo[1,2-a]pyrazine;

(7R,8aS)-7-[(5-cyclopropylpyrazin-2-yl)oxy]-2-[(2,4-difluorophenyl)sulfonyl]-octahydropyrrolo[1,2-a]pyrazine;

(7R,8aS)-7-[(5-cyclopropylpyrazin-2-yl)oxy]-2-{[4-(trifluoromethyl)pyridin-2-yl]sulfonyl}octahydropyrrolo[1,2-a]pyrazine;

3-{[(7R,8aS)-7-[(5-cyclopropylpyrazin-2-yl)oxy]hexahydropyrrolo[1,2-a]pyrazin-2(1H)-yl]sulfonyl}-5-(trifluoromethyl)benzonitrile;

4-{[(7R,8aS)-7-[(5-cyclopropylpyrazin-2-yl)oxy]hexahydropyrrolo[1,2-a]pyrazin-2(1H)-yl]sulfonyl}-2-(trifluoromethyl)benzonitrile;

(7R,8aS)-7-[(5-cyclopropylpyrazin-2-yl)oxy]-2-{[6-(trifluoromethyl)pyridin-2-yl]sulfonyl}octahydropyrrolo[1,2-a]pyrazine;

(7R,8aS)-7-[(5-cyclopropylpyrazin-2-yl)oxy]-2-{[5-(trifluoromethyl)pyridin-2-yl]sulfonyl}octahydropyrrolo[1,2-a]pyrazine;

2-chloro-5-{[(7R,8aS)-7-[(5-cyclopropylpyrazin-2-yl)oxy]hexahydropyrrolo[1,2-a]pyrazin-2(1H)-yl]sulfonyl}benzonitrile;

(7R,8aS)-7-{[6-(trifluoromethyl)pyridin-3-yl]oxy}-2-{[6-(trifluoromethyl)pyridin-2-yl]sulfonyl}octahydropyrrolo[1,2-a]pyrazine;

(7S,8aS)-7-[(5-cyclopropylpyrazin-2-yl)oxy]-2-{[6-(morpholin-4-yl)pyridin-3-yl]sulfonyl}octahydropyrrolo[1,2-a]pyrazine;

(7S,8aS)-2-[(5-tert-butyl-2-methoxyphenyl)sulfonyl]-7-[(5-cyclopropylpyrazin-2-yl)oxy]octahydropyrrolo[1,2-a]pyrazine;

(7S,8aS)-7-[(5-cyclopropylpyrazin-2-yl)oxy]-2-[(5-methyl-2-thienyl)sulfonyl]-octahydropyrrolo[1,2-a]pyrazine;

(7S,8aS)-2-[(5-bromopyridin-3-yl)sulfonyl]-7-[(5-cyclopropylpyrazin-2-yl)oxy]-octahydropyrrolo[1,2-a]pyrazine;

(7S,8aS)-7-[(5-cyclopropylpyrazin-2-yl)oxy]-2-[(5-cyclopropylpyridin-3-yl)sulfonyl]-octahydropyrrolo[1,2-a]pyrazine;

(7S,8aS)-2-[(6-chloropyridin-3-yl)sulfonyl]-7-[(5-cyclopropylpyrazin-2-yl)oxy]-octahydropyrrolo[1,2-a]pyrazine;

5-{[(7S,8aS)-2-{[3-(trifluoromethyl)phenyl]sulfonyl}octahydropyrrolo[1,2-a]pyrazin-7-yl]oxy}-1,3-benzoxazole;

(7S,8aS)-2-{[3-(trifluoromethyl)phenyl]sulfonyl}-7-{[6-(trifluoromethyl)pyridin-3-yl]oxy}octahydropyrrolo[1,2-a]pyrazine;

2-methyl-6-{[(7S,8aS)-2-{[3-(trifluoromethyl)phenyl]sulfonyl}octahydropyrrolo[1,2-a]pyrazin-7-yl]oxy}-1,3-benzoxazole;

(7S,8aS)-7-(4-fluoro-3-methylphenoxy)-2-{[3-(trifluoromethyl)phenyl]sulfonyl}-octahydropyrrolo[1,2-a]pyrazine;

(7S,8aS)-7-[(5-methylpyrazin-2-yl)oxy]-2-{[3-(trifluoromethyl)phenyl]sulfonyl}-octahydropyrrolo[1,2-a]pyrazine;

(7S,8aS)-7-[(6-methylpyrazin-2-yl)oxy]-2-{[3-(trifluoromethyl)phenyl]sulfonyl}-octahydropyrrolo[1,2-a]pyrazine;

(7S,8aS)-7-{[6-chloro-5-(trifluoromethyl)pyridin-3-yl]oxy}-2-{[3-(trifluoromethyl)-phenyl]sulfonyl}octahydropyrrolo[1,2-a]pyrazine;

(7S,8aS)-2-{[3-(trifluoromethyl)phenyl]sulfonyl}-7-{[5-(trifluoromethyl)pyridin-2-yl]oxy}octahydropyrrolo[1,2-a]pyrazine;

(7S,8aS)-2-{[3-(trifluoromethyl)phenyl]sulfonyl}-7-{[6-(trifluoromethyl)pyridin-3-yl]oxy}octahydropyrrolo[1,2-a]pyrazine;

6-{[(7R,8aS)-2-{[3-(trifluoromethyl)phenyl]sulfonyl}octahydropyrrolo[1,2-a]pyrazin-7-yl]oxy}nicotinonitrile;

5-{[(7R,8aS)-2-{[3-(trifluoromethyl)phenyl]sulfonyl}octahydropyrrolo[1,2-a]pyrazin-7-yl]oxy}pyridine-2-carbonitrile;

(7S,8aS)-7-[(6-bromopyridin-3-yl)oxy]-2-{[3-(trifluoromethyl)phenyl]sulfonyl}-octahydropyrrolo[1,2-a]pyrazine;

(7S,8aS)-7-[(6-cyclopropylpyridin-3-yl)oxy]-2-{[3-(trifluoromethyl)phenyl]-sulfonyl}octahydropyrrolo[1,2-a]pyrazine;

(7S,8aS)-7-[(5-bromopyridin-2-yl)oxy]-2-{[3-(trifluoromethyl)phenyl]-sulfonyl}octahydropyrrolo[1,2-a]pyrazine;

(7S,8aS)-7-[(5-cyclopropylpyridin-2-yl)oxy]-2-{[3-(trifluoromethyl)phenyl]-sulfonyl}octahydropyrrolo[1,2-a]pyrazine;

(7S,8aS)-7-[(6-bromopyridin-2-yl)oxy]-2-{[3-(trifluoromethyl)phenyl]-sulfonyl}octahydropyrrolo[1,2-a]pyrazine;

(7S,8aS)-7-[(6-cyclopropylpyridin-2-yl)oxy]-2-{[3-(trifluoromethyl)phenyl]-sulfonyl}octahydropyrrolo[1,2-a]pyrazine;

(7S,8aS)-7-[(5-bromo-1,3-thiazol-2-yl)oxy]-2-{[3-(trifluoromethyl)phenyl]-sulfonyl}octahydropyrrolo[1,2-a]pyrazine;

(7S,8aS)-7-[(5-cyclopropyl-1,3-thiazol-2-yl)oxy]-2-{[3-(trifluoromethyl)phenyl]-sulfonyl}octahydropyrrolo[1,2-a]pyrazine;

(7R,8aS)-7-[(5-cyclopropylpyrazin-2-yl)oxy]-2-[(2,3-difluorophenyl)sulfonyl]-octahydropyrrolo[1,2-a]pyrazine;

(7S,8aS)-7-[(5-cyclopropylpyrazin-2-yl)oxy]-2-{[3-fluoro-2-(piperidin-1-yl)phenyl]sulfonyl}octahydropyrrolo[1,2-a]pyrazine;

(7S,8aS)-7-[(4-tert-butylbenzyl)oxy]-2-{[3-(trifluoromethyl)phenyl]sulfonyl}-octahydropyrrolo[1,2-a]pyrazine;

(7S,8aS)-7-{[4-(trifluoromethoxy)benzyl]oxy}-2-{[3-(trifluoromethyl)phenyl]-sulfonyl}octahydropyrrolo[1,2-a]pyrazine;

(7S,8aS)-7-{[4-(trifluoromethyl)benzyl]oxy}-2-{[3-(trifluoromethyl)phenyl]-sulfonyl}octahydropyrrolo[1,2-a]pyrazine;

(7S,8aS)-7-[(5-cyclopropylpyrazin-2-yl)oxy]-2-{[4-(1,1-difluoroethyl)phenyl]-sulfonyl}octahydropyrrolo[1,2-a]pyrazine;

(7S,8aS)-7-[(5-cyclobutylpyrazin-2-yl)oxy]-2-{[3-(trifluoromethyl)phenyl]-sulfonyl}octahydropyrrolo[1,2-a]pyrazine;

(7S,8aS)-7-[(5-cyclobutylpyrazin-2-yl)oxy]-2-{[4-(trifluoromethyl)phenyl]-sulfonyl}octahydropyrrolo[1,2-a]pyrazine;

(7S,8aS)-2-(biphenyl-3-ylsulfonyl)-7-[(5-cyclopropylpyrazin-2-yl)oxy]octahydropyrrolo[1,2-a]pyrazine;

(7S,8aS)-7-[(5-cyclopropylpyrazin-2-yl)oxy]-2-[(4-isopropylphenyl)sulfonyl]-octahydropyrrolo[1,2-a]pyrazine;

(7S,8aS)-7-[(5-cyclopropylpyrazin-2-yl)oxy]-2-[(3-methoxyphenyl)sulfonyl]-octahydropyrrolo[1,2-a]pyrazine;

(7S,8aS)-7-[(5-cyclopropylpyrazin-2-yl)oxy]-2-{[4-methoxy-3-(trifluoromethyl)-phenyl]sulfonyl}octahydropyrrolo[1,2-a]pyrazine;

1-(3-{[(7R,8aS)-7-[(5-cyclopropylpyrazin-2-yl)oxy]hexahydropyrrolo[1,2-a]pyrazin-2(1H)-yl]sulfonyl}phenyl)ethanone;

(7S,8aS)-7-[(5-cyclopropylpyrazin-2-yl)oxy]-2-{[3-(1,1-difluoroethyl)phenyl]-sulfonyl}octahydropyrrolo[1,2-a]pyrazine;

(7S,8aS)-7-[(5-cyclopropylpyrazin-2-yl)oxy]-2-[(4-methylphenyl)sulfonyl]-octahydropyrrolo[1,2-a]pyrazine;

(7S,8aR)-7-[(5-cyclopropylpyrazin-2-yl)oxy]-2-{[3-(trifluoromethyl)phenyl]-sulfonyl}octahydropyrrolo[1,2-a]pyrazine;

(7R,8aS)-2-{[3-bromo-5-(trifluoromethyl)phenyl]sulfonyl}-7-[(5-cyclopropylpyrazin-2-yl)oxy]octahydropyrrolo[1,2-a]pyrazine;

(7S,8aS)-2-[(3-tert-butylphenyl)sulfonyl]-7-{[5-(prop-1-en-2-yl)pyrazin-2-yl]oxy}-octahydropyrrolo[1,2-a]pyrazine;

(7S,8aS)-7-[(5-cyclopropylpyrazin-2-yl)oxy]-2-(2,3-dihydro-1-benzofuran-5-yl-sulfonyl)octahydropyrrolo[1,2-a]pyrazine;

(7S,8aS)-7-{[5-(prop-1-en-2-yl)pyrazin-2-yl]oxy}-2-{[3-(trifluoromethyl)phenyl]-sulfonyl}octahydropyrrolo[1,2-a]pyrazine;

(7S,8aS)-7-{[5-(prop-1-en-2-yl)pyrazin-2-yl]oxy}-2-{[4-(trifluoromethyl)phenyl]-sulfonyl}octahydropyrrolo[1,2-a]pyrazine;

(7S,8aS)-2-[(3-tert-butylphenyl)sulfonyl]-7-[(5-isopropylpyrazin-2-yl)oxy]-octahydropyrrolo[1,2-a]pyrazine;

(7S,8aS)-7-[(5-isopropylpyrazin-2-yl)oxy]-2-{[3-(trifluoromethyl)phenyl]-sulfonyl}octahydropyrrolo[1,2-a]pyrazine;

(7S,8aS)-7-[(5-cyclopropylpyrazin-2-yl)oxy]-2-[(3,4,5-trifluorophenyl)sulfonyl]-octahydropyrrolo[1,2-a]pyrazine;

(7S,8aS)-2-[(3-chloro-2-fluorophenyl)sulfonyl]-7-[(5-cyclopropylpyrazin-2-yl)-oxy]octahydropyrrolo[1,2-a]pyrazine;

(7S,8aS)-7-[(5-cyclopropylpyrazin-2-yl)oxy]-2-[(2-fluoro-5-methylphenyl)-sulfonyl]-octahydropyrrolo[1,2-a]pyrazine;

(7S,8aS)-7-[(5-cyclopropylpyrazin-2-yl)oxy]-2-[(2,6-difluorophenyl)sulfonyl]-octahydropyrrolo[1,2-a]pyrazine;

(7R,8aS)-7-[(5-cyclopropylpyrazin-2-yl)oxy]-2-[(2,3,4-trifluorophenyl)sulfonyl]-octahydropyrrolo[1,2-a]pyrazine;

(7S,8aS)-2-[(5-chloro-2-fluorophenyl)sulfonyl]-7-[(5-cyclopropylpyrazin-2-yl)oxy]-octahydropyrrolo[1,2-a]pyrazine;

(7S,8aS)-7-[(5-cyclopropylpyrazin-2-yl)oxy]-2-[(3-fluoro-4-methylphenyl)-sulfonyl]-octahydropyrrolo[1,2-a]pyrazine;

(7R,8aS)-7-[(5-cyclopropylpyrazin-2-yl)oxy]-2-[(3,5-difluorophenyl)sulfonyl]-octahydropyrrolo[1,2-a]pyrazine;

(7S,8aS)-7-[(5-cyclopropylpyrazin-2-yl)oxy]-2-[(3,5-dimethylphenyl)sulfonyl]-octahydropyrrolo[1,2-a]pyrazine;

(7R,8aS)-2-{[4-bromo-3-(trifluoromethyl)phenyl]sulfonyl}-7-[(5-cyclopropylpyrazin-2-yl)oxy]octahydropyrrolo[1,2-a]pyrazine;

(7S,8aS)-7-[(5-cyclopropylpyrazin-2-yl)oxy]-2-[(4-fluoro-2-methylphenyl)-sulfonyl]-octahydropyrrolo[1,2-a]pyrazine;

(7S,8aS)-2-[(4-chloro-2-fluorophenyl)sulfonyl]-7-[(5-cyclopropylpyrazin-2-yl)-oxy]octahydropyrrolo[1,2-a]pyrazine;

(7R,8aS)-7-[(5-cyclopropylpyrazin-2-yl)oxy]-2-[(2,5-difluorophenyl)sulfonyl]-octahydropyrrolo[1,2-a]pyrazine;

(7S,8aS)-2-[(3-chloro-4-methylphenyl)sulfonyl]-7-[(5-cyclopropylpyrazin-2-yl)oxy]octahydropyrrolo[1,2-a]pyrazine;

(7S,8aS)-2-[(4-bromo-3-methylphenyl)sulfonyl]-7-[(5-cyclopropylpyrazin-2-yl)oxy]octahydropyrrolo[1,2-a]pyrazine;

(7R,8aS)-2-{[2-bromo-5-(trifluoromethyl)phenyl]sulfonyl}-7-[(5-cyclopropylpyrazin-2-yl)oxy]octahydropyrrolo[1,2-a]pyrazine;

(7S,8aS)-7-[(5-cyclopropylpyrazin-2-yl)oxy]-2-(mesitylsulfonyl)octahydropyrrolo-[1,2-a]pyrazine;

(7S,8aS)-2-(biphenyl-4-ylsulfonyl)-7-[(5-cyclopropylpyrazin-2-yl)oxy]octahydropyrrolo[1,2-a]pyrazine;

(7S,8aS)-2-[(3-bromophenyl)sulfonyl]-7-[(5-cyclopropylpyrazin-2-yl)oxy]-octahydropyrrolo[1,2-a]pyrazine;

(7S,8aS)-2-{[2,5-bis(trifluoromethyl)phenyl]sulfonyl}-7-[(5-cyclopropylpyrazin-2-yl)oxy]octahydropyrrolo[1,2-a]pyrazine;

(7S,8aS)-7-[(5-cyclopropylpyrazin-2-yl)oxy]-2-[(5-fluoro-2-methylphenyl)-sulfonyl]-octahydropyrrolo[1,2-a]pyrazine;

(7R,8aS)-7-[(5-cyclopropylpyrazin-2-yl)oxy]-2-[(2,5-dichloro-3-thienyl)sulfonyl]-octahydropyrrolo[1,2-a]pyrazine;

(7S,8aS)-2-[(5-chloro-2-thienyl)sulfonyl]-7-[(5-cyclopropylpyrazin-2-yl)oxy]-octahydropyrrolo[1,2-a]pyrazine;

(7S,8aS)-2-[(4-chlorophenyl)sulfonyl]-7-[(5-cyclopropylpyrazin-2-yl)oxy]-octahydropyrrolo[1,2-a]pyrazine;

(7S,8aS)-7-[(5-cyclopropylpyrazin-2-yl)oxy]-2-[(4-fluorophenyl)sulfonyl]-octahydropyrrolo[1,2-a]pyrazine;

(7S,8aS)-7-[(5-cyclopropylpyrazin-2-yl)oxy]-2-[(3-fluorophenyl)sulfonyl]-octahydropyrrolo[1,2-a]pyrazine;

(7S,8aS)-7-[(5-cyclopropylpyrazin-2-yl)oxy]-2-[(3-methylphenyl)sulfonyl]-octahydropyrrolo[1,2-a]pyrazine;

2-{[(7R,8aS)-7-[(5-cyclopropylpyrazin-2-yl)oxy]hexahydropyrrolo[1,2-a]pyrazin-2(1H)-yl]sulfonyl}benzonitrile;

(7S,8aS)-7-[(5-cyclopropylpyrazin-2-yl)oxy]-2-[(4-methoxyphenyl)sulfonyl]-octahydropyrrolo[1,2-a]pyrazine;

(7S,8aS)-7-[(5-cyclopropylpyrazin-2-yl)oxy]-2-[(3,5-dichlorophenyl)sulfonyl]-octahydropyrrolo[1,2-a]pyrazine;

(7S,8aS)-7-[(5-cyclopropylpyrazin-2-yl)oxy]-2-[(2,3-dichlorophenyl)sulfonyl]-octahydropyrrolo[1,2-a]pyrazine;

(7S,8aS)-2-[(4-bromophenyl)sulfonyl]-7-[(5-cyclopropylpyrazin-2-yl)oxy]-octahydropyrrolo[1,2-a]pyrazine;

(7S,8aS)-7-[(5-cyclopropylpyrazin-2-yl)oxy]-2-[(3,4-dichlorophenyl)sulfonyl]-octahydropyrrolo[1,2-a]pyrazine;

(7S,8aS)-7-[(5-cyclopropylpyrazin-2-yl)oxy]-2-[(2,5-dichlorophenyl)sulfonyl]-octahydropyrrolo[1,2-a]pyrazine;

4-{[(7R,8aS)-7-[(5-cyclopropylpyrazin-2-yl)oxy]hexahydropyrrolo[1,2-a]pyrazin-2(1H)-yl]sulfonyl}benzonitrile;

(7S,8aS)-7-[(5-cyclopropylpyrazin-2-yl)oxy]-2-[(2,4-dichlorophenyl)sulfonyl]-octahydropyrrolo[1,2-a]pyrazine;

(7S,8aS)-7-[(5-cyclopropylpyrazin-2-yl)oxy]-2-(1-naphthylsulfonyl)octahydropyrrolo[1,2-a]pyrazine;

(7S,8aS)-7-[(5-cyclopropylpyrazin-2-yl)oxy]-2-(2-naphthylsulfonyl)octahydropyrrolo[1,2-a]pyrazine;

(7S,8aS)-7-[(5-cyclopropylpyrazin-2-yl)oxy]-2-[(4-propylphenyl)sulfonyl]-octahydropyrrolo[1,2-a]pyrazine;

(7S,8aS)-7-[(5-cyclopropylpyrazin-2-yl)oxy]-2-[(2-methylphenyl)sulfonyl]-octahydropyrrolo[1,2-a]pyrazine;

3-{[(7R,8aS)-7-[(5-cyclopropylpyrazin-2-yl)oxy]hexahydropyrrolo[1,2-a]pyrazin-2(1H)-yl]sulfonyl}benzonitrile;

(7S,8aS)-7-[(5-cyclopropylpyrazin-2-yl)oxy]-2-[(2,5-dimethoxyphenyl)sulfonyl]-octahydropyrrolo[1,2-a]pyrazine;

(7S,8aS)-2-[(3-chloro-4-fluorophenyl)sulfonyl]-7-[(5-cyclopropylpyrazin-2-yl)oxy]-octahydropyrrolo[1,2-a]pyrazine;

(7S,8aS)-7-[(5-isopropylpyrazin-2-yl)oxy]-2-{[4-(trifluoromethyl)phenyl]-sulfonyl}octahydropyrrolo[1,2-a]pyrazine;

5-{[(7R,8aS)-7-[(5-cyclopropylpyrazin-2-yl)oxy]hexahydropyrrolo[1,2-a]pyrazin-2(1H)-yl]sulfonyl}-1-methyl-1,3-dihydro-2H-indol-2-one;

(7S,8aS)-7-[(5-cyclopropylpyrazin-2-yl)oxy]-2-[(5-ethyl-2-thienyl)sulfonyl]-octahydropyrrolo[1,2-a]pyrazine;

(7S,8aS)-7-[(5-cyclopropylpyrazin-2-yl)oxy]-2-[(1-ethyl-1H-pyrazol-4-yl)-sulfonyl]-octahydropyrrolo[1,2-a]pyrazine;

(7R,8aS)-7-[(2-cyclopropylpyrimidin-4-yl)oxy]-2-{[3-(trifluoromethyl)phenyl]-sulfonyl}octahydropyrrolo[1,2-a]pyrazine;

(7S,8aS)-7-[(2-cyclopropylpyrimidin-4-yl)oxy]-2-{[4-(trifluoromethyl)phenyl]-sulfonyl}octahydropyrrolo[1,2-a]pyrazine;

(7S,8aS)-2-[(5-tert-butyl-2-methylphenyl)sulfonyl]-7-[(5-cyclopropylpyrazin-2-yl)oxy]octahydropyrrolo[1,2-a]pyrazine;

(7S,8aS)-7-[(5-cyclopropylpyrazin-2-yl)oxy]-2-(5,6,7,8-tetrahydronaphthalen-2-ylsulfonyl)octahydropyrrolo[1,2-a]pyrazine;

(7S,8aS)-7-[(5-cyclopropylpyrazin-2-yl)oxy]-2-[(4-methoxy-3-methylphenyl)-sulfonyl]octahydropyrrolo[1,2-a]pyrazine;

(7S,8aS)-2-{[4-chloro-3-(trifluoromethyl)phenyl]sulfonyl}-7-[(5-cyclopropylpyrazin-2-yl)oxy]octahydropyrrolo[1,2-a]pyrazine;

(7S,8aS)-2-{[2-chloro-5-(trifluoromethyl)phenyl]sulfonyl}-7-[(5-cyclopropylpyrazin-2-yl)oxy]octahydropyrrolo[1,2-a]pyrazine;

(7R,8aS)-7-[(5-cyclopropylpyrazin-2-yl)oxy]-2-{[2-methoxy-5-(trifluoromethyl)-phenyl]sulfonyl}octahydropyrrolo[1,2-a]pyrazine;

(7S,8aS)-7-[(5-cyclopropylpyrazin-2-yl)oxy]-2-(2,3-dihydro-1H-inden-5-yl-sulfonyl)octahydropyrrolo[1,2-a]pyrazine;

(7S,8aS)-7-[(5-cyclopropylpyrazin-2-yl)oxy]-2-[(3,4-dimethylphenyl)sulfonyl]-octahydropyrrolo[1,2-a]pyrazine;

(7S,8aS)-7-[(5-cyclopropylpyrazin-2-yl)oxy]-2-{[3-(1-methyl-1H-pyrazol-5-yl)-phenyl]sulfonyl}octahydropyrrolo[1,2-a]pyrazine;

(7S,8aS)-7-[(5-cyclopropylpyrazin-2-yl)oxy]-2-{[2-methyl-6-(trifluoromethyl)-pyridin-3-yl]sulfonyl}octahydropyrrolo[1,2-a]pyrazine;

(7R,8aS)-7-[(5-cyclopropylpyrazin-2-yl)oxy]-2-{[2-(morpholin-4-yl)-5-(trifluoromethyl)phenyl]sulfonyl}octahydropyrrolo[1,2-a]pyrazine;

(7S,8aS)-7-[(5-cyclopropylpyrazin-2-yl)oxy]-2-{[3-(methoxymethyl)phenyl]-sulfonyl}octahydropyrrolo[1,2-a]pyrazine;

(7R,8aS)-7-[(5-cyclopropylpyrazin-2-yl)oxy]-2-{[4-methyl-3-(trifluoromethyl)-phenyl]sulfonyl}octahydropyrrolo[1,2-a]pyrazine;

5-{[(7R,8aS)-7-[(5-cyclopropylpyrazin-2-yl)oxy]hexahydropyrrolo[1,2-a]pyrazin-2(1H)-yl]sulfonyl}-2-fluorobenzonitrile;

2-{[(7R,8aS)-7-[(5-cyclopropylpyrazin-2-yl)oxy]hexahydropyrrolo[1,2-a]pyrazin-2(1H)-yl]sulfonyl}-4-methylbenzonitrile;

(7S,8aS)-7-[(5-cyclopropylpyrazin-2-yl)oxy]-2-[(1-isopropyl-3-methyl-1H-pyrazol-4-yl)sulfonyl]octahydropyrrolo[1,2-a]pyrazine;

(7S,8aS)-2-{[4-chloro-3-(trifluoromethyl)phenyl]sulfonyl}-7-ethoxyoctahydro-pyrrolo[1,2-a]pyrazine;

(7S,8aS)-7-[(5-cyclopropylpyrazin-2-yl)oxy]-2-[(3,3,3-trifluoropropyl)-sulfonyl]octahydropyrrolo[1,2-a]pyrazine;

(7S,8aS)-2-(butylsulfonyl)-7-[(5-cyclopropylpyrazin-2-yl)oxy]octahydropyrrolo[1,2-a]pyrazine;

(7S,8aS)-7-[(5-cyclopropylpyrazin-2-yl)oxy]-2-(2-thienylsulfonyl)octahydropyrrolo[1,2-a]pyrazine;

(7S,8aS)-2-(benzylsulfonyl)-7-[(5-cyclopropylpyrazin-2-yl)oxy]octahydropyrrolo[1,2-a]pyrazine;

(7S,8aS)-7-[(5-cyclopropylpyrazin-2-yl)oxy]-2-(isopropylsulfonyl)octahydropyrrolo[1,2-a]pyrazine;

(7S,8aS)-7-[(5-cyclopropylpyrazin-2-yl)oxy]-2-{[6-(trifluoromethyl)pyridin-3-yl]sulfonyl}octahydropyrrolo[1,2-a]pyrazine;

(7S,8aS)-7-[(5-cyclopropylpyrazin-2-yl)oxy]-2-[(4-methylpyridin-2-yl)sulfonyl]-octahydropyrrolo[1,2-a]pyrazine;

(7R,8aS)-7-[(5-cyclopropylpyrazin-2-yl)oxy]-2-[(6-methoxypyridin-3-yl)sulfonyl]-octahydropyrrolo[1,2-a]pyrazine;

3-{[(7R,8aS)-7-[(5-cyclopropylpyrazin-2-yl)oxy]hexahydropyrrolo[1,2-a]pyrazin-2(1H)-yl]sulfonyl}-N,N-dimethylbenzamide;

(7R,8aS)-7-[(5-cyclopropylpyrazin-2-yl)oxy]-2-[(5-fluoropyridin-3-yl)sulfonyl]-octahydropyrrolo[1,2-a]pyrazine;

5-{[(7R,8aS)-7-[(5-cyclopropylpyrazin-2-yl)oxy]hexahydropyrrolo[1,2-a]pyrazin-2(1H)-yl]sulfonyl}-3,3-dimethyl-1,3-dihydro-2H-indol-2-one;

2-{[(7R,8aS)-7-[(5-cyclopropylpyrazin-2-yl)oxy]hexahydropyrrolo[1,2-a]pyrazin-2(1H)-yl]sulfonyl}-4-(trifluoromethyl)benzonitrile;

(7S,8aS)-2-[(6-tert-butylpyridin-2-yl)sulfonyl]-7-{[5-(prop-1-en-2-yl)pyrazin-2-yl]oxy}octahydropyrrolo[1,2-a]pyrazine;

(7S,8aS)-2-[(6-tert-butylpyridin-2-yl)sulfonyl]-7-[(5-isopropylpyrazin-2-yl)oxy]octahydropyrrolo[1,2-a]pyrazine;

(7S,8aS)-7-{[5-(prop-1-en-2-yl)pyrazin-2-yl]oxy}-2-{[6-(trifluoromethyl)pyridin-2-yl]sulfonyl}octahydropyrrolo[1,2-a]pyrazine;

(7S,8aS)-7-[(5-isopropylpyrazin-2-yl)oxy]-2-{[6-(trifluoromethyl)pyridin-2-yl]-sulfonyl}octahydropyrrolo[1,2-a]pyrazine;

(7S,8aS)-7-{[5-(1-methylcyclopropyl)pyrazin-2-yl]oxy}-2-{[3-(trifluoromethyl)-phenyl]sulfonyl}octahydropyrrolo[1,2-a]pyrazine;

7-[(5-cyclopropylpyrazin-2-yl)oxy]-2-{[3-(trifluoromethyl)phenyl]sulfonyl}-hexahydropyrrolo[1,2-a]pyrazin-6(2H)-one;

(7S,8aR)-7-[(5-cyclopropylpyrazin-2-yl)oxy]-2-{[3-(trifluoromethyl)phenyl]-sulfonyl}hexahydropyrrolo[1,2-a]pyrazin-6(2H)-one;

(7S,8aS)-7-[(5-cyclopropylpyrazin-2-yl)oxy]-2-{[3-(trifluoromethyl)phenyl]-sulfonyl}hexahydropyrrolo[1,2-a]pyrazin-6(2H)-one;

(7S,8aR)-7-[(5-cyclopropylpyrazin-2-yl)oxy]-2-{[3-(trifluoromethyl)phenyl]-sulfonyl}hexahydropyrrolo[1,2-a]pyrazin-6(2H)-one;

(7S,8aS)-7-[(5-cyclopropylpyrazin-2-yl)oxy]-2-{[3-(trifluoromethyl)phenyl]-sulfonyl}hexahydropyrrolo[1,2-a]pyrazin-6(2H)-one;

7-[(5-cyclopropylpyrazin-2-yl)oxy]-2-{[4-(trifluoromethyl)phenyl]-sulfonyl}hexahydropyrrolo[1,2-a]pyrazin-6(2H)-one;

(8aS)-7-(3-fluorobenzyl)-2-{[4-(trifluoromethyl)phenyl]-sulfonyl}hexahydropyrrolo[1,2-a]pyrazin-6(2H)-one;

(8aS)-7-(3-fluorobenzyl)-2-{[3-(trifluoromethyl)phenyl]-sulfonyl}hexahydropyrrolo[1,2-a]pyrazin-6(2H)-one;

(7S,8aS)-7-[(3-fluorophenyl)(hydroxy)methyl]-2-{[3-(trifluoromethyl)phenyl]-sulfonyl}hexahydropyrrolo[1,2-a]pyrazin-6(2H)-one;

(7S,8aS)-7-[(3-fluorophenyl)(hydroxy)methyl]-2-{[3-(trifluoromethyl)phenyl]-sulfonyl}hexahydropyrrolo[1,2-a]pyrazin-6(2H)-one;

2-{[3-(trifluoromethyl)phenyl]sulfonyl}-7-{[5-(trifluoromethyl)pyridin-2-yl]-oxy}hexahydropyrrolo[1,2-a]pyrazin-6(2H)-one;

(7S,8aS)-7-[(5-cyclopropylpyrazin-2-yl)oxy]-2-{[3-(trifluoromethyl)benzyl]-sulfonyl}octahydropyrrolo[1,2-a]pyrazine;

(7S,8aS)-7-[(5-cyclopropylpyrazin-2-yl)oxy]-2-[(4,4,4-trifluorobutyl)sulfonyl]-octahydropyrrolo[1,2-a]pyrazine;

(8aR)-7-[(5-cyclopropylpyrazin-2-yl)oxy]-2-{[3-(trifluoromethyl)phenyl]-sulfonyl}hexahydropyrrolo[1,2-a]pyrazin-6(2H)-one;

(8aS)-7-[3-(trifluoromethyl)benzyl]-2-{[3-(trifluoromethyl)phenyl]sulfonyl}-hexahydropyrrolo[1,2-a]pyrazin-6(2H)-one;

(8aS)-7-[3-(trifluoromethyl)benzyl]-2-{[4-(trifluoromethyl)phenyl]sulfonyl}-hexahydropyrrolo[1,2-a]pyrazin-6(2H)-one;

3-{[(8aS)-6-oxo-7-[3-(trifluoromethyl)benzyl]hexahydropyrrolo[1,2-a]pyrazin-2(1H)-yl]sulfonyl}benzonitrile;

(7S,8aS)-2-{[4-(trifluoromethyl)phenyl]sulfonyl}-7-{[5-(trifluoromethyl)pyridin-2-yl]oxy}octahydropyrrolo[1,2-a]pyrazine;

3-{[(7R,8aS)-7-{[5-(trifluoromethyl)pyridin-2-yl]oxy}hexahydropyrrolo[1,2-a]pyrazin-2(1H)-yl]sulfonyl}benzonitrile;

(7S,8aS)-2-{[4-(trifluoromethyl)phenyl]sulfonyl}-7-{[6-(trifluoromethyl)pyridin-3-yl]oxy}octahydropyrrolo[1,2-a]pyrazine;

3-{[(7R,8aS)-7-{[6-(trifluoromethyl)pyridin-3-yl]oxy}hexahydropyrrolo[1,2-a]pyrazin-2(1H)-yl]sulfonyl}benzonitrile;

(7S,8aS)-2-{[3-(trifluoromethyl)phenyl]sulfonyl}-7-{[6-(trifluoromethyl)pyridin-2-yl]oxy}octahydropyrrolo[1,2-a]pyrazine; and (7S,8aS)-2-{[3-(trifluoromethyl)phenyl]sulfonyl}-7-{[5-(trifluoromethyl)pyridin-3-yl]oxy}octahydropyrrolo[1,2-a]pyrazine.

18. The compound or salt of claim 1 that is (7R,8aS)-7-[(5-cyclopropylpyrazin-2-yl)oxy]-2-{[3-(trifluoromethyl)phenyl]-sulfonyl}octahydropyrrolo[1,2-a]pyrazine, or a pharmaceutically acceptable salt thereof.

19. A pharmaceutical composition comprising a therapeutically effective amount of a compound of claim 1, or a pharmaceutically acceptable salt thereof, in combination with a pharmaceutically acceptable carrier.

20. The pharmaceutical composition of claim 19, wherein the compound or pharmaceutically acceptable salt thereof is (7R,8aS)-7-[(5-cyclopropylpyrazin-2-yl)oxy]-2-{[3-(trifluoromethyl)phenyl]-sulfonyl}-octahydropyrrolo[1,2-a]pyrazine.

21. A compound of Formula (II):

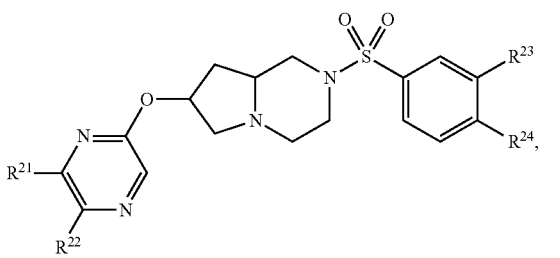

or a salt thereof, wherein:

$R^{21}$ and $R^{22}$ are independently selected from the group consisting of hydrogen, $C_{1-3}$ alkyl, and cyclopropyl; and one of $R^{23}$ and $R^{24}$ is hydrogen, and the other of $R^{23}$ and $R^{24}$ is halomethyl.

22. The compound of claim 21, or a salt thereof, wherein one of $R^{23}$ and $R^{24}$ is hydrogen, and the other of $R^{23}$ and $R^{24}$ is trifluoromethyl.

23. The compound of claim 21, or a salt thereof, wherein:
$R^{21}$ is hydrogen; and
$R^{22}$ is selected from the group consisting of hydrogen, isopropyl, and cyclopropyl; and
one of $R^{23}$ and $R^{24}$ is hydrogen, and the other of $R^{23}$ and $R^{24}$ is halomethyl.

24. The compound of claim 21, or a salt thereof, wherein:
$R^{21}$ is selected from the group consisting of hydrogen, isopropyl, and cyclopropyl; and
$R^{22}$ is hydrogen; and
one of $R^{23}$ and $R^{24}$ is hydrogen, and the other of $R^{23}$ and $R^{24}$ is halomethyl.

25. The compound of claim 21, or a salt thereof, wherein the compound is selected from the group consisting of:

(7R,8aS)-7-[(5-cyclopropylpyrazin-2-yl)oxy]-2-{[3-(trifluoromethyl)phenyl]-sulfonyl}octahydropyrrolo[1,2-a]pyrazine;

(7R,8aS)-7-(pyrazin-2-yloxy)-2-{[3-(trifluoromethyl)phenyl]sulfonyl}-octahydropyrrolo[1,2-a]pyrazine;

(7R,8aS)-7-[(6-cyclopropylpyrazin-2-yl)oxy]-2-{[3-(trifluoromethyl)phenyl]-sulfonyl}octahydropyrrolo[1,2-a]pyrazine;

(7R,8aS)-7-[(5-cyclopropylpyrazin-2-yl)oxy]-2-{[4-(trifluoromethyl)phenyl]-sulfonyl}octahydropyrrolo[1,2-a]pyrazine;

(7R,8aS)-7-[(6-cyclopropylpyrazin-2-yl)oxy]-2-{[4-(trifluoromethyl)phenyl]-sulfonyl}octahydropyrrolo[1,2-a]pyrazine; and (7R,8aS)-7-[(5-isopropyl pyrazin-2-yl)oxy]-2-{[4-(trifluoromethyl)phenyl]-sulfonyl}octahydropyrrolo[1,2-a]pyrazine.

* * * * *